(12) United States Patent
Gregor et al.

(10) Patent No.: US 8,815,906 B2
(45) Date of Patent: Aug. 26, 2014

(54) TYROSINE KINASE INHIBITORS

(75) Inventors: Vlad Edward Gregor, Del Mar, CA (US); Christina Gregor, legal representative, Del Mar, CA (US); Yahua Liu, San Diego, CA (US); Alexey Vyacheslavovich Anikin, Ivanteevka (RU); Charles Chamchoumis Mikel, Escondido, CA (US); Douglas Eric McGrath, Carlsbad, CA (US); Goverdhan Reddy Vavilala, Morrisville, NC (US); Jason Conrad Pickens, Chula Vista, CA (US); Aleksander Kadushkin, Zheleznodorozhnyi (RU); Luyong Jiang, San Marcos, CA (US); Mohan Santhanam Thiruvazhi, San Diego, CA (US); Sergey Zozulya, Shrewsbury, MA (US); Rajendran Vairagoundar, Portage, MI (US); Tong Zhu, San Diego, CA (US); Alexander Chucholowski, San Diego, CA (US); Zheng Yan, San Diego, CA (US); Alisher Khasanov, Escondido, CA (US)

(73) Assignee: Chembridge Corporation, San Diego, CA (US)

( * ) Notice: Subject to any disclaimer, the term of this patent is extended or adjusted under 35 U.S.C. 154(b) by 952 days.

(21) Appl. No.: 12/922,891

(22) PCT Filed: Mar. 18, 2009
(Under 37 CFR 1.47)

(86) PCT No.: PCT/US2009/001691
§ 371 (c)(1),
(2), (4) Date: Sep. 4, 2012

(87) PCT Pub. No.: WO2009/117097
PCT Pub. Date: Sep. 24, 2009

(65) Prior Publication Data
US 2013/0053376 A1    Feb. 28, 2013

Related U.S. Application Data

(60) Provisional application No. 61/038,032, filed on Mar. 19, 2008.

(51) Int. Cl.
*C07D 401/14* (2006.01)
*A61K 31/4439* (2006.01)
*A61K 31/4545* (2006.01)

(52) U.S. Cl.
CPC ........... *C07D 401/14* (2013.01); *A61K 31/4439* (2013.01); *A61K 31/4545* (2013.01)
USPC ........... 514/318; 514/338; 546/193; 546/194; 546/273.1

(58) Field of Classification Search
None
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie et al. | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis et al. | |
| 8,063,225 B2 * | 11/2011 | Gregor et al. | 546/273.1 |

FOREIGN PATENT DOCUMENTS

| | | |
|---|---|---|
| WO | WO 2004/063151 | 7/2004 |
| WO | WO 2004/096807 | 11/2004 |
| WO | WO 2005/009389 | 2/2005 |
| WO | WO 2006/108488 | 10/2006 |
| WO | WO 2008/021369 | 2/2008 |
| WO | WO 2008/022747 | 2/2008 |

OTHER PUBLICATIONS

West, Anthony R., Solid State Chemistry and its Applications, Wiley, New York, 1988, pp. 358 & 365.*
Wu et al., Toxicology, 236, pp. 1-6, 2007.*
Yu et al., "Physical characterization of, etc.," PSTT, vl. 1(3), 118-127 (1998).

(Continued)

*Primary Examiner* — Zinna Northington Davis
(74) *Attorney, Agent, or Firm* — Mark S. Cohen; Pearl Cohen Zedek Latzer Baratz LLP

(57) ABSTRACT

Provided are compounds of the formula (I): or a stereoisomer, tautomer, salt, hydrate or prodrug thereof that modulate tyrosine kinase activity, compositions comprising the compounds and methods of their use.

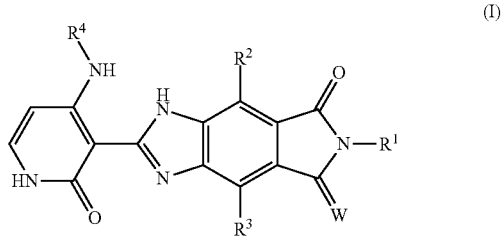

(I)

26 Claims, No Drawings

(56) References Cited

OTHER PUBLICATIONS

Kirk-Othmer Encyclopedia of Chemical Technology, 8, pp. 95-147 (2002).
Vippagunta et al., "Crystalline Solids", Advanced Drug Delivery Reviews 48 (2001) 3-26.
Guillory (in Brittain ed.), "Polymorphism in Pharmaceutical Solids.," NY: Marcel Dekker, Inc., 1999, 1-2, 125-181, 183-226.
Jain et al., "Polymorphism in Pharmacy", Indian Drugs, 1986, 23(6) 315-329.
Jens T. Carstensen, Drug Stability: Principles & Practice, 2d. Ed., Marcel Dekker, NY, NY, 1995, pp. 379-380.
Gunby et al., "An enzyme-linked immunosorbent assay to screen for inhibitors of the oncogenic anaplastic lymphoma kinase," Haematologica, 2005, 90, 988-990.
Bonvini et al., "Nucleophosmin-Anaplastic Lymphoma Kinase (NPM-ALK), a Novel Hsp90-Client Tyrosine Kinase: Down-Regulation of NPM-ALK Expression and Tyrosine Phosphorylation in ALK+ CD30+ Lymphoma Cells by the Hsp90 Antagonist 17-Allylamino,17-demethoxygeldanamycin ," Cancer. Res. 2002, 62, 1559-1566.
Turturro et al., "Model of Inhibition of the NPM-ALK Kinase Activity by Herbimycin A," Clin. Cancer Res. 2002, 8, 240-245.
Morris et al., "ALK, the chromosome 2 gene locus altered by the t(2;5) in non-Hodgkin's lymphoma, encodes a novel neural receptor tyrosine kinase that is highly related to leukocyte tyrosine kinase (LTK)," Oncogene, 1997, 14:2175-2188.
Iwahara et al., "Molecular characterization of ALK, a receptor tyrosine kinase expressed specifically in the nervous system," Oncogene, 1997, 14:439-449.
Stoica et al., "Identification of anaplastic lymphoma kinase as a receptor for the growth factor pleiotrophin," J Biol Chem, 2001, 276(20): 16772-16779.
Stoica et al., "Pleiotrophin Signaling through Anaplastic Lymphoma Kinase Is Rate-limiting for Glioblastoma Growth," J Biol Chem, 2002, 277(16):14153-14158.
Morris et al., "Fusion of a kinase gene, ALK, to a nucleolar protein gene, NPM, in non-Hodgkin's lymphoma," Science, 1994, 263: 1281-1284.
Pulford et al, "Anaplastic lymphoma kinase proteins in growth control and cancer," J Cell Physiol, 2004, 199:330-358.
Sauville et al, J. CHn. Oncol, 2001, 19, 2319-2333.
International Search Report of corresponding PCT Application No. PCT/US09/01691 dated Sep. 24, 2009.
Cahn et al., "Specification of Molecular Chirality" 1966, Angew. Chem. 78: 413-447, Angew Chem. Int. Ed. Engl. 5: 385-414.
Prelog and Helmchen, "Basic principles of the CIP-system and proposals for a revision" 1982, Angew. Chem. 94:614-631, Angew. Chem. Int. Ed. Engl. 21:567-583.
Mata and Lobo, "The CIP sequence rules: analysis and proposal for a revision",1993, Tetrahedron: Asymmetry 4:657-668.
Wagner, "Stereospecific synthesis of amphetamines", 2003, Tetrahedron: Asymmetry 14(15), 2119-2125.
Goodman, "Synthesis and evaluation of radioiodinated 2-(2(RS)-aminopropyl)-5-iodothiophenes as brain imaging agents" J. Med. Chem. Jan. 24, 1992;35(2):280-5.

\* cited by examiner

TYROSINE KINASE INHIBITORS

CROSS-REFERENCE TO RELATED APPLICATIONS

This application is a National Phase Application of PCT International Application No. PCT/US09/01691, International Filing Date Mar. 18, 2009, which claims priority of U.S. Ser. No. 61/038,032, filed Mar. 19, 2008, all of which are hereby incorporated by reference in their entirety.

FIELD

The present disclosure relates to the field of tyrosine kinase enzyme inhibition, in particular anaplastic lymphoma kinase (ALK) inhibition using novel small molecules. Provided are compounds capable to modulate ALK activity, compositions that comprise the compounds and methods of using the compounds for the treatment or prevention of diseases or conditions that are characterized by ALK activity or expression.

BACKGROUND

The anaplastic lymphoma kinase (ALK) is a receptor tyrosine kinase that belongs to the insulin receptor superfamily and is normally expressed in neural tissues during embryogenesis (Morris et al., *Oncogene,* 1997, 14:2175-2188; Iwahara et al., *Oncogene,* 1997, 14:439-449). In particular, transcripts of ALK gene are highly expressed in specific regions of the central nervous system, including the diencephalon, midbrain, and the ventral half of the spinal cord. In the peripheral nervous system, ALK expression has been detected in the trigeminal, sympathetic, and enteric ganglia. After birth, expression diminishes, but still persists in certain areas such as the olfactory bulb and thalamus. Despite the apparent function of ALK in the development of the nervous system, the physiologic role of ALK is still largely unclear. While the recent studies are proposing that pleiotrophin (PTN) and midkine (MK) are cognate ligands for ALK (Stoica et al., *J Biol Chem,* 2001, 276(20):16772-16779; Stoica et al., *J Biol Chem,* 2002, 277(16):14153-14158), exact mechanisms and biological consequences of ligand-dependent ALK activation are not fully understood at this time.

ALK was initially identified because of its involvement in the human non-Hodgkin lymphoma subtype known as anaplastic large cell lymphoma (ALCL). Many cases of ALCL are associated with a reciprocal translocation, t(2; 5)(p23; q35), which juxtaposes the gene at 5q35 encoding nucleophosmin (NPM), a nucleolar-associated phosphoprotein, with the gene for a receptor tyrosine kinase, the anaplastic lymphoma kinase (ALK), at 2p23. The resulting fusion gene encodes a chimeric 80-kD protein in which 40% of the N-terminal portion of NPM is fused to the complete intracytoplasmic portion of ALK containing the functional tyrosine kinase domain (Morris et al., Science, 1994, 263:1281-1284). Constitutive activation of the NPM-ALK kinase domain stimulates anti-apoptotic and mitogenic signaling pathways such as PI3K-AKT, JAK-STAT, and PLCγ, resulting in cellular transformation (Bai, 1998; Slupianek, 2001; Zamo 2002). The transforming activity of NPM/ALK is dependent on its kinase activity (Bischof 1997). While the most frequently occurring oncogenic ALK fusion in ALK-positive ALCL cases ("ALKomas") is the NPM-ALK (~80% of ALK-positive ALCL cases), other ALK gene fusions have been consequently identified in human hematological and solid cancers. These include TPM3-ALK (fusion of non-muscle tropomyosin 3 with ALK), TPM4-ALK, ATIC-ALK, CLTC-ALK, RanBP2-ALK, TFGL/S-ALK, CARS-ALK, MSN-ALK and others.

All known ALK fusion proteins share the essential feature of having some type of the oligomerization domain in the sequence of the ALK fusion partner which mediates constituitive self-association of the ALK fusion that causes constant, ligand-independent ALK kinase domain activation. Similarly to NPM-ALK, the related ALK fusion proteins have been shown to possess transforming and oncogenic potential, apparently mediated by their constitutive kinase activity. Although ALK-positive lymphomas have a relatively benign prognosis, about 40% of patients do not respond or relapse after the standard therapy (CHOP). CHOP (cyclophosphamide, hydroxydoxorubicin, oncovin, prednisone) and CHOP-like multi-agent combination chemotherapy regimens that are used for conventional treatment of non-Hodgkin lymphomas including ALCL are associated with considerable acute and chronic toxicities, a problem specifically bothersome in pediatric patients. Therefore, a highly effective and targeted therapy would be beneficial and highly warranted not only for relapsed patients but also as first-line therapy if well tolerated and efficacious.

In addition to ALKomas, several research groups have also described the presence of the NPM-ALK and the related fusion proteins like CLTC-ALK in a rare form of B-cell non-Hodgkin lymphoma. Rearrangements of ALK gene have been also identified in the inflammatory fibroblastic tumors (IMT). These rare spindle cell proliferations involve malignant myofibroblasts and infiltrating non-malignant inflammatory cells in a collagenous matrix and occur primarily in the soft tissue of children and young adults.

More recently, a novel oncogenic ALK fusion, EML4-ALK, comprising portions of the echinoderm microtubule-associated protein-like 4 (EML4) gene and the anaplastic lymphoma kinase (ALK) gene, has been implicated in a subset of non-small cell lung cancer (NSCLC) (Soda, 2007). Mouse 3T3 fibroblast cells forced to express this fusion tyrosine kinase generated transformed foci in culture and subcutaneous tumors in nude mice. The EML4-ALK fusion transcript was detected in 6.7% of the 75 NSCLC patients examined; these individuals were distinct from those harboring mutations in the epidermal growth factor receptor gene. Presence of the oncogenic TPM4-ALK fusion was also detected by proteomics methods in esophageal cancer samples from patients in Iran (Jazii, 2006) and China (Du, 2007). These findings strongly suggest that EML4-ALK and TPM4-ALK fusions are promising candidates for a therapeutic target in a sizable subset of NSCLC and possibly in some esophageal carcinomas.

Certain additional facts concerning the possible relevance of deregulated full-length ALK signaling in some types of cancer and utility of the non-rearranged, full-length ALK as a therapeutic target are noteworthy. The small secreted growth factors pleiotrophin (PTN) and midkine (MK) have been shown to activate signaling of the normal, full-length ALK receptor protein (Stoica et al., 2001, supra; Stoica et al., 2002, supra). While the exact mechanism and biological significance of ALK stimulation by the different molecular forms of these ligands are not completely understood at this time (Lu, 2005; Perez-Pinera, 2007), a functional connection between PTN and/or midkine and ALK is well established. A large number of studies provide evidence that PTN and MK contribute to tumor growth, abnormal tumor-associated angiogenesis and metastasis (Kadamatsu, 2004; Bernard-Pierrot 2002). For example, both PTN and ALK have been found to be overexpressed in human glioblastomas, and downregulation of ALK expression by ribozymes was shown to suppress human glioblastoma xenograft growth in mice and to prolong the survival of the tumor-bearing animals (Powers 2002; Grzhelinsky 2005). Expression or overexpression of the full-length ALK receptor in certain neuroblastomas, diffuse large B-cell non-Hodgkin lymphomas, leiomyosarcomas, and malignant peripheral nerve sheath sarcomas have been reported (Pullford et al., *J Cell Physiol*, 2004, 199:330-358). Similarly, it has been reported that cell lines established from common solid tumors of ectodermal origin, such as melanoma and breast cancer, exhibit ALK receptor mRNA expression (Pulford, 2004, supra). Additional analyses should elucidate the role of ALK signaling in the genesis and progression of these various cancers aver the next few years.

Studies in which the mouse Alk gene was knocked-out demonstrate that ALK-negative mice show no evident gross anatomical, histological or functional abnormalities and have a normal lifespan (Pulford, 2004, supra). Therefore, the physiological functions of Alk, which is normally expressed primarily in neural tissues, appear to be largely redundant. These observations suggest that therapeutic approaches targeting the aberrant oncogenic functions of ALK are not likely to be associated with limiting toxicities due to concomitant inhibition of normal ALK functions.

Therefore, both the various cytoplasmic ALK fusion proteins and the full-length ALK in its transmembrane receptor form are valid molecular targets for anticancer drugs. Consequently, a small-molecule inhibitors of ALK kinase are likely to be a drug for suppressing of tumor growth and angiogenesis.

Recently reported preclinical studies have provided compelling proof of principle for the efficacy of the inhibition of NPM-ALK in ALK-positive ALCL, with marked anti-tumor activity observed experimentally. For instance, studies performed by Novartis demonstrated regression of established lymphoma tumors formed by subcutaneous injection of the human NPM-ALK-positive ALCL cell line Karpas-299 in mice when the animals were treated with the small molecule ALK kinase inhibitor NVP-TAE684 (Galkin, 2007).

Other experimental approaches for the inhibition of oncogenic ALK signaling have also indicated that the agents blocking this signaling are likely to possess very potent anticancer capabilities. Piva and colleagues recently showed that siRNA (small inhibitory ribonucleic acid)-mediated inhibition of NPM-ALK signaling markedly diminished the development of ALCL xenografts in mice (Piva, 2006). Collectively, these data indicate that the inhibition of the aberrant, cancer-causing activity of ALK fusion proteins in ALCL, as well as other ALK-driven malignancies, using small molecule inhibitors is very likely to produce marked anti-tumor responses.

WO 2004/063151 reported a tyrosine kinase inhibitory activity of pyridones. Pyrroloquinixalinediones and their derivatives were shown to exhibit HIV integrase inhibitory activity (WO2004/096807).

Only a few inhibitors with activity against ALK have been reported. Sauville (Sauville et al, *J. Clin. Oncol.*, 2001, 19, 2319-2333) disclosed a derivative of the natural product staurosporine having an anti-tumor activity in a patient with an ALK-positive anaplastic large cell lymphoma that was refractory to conventional chemo- and radio-therapy. It is important to note that the compound's ability to inhibit ALK was not tested in this study, thus, it has not been formally proven that it is an ALK inhibitor. Indeed, a recent report suggests that staurosporine possesses minimal ability to directly inhibit ALK (Gunby et al., *Haematologica*, 2005, 90, 988-990). The naturally occurring, structurally related benzoquinone analogues, geldanamycin and 17-allylamino-17-demethoxygeldanamycin (Bonvini et al., *Cancer. Res.* 2002, 62, 1559-1566) and herbimycin A (Turturro et al., *Clin. Cancer Res.* 2002, 8, 240-245) have been reported to exert ALK inhibition via heat shock protein pathways, enhancing the proteasome-mediated degradation of the ALK protein. Most recently, a series of pyrazolo[3,4-c]isoquinoline derivatives with ALK-inhibitory activity was published in WO 2005009389.

One of the challenges of developing an ATP-competitive small-molecule ALK inhibitor is to provide sufficient selectivity of the compound for ALK versus inhibition of other structurally related protein kinases. Due to the existence of about 520 evolutionary related protein kinases in the human genome, this could be a demanding task. In particular, inhibition of the insulin receptor kinase which is closely structurally related to ALK is highly undesirable due to the risk of blocking insulin action and the resultant hyperglycemia.

Another highly related RTK is Insulin-Like Growth Factor Receptor I (IGF1R). In the recent years, IGF1R emerged as an attractive oncology target in a broad variety of malignancies (Riedman and Macaulay, 2006; Tao et al 2007). However, suppression of IGF1R signaling may potentially have undesirable side-effects in a clinical context where normal cell/tissue proliferation and development are essential, such as treating pediatric patients (ALCL). Therefore, a sufficiently high selectivity of ALK inhibition versus inhibition of such related RTKs as Insulin Receptor and IGF is likely to be a desirable trait in a clinical ALK inhibitor. Conversely, inhibition of a small subset of therapeutically relevant PTKs (multitargeting), in addition to ALK, can improve the efficacy of an oncology drug, especially for solid tumors which are often heterogeneous and have complicated tumor biology.

Another group of tyrosine kinases evolutionary and structurally related to ALK is Ret, Ros, Axl and kinases that are members of Trk family (Trk A, B and C).

RET is a receptor tyrosine kinase that has a role in transducing growth and differentiation signals in tissues derived from the neural crest and is required for normal development of the sympathetic, parasympathetic and enteric nervous systems and the kidney. Gain of function mutations of Ret are associated with the development of several types of human cancers, including medullar thyroid carcinoma and multiple endocrine neoplasias type II and III (or MEN2A and MEN2B). RET mutations have been also identified in a small percentage of pheochromocytomas. Chromosomal rearrangements involving the RET gene are one of the most common causes of a sporadic form of thyroid cancer called papillary thyroid carcinoma (also known as RET/PTC). There is a compelling experimental evidence that thyroid cell transformation to PTC is driven by hyperactivated Ret (Santoro, 2004]. Kinase inhibitors with activity against RET are currently in preclinical or clinical development for these types of cancers.

ROS is a receptor tyrosine kinase that has been found to be constitutively activated in a subset of glioblastomas as a result of genomic translocations (Charest, 2003; Charest, 2006) and may represent an emerging therapeutic target in this highly malignant and deadly brain tumor.

AXL is a unique tyrosine kinase receptor, implicated in the inhibition of apoptosis as well as promoting neovascularization, and it is emerging as a viable therapeutic target in a number of malignancies, both solid and hematologic (Holland, 2005). In particular, it is a chronic myelogenous leukemia-associated oncogene (O'Bryan, 1991; Jannsen, 1991) and is also associated with colon, prostate cancer and melanoma (Van Ginkel, 2004; Sainaghi, 2005). Overexpression of Axl in myeloid cells has been shown to be involved in Type II diabetes (Augustine, 1999). Modulation of Axl activity by small-molecule kinase inhibitors may have utility in therapy of the disease states mentioned above.

TrkA is a receptor tyrosine kinase that belongs to a subfamily of tyrosine kinases that also includes TrkB, and TrkC. TrkB and TrkC are structurally closely related to TrkA, but respond to different ligands in the neurotrophin (NT) family. Nerve growth factor (NGF) signaling through TrkA has been well characterized and is similar to signal transduction mechanisms of other tyrosine kinase receptors. As outlined in more detail below, TrkA is a well validated or a potential drug target in a variety of malignancies as well as in neuropathic pain and certain inflammatory diseases. The roles of the two other members of the neurothropin receptor TK family, TrkB and TrkC, in disease states has received less attention, however the emerging evidence implicates both of them in several types of neoplasias.

TrkA gene was originally described as a chimeric oncogene in colon cancer (Martin-Zanca, 1986] and its activating genomic translocations are common in papillary thyroid carcinomas (Bongarzone, 1989; Pierotti, 2006) and occur in breast cancer as well (Brzezianska, 2007). Hyperactivating deletion or fusion mutations of TrkA and TrkC were also identified in some acute myeloid leukemias as well as solid tumors (Reuther, 2000; Eguchi, 2005).

Overexpression of TrkA in malignant versus normal tissues and association with poor prognosis was shown in prostate, pancreatic cancers, melanomas, mesotheliomas (Festuccia, 2007; Myknyoczki, 1999; Florenes, 2004; Davidson, 2004). TrkA is overexpressed in the majority of prostate carcinomas, and is further increased in androgen-independent tumors (Papatsoris, 2007). In prostatic carcinomas, an autocrine loop involving NGF and TrkA is responsible for tumor progression (Djakiew, 1993). An autocrine NGF/TrkA loop and mitogenic role of NGF has been demonstrated in breast cancer cells as well (Chiarenza, 20011; Dolle, 2003). It has also been shown that NGF signaling has angiogenesis-promoting effect (Cantarella, 2002).

TrkB, sometimes in conjunction with its ligand BDNF, is often overexpressed in a variety of human cancers, ranging from neuroblastomas to pancreatic ductal adenocarcinomas, in which it may allow tumor expansion and contribute to resistance to anti-tumor agents. TrkB acts as a potent suppressor of anoikis (detachment-induced apoptosis), which is associated with the acquisition of an aggressive tumorigenic and metastatic phenotype in vivo (Desmet, 2006; Douma, 2004). In summary, Trk family members have been implicated as oncogenes in a number of neoplasms including prostate, thyroid, pancreatic, colon, breast, ovarian cancers, melanomas and some leukemias. For prostate cancer and thyroid carcinomas, TrkA is especially well validated as a drug target.

Strong and diverse experimental evidence suggests that nerve growth factor (NGF), signaling through TrkA pathway, is a mediator of some persistent pain states, including neuropathic and inflammatory pain (Pezet, 2006; Hefti, 2006; Bennet, 2001). Function-neutralizing anti-NGF and anti-TrkA antibodies demonstrated therapeutic effect in models of inflammatory, neuropathic, skeletal and cancer pain (Ugolini, 2007; Koewler, 2007; Sevcik, 2005). In such disease states as prostate cancer with metastatic bone pain and pancreatic cancer with perineural invasion, cancer progression, pain and TrkA signaling has been shown to be all positively correlated (Dang, 2006; Halvorson, 2005). Inhibition of the NGF/TrkA pathway appears to be very well validated for treatment of chronic pain of different natures: (i) inflammatory pain; (ii) neuropathic pain and (iii) cancer pain.

It is noteworthy that in the skin, TrkA receptor mediates the ability of NGF to stimulate keratinocytes proliferation and inhibit keratinocytes apoptosis. NGF is produced by keratinocytes to stimulate their cell proliferation with an autocrine loop and melanocyte proliferation with a paracrine pathway (Di Marco, 1993; Pincelli, 2000). NGF/TrkA signaling also modulates inflammation (Frossard, 2004) and proliferation of terminal cutaneous nerves (Raychaudhury, 2004), components of psoriasis and atopic dermatitis. Murine models for psoriasis and atopic dermatitis have been established and K252a and AG879, both potent non-clinical TrkA inhibitors, were demonstrated to have therapeutic effect [Raychaudhury, 2004) Takano, 2007) in the models. This data indicates that TrkA is a potential drug target in skin disorders characterized by keratinocytes hyperproliferation.

Thus, blocking the ALK activity represents a rational, targeted approach to therapy of various diseases. As there are several tyrosine kinases that are evolutionary and structurally related to ALK, such as Ret, Ros, Axl and members of Trk family, there is an opportunity to either identify a multitargeted kinase inhibitor with a potential utility in other types of malignancies not targeted by selective ALK inhibition, or to fine-tune the inhibition selectivity towards a particular kinase of interest by lead optimization.

SUMMARY

Provided herein are selective ALK activity inhibitors, compositions that comprise the compounds and methods of using the compounds for the treatment or prevention of diseases or conditions that are characterized by ALK activity or expression in mammals.

Provided herein are selective inhibitors of tyrosine kinases evolutionary and structurally related to ALK, such as Ret, Ros, Axl and members of Trk family (TrkA, B and C) and are useful for the treatment or prevention of diseases or conditions characterized by aberrant ALK, RET, ROS, Axl and Trk family of tyrosine kinase activity or expression in mammals.

The compounds provided herein are selective inhibitors of ALK, RET, ROS, Axl and Trk family of tyrosine kinases as compared to the inhibitory activity of one or more other tyrosine kinases such as IRK (Insulin Receptor Kinase) or IGF1R.

The compounds provided herein can be used to treat and/or prevent a mammal affected by a neoplastic disease, in particular ALK-positive anaplastic large cell lymphoma, inflammatory myofibroblastic tumors, diffuse large B-cell non-Hodgkin lymphoma, non-small cell lung cancer, esophageal carcinoma, breast cancer, neuroblastoma and glioblastoma.

Certain compounds provided herein have therapeutic utility in treating various types of neoplasms and other disease states, caused by the aberrant activity of Alk, RET, ROS, AXL and TRK family tyrosine kinases. In particular, provided compounds potently inhibit the catalytic activity of TrkA and/or other Trk family kinases and thereby provide new treatment strategies for patients afflicted with cancer, chronic pain and certain hyperproliferative skin diseases.

The compounds provided herein can be used to treat and/or prevent a mammal affected by tyrosine kinase related disorder such as cancer selected from, but not limited to, astrocytoma, basal or squamous cell carcinoma, brain cancer, gliobastoma, bladder cancer, breast cancer, colorectal cancer, chrondrosarcoma, cervical cancer, adrenal cancer, choriocarcinoma, esophageal cancer, endometrial carcinoma, erythroleukemia, Ewing's sarcoma, gastrointestinal cancer, head and neck cancer, hepatoma, glioma, hepatocellular carcinoma, leukemia, leiomyoma, melanoma, non-small cell lung cancer, neural cancer, ovarian cancer, pancreatic cancer, prostate cancer, renal cell carcinoma, rhabdomyosarcoma, small cell lung cancer, thyoma, thyroid cancer, testicular cancer and osteosarcoma.

The compounds provided herein can be used to treat and/or prevent a mammal affected by tyrosine kinase related disorder such as hyperproliferative skin disease selected from, but not limited to, psoriasis, acne vulgaris, acne rosacea, actinic keratosis, solar keratosis, Bowen's disease, ichthyosis, hyperkeratosis, disorders of keratinization such as Darrier's disease, palmoplanter keratoderma, pityriasis rubra pilaris, epidermal naevoid syndrome, erythrokeratoderma variabilis, epidermolytic hyperkeratosis, non-bullous ichthyosiform erythroderma, cutaneous lupus erythematosus and lichen planus.

In one aspect, provided are compounds of the formula (I) or a stereoisomer, tautomer, salt, hydrate or prodrug thereof:

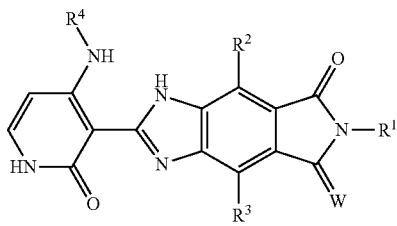

wherein:
$R^2$ and $R^3$ are each independently hydrogen, lower alkyl, lower alkoxy, halogen, cyano, lower alkylamino or di-lower alkylamino;
W is O, S, or $NR^e$, wherein
$R^e$ is selected from hydrogen or lower alkyl;
or W represents bonding of two hydrogen atoms to a carbon atom, forming an optionally substituted methylene group:

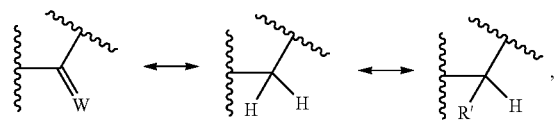

wherein
$R^f$ is selected from hydrogen or lower alkyl;
$R^4$ is

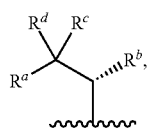

wherein
$R^a$ is optionally substituted aryl or heteroaryl;
$R^b$ is lower alkyl, trifluoromethyl, hydroxymethyl, methoxymethyl, aminomethyl, di-lower alkylaminomethyl or heterocyclylaminomethyl;
$R^c$ is selected from hydrogen, hydroxy, lower alkoxy, or lower alkyl;
$R^d$ is selected from hydrogen, or lower alkyl; and
$R^1$ is as described below.

In another aspect, provided are compounds of the formula (I) that are ALK inhibitors, selective especially with respect to IGF1R and/or IRK.

In yet another aspect, provided are pharmaceutical compositions comprising one or more compounds of the formula (I) or a stereoisomer, tautomer, salt, hydrate or prodrug thereof useful for treatment of a disease or condition characterized by Alk activity or expression.

In yet another aspect, provided are pharmaceutical compositions comprising one or more compounds of the formula (I) or a stereoisomer, tautomer, salt, hydrate or prodrug thereof useful for treatment of a disease or condition characterized by Alk, RET, ROS, AXL and TRK family tyrosine kinases activity or expression.

A disease or condition characterized by ALK activity or expression includes but is not limited to ALK-positive anaplastic large cell lymphoma, an inflammatory myofibroblastic tumor, diffuse large B-cell non-Hodgkin lymphoma, non-small cell lung cancer, esophageal carcinoma, breast cancer, neuroblastoma and glioblastoma.

A disease or condition characterized by ALK, RET, ROS, AXL and TRK family tyrosine kinases activity or expression includes but is not limited to cancer, chronic pain and certain hyperproliferative skin diseases.

In yet another aspect, provided are methods for treating a disease or disorder characterized by ALK activity or expression comprising administration to mammal one or more compounds of the formula (I).

In yet another aspect, provided are methods for treating a disease or disorder characterized by ALK, RET, ROS, AXL and TRK family tyrosine kinases activity or expression comprising administration to mammal one or more compounds of the formula (I).

DETAILED DESCRIPTION

Definitions

When describing the compounds, pharmaceutical compositions containing such compounds and methods of using such compounds and compositions, the following terms have the following meanings unless otherwise indicated. When two terms referring to chemical groups are combined, the combined term refers to the groups covalently linked in either orientation, unless specified otherwise. For instance, the term "acylamino" can refer to either "—C(O)—N(R)—" or to "—N(R)—C(O)—" unless specified otherwise and similarly sulfonamido or aminosulfonyl can refer to either —S(O$_2$)—N(R)— or —N(R)—S(O$_2$)—.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups, in one embodiment having up to about 11 carbon atoms, in another embodiment, as a lower alkyl, from 1 to 8 carbon atoms, and in yet another embodiment, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyl" as defined below.

"Substituted alkyl" includes those groups recited in the definition of "substituted" herein, and in one embodiment refers to an alkyl group having 1 or more substituents, in another embodiment, from 1 to 5 substituents, and yet in another embodiment, from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, alkylthio, substituted alkylthio, arylthio, thioketo, thiol, alkyl-S(O)—, aryl-S(O)—, alkyl-S(O)$_2$—, and aryl-S(O)$_2$—.

"Alkylene" refers to divalent saturated aliphatic hydrocarbyl groups in one embodiment having up to about 11 carbon atoms and in another embodiment having 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups having in one embodiment up to about 11 carbon atoms, in another embodiment from 2 to 8 carbon atoms, and in yet another embodiment from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH3)═CH2), vinyl and substituted vinyl, and the like.

"Substituted alkenyl" includes those groups recited in the definition of "substituted" herein, and particularly refers to an alkenyl group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Alkenylene" refers to divalent olefinically unsaturated hydrocarbyl groups particularly having in one embodiment up to about 11 carbon atoms and in another embodiment 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically unsaturated hydrocarbyl groups particularly having in one embodiment up to about 11 carbon atoms and in another embodiment 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C═CH), propargyl (—CH$_2$C═CH), and the like.

"Substituted alkynyl" includes those groups recited in the definition of "substituted" herein, and particularly refers to an alkynyl group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Alkanoyl" as used herein, which can include "acyl", refers to the group R—C(O)—, where R is hydrogen or alkyl as defined above.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having in one embodiment 1 or more substituents, in another embodiment from 1 to 5 substituents, and yet in another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Heteroalkyl" refers to an alkyl chain as specified above, having one or more heteroatoms selected from O, S, or N.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as indacene, s indacene, indane, indene, naphthalene, octacene, octaphene, octalene, ovalene, penta 2,4 diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted in one embodiment with 1 or more substituents, in another embodiment from 1 to 5 substituents, and in yet another embodiment from 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, alkylthio, substituted alkylthio, arylthio, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring. In certain embodiments, a bicyclic compound provided herein comprises a fused aryl.

"Amino" refers to the radical —NH$_2$.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Azido" refers to the radical —N$_3$.

"Carbamoyl" refers to the radical —C(O)N(R)$_2$ where each R group is independently hydrogen, alkyl, cycloalkyl or aryl, as defined herein, which may be optionally substituted as defined herein.

"Carboxy" refers to the radical —C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Particular halo groups are either fluoro or chloro.

"Hydroxy" refers to the radical —OH.

"Nitro" refers to the radical —NO$_2$.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" or "heteroaromatic" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, □-carboline, chromane, chromene, cinnoline, furan, imidazole, indazole, indole, indoline, indolizine, isobenzofuran, isochromene, isoindole, isoindoline, isoquinoline, tetrahydroisoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, tetrahydroquinoline, quinolizine, quinoxaline, tetrazole, thiadiazole, thiazole, thiophene, triazole, xanthene, and the like. Particularly, heteroaryl can include other saturated ring systems, and can therefore be derived from indoline, indolizine, tetrahydroquinoline, and tetrahydroisoquinoline. In certain embodiments, the heteroaryl group is between 5-20 membered heteroaryl, with 5-10 membered heteroaryl being useful in certain embodiments. Particular heteroaryl groups are those derived from thiophene, pyrrole, benzothiophene, benzofuran, indole, pyridine, pyrimidine, quinoline, tetrahydroquinoline, isoquinoline, tetrahydroisoquinoline, imidazole, oxazole and pyrazine.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl.

"Sulfanyl" refers to the radical HS—. "Substituted sulfanyl" refers to a radical such as RS— wherein R is any substituent described herein. In certain embodiments, "substituted sulfanyl" refers to a radical —SR where R is an alkyl or cycloalkyl group as defined herein that may be optionally substituted as defined herein. Alkylthio or arylthio refer to the above sulfanyl group. Representative examples include, but are not limited to, methylthio; ethylthio, propylthio, butylthio, phenylthio and the like.

"Sulfinyl" refers to the radical —S(O)H. "Substituted sulfinyl" refers to a radical such as S(O)—R wherein R is any substituent described herein.

"Sulfonyl" refers to the divalent radical —S(O2)-. "Substituted sulfonyl" refers to a radical such as —S($O_2$)—R wherein R is any substituent described herein. "Aminosulfonyl" or "Sulfonamide" refers to the radical $H_2N$(O-2)S—, and "substituted aminosulfonyl" "substituted sulfonamide" refers to a radical such as R2N(O-2)S— wherein each R is independently any substituent described herein. In particular embodiments, R is selected from H, lower alkyl, alkyl, aryl and heteroaryl.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms as long as the heteroaromatic ring is chemically feasible and stable.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like. The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations and the like.

"Solvate" refers to a compound provided herein or a salt thereof, that further includes a stoichiometric or non-stoichiometric amount of solvent bound by non-covalent intermolecular forces. Where the solvent is water, the solvate is a hydrate.

It is to be understood that compounds having the same molecular formula but differing in the nature or sequence of bonding of their atoms or in the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78:413-447, *Angew. Chem.*, Int. Ed. Engl. 5:385-414 (errata: *Angew. Chem.*, Int. Ed. Engl. 5:511); Prelog and Helmchen, 1982, *Angew. Chem.* 94:614-631, *Angew. Chem.* Internat. Ed. Eng. 21:567-583; Mata and Lobo, 1993, *Tetrahedron*: Asymmetry 4:657-668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture".

In certain embodiments, the compounds provided herein may possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, provided are the stereoisomers of the compounds depicted herein upon use of stereoisomerically pure intermediates in their synthesis, such as pure enantiomers, or diastereomers as building blocks, prepared by chiral synthesis methodologies, or resolution by formation of diastereomeric salts with chiral acid or base and their separation, or separation by means of chromatography, including using chiral stationary phase. The racemic, or diastereomeric mixtures of compounds provided herein can also be separated by means of chromatography, including chiral stationary phase chromatography.

In certain embodiments, the compounds provided herein are "stereochemically pure." A stereochemically pure compound has a level of stereochemical purity that would be recognized as "pure" by those of skill in the art. Of course, this level of purity will be less than 100%. In certain embodiments, "stereochemically pure" designates a compound that is substantially free of alternate isomers. In particular embodiments, the compound is 85%, 90%, 91%, 92%, 93%, 94%, 95%, 96%, 97%, 98%, 99%, 99.5% or 99.9% free of other isomers.

As used herein, the terms "disorder" and "disease" are used interchangeably to refer to a condition in a subject. Certain conditions may be characterized as more than one disorder. For example, certain conditions may be characterized as both non-cancerous proliferative disorders and inflammatory disorders.

As used herein, the term "effective amount" refers to the amount of a compound provided herein which is sufficient to reduce or ameliorate the severity, duration of a disorder, cause regression of a disorder, prevent the recurrence, development, or onset of one or more symptoms associated with a disorder, or enhance or improve the prophylactic or therapeutic effect(s) of another therapy.

As used herein, the term "in combination" refers to the use of more than one therapies. The use of the term "in combination" does not restrict the order in which therapies (e.g., prophylactic and/or therapeutic agents) are administered to a subject with a disorder. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject with a disorder.

As used herein, the terms "prophylactic agent" and "prophylactic agents" as used refer to any agent(s) which can be used to prevent disorder or one or more symptoms thereof. In certain embodiments, the term "prophylactic agent" refers to a compound provided herein. In certain other embodiments, the term "prophylactic agent" does not refer a compound provided herein. In certain embodiments, a prophylactic agent is an agent which is known to be useful for, or has been or is currently being used to the prevent or impede the onset, development, progression and/or severity of a disorder. Prophylactic agents may be characterized as different agents based upon one or more effects that the agents have in vitro and/or in vivo. For example, an anti-angiogenic agent may also be characterized as an immunomodulatory agent.

As used herein, the terms "prevent," "preventing" and "prevention" refer to the prevention of the recurrence, onset, or development of one or more symptoms of a disorder in a subject resulting from the administration of a therapy, or the administration of a combination of therapies.

As used herein, the phrase "prophylactically effective amount" refers to the amount of a therapy which is sufficient to result in the prevention of the development, recurrence or onset of one or more symptoms associated with a disorder, or to enhance or improve the prophylactic effect(s) of another therapy.

As used herein, the terms "subject" and "patient" are used interchangeably herein. The terms "subject" and "subjects" refer to an animal, in certain embodiments a mammal including a non-primate (e.g., a cow, pig, horse, cat, dog, rat, and mouse) and a primate (e.g., a monkey such as a cynomolgous monkey, a chimpanzee and a human), and more particularly a human. In another embodiment, the subject is a farm animal (e.g., a horse, a cow, a pig, etc.) or a pet (e.g., a dog or a cat). In certain embodiments, the subject is a human.

As used herein, the term "synergistic" refers to a combination of a compound provided herein and another therapy which has been or is currently being used to prevent, manage or treat a disorder, which is more effective than the additive effects of the therapies. A synergistic effect of a combination of therapies permits the use of lower dosages of one or more of the therapies and/or less frequent administration of said therapies to a subject with a disorder. The ability to utilize lower dosages of a therapy and/or to administer said therapy less frequently reduces the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies may avoid or reduce adverse or unwanted side effects associated with the use of either therapy alone.

As used herein, the terms "therapeutic agent" and "therapeutic agents" refer to any agent(s) which can be used in the treatment, management, or amelioration of a disorder or one or more symptoms thereof. In certain embodiments, the term "therapeutic agent" refers to a compound provided herein. In certain other embodiments, the term "therapeutic agent" does not refer to a compound provided herein. In certain embodiments, a therapeutic agent is an agent which is known to be useful for, or has been or is currently being used for the treatment, management, prevention, or amelioration a disorder or one or more symptoms thereof. Therapeutic agents may be characterized as different agents based upon one or more effects the agents have in vivo and/or in vitro, for example, an anti-inflammatory agent may also be characterized as an immunomodulatory agent.

As used herein, the term "therapeutically effective amount" refers to that amount of a therapy sufficient to result in the amelioration of one or more symptoms of a disorder, prevent advancement of a disorder, cause regression of a disorder, or to enhance or improve the therapeutic effect(s) of another therapy. In a specific embodiment, with respect to the treatment of cancer, an effective amount refers to the amount of a therapy that inhibits or reduces the proliferation of cancerous cells, inhibits or reduces the spread of tumor cells (metastasis), inhibits or reduces the onset, development or progression of one or more symptoms associated with cancer, or reduces the size of a tumor. In certain embodiments, a therapeutically effective of a therapy reduces the proliferation of cancerous cells or the size of a tumor by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, relative to a control or placebo such as phosphate buffered saline ("PBS").

As used herein, the terms "therapies" and "therapy" can refer to any protocol(s), method(s), and/or agent(s) that can be used in the prevention, treatment, management, or amelioration of a disorder or one or more symptoms thereof. In certain embodiments, the terms "therapy" and "therapies" refer to chemotherapy, radiation therapy, hormonal therapy, biological therapy, and/or other therapies useful in the prevention, management, treatment or amelioration of a disorder or one or more symptoms thereof known to one of skill in the art (e.g., skilled medical personnel).

As used herein, the terms "treat", "treatment" and "treating" refer to the reduction or amelioration of the progression, severity and/or duration of a disorder, or the amelioration of one or more symptoms thereof resulting from the administration of one or more therapies.

As used herein, the term "modulation" or "modulating" refers to the alteration of the catalytic activity of a tyrosine kinase. In particular, modulating can refer to the activation or to the inhibition of the tyrosine kinase. The tyrosine kinase can be any tyrosine kinase known to those of skill in the art. In certain embodiments, the tyrosine kinase is a receptor tyrosine kinase or an intracellular tyrosine kinase.

As used herein, the term "ALK" refers to anaplastic lymphoma kinase.

The definitions used herein are according to those generally accepted in the pertinent art and those specified herein.

Compounds

In one embodiment, provided are compounds of the formula (I) or a stereoisomer, tautomer, salt, hydrate or prodrug thereof:

wherein:

$R^2$ and $R^3$ are each independently hydrogen, lower alkyl, lower alkoxy, halogen, cyano, amino, lower alkylamino, or di-lower alkylamino;

W is O, S, or $NR^e$, wherein $R^e$ is selected from hydrogen or lower alkyl;

or W represents bonding of two hydrogen atoms to a carbon atom, forming an optionally substituted methylene group:

wherein $R^f$ is selected from hydrogen or lower alkyl;

$R^4$ is wherein $R^a$ is optionally substituted aryl or heteroaryl, $R^b$ is lower alkyl, trifluoromethyl, hydroxymethyl, methoxymethyl, aminomethyl, lower alkylaminomethyl, di-lower alkylaminomethyl or heterocyclylaminomethyl;

$R^c$ is selected from hydrogen, hydroxy, lower alkoxy, or lower alkyl;

$R^d$ is selected from hydrogen, or lower alkyl; and $R^1$ is independently selected from optionally substituted heterocyclyl, heterocyclylalkyl, heteroaryl, heteroarylalkyl, heterocyclyloxyalkyl, heteroalkyl, heterocyclylaminoalkyl, aminoalkyl, lower alkylaminoalkyl, di-(lower alkyl)-aminoalkyl, aminocycloalkyl, alkylaminocycloalkyl, di-(lower alkyl)-aminocycloalkyl, di-(lower alkyl)-aminocycloalkylalkyl, wherein the substituents are selected from hydrogen, lower alkyl, hydroxy, lower alkoxy, amino, amidino, carboxamido, sulfonamido, hydroxy, cyano, primary, secondary or tertiary amino, halo, azido, lower alkoxyalkyl, cyanoalkyl, azidoalkyl, haloalkyl, hydroxyalkyl, methanesulfonylalkyl, primary, secondary or tertiary amino-alkyl, optionally substituted aryl, heteroaryl, heteroalkyl, heterocyclyl, cycloalkyl, alkenyl and alkynyl.

In another embodiment, $R^2$ and $R^3$ are hydrogen or methyl.

In yet another embodiment, W is

In one embodiment, $R^a$ is optionally substituted thienyl or phenyl wherein the optional substituents are alkyl, alkoxy or halo.

In another embodiment, $R^a$ is optionally substituted thienyl or phenyl wherein the optional substituents are methyl, methoxy or fluoro.

In yet another embodiment, $R^a$ is thiophen, phenyl, methylthiophen, methylphenyl, fluoromethylphenyl, fluoromethoxyphenyl, trifluorophenyl or tetrafluorophenyl.

In another embodiment, $R^c$ and $R^d$ are hydrogen or hydroxy.

In one embodiment, $R^b$ is alkyl.

In another embodiment, $R^b$ is methyl.

In another embodiment, $R^1$ includes, but is not limited to:

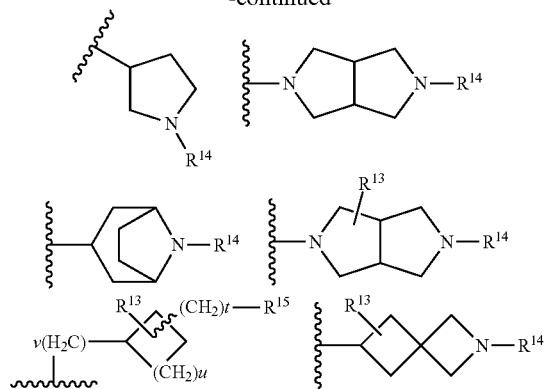

wherein:

R[13] is selected from hydrogen, lower alkyl, heteroalkyl, heterocyclyl, cycloalkyl and heterocycloalkyl;

R[14] is selected from hydrogen, hydroxy, lower alkoxy, di-(lower alkyl)amino, lower alkyl, heteroalkyl, heterocyclyl, cycloalkyl, heterocycloalkyl, lower alkoxyalkyl, cyanoalkyl, azidoalkyl, nitroalkyl, ketoalkyl, methanesulfonylalkyl, aminoalkyl, lower alkylaminoalkyl, di-(lower alkyl)aminoalkyl, optionally substituted aryl, heteroaryl, arylalkyl, and heteroarylalkyl;

R[15] is selected from hydrogen, amino, lower alkylamino, di-(lower alkyl)amino, hydroxy, lower alkoxy, heteroalkyl, lower alkoxyalkyl, aminoalkyl, lower alkylaminoalkyl and di-(lower alkyl)aminoalkyl;

a is an integer from 0 to 4; and t, u, v are independent integers from 0 to 5.

It is understood that if any of the integers is (are) 0 (zero), it means a covalent chemical bond.

In another embodiment, R[1] is further selected from:

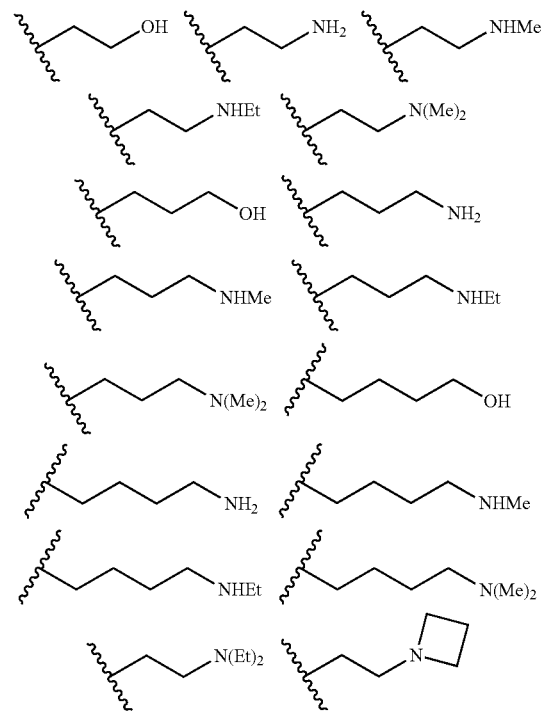
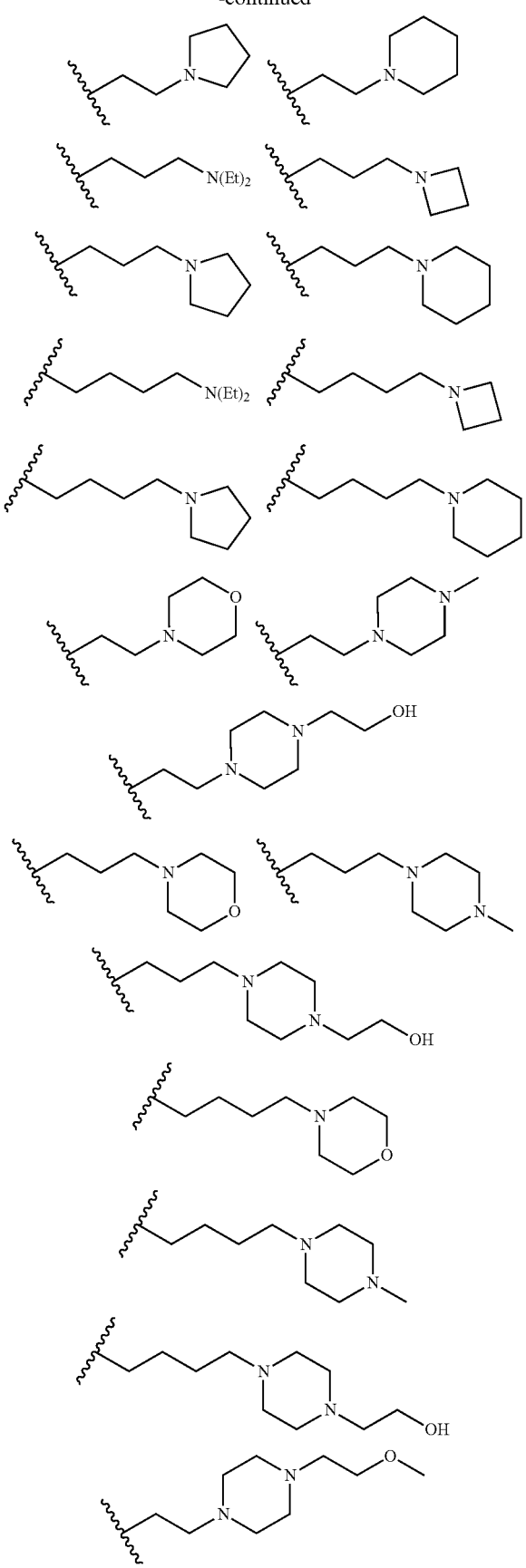

21
-continued
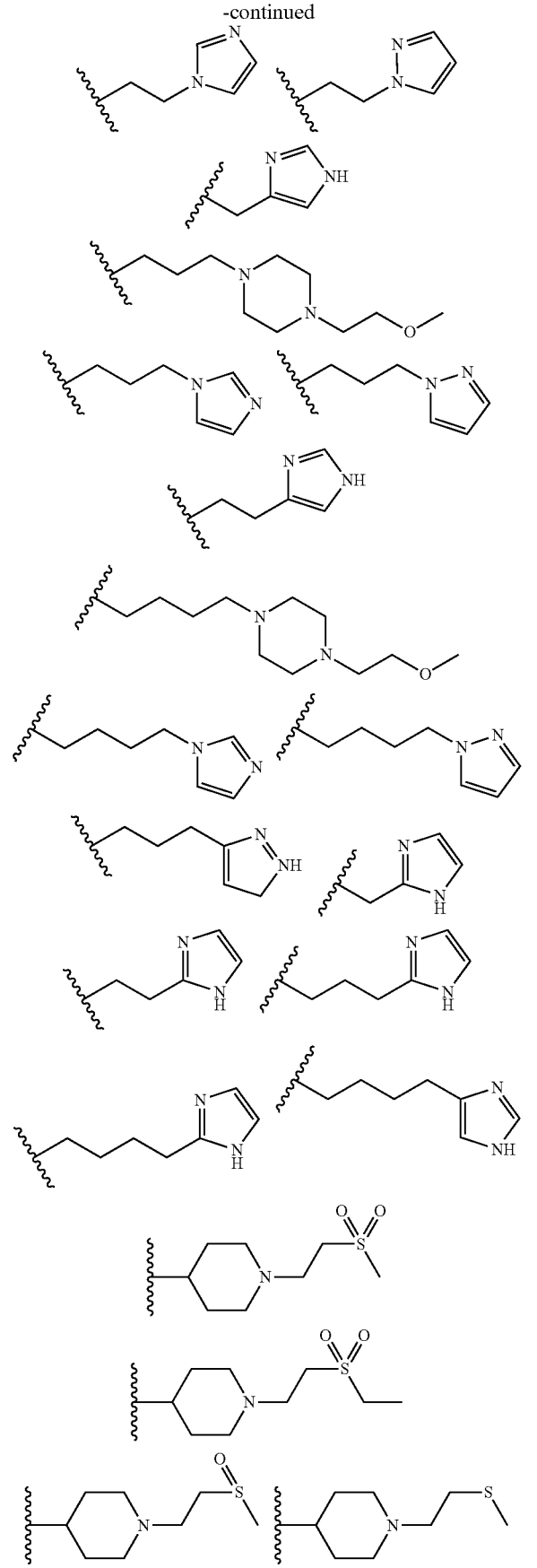
22
-continued
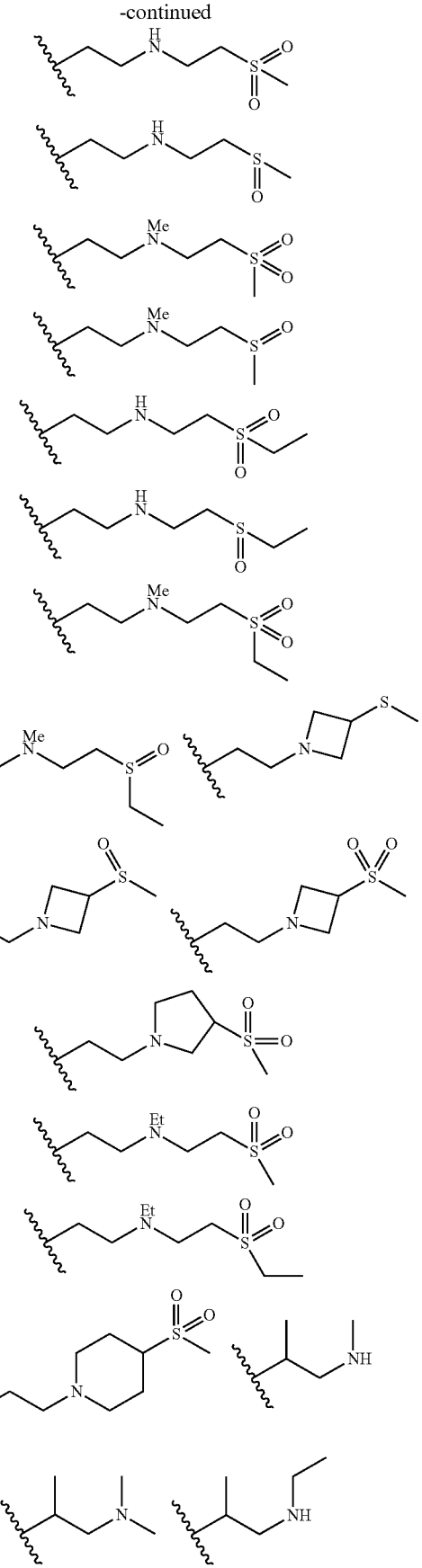

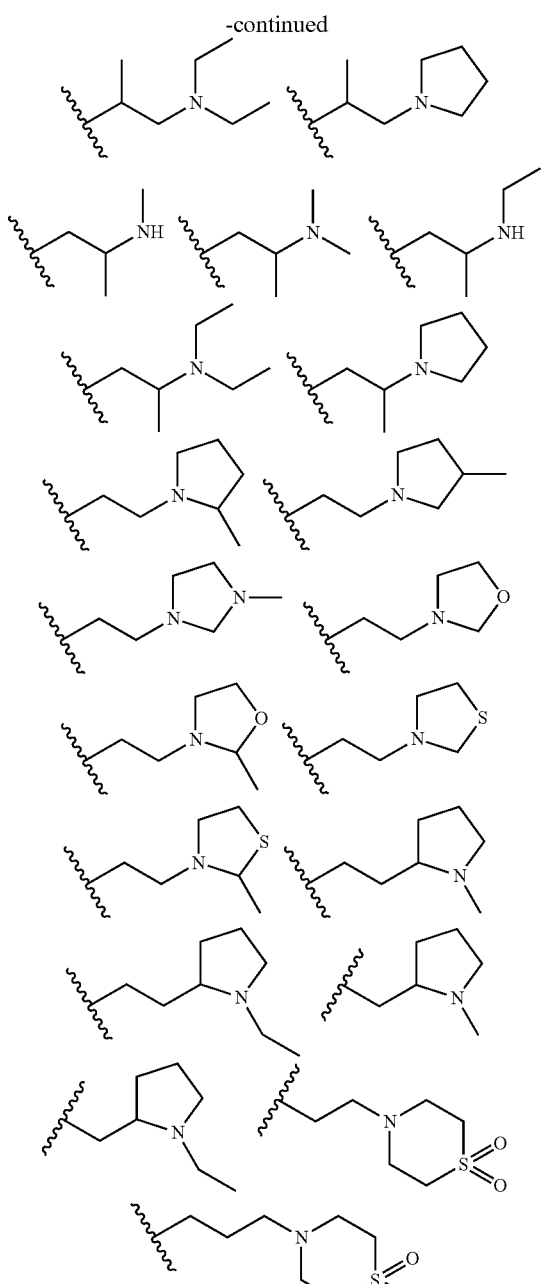

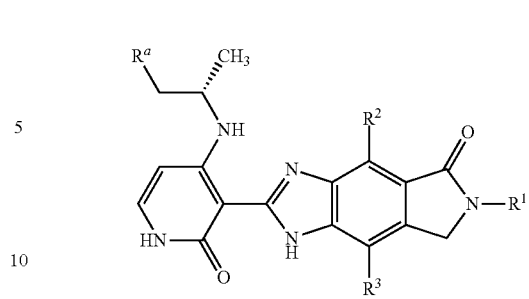

wherein the substituents are as defined above.

The compounds provided herein are selective ALK inhibitors, especially compared to IGF1R and/or IR (insulin receptor) inhibition.

The following exemplary compounds according to formula (I) were prepared according to the methods described herein:

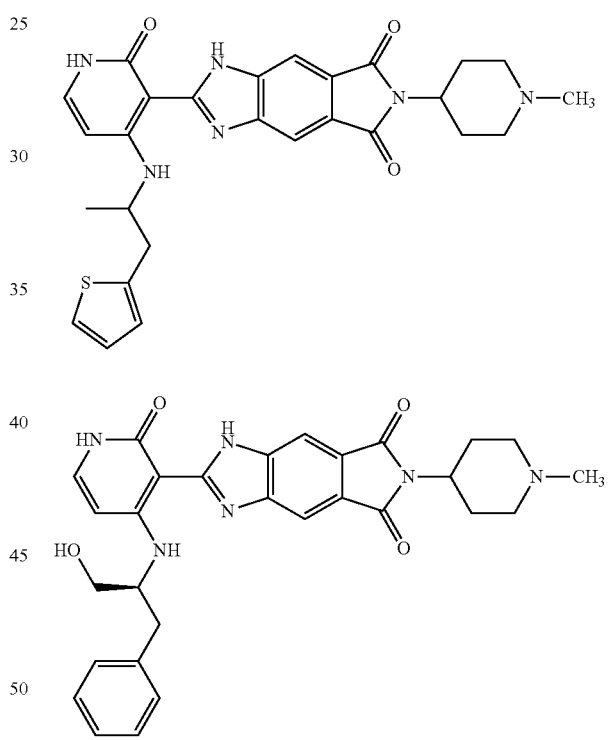

In certain embodiments, one or more of the $R^1$ methylene chain between the connection and the heteroatom is optionally substituted by one or more hydrogen, lower alkyl, hydroxy, hydroxy-lower alkyl, lower alkoxy, carboxamido or sulfonamido.

In certain embodiments, the $R^1$ methylene groups is optionally substituted by a heteroatom selected from O and S, or NR*, S=O, or S(=O)$_2$, wherein R* is selected from hydrogen, hydroxy, lower alkyl, lower alkoxy, heteroalkyl, hydroxyalkyl, aminoalkyl, lower alkylaminoalkyl and di-(lower alkyl)aminoalkyl.

In certain embodiments, any $R^1$ ring is optionally substituted by a lower alkyl or heteroalkyl group.

In another embodiment, provided are compounds of the formula (Ia) or a stereoisomer, tautomer, salt, hydrate or prodrug thereof:

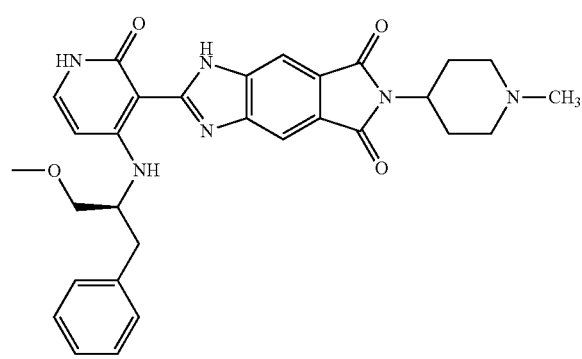

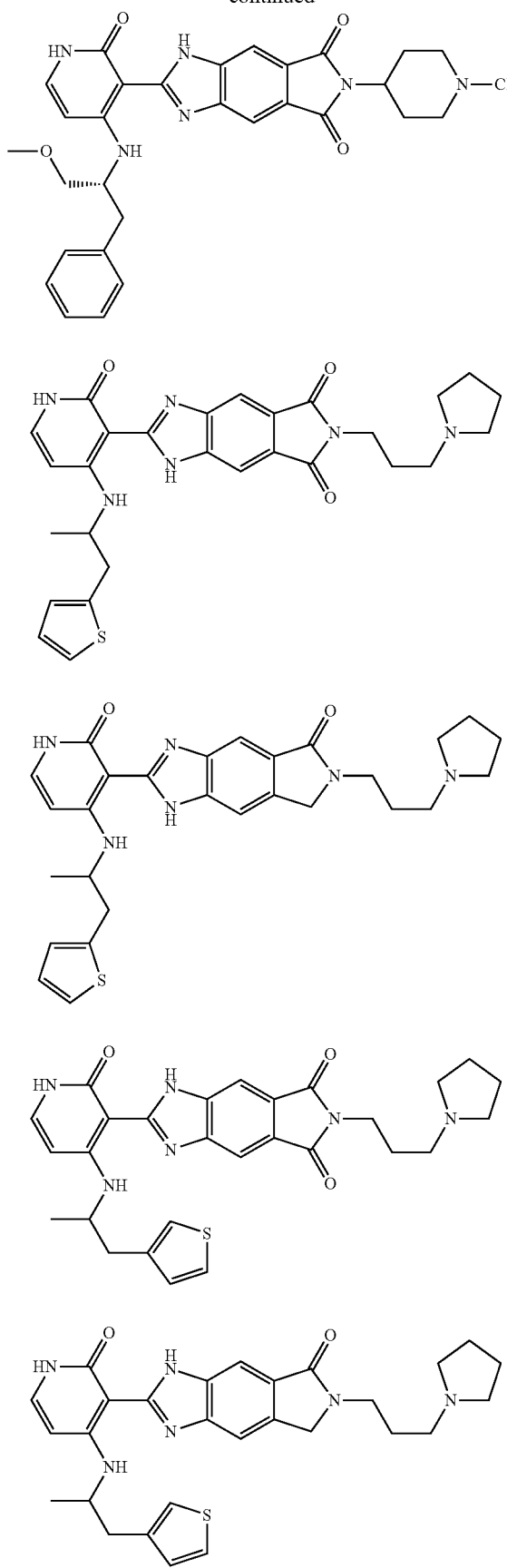
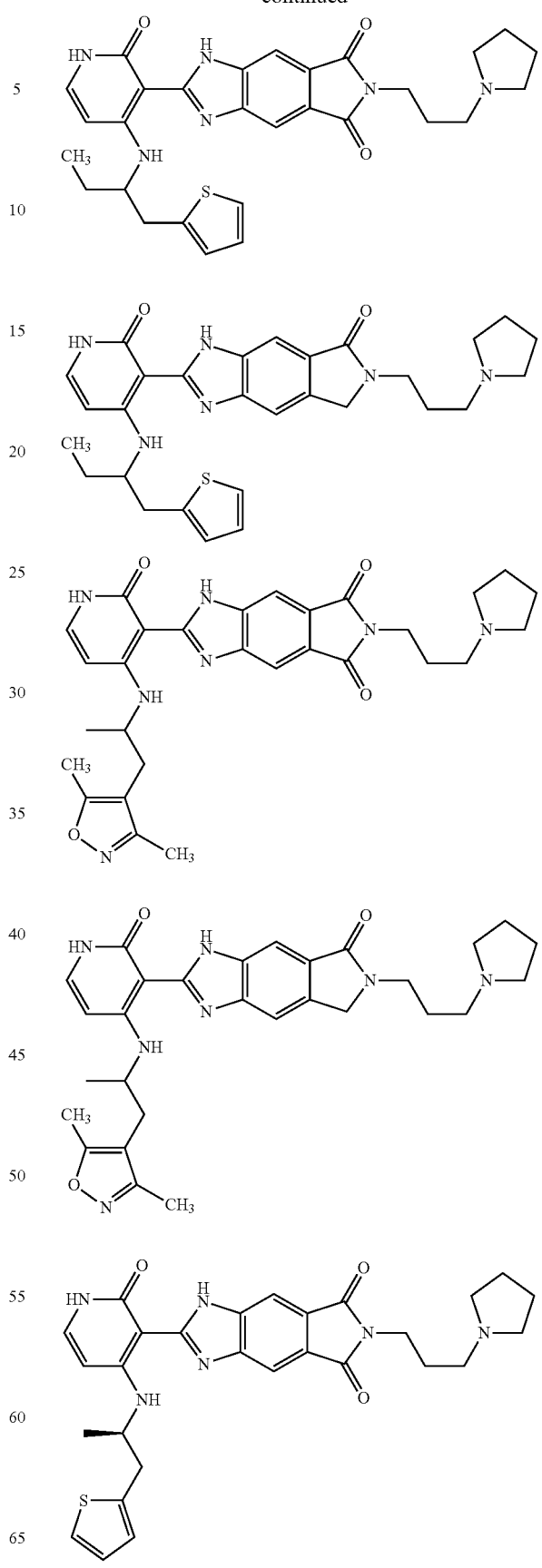

27
-continued
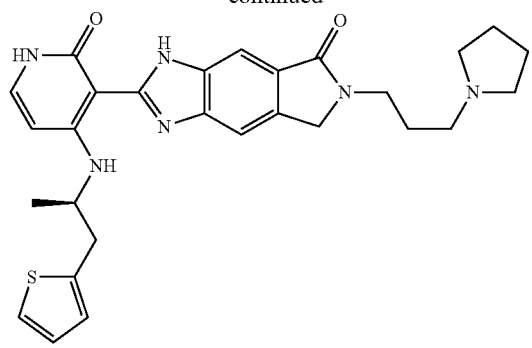
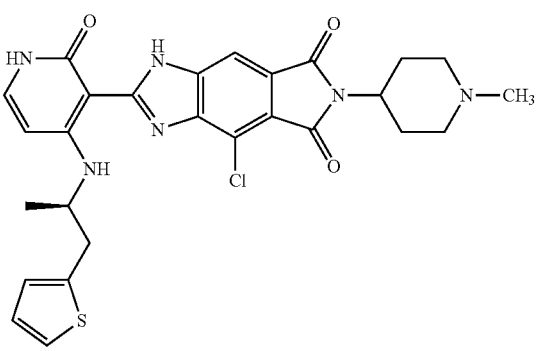
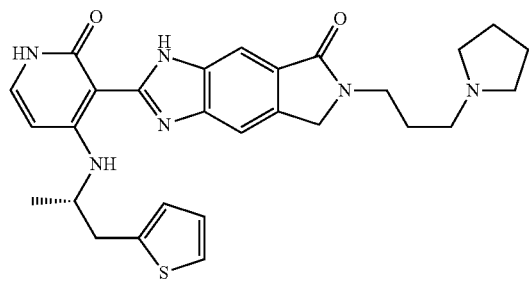
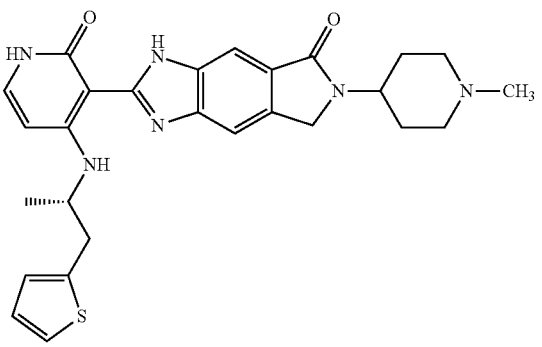
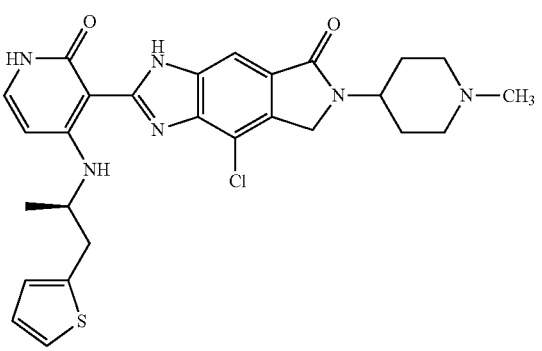
28
-continued
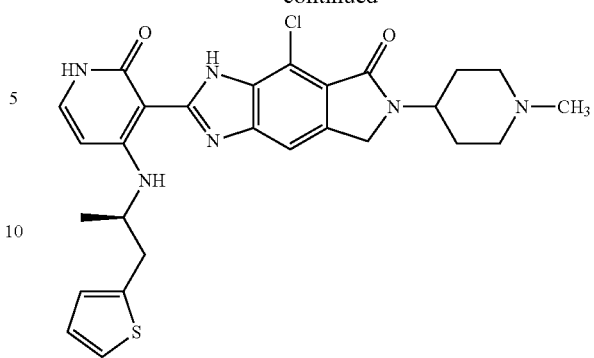
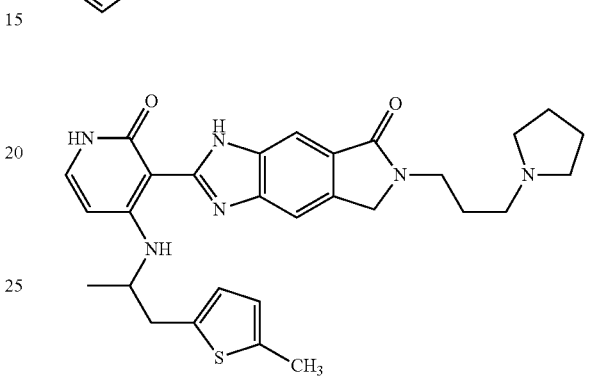
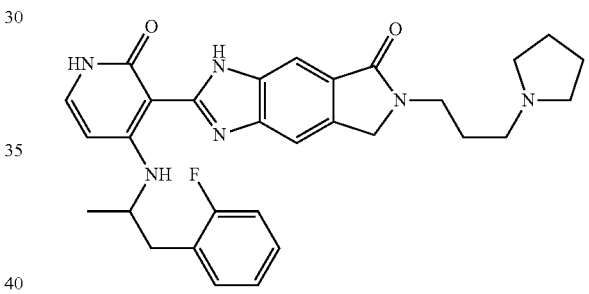
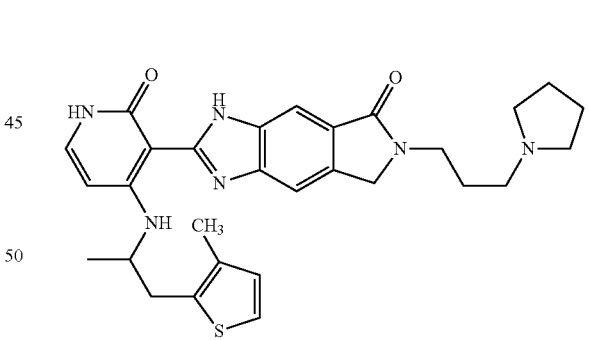
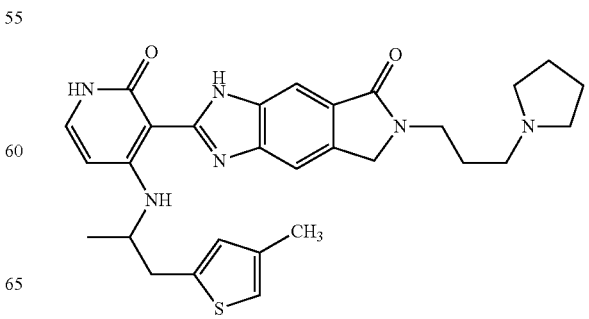

-continued
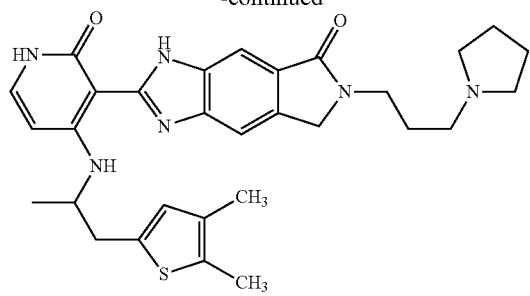
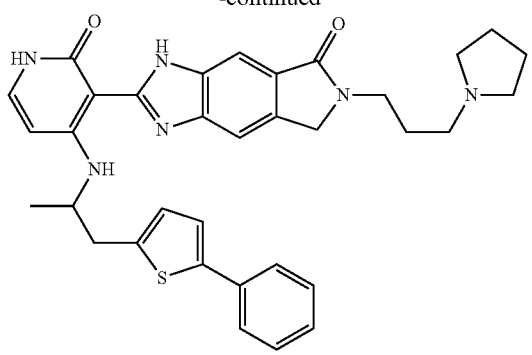
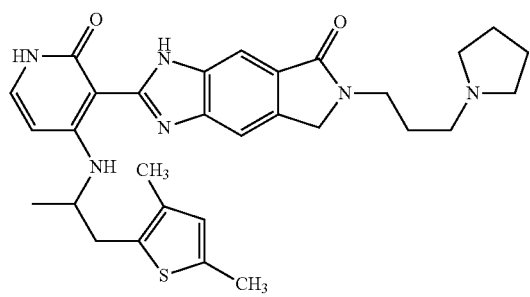
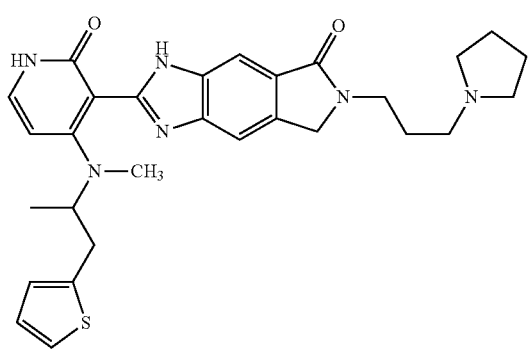
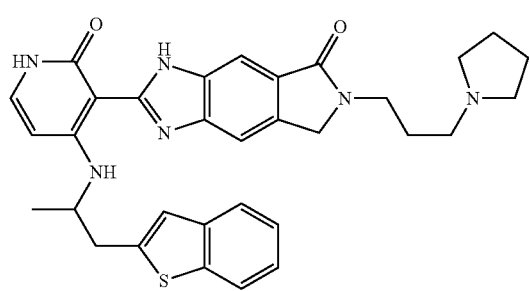
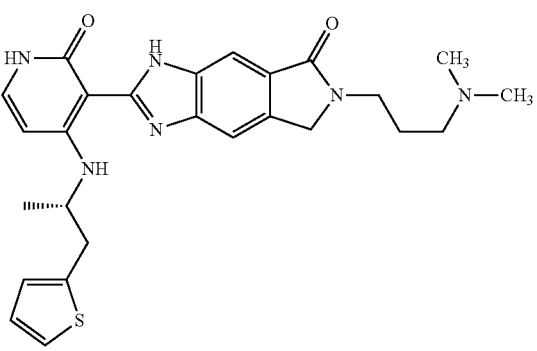
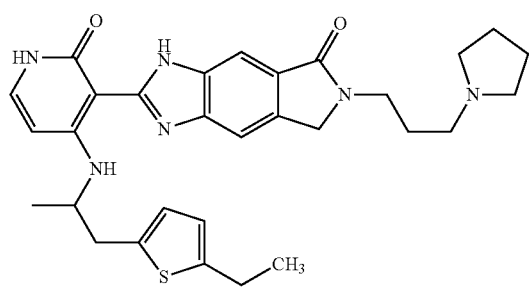
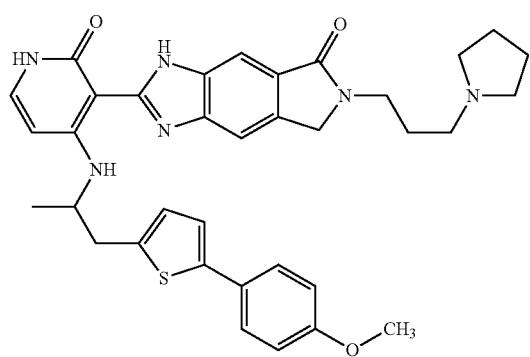
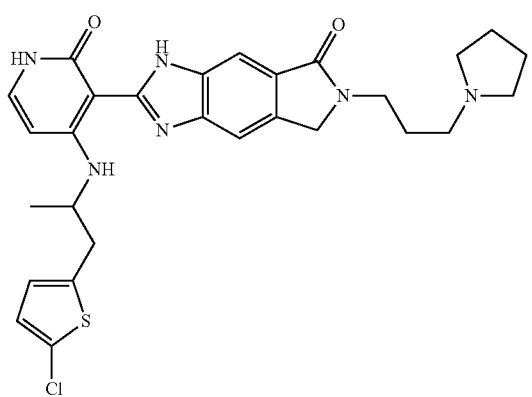

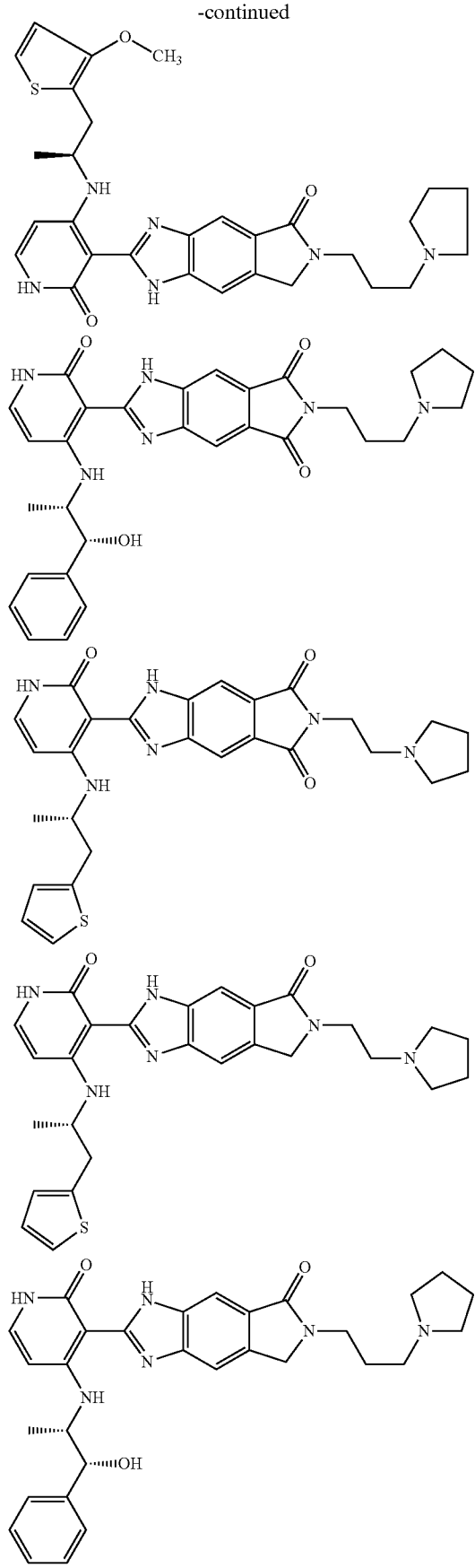
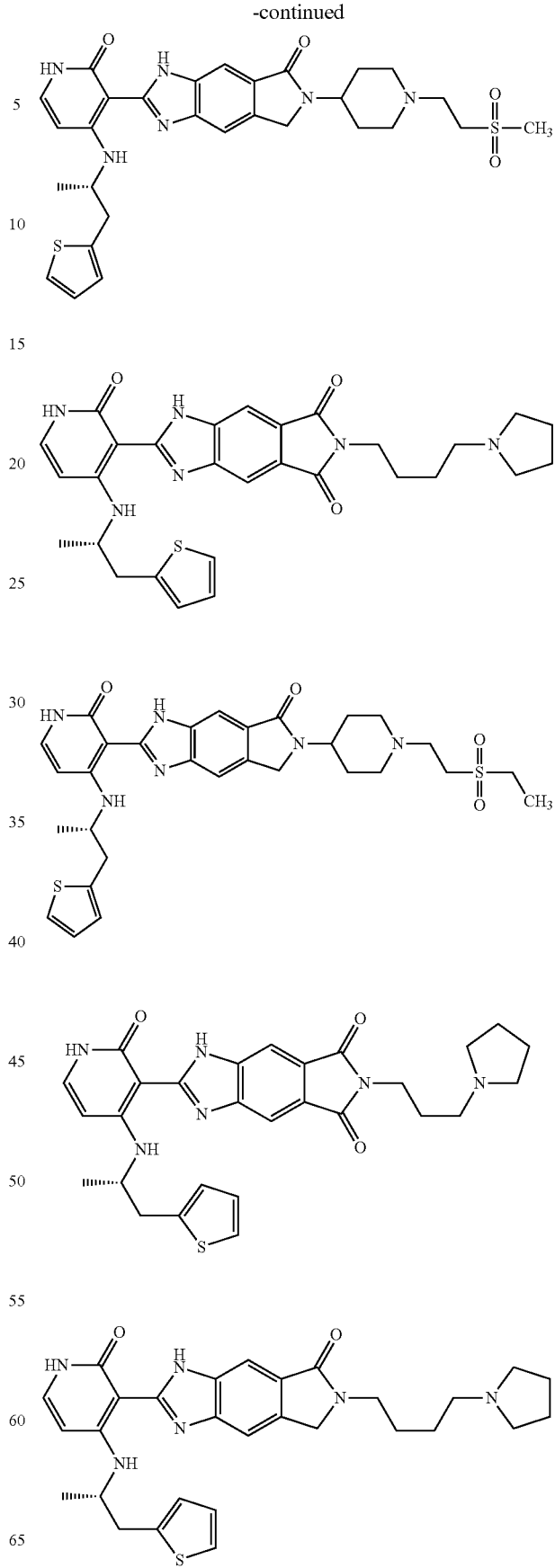

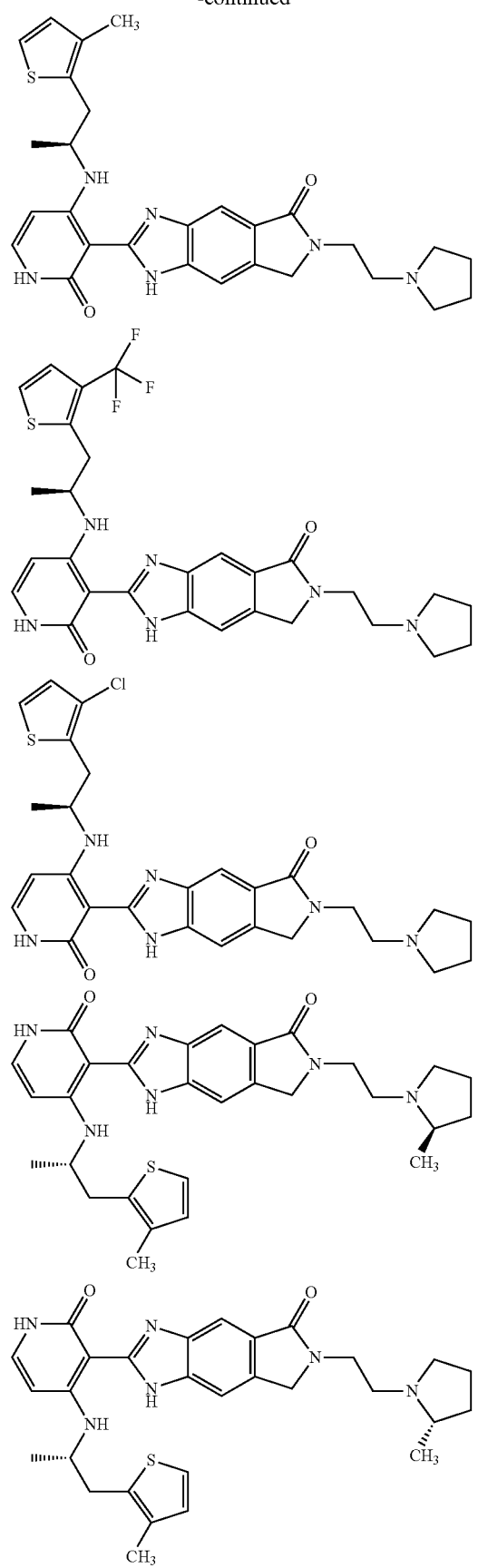
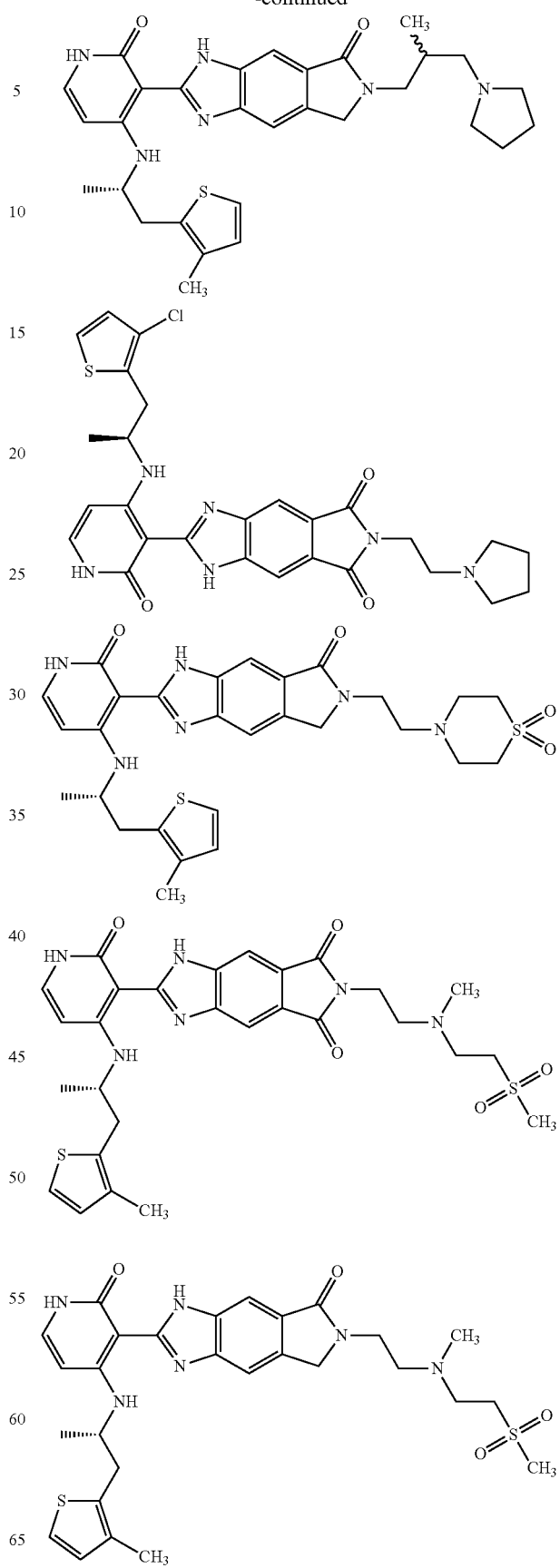

35
-continued
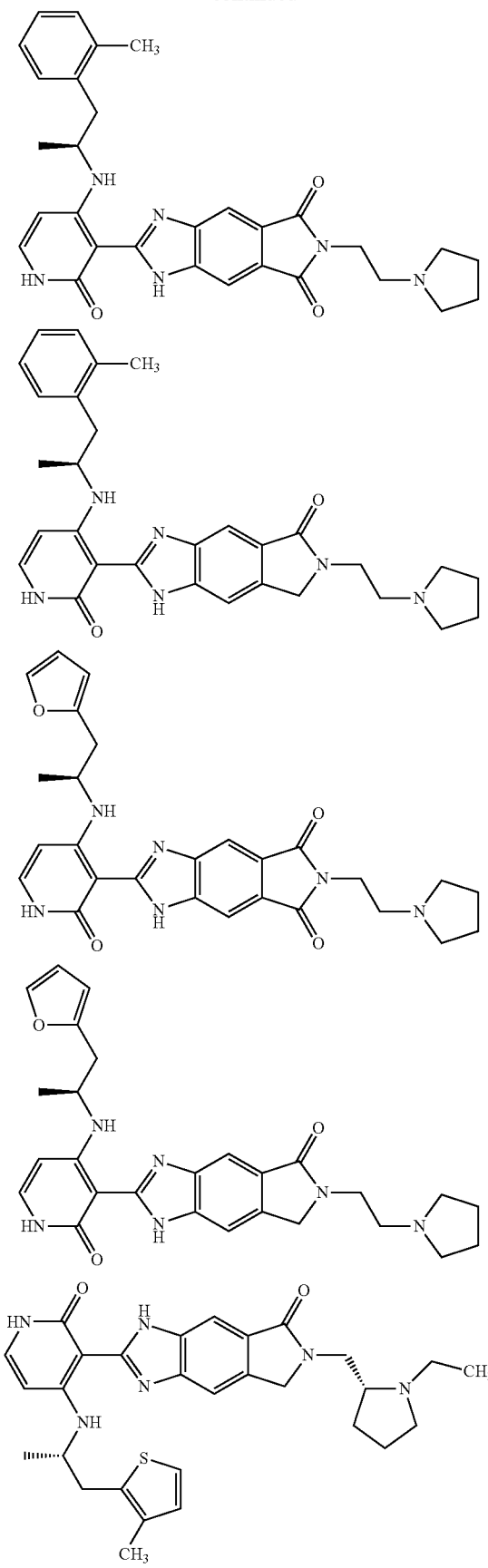
36
-continued
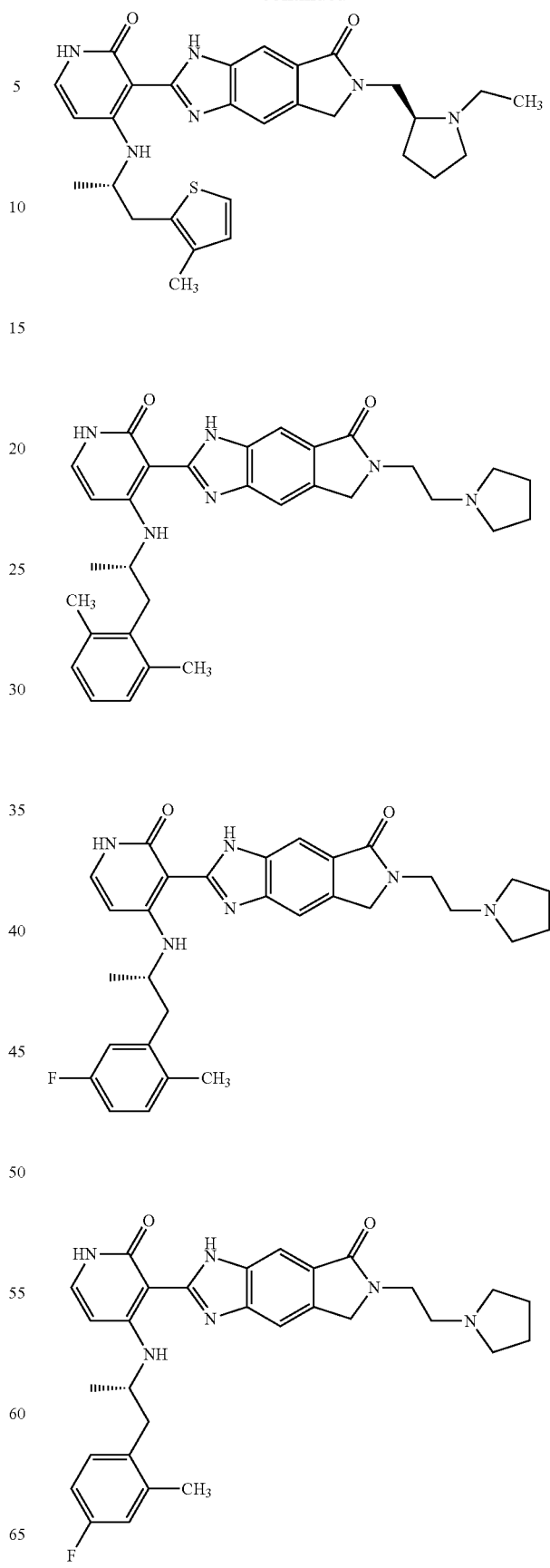

37
-continued
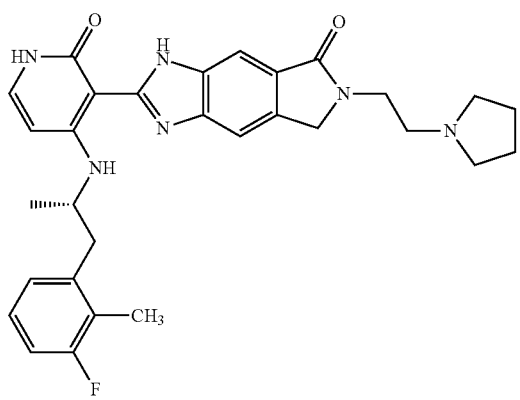
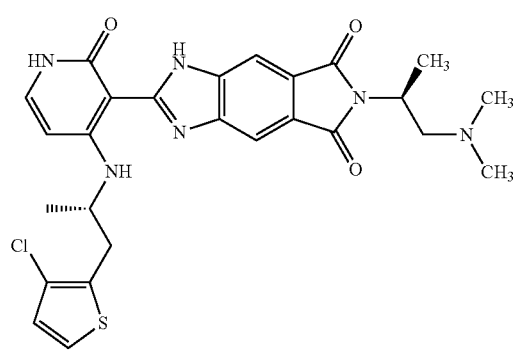
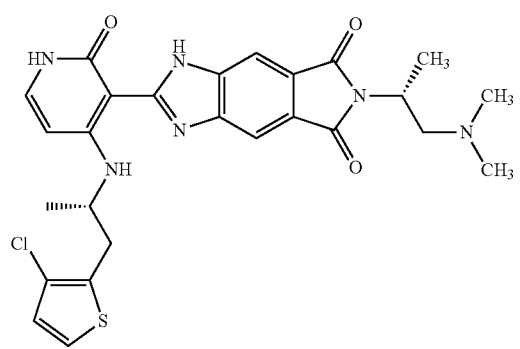
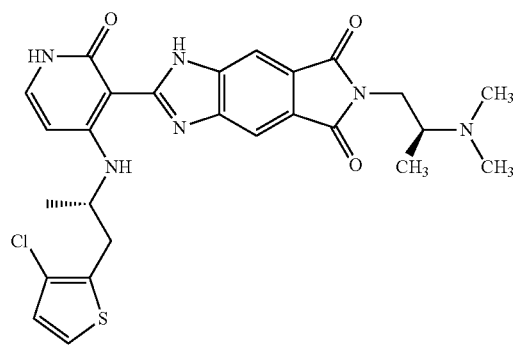
38
-continued
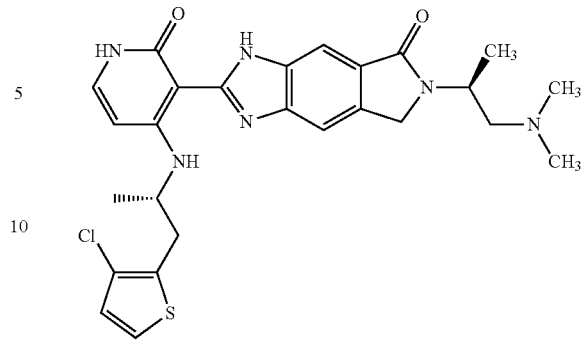
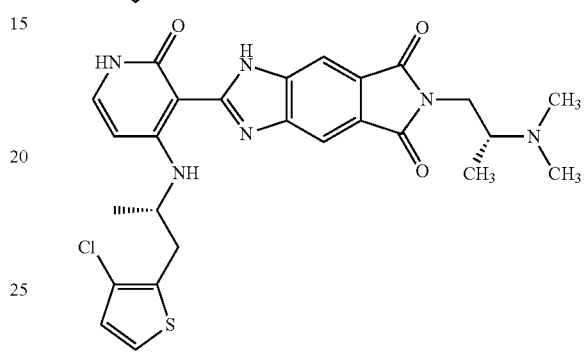
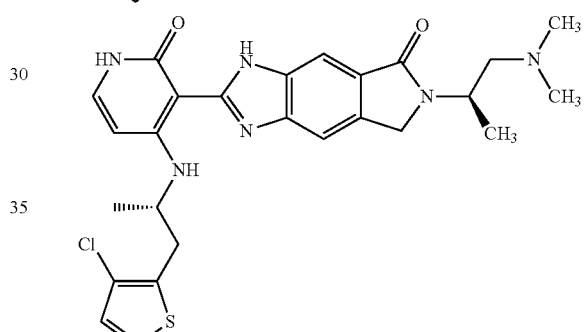
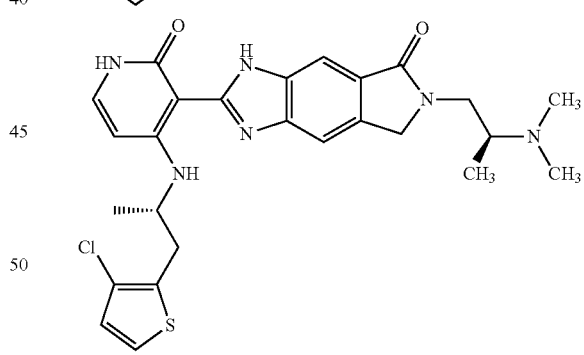
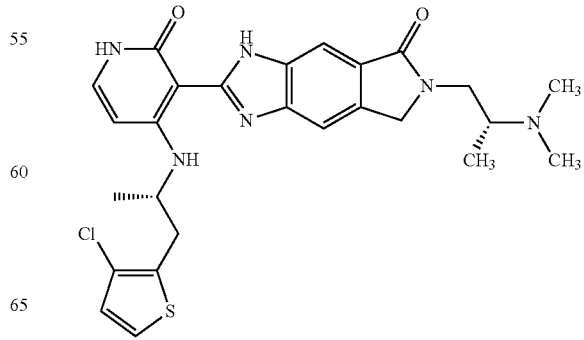

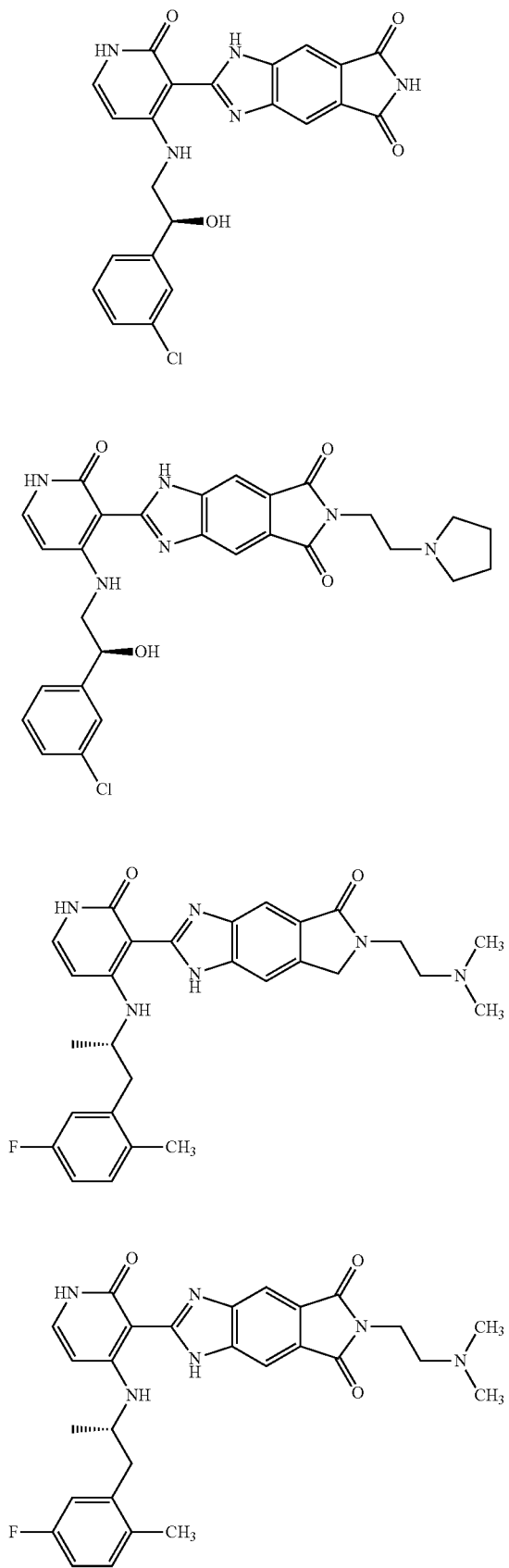

41
-continued
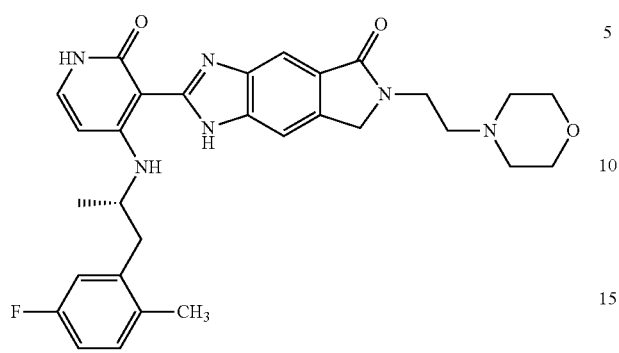
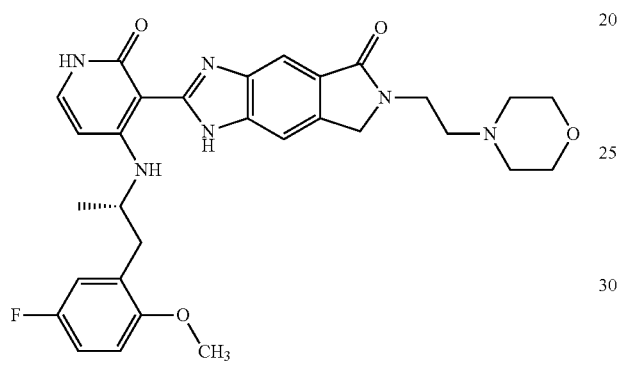
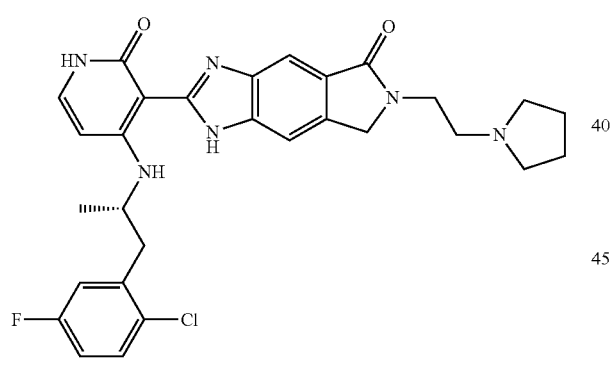
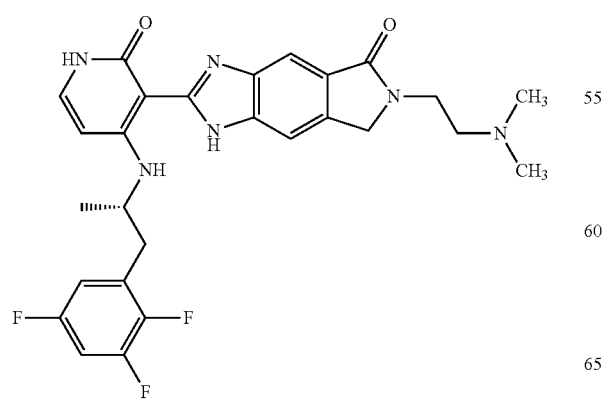
42
-continued
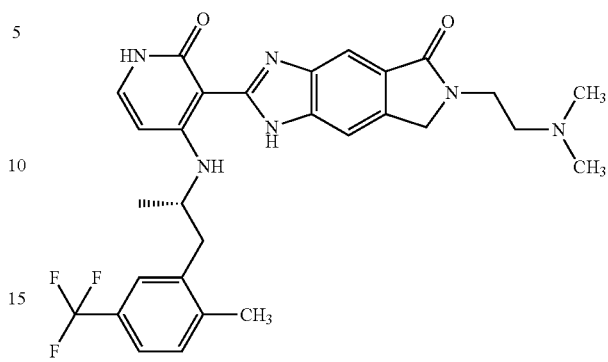
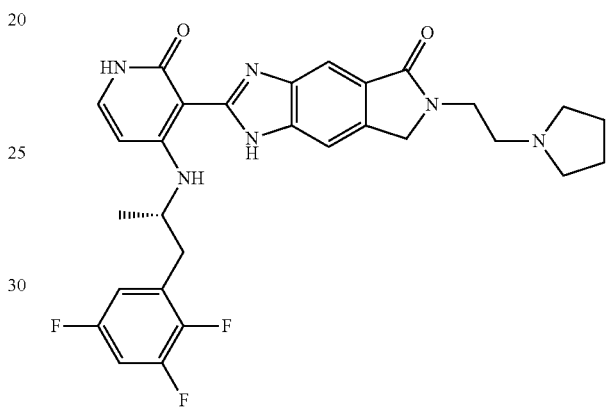
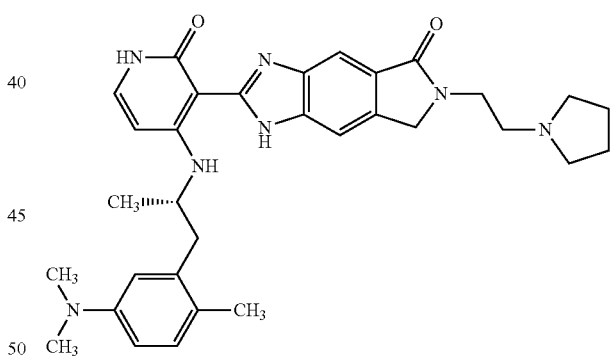
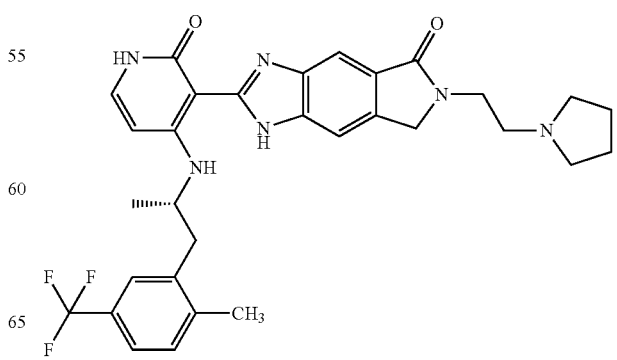

43
-continued
44
-continued
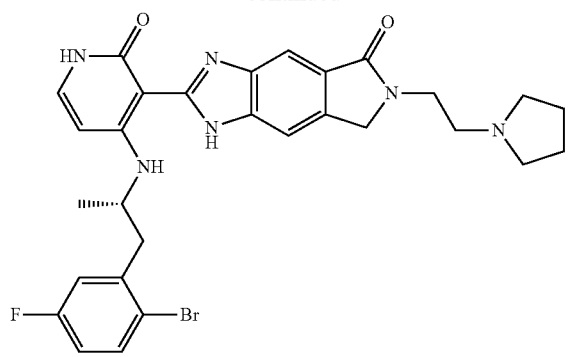
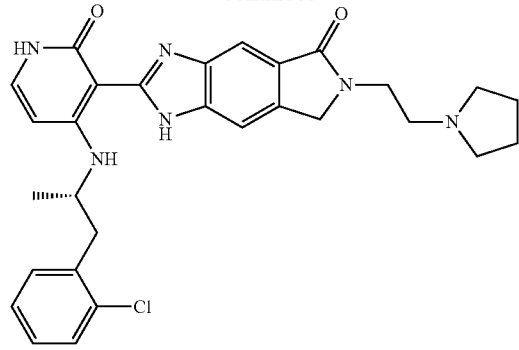
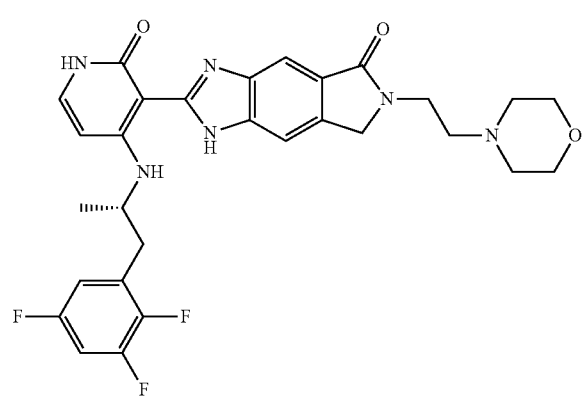
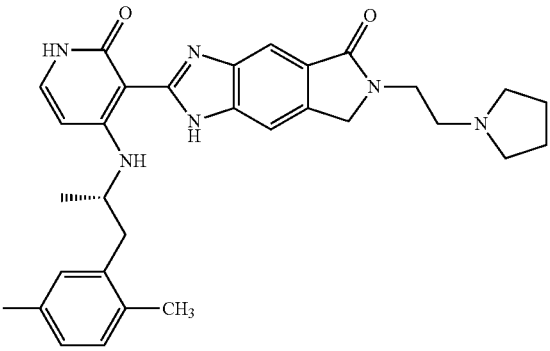
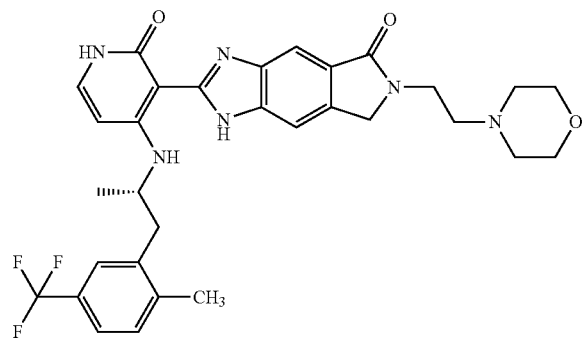
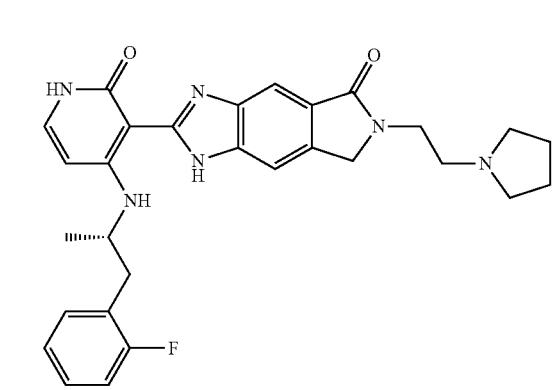
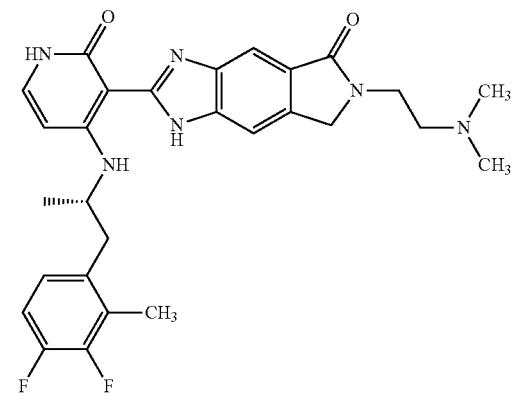

45
-continued
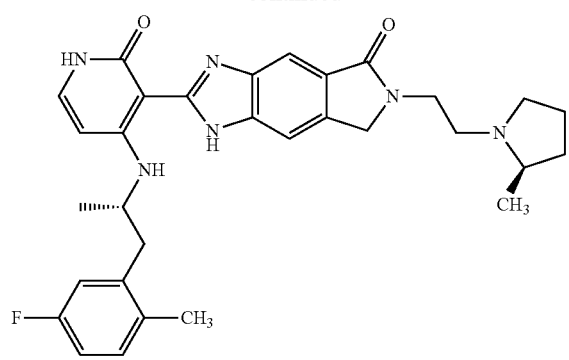
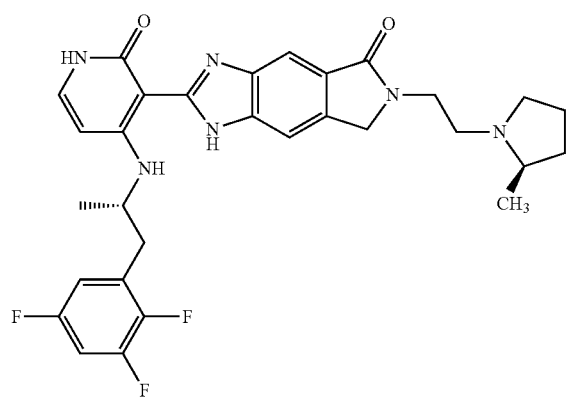
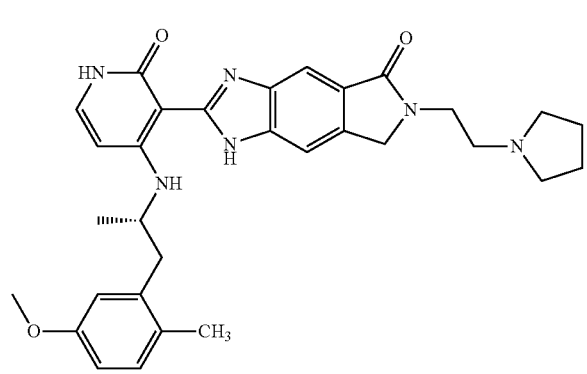
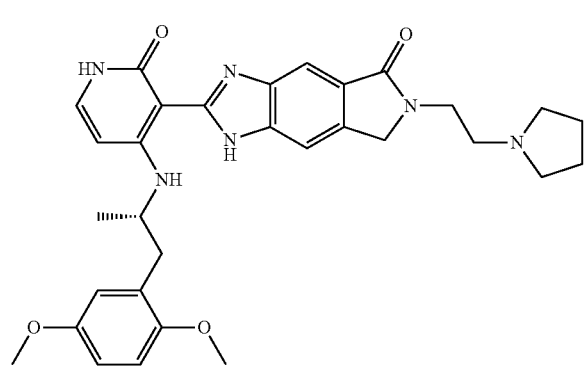
46
-continued
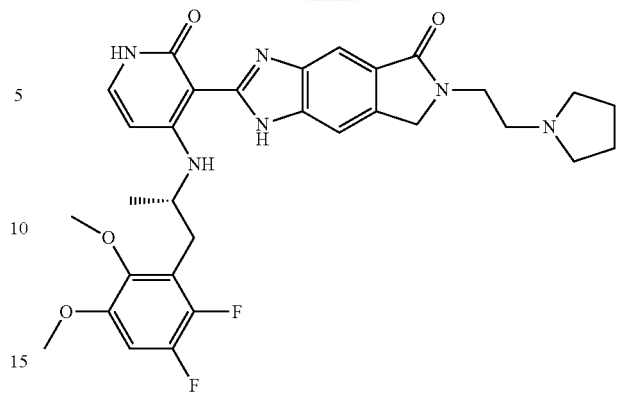
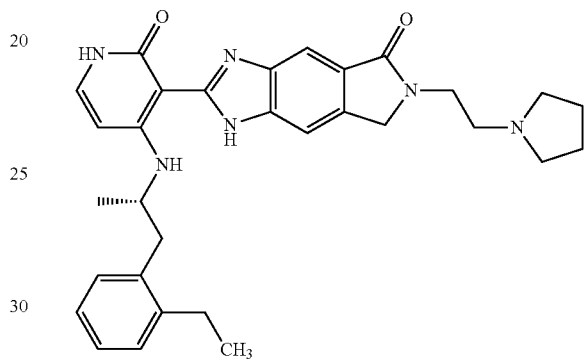
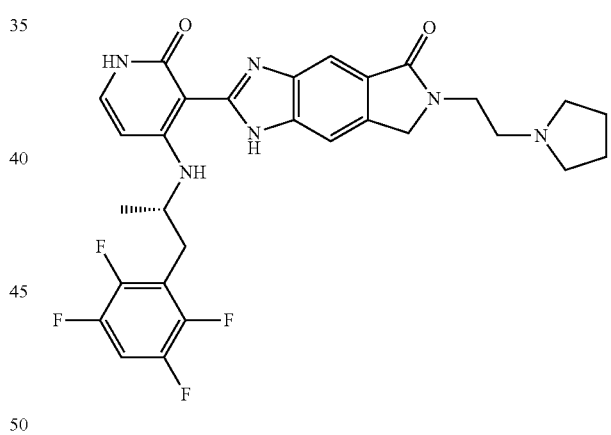
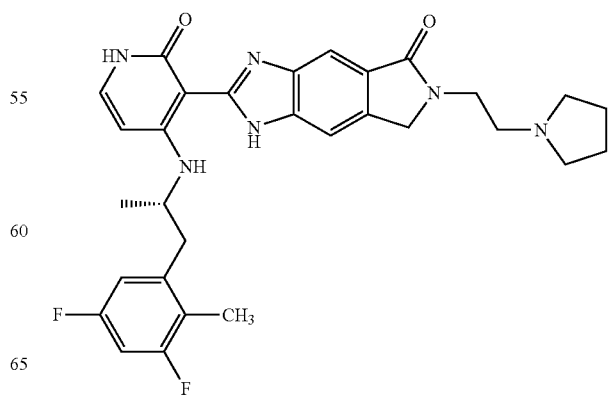

47
-continued
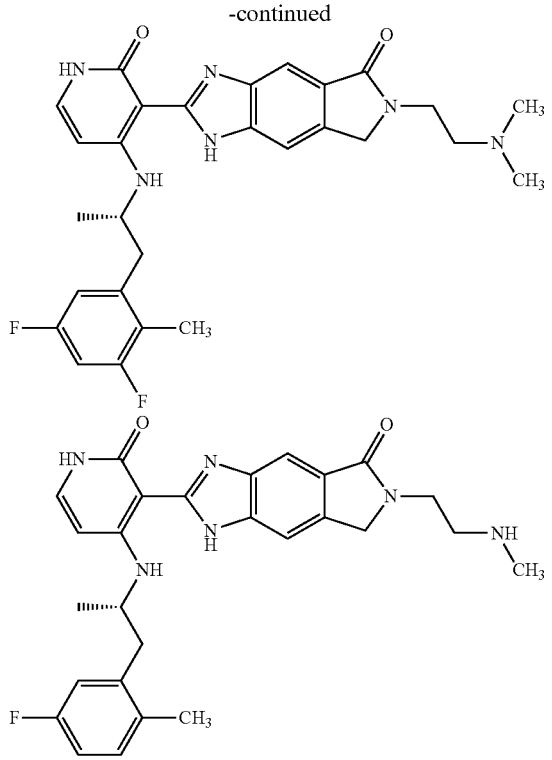
48
-continued
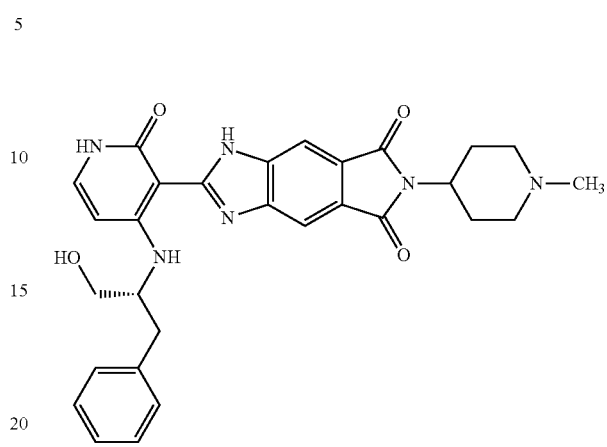
All compounds include tautomeric forms, as exemplified by, but not limited to the following:
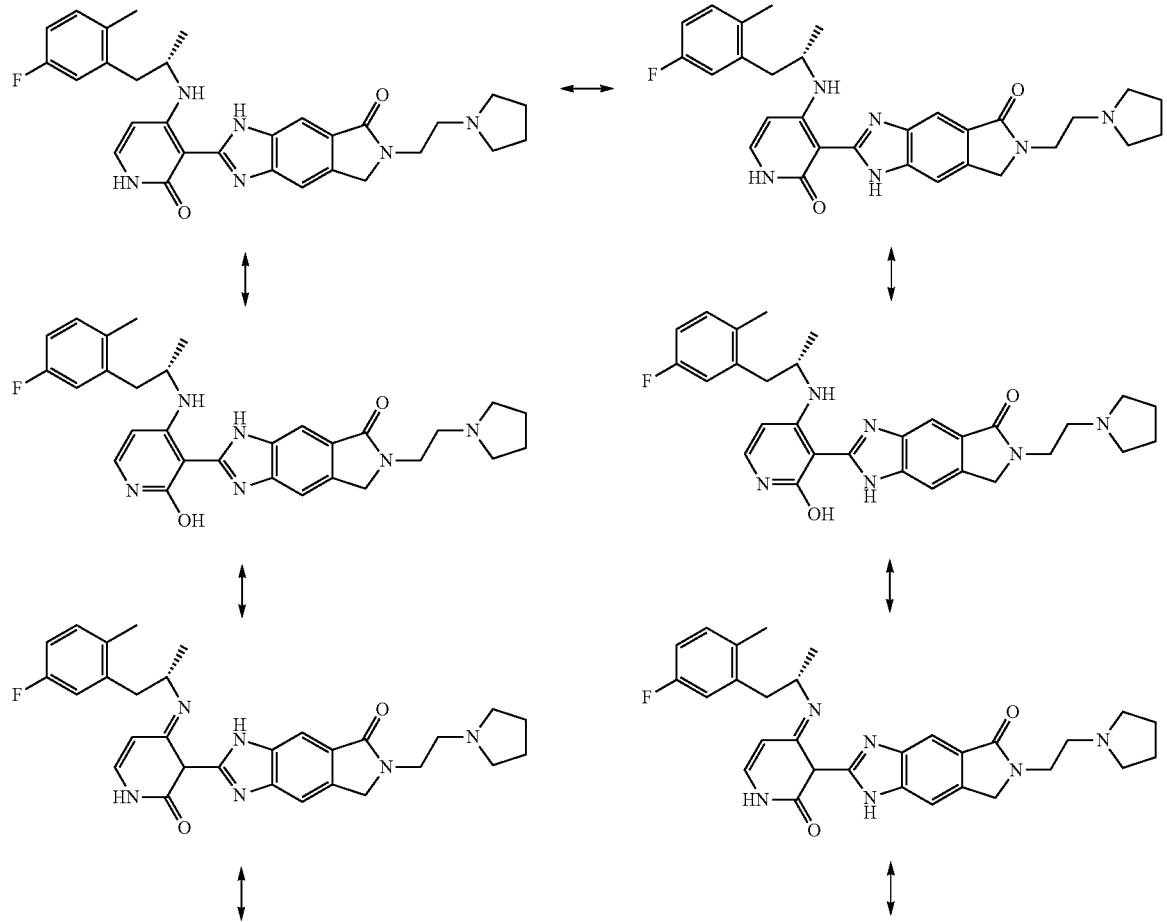

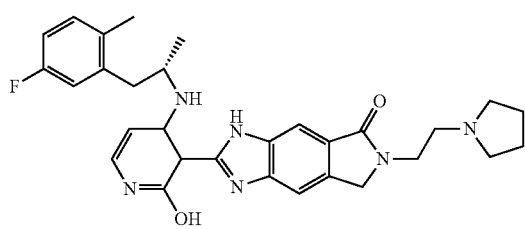
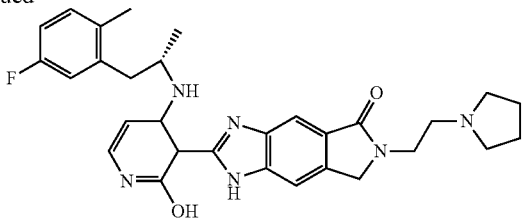
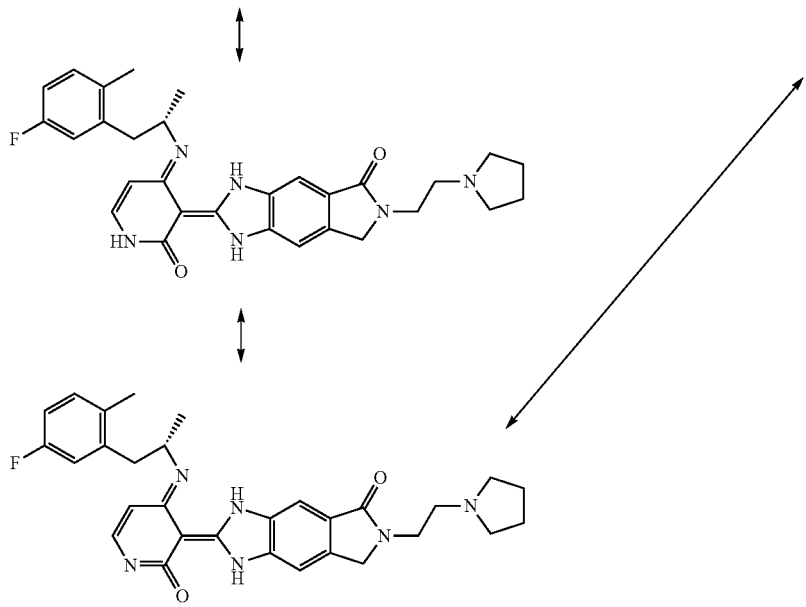

Included are also without limitation their corresponding prodrugs, such as are known in the art. They include esters, such as acetate, propionate and other esters of fatty acids, aminoacids natural and unnatural, such as glycine, valine esters and the like, amides such as acetamides, propionamides and other amides of fatty or aromatic acids, aminoacids, such as glycinamide and other aminonoacids natural or unnatural, ethers, such as methoxy or ethoxy, methoxyethyl, ethoxyethyl, hydroxyethyl, propyleneglycol ethers and/or polyethyleneglycol ethers and/or polypropylene glycol ethers.

Methods of Use

In one aspect, provided are methods for modulating the activity of a tyrosine kinase. In one embodiment, the methods comprise the step of contacting the tyrosine kinase with a compound provided herein. The contacting can be in any environ known to those of skill in the art, for instance, in vitro, in vivo, ex vivo or otherwise. In certain embodiments, provided are methods of modulating the activity of a tyrosine kinase in a mammal in need thereof comprising contacting the tyrosine kinase with a compound provided herein. Modulating can refer to the activation or to the inhibition of the tyrosine kinase. The tyrosine kinase can be any tyrosine kinase known to those of skill in the art. In certain embodiments, the tyrosine kinase is a receptor tyrosine kinase or an intracellular tyrosine kinase.

In certain embodiments, the receptor tyrosine kinase is selected from the group consisting of EGFR, HBER2, HER3, HER4, IR, IGF1R, IRR, PDGFRα, PDGFRβ, TrkA, TrkB, TrkC, HGFR, CSFIR, C-Kit, C-fms, Flk4, KDR/Flk-1, Flt-1, FGF1R, FGF2R, FGF3R and FGF4R.

In certain embodiments, the intracellular tyrosine kinase is selected from the group consisting of Alk, Src, Frk, Btk, Csk, Abl, ZAP70, Fes, Fps, Fak, Jak1, Jak2, Jak3, Jak4, Ack, Yes, Fyn, Lyn, Lck, Blk, Hck, Fgr and Yrk.

In specific embodiments, the intracellular tyrosine kinase is Alk.

In another specific embodiment, the tyrosine kinases are those that are evolutionary and structurally related to ALK, such as Ret, Ros, Axl and members of Trk family (Trk A, B and C).

In another aspect, provided are methods for treating or preventing a tyrosine kinase related disorder in a subject in need thereof. In one embodiment, the methods comprise administering to the subject an amount of a disclosed compound effective to treat or prevent the disorder. The compound can be in the form of a pharmaceutical composition or a unit dose as described below.

A tyrosine kinase related disorder can be any disorder known to those of skill in the art to be related to tyrosine kinase activity. Such disorders include those related to excessive tyrosine kinase activity, those related to reduced tyrosine kinase activity and to those that can be treated or prevented by modulation of tyrosine kinase activity. Excessive tyrosine kinase activity can arise as the result of, for example: (1) tyrosine kinase expression in cells which normally do not express tyrosine kinases; (2) increased tyrosine kinase expression leading to unwanted cell proliferation, differentiation and/or growth; or, (3) decreased tyrosine kinase expression leading to unwanted reductions in cell proliferation, differentiation and/or growth.

The tyrosine kinase related disorder can be a cancer selected from, but not limited to, astrocytoma, basal or squamous cell carcinoma, brain cancer, gliobastoma, bladder cancer, breast cancer, colorectal cancer, chrondrosarcoma, cervical cancer, adrenal cancer, choriocarcinoma, esophageal cancer, endometrial carcinoma, erythroleukemia, Ewing's sarcoma, gastrointestinal cancer, head and neck cancer, hepatoma, glioma, hepatocellular carcinoma, leukemia, leiomyoma, melanoma, non-small cell lung cancer, neural cancer, ovarian cancer, pancreatic cancer, prostate cancer, renal cell carcinoma, rhabdomyosarcoma, small cell lung cancer, thyoma, thyroid cancer, testicular cancer and osteosarcoma.

The tyrosine kinase related disorder can be an IGFR-related disorder selected from diabetes, an autoimmune disorder, Alzheimer's and other cognitive disorders, a hyperproliferation disorder, aging, cancer, acromegaly, Crohn's disease, endometriosis, diabetic retinopathy, restenosis, fibrosis, psoriasis, osteoarthritis, rheumatoid arthritis, an inflammatory disorder and angiogenesis.

Other disorders which might be treated with compounds provided herein include, without limitation, immunological and cardiovascular disorders such as atherosclerosis.

A disease or condition characterized by ALK activity or expression includes but is not limited to ALK-positive anaplastic large cell lymphoma, an inflammatory myofibroblastic tumor, diffuse large B-cell non-Hodgkin lymphoma, non-small cell lung cancer, esophageal carcinoma, breast cancer, neuroblastoma and glioblastoma.

Compositions and Methods of Administration

In certain aspects, provided are compostions comprising a compound provided herein. The compositions can be used, for example, in the methods of use described above.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and one or more pharmaceutically acceptable carriers or excipients or diluents. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

On one embodiment, pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose-free compositions provided herein can comprise excipients that are well known in the art and are listed, for example, in the U.S. Pharmocopia (USP) SP (XXI)/NF (XVI). In one embodiment, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pregelatinized starch, and magnesium stearate.

Provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are in certain embodiments anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are in certain embodiments packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent in certain embodiments in purified form, together with a suitable amount of carrier so as to provide the form for proper administration to the patient. The formulation should suit the mode of administration. In certain embodiments, the pharmaceutical compositions or single unit dosage forms are sterile and in suitable form for administration to a subject, in certain embodiments an animal subject, such as a mammalian subject, particularly a human subject.

A pharmaceutical composition provided herein is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration.

In a specific embodiment, the composition is formulated in accordance with routine procedures as a pharmaceutical composition adapted for intravenous, subcutaneous, intramuscular, oral, intranasal or topical administration to human beings.

In an embodiment, a pharmaceutical composition is formulated in accordance with routine procedures for subcutaneous administration to human beings. In one embodiment, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms provided herein will typically vary depending on their use. For example, a dosage form used in the acute treatment of inflammation or a related disorder may contain larger amounts of one or more of the active ingredients it comprises than a dosage form used in the chronic treatment of the same disease. Also, the therapeutically effective dosage form may vary among different types of cancer. Similarly, a parenteral dosage form may contain smaller amounts of one or more of the active ingredients it comprises than an oral dosage form used to treat the same disease or disorder. These and other ways in which specific dosage forms provided herein will vary from one another will be readily apparent to those skilled in the art. See, e.g., Remington's Pharmaceutical Sciences, 18th ed., Mack Publishing, Easton Pa. (1990).

The ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day. Particular dosage forms have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the compound.

Oral Dosage Forms

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

In certain embodiments, the oral dosage forms are solid and prepared under anhydrous conditions with anhydrous ingredients, as described in detail in the sections above. However, the scope extends beyond anhydrous, solid oral dosage forms. As such, further forms are described herein.

Typical oral dosage forms provided herein are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Controlled Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients. Thus provided are single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are in certain embodiments sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms provided herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients provided herein. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Dosage & Frequency of Administration

The amount of the compound or composition which will be effective in the prevention, treatment, management, or amelioration of a disorder or one or more symptoms thereof will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems.

Exemplary doses of a compound include milligram or microgram amounts of the active peptide per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). In one embodiment, the recommended daily dose range of a compound provided herein for the conditions described herein lie within the range of from about 0.01 mg to about 1000 mg per day, given as a single once-a-day dose in certain embodiments as divided doses throughout a day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the compounds provided herein are also encompassed by the above described dosage amounts and dose frequency schedules. Further, when a patient is administered multiple dosages of a compound provided herein, not all of the dosages need be the same. For example, the dosage administered to the patient may be increased to improve the prophylactic or therapeutic effect of the compound or it may be decreased to reduce one or more side effects that a particular patient is experiencing.

In certain embodiments, administration of the same compound provided herein may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

Biological Assays

The following assays can be employed in ascertaining the activity of a small-molecule compound as an inhibitor of the catalytic kinase activity of various tyrosine kinases.

Kinase Assays

To determine inhibition of several tyrosine kinases, such as IGF1R, InsR, Alk, TrkA and Jak2, kinase assays are conducted using either Kinase-Glo (Promega) or AlphaScreen (PerkinElmer) kinase assay platforms. The Kinase-Glo Luminescent Kinase Assay is a homogeneous method for measuring kinase activity by determining the amount of ATP remaining after a kinase reaction. The luminescent signal is proportional to the amount of ATP and inversely proportional to the amount of kinase activity. Tyrosine kinase PT66 AlphaScreen Assay is a high-sensitivity homogeneous, anti-phosphotyrosine antibody-mediated luminescent proximity method measuring incorporation of phosphate in synthetic poly(Glu-Tyr) substrate. The kinase preparations used consist of purified recombinant, 6×His- or GST-tagged kinase domain fragments of the corresponding RTKs expressed in baculovirus system.

Enzymatic Kinase Assay for High-Throughput Screening of Candidate Small Molecule ALK Inhibitors High-throughput enzymatic assay may be used to examine ALK activity, modified from the AlphaScreen™ (Amplified Luminescent Proximity Homogeneous Assay) technology marketed by PerkinElmer Life Sciences (Boston, Mass.). This methodology was adapted to assess NPM-ALK activity based on the ability of the constitutively active purified fusion kinase to phosphorylate a biotinylated poly(GT) substrate peptide. NPM-ALK activity is indicated in this assay by a shift in the incident 680 nM wavelength light to an emitted wavelength between 520-620 nM when "donor" and "acceptor" beads come into proximity due to tyrosine phosphorylation by the purified kinase of a biotinylated-poly(GT) (G:T=4:1) peptide bound to the streptavidin-coated "donor" bead and recognition of this phosphorylation by anti-phosphotyrosine antibody bound to the "acceptor" bead. "Donor" beads contain a photosensitizer that converts ambient oxygen to the excited singlet state when exposed to laser light at 680 nM. These singlet oxygen molecules diffuse to react with a thioxene derivative in "acceptor" beads that are in proximity to the "donor" beads (if separated by <200 nM), in turn shifting the emission wavelength to 520-620 nM. In the complete absence of NPM-ALK activity, the incident and emitted wavelengths are identical (i.e., 680 nM); partial degrees of kinase inhibition can be quantitatively scored based on the amount of wavelength shift.

Compounds with a range of concentrations 40 µM, 20 µM, 10 µM, 5 µM, 2.5 µM, 1.25 µM, 0.625 µM, 0.3125 µM, 0.15625 µM and 0.078125 µM were incubated with NPM-ALK, which was produced in insect cells as a 6×HIS-tagged fusion protein and purified using nickel-charged resin chromatography, for 30 minutes at RT in the presence of 10 µM ATP and 7.0 ng biotinylated poly-GT. A 1:1 mixture of receptor and donor beads was then added to the reaction and incubated for an additional 60 minutes at RT. The assay was conducted on a MultiPROBE liquid handling workstation (PerkinElmer) in a 384-well plate format with a total reaction volume of 40 µL per well. Working stocks of all compounds were dissolved in 100% DMSO and serial dilutions of the compounds were performed using kinase buffer (50 mM Tris-HCl (pH 7.5), 5 mM MgCl2, 5 mM MnCl2, 2 mM DTT (added freshly before use), 0.01% Tween-20) containing 5% DMSO. Control samples included on all assays included kinase buffer containing 5% DMSO without compound, as well as staurosporine, which we have shown to inhibit NPM-ALK with a Ki of ~30-50 nM. Data were collected as optical readings at 520-680 nm on a Fusion™ microplate analyzer (PerkinElmer), and $IC_{50}$ and $K_i$ values calculated using PRISM3.0 software (GraphPad Software, Inc., San Diego, Calif.). The same assay was also used with minor modifications to assess the $IC_{50}$ and $K_i$ values for selected compounds against five other tyrosine kinases (IRK, IGF1R, Flt3, Abl, Src), all of which were purchased from commercial vendors. PolyGT-Biotin was bought from CIS Biointernational Cat. #61GT0BLD; ATP—from Sigma Cat. #A7699; sodium orthovanadate—from Sigma Cat. #S-6508; phosphotyrosine (PT66) assay kit from PerkinElmer Cat. #6760602M; automated workstation tips (20 µL): PerkinElmer Cat. #6000657; and OptiPlate-384 (white)—from PerkinElmer Cat. #6007299.

Cell-Based XTT Assay for Screening of Small Molecule Inhibitors

The IL-3-dependent lymphoid cell line BaF3 or BaF3 rendered IL-3-independent by engineered expression of NPM-ALK were used in parallel to test each candidate inhibitor. Control wells contained DMSO solvent without test compound. Specific inhibition of ALK signaling is indicated in the assay by impairment of NPM-ALK-expressing BaF3 cell growth without alterations in the growth of parental BaF3. This colorimetric assay of cell proliferation and viability is based upon reduction of the yellow monotetrazolium salt XTT to a water-soluble orange formazan dye, a reaction catalyzed by mitochondrial dehydrogenases in living cells only (Cell Proliferation Kit II, Cat. #1 465 015, Roche Biochemicals). In addition to testing compounds for their ability to impair the growth of BaF3 cells engineered to express NPM-ALK, the NPM-ALK-positive human lymphoma cell line Karpas-299 (Deutsche Sammlung von Mikroorganismen and Zellkulturen GmbH (DSMZ) no. ACC 31), the human BCR-ABL-positive chronic myeloid leukemia cell line K562 (American Type Culture Collection (ATCC) no. CCL-243), and the human T-cell leukemia line Jurkat (DSMZ no. ACC 282) were tested in these assays.

Each compound stock in 100% DMSO was first diluted using 8% DMSO/culture medium to produce a working stock of 250 µM compound. This working stock was then used to perform serial 1:1 dilutions (i.e., 125 µM, 62.5 µM, 31.25 µM, 15.625 µM, 7.8125 µM, and 3.90625 µM) using DMSO-free culture medium. Twenty (20) µL of each of these dilutions was then added to the cells ($2 \times 10^4$ cells in 80 µL culture medium per 96-well) to obtain the final test compound concentrations (i.e., 25 µM, 12.5 µM, 6.25 µM, 3.125 µM, 1.5625 µM, and 0.78125 µM). The maximum final DMSO concentration in the assays was 2.61%, which was found to have no effect on cell viability and proliferation. The assays were read and the cellular $IC_{50}$s determined 72 hrs. following addition of the test compounds to the cultures.

Compounds according to formula (1) can be prepared according to any method apparent to those skilled in the art. Provided below are exemplary methods for their preparation.

Scheme 1

Synthesis of substituted-6,7-dihydroimidazo[4,5-f]isoindol-5(1H)-ones: General Approach 1:

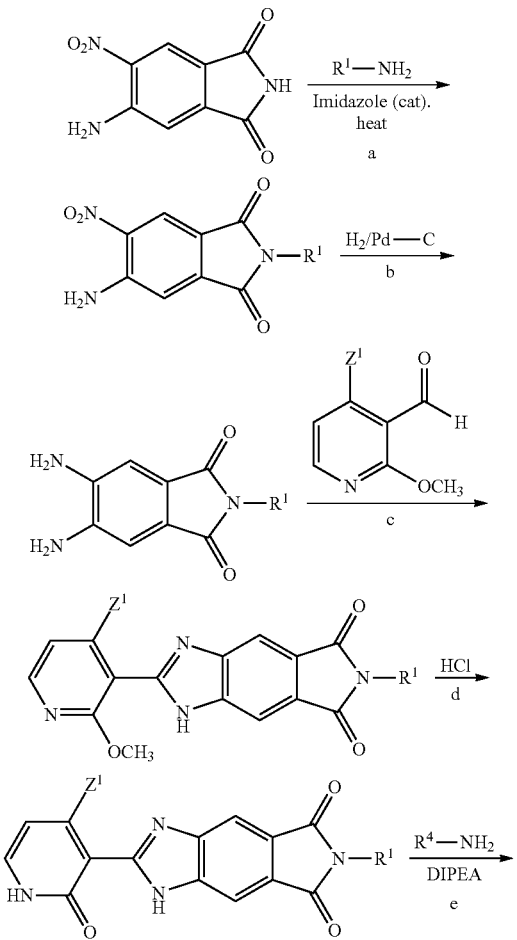

-continued

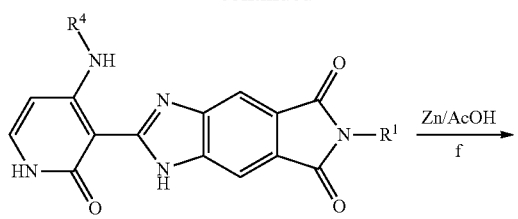

wherein $Z^1$ is Cl or I; and

AR is selected from optionally substituted aryl or heteroaryl.

This description will be used in the following text.

Scheme 2
Synthesis of Amines $R^4$—NH2

General Approach 2:

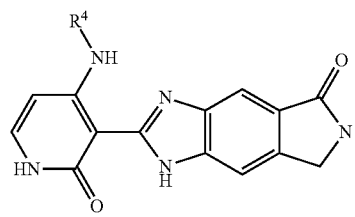

This scheme was described in *J. Med. Chem.* 35 (1992), 280-285. The racemic compounds can be resolved by any of the resolution methods known in the art, including but not limited to chiral chromatography (e.g.: chromatography on a chiral support column), formation of diastereomeric compounds, either ionic, or covalent, such as chiral tartrate salts or salts with any feasible chiral acid, carboxylic, or sulfonic. As an example of covalent compounds the corresponding diastereomeric amides, such as chiral mandelamides, formed by standard non-racemizing amide coupling reactions, followed by separation either by chromatography, or fractional crystallization.

Scheme 3
Synthesis of Amines $R^4$—NH2

General Approach 3:

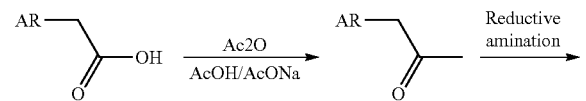

-continued

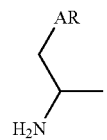

Scheme 4
Synthesis of Chiral Amines $R^4$—NH2

General Approach 4:

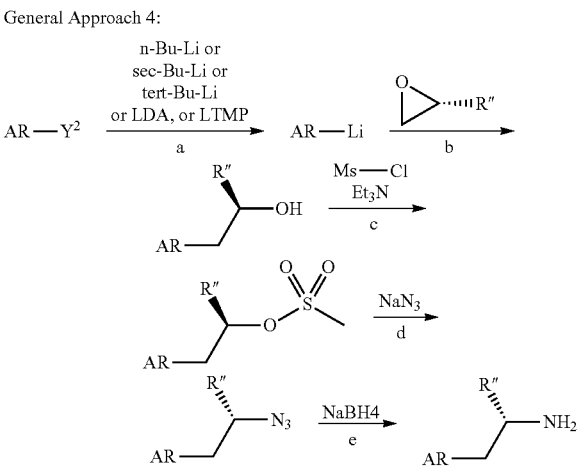

wherein $Y^2$ is selected from hydrogen, bromo or iodo.

The synthesis of the chiral and/or racemic amines is according to the above general scheme and is a modification of the approach described in: Wagner, Jared M.; McElhinny, Charles J.; Lewin, Anita H.; Carroll, F. Ivy Tetrahedron: Asymmetry (2003), 14(15), 2119-2125.

The non-limiting examples are described below.

EXAMPLES

Example 1

General Procedure 1

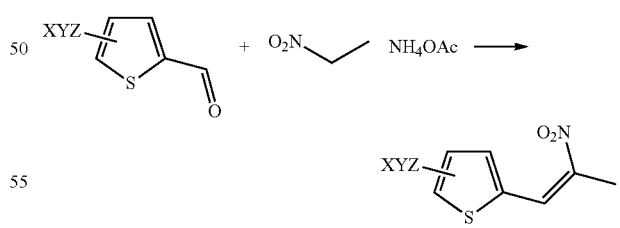

General Procedure 1. (*J. Med. Chem.* 35 (1992), 280-285). A mixture of substituted thiophene-2-carbaldehyde (10.0 mmol), nitroethane (10 ml), NH₄OAc (5.0 mmol) was stirred at 110° C. for 4 h. After cooling to RT the solvent was evaporated, the residue was dissolved in ether (50 ml), washed with water (2×50 ml), the solution was dried over Na₂SO₄, evaporated. The residue was recrystallized from methanol. Precipitate was collected by filtration, washed with cold (−20° C.) methanol, dried on air.

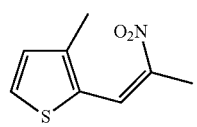

3-methyl-2-(2-nitroprop-1-en-1-yl)thiophene was prepared according to General Procedure 1. Yellow solid, yield 9%.

$^1$H NMR (300 MHz, CDCl$_3$) δ 8.39 (s, 1H), 7.55 (d, J 5.1 Hz, 1H), 7.01 (d, J 5.1 Hz, 1H), 2.57 (s, 3H), 2.43 (s, 3H).

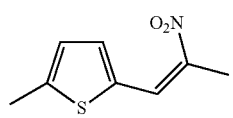

2-methyl-5-(2-nitroprop-1-en-1-yl)thiophene was prepared according to General Procedure 1. Orange solid, yield 49%.

$^1$H NMR (300 MHz, DMSO) δ 8.32 (s, 1H), 7.60 (d, J 3.6 Hz, 1H), 7.03 (d, J 3.6 Hz, 1H), 2.55 (s, 3H), 2.44 (s, 3H).

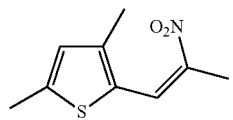

3,5-dimethyl-2-(2-nitroprop-1-en-1-yl)thiophene was prepared according to General Procedure 1. Orange solid, yield 58%.

$^1$H NMR (300 MHz, CDCl$_3$) δ 8.36 (s, 1H), 6.71 (s, 1H), 2.52 (s, 6H), 2.37 (s, 3H).

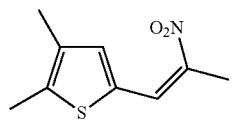

2,3-dimethyl-5-(2-nitroprop-1-en-1-yl)thiophene was prepared according to General Procedure 1. Brown solid, yield 98%.

$^1$H NMR (300 MHz, CDCl$_3$) δ 8.19 (s, 1H), 7.14 (s, 1H), 2.42 (s, 3H), 2.38 (s, 3H), 2.21 (s, 3H).

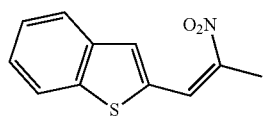

2-(2-nitroprop-1-en-1-yl)-1-benzothiophene was prepared according to General Procedure 1. Yellow solid, yield 100%.

$^1$H NMR (300 MHz, CDCl$_3$) δ 8.35 (s, 1H), 7.89 (m, 2H), 8.67 (s, 1H), 7.42 (m, 2H), 2.65 (s, 3H).

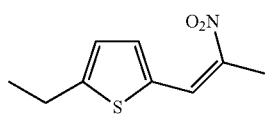

2-ethyl-5-(2-nitroprop-1-en-1-yl)thiophene was prepared according to General Procedure 1. Brown solid, yield 45%.

$^1$H NMR (300 MHz, CDCl$_3$) δ 8.24 (s, 1H), 6.90 (s, 1H), 2.85 (q, J 7.0 Hz 2H), 2.54 (s, 3H), 1.37 (t, J 7.0 Hz, 3H).

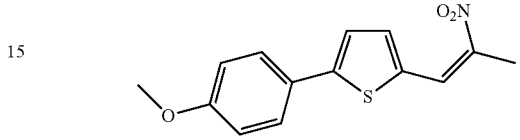

2-(4-methoxyphenyl)-5-(2-nitroprop-1-en-1-yl)thiophene was prepared according to General Procedure 1 using DCM instead of ether. Orange solid, yield 64%.

$^1$H NMR (300 MHz, CDCl$_3$) δ 8.25 (s, 1H), 7.64 (m, 2H), 7.19 (m, 2H), 6.93 (m, 2H), 3.84 (s, 3H), 2.60 (s, 3H).

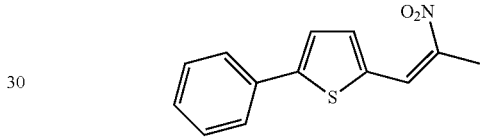

2-(2-nitroprop-1-en-1-yl)-5-phenylthiophene was prepared according to General Procedure 1. Orange solid, yield 73%.

$^1$H NMR (300 MHz, CDCl$_3$) δ 8.25 (s, 1H), 7.71 (m, 2H), 7.41 (m, 5H), 2.65 (s, 3H).

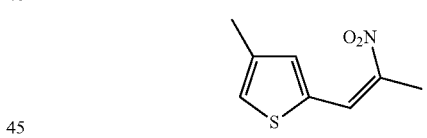

4-methyl-2-(2-nitroprop-1-en-1-yl)thiophene was prepared according to General Procedure 1. Yellow solid, yield 40%.

$^1$H NMR (300 MHz, CDCl$_3$) δ 8.23 (s, 1H), 7.20 (s, 2H), 2.50 (s, 3H), 2.30 (s, 3H).

General Procedure 2

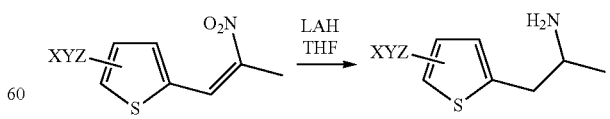

General Procedure 2. To a suspension of LAH (0.30 mol) in dry THF (150 ml) a solution of 2-(2-nitroprop-1-en-1-yl) thiophene (0.050 mol) in THF (50 ml) was added dropwise over 30 min at 40-50° C. The reaction mixture was stirred overnight at 60° C. After cooling to RT saturated K$_2$CO$_3$ (200 ml) was added carefully, extracted with EtOAc (2×200 ml). Extract was dried over Na$_2$SO$_4$, evaporated.

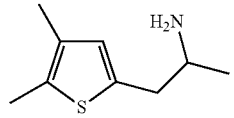

1-(4,5-dimethyl-2-thienyl)propan-2-amine was prepared according to General Procedure 2. Brown oil, yield 52%.
LCMS [M+H]$^+$ 170.2.

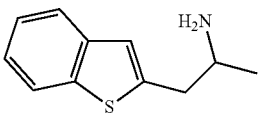

1-(1-benzothien-2-yl)propan-2-amine was prepared according to General Procedure 2. Brown oil, yield 38%.
LCMS [M+H]$^+$ 192.2.

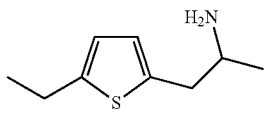

1-(5-ethyl-2-thienyl)propan-2-amine was prepared according to General Procedure 2. Brown oil, yield 47%.
LCMS [M+H]$^+$ 170.2.

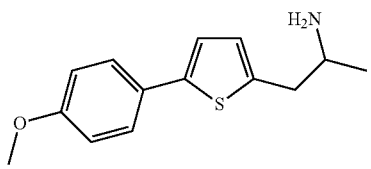 [SMILES: COc1ccc(-c2ccc(CC(C)N)s2)cc1]

1-[5-(4-methoxyphenyl)-2-thienyl]propan-2-amine was prepared according to General Procedure 2. Brown solid, yield 44%.
LCMS [M+H]$^+$ 248.3.

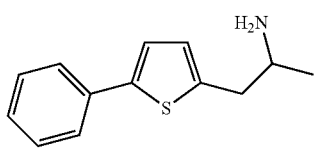

1-(5-phenyl-2-thienyl)propan-2-amine was prepared according to General Procedure 2. Brown oil, yield 58%.
LCMS [M+H]$^+$ 218.3.

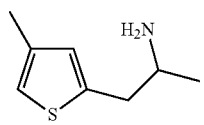

1-(4-methyl-2-thienyl)propan-2-amine was prepared according to General Procedure 2. Brown oil, yield 46%.
LCMS [M+H]$^+$ 156.3.

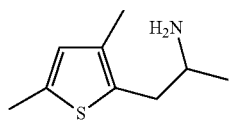

1-(3,5-dimethyl-2-thienyl)propan-2-amine was prepared according to General Procedure 2. Brown oil, yield 39%.
LCMS [M+H]$^+$ 170.3.

General Procedure 3

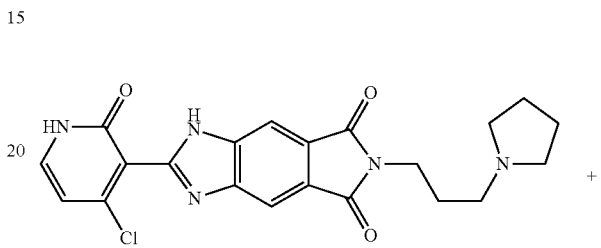

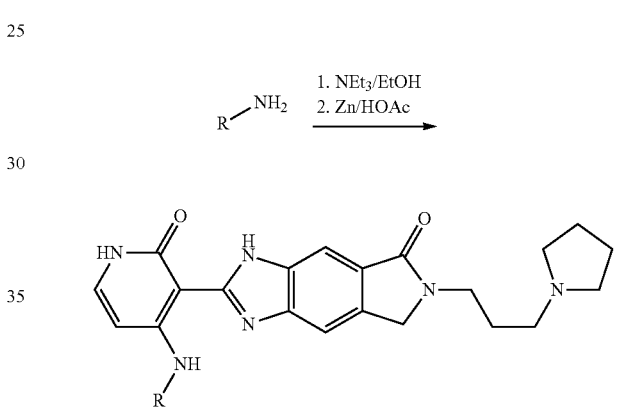

R—NH$_2$ depicts a generic promary amine.

General Procedure 3. A mixture of chloropyridone (0.05 mmol), amine (0.05 mmol), EtOH (1.0 ml) and NEt3 (0.1 ml) was stirred at 100° C. overnight. The solvent was evaporated. Acetic acid (2.0 ml) and Zn (dust, 0.1 g) were added, the mixture was stirred at 110° C. for 5 h. Solids were removed by filtration, filtrate was evaporated, and the residue was separated by preparative TLC (CH$_2$Cl$_2$-MeOH—NH$_4$OH, 100:10:1).

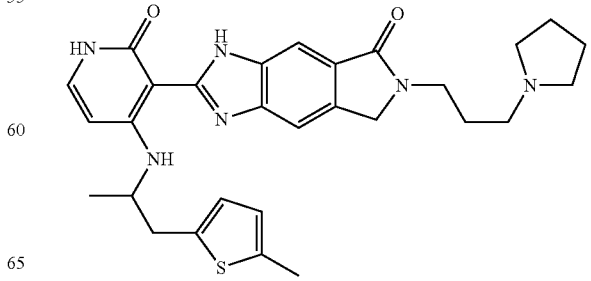

2-(4-{[1-methyl-2-(5-methyl-2-thienyl)ethyl]amino}-2-oxo-1,2-dihydropyridin-3-yl)-6-(3-pyrrolidin-1-ylpropyl)-6,7-dihydroimidazo[4,5-f]isoindol-5(3H)-one was prepared according to General procedure 3.

LCMS [M+H]+ 531.6.

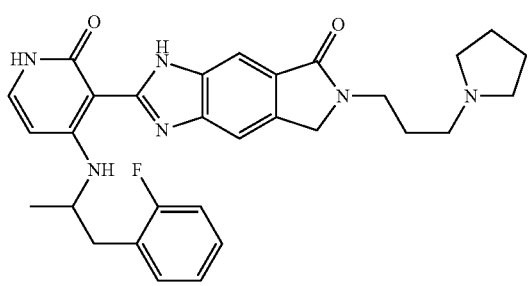 [SMILES: CC(Cc1ccccc1F)Nc1cc[nH]c(=O)c1-c1nc2cc3c(cc2[nH]1)C(=O)N(CCCN1CCCC1)C3]

2-(4-{[2-(2-fluorophenyl)-1-methylethyl]amino}-2-oxo-1,2-dihydropyridin-3-yl)-6-(3-pyrrolidin-1-ylpropyl)-6,7-dihydroimidazo[4,5-f]isoindol-5(3H)-one was prepared according to General procedure 3.

LCMS [M+H]+ 529.3.

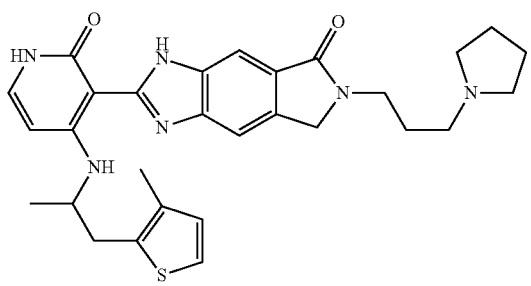 [SMILES: Cc1ccsc1CC(C)Nc1cc[nH]c(=O)c1-c1nc2cc3c(cc2[nH]1)C(=O)N(CCCN1CCCC1)C3]

2-(4-{[1-methyl-2-(3-methyl-2-thienyl)ethyl]amino}-2-oxo-1,2-dihydropyridin-3-yl)-6-(3-pyrrolidin-1-ylpropyl)-6,7-dihydroimidazo[4,5-f]isoindol-5(3H)-one was prepared according to General procedure 3.

LCMS [M+H]+ 531.3.

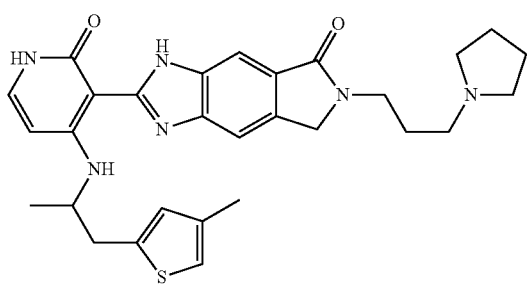 [SMILES: Cc1csc(CC(C)Nc2cc[nH]c(=O)c2-c2nc3cc4c(cc3[nH]2)C(=O)N(CCCN2CCCC2)C4)c1]

2-(4-{[1-methyl-2-(4-methyl-2-thienyl)ethyl]amino}-2-oxo-1,2-dihydropyridin-3-yl)-6-(3-pyrrolidin-1-ylpropyl)-6,7-dihydroimidazo[4,5-f]isoindol-5(3H)-one was prepared according to General procedure 3.

LCMS [M+H]+ 531.3

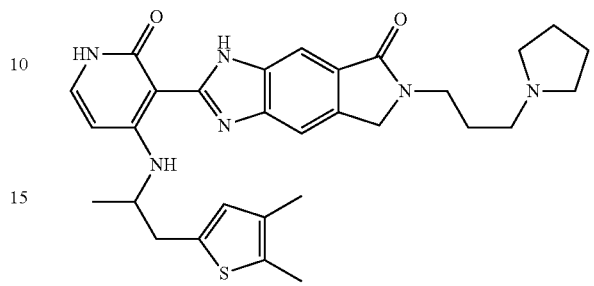

2-(4-{[2-(4,5-dimethyl-2-thienyl)-1-methylethyl]amino}-2-oxo-1,2-dihydropyridin-3-yl)-6-(3-pyrrolidin-1-ylpropyl)-6,7-dihydroimidazo[4,5-f]isoindol-5(3H)-one was prepared according to General procedure 3.

LCMS [M+H]+ 545.3.

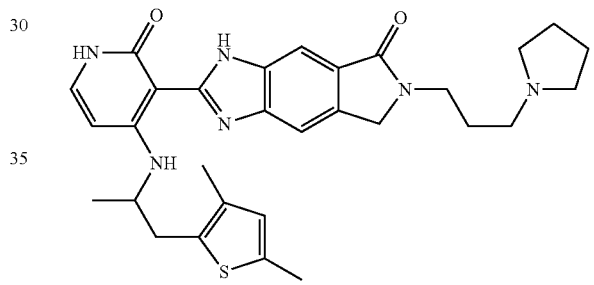

2-(4-{[2-(3,5-dimethyl-2-thienyl)-1-methylethyl]amino}-2-oxo-1,2-dihydropyridin-3-yl)-6-(3-pyrrolidin-1-ylpropyl)-6,7-dihydroimidazo[4,5-f]isoindol-5(3H)-one was prepared according to General procedure 3.

LCMS [M+H]+ 545.3.

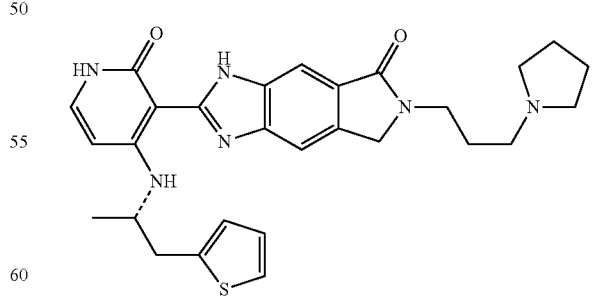

2-(4-{[(1S)-1-methyl-2-(2-thienyl)ethyl]amino}-2-oxo-1,2-dihydropyridin-3-yl)-6-(3-pyrrolidin-1-ylpropyl)-6,7-dihydroimidazo[4,5-f]isoindol-5(3H)-one was prepared according to General procedure 3.

LCMS [M+H]+ 517.4.

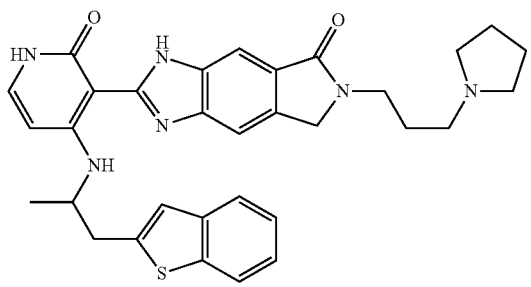 [SMILES: CC(Cc1cc2ccccc2s1)Nc1cc[nH]c(=O)c1-c1nc2cc3c(cc2[nH]1)C(=O)N(CCCN1CCCC1)C3]

2-(4-{[2-(1-benzothien-2-yl)-1-methylethyl]amino}-2-oxo-1,2-dihydropyridin-3-yl)-6-(3-pyrrolidin-1-ylpropyl)-6,7-dihydroimidazo[4,5-f]isoindol-5(3H)-one was prepared according to General procedure 3.

LCMS [M+H]+ 567.3.

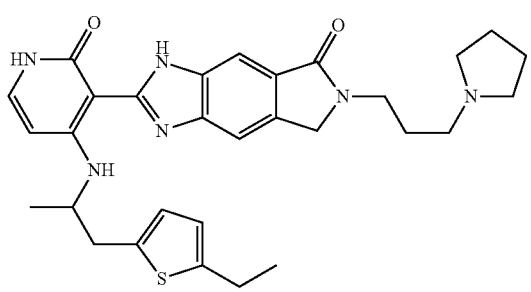 [SMILES: CCc1ccc(CC(C)Nc2cc[nH]c(=O)c2-c2nc3cc4c(cc3[nH]2)C(=O)N(CCCN2CCCC2)C4)s1]

2-(4-{[2-(5-ethyl-2-thienyl)-1-methylethyl]amino}-2-oxo-1,2-dihydropyridin-3-yl)-6-(3-pyrrolidin-1-ylpropyl)-6,7-dihydroimidazo[4,5-f]isoindol-5(3H)-one was prepared according to General procedure 3.

LCMS [M+H]+ 545.5.

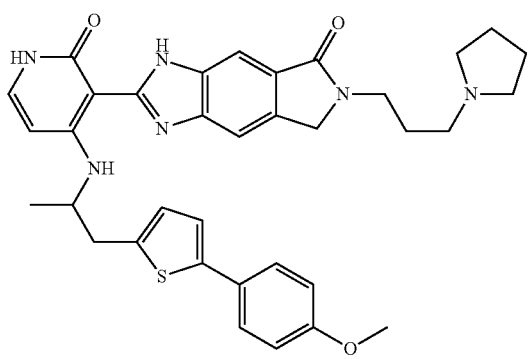 [SMILES: COc1ccc(-c2ccc(CC(C)Nc3cc[nH]c(=O)c3-c3nc4cc5c(cc4[nH]3)C(=O)N(CCCN3CCCC3)C5)s2)cc1]

2-[4-({2-[5-(4-methoxyphenyl)-2-thienyl]-1-methylethyl}amino)-2-oxo-1,2-dihydropyridin-3-yl]-6-(3-pyrrolidin-1-ylpropyl)-6,7-dihydroimidazo[4,5-f]isoindol-5(3H)-one was prepared according to General procedure 3.

LCMS [M+H]+ 623.5.

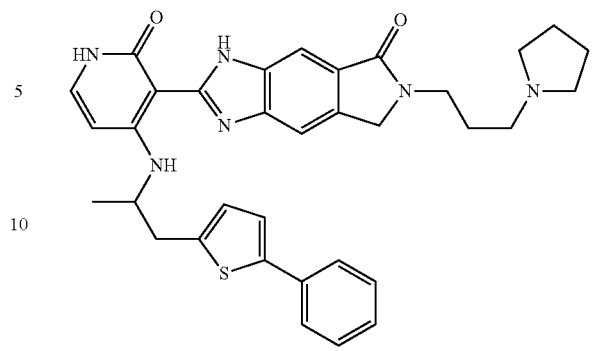

2-(4-{[1-methyl-2-(5-phenyl-2-thienyl)ethyl]amino}-2-oxo-1,2-dihydropyridin-3-yl)-6-(3-pyrrolidin-1-ylpropyl)-6,7-dihydroimidazo[4,5-f]isoindol-5(3H)-one was prepared according to General procedure 3.

LCMS [M+H]+ 593.5.

General Procedure 4

((2R)-1-(aryl)propan-2-ols)

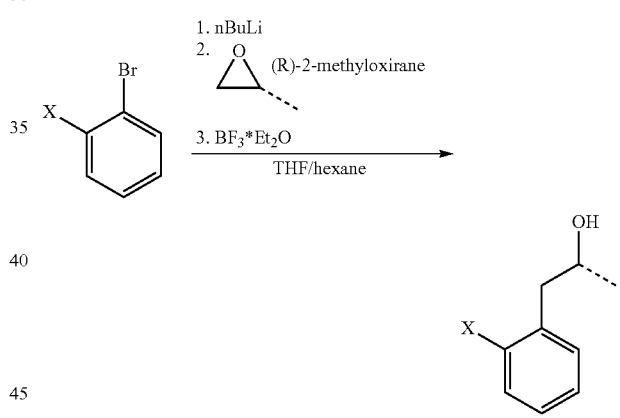

X = F, Cl

General Procedure 4. Substituted bromobenzene (20 mmol) was dissolved in dry THF (100 ml), the solution was cooled to −100° C. (heptane-liquid nitrogen) under Ar. nBuLi (12.5 ml of 1.6 M in hexane, 20 mmol) was added dropwise over 10 min at the temperature between −95° C. and −105° C., the mixture was stirred for 10 min at the same temperature. Than (R)-propyleneoxide (1.82 ml, 26 mmol) was added dropwise over 5 min and the mixture was stirred for 5 min at the temperature between −95° C. and −105° C. BF$_3$*Et$_2$O (2.17 ml, 30 mmol) was added dropwise over 5 min, the mixture was stirred for 1 h at the temperature between −95° C. and −105° C., saturated NH$_4$Cl (10 ml) was added at the same temperature and than the mixture was stirred overnight wile the temperature was increasing to RT. Water (50 ml) was added, extracted with hexane-EtOAc (1:1, 2×50 ml), extract was dried over Na$_2$SO$_4$, evaporated. The residue was separated on SiO$_2$ (50 ml, hexane-EtOAc 10:1).

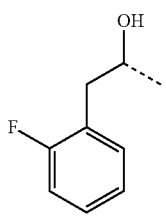

(R)-1-(2-fluorophenyl)propan-2-ol (2R)-1-(2-fluorophenyl)propan-2-ol was prepared according to General procedure 4. $^1$H NMR (400 MHz, DMSO-$d_6$) δ 7.31-7.20 (m, 2H), 7.13-7.08 (m, 2H), 4.61 (d, J 4.9 Hz, 1H), 3.89-3.79 (m, 1H), 2.71 (dd, J J 6.4 and 13.2 Hz, 1H), 2.60 (dd, J 6.4 and 13.4 Hz, 1H), 1.03 (d, J 6.1 Hz, 3H).

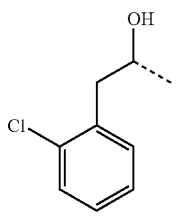

(R)-1-(2-chlorophenyl)propan-2-ol (2R)-1-(2-chlorophenyl)propan-2-ol was prepared according to General procedure 4. $^1$H NMR (400 MHz, DMSO-$d_6$) δ 7.41-7.32 (m, 2H), 7.27-7.19 (m, 2H), 4.62 (d, J 5.1 Hz, 1H), 3.94-3.85 (m, 1H), 2.80 (dd, J 6.8 and 13.2 Hz, 1H), 2.72 (dd, J 6.2 and 13.2 Hz, 1H), 1.06 (d, J 6.2 Hz, 3H).

General Procedure 5 ((2S)-1-arylpropan-2-amine))

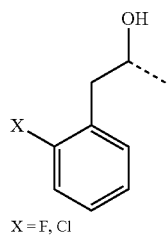

X = F, Cl

General Procedure 5. To a solution of (2R)-1-arylpropan-2-ol (10 mmol) and NEt3 (2.1 ml, 15 mmol) in DCM (10 ml) MSCl (0.85 ml, 11 mmol) was added dropwise over 5 min at 0° C. The reaction mixture was stirred at RT for 4 h. Than the reaction mixture was washed with water (10 ml), organic layer was separated, dried over Na2SO4. The solvent was evaporated. DMSO (5.0 ml) and NaN3 were added, the mixture was stirred for 2 h at 80° C., cooled to RT, hexane (20 ml) was added, the mixture was washed with water (2×20 ml), and organic layer was dried over Na$_2$SO$_4$, evaporated. The residue was dissolved in THF (10 ml), PPh$_3$ was added in portions, at RT and stirring. The reaction mixture was stirred for 4 h at RT, than NH$_4$OH (10 ml of 25%) was added, stirred overnight at 40° C. After cooling to RT 1N HCl (20 ml) was added, the mixture was washed with DCM (2×20 ml), the aqueous phase was basified with 1N NaOH to pH 9-10, extracted with DCM (2×20 ml). Extract was dried over Na2SO4, evaporated.

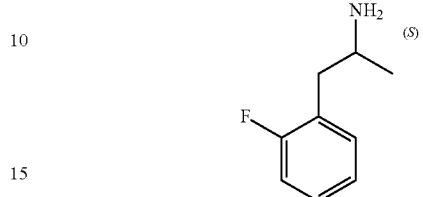

(2S)-1-(2-fluorophenyl)propan-2-amine was prepared according to General procedure 5. Colorless oil, Yield 50%.

$^1$H NMR (400 MHz, DMSO-$d_6$) δ 7.29-7.20 (m, 2H), 7.14-7.09 (m, 2H), 3.05-2.97 (m, 1H), 2.57-2.50 (m, 2H), 0.94 (d, J 6.1 Hz, 3H).

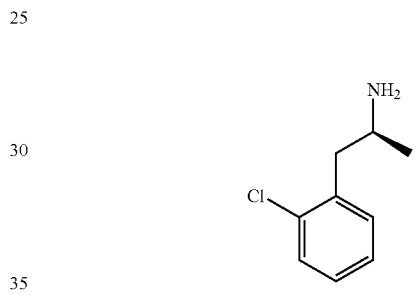

(2S)-1-(2-chlorophenyl)propan-2-amine was prepared according to General procedure 5. Colorless oil, Yield 55%.

$^1$H NMR (400 MHz, DMSO-$d_6$) δ 7.41-7.38 (m, 1H), 7.33-7.19 (m, 3H), 3.11-3.03 (m, 1H), 2.66 (d, J 6.8 Hz, 2H), 0.96 (d, J 6.4 Hz, 3H).

General Procedure 6

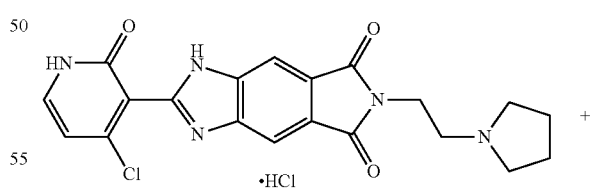

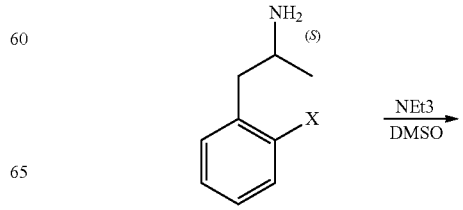

73

-continued

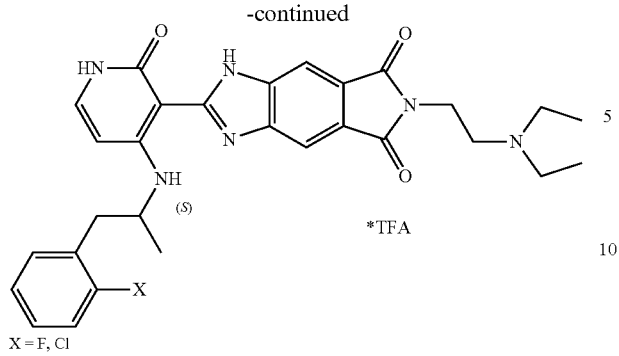

X = F, Cl

General Procedure 6. A mixture of chloropyridone (0.4 mmol), amine (0.4 mmol), NEt3 (0.5 ml) and DMSO (2.0 ml) was stirred overnight at 85° C. The product was isolated by preparative HPLC on C18 column (acetonitrile-01% TFA 5:95 to 95:5 v/v).

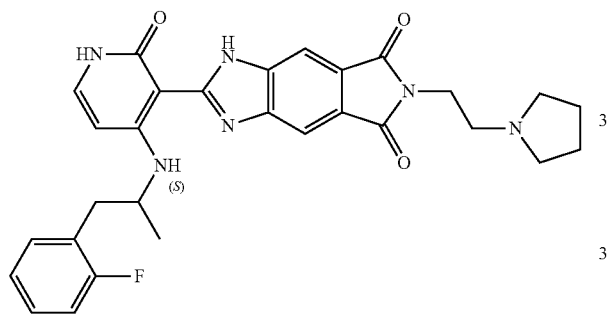

2-(4-{[(1S)-2-(2-fluorophenyl)-1-methylethyl]amino}-2-oxo-1,2-dihydropyridin-3-yl)-6-(2-pyrrolidin-1-ylethyl)imidazo[4,5-f]isoindole-5,7(1H,6H)-dione was prepared according to General procedure 6.

LCMS [M+H]$^+$ 529.2

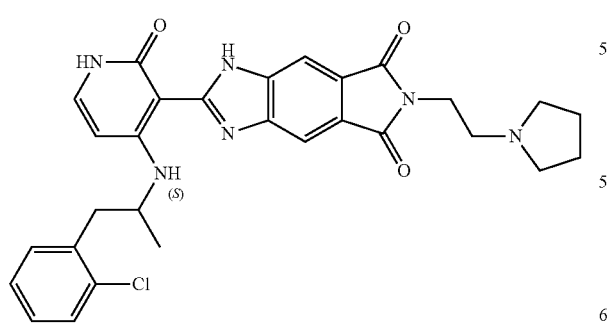

2-(4-{[(1S)-2-(2-chlorophenyl)-1-methylethyl]amino}-2-oxo-1,2-dihydropyridin-3-yl)-6-(2-pyrrolidin-1-ylethyl)imidazo[4,5-f]isoindole-5,7(1H,6H)-dione was prepared according to General procedure 6.

LCMS [M+H]$^+$ 545.2

74

5-Methoxy-2-methylaniline

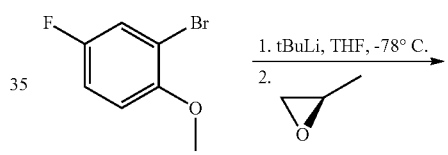

5-Methoxy-2-methylaniline: To a solution of 4-methoxy-1-methyl-2-nitrobenzene (18.0 g, 108 mmol) in 160 mL of DME was added Pd/C (10%, 0.9 g) under nitrogen. Then hydrazine hydrate (16.17 g, 323 mmol) was added dropwise. The mixture was heated and stirred under reflux for 4 h. Then another 3 mL of hydrazine hydrate was added and stirred under reflux for 2d. Then the reaction mixture was cooled to RT, filtered through celite and evaporated to dryness to give 5-methoxy-2-methylaniline as yellow oil that solidified upon drying under vacuum to give 14.8 g (100%). $^1$H NMR (300 MHz, CDCl$_3$): δ 6.94 (d, J=7.53 Hz, 1H), 6.28 (d, J=7.53 Hz, 1H), 6.26 (s, 1H), 3.78 (s, 3H), 3.5 (br, 1H), 2.10 (s, 3H), 1.6 (br, 1H).

(2R)-1-(5-Fluoro-2-methoxyphenyl)propan-2-ol

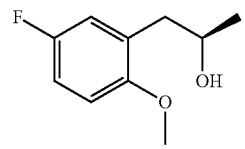

(R)-2-methyloxirane (2R)-1-(5-Fluoro-2-methoxyphenyl)propan-2-ol: A solution of 2-bromo-4-fluoro-1-methoxybenzene (2.0 g, 9.75 mmol) in 20 mL of anhydrous THF was cooled to −78° C. Then 1.7M solution of t-BuLi in pentane (13.0 mL, 22.1 mmol) was added dropwise. The mixture was stirred at −78° C. for 10 min, then R-(+)-propylene oxide (670 mg, 11.55 mmol) was added and the mixture was allowed to warm to 0° C. overnight. The mixture was quenched with 2 mL of sat. NH$_4$Cl and then conc. HCl was added dropwise to pH 8. The mixture was extracted with EtOAc (2×20 mL), the extract was dried over Na$_2$SO$_4$ and evaporated to give crude oil, which was purified by column (silica gel, EtOAc/hexane 1:9) to give (2R)-1-(5-fluoro-2-methoxyphenyl)propan-2-ol (531 mg, 30%). $^1$H NMR (300 MHz, CDCl$_3$): δ 6.88 (m, 2H), 6.78 (m, 1H), 4.06 (m, 1H), 3.81 (s, 3H), 2.66-2.84 (m, 2H), 1.92 (d, J=3.96 Hz, 1H), 1.22 (d, J=6.21 Hz, 3H).

N-(3-Iodo-4-methylphenyl)-N,N-dimethylamine

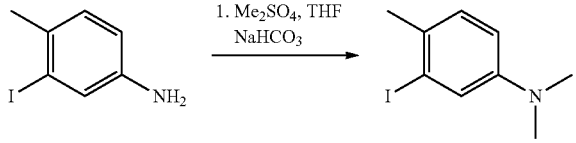

N-(3-Iodo-4-methylphenyl)-N,N-dimethylamine: To a solution of 3-iodo-4-methylaniline (5.0 g, 21.46 mmol) in 30 mL of THF was added NaHCO$_3$ anh. (5.0 g, 60 mmol). The mixture was stirred and dimethylsulfate (5.92 g, 47 mmol) was carefully added. The mixture was stirred for 16 h, then 12 mL of sat. NaHCO$_3$ was added and extracted with EtOAc (2×30 mL). The extract was dried over Na$_2$SO$_4$ and evaporated to give crude oil, which was purified by column (silica gel, DCM/hexane 1:9) to give N-(3-iodo-4-methylphenyl)-N,N-dimethylamine (2.83 g, 51%) as yellow oil. $^1$H NMR (300 MHz, CDCl$_3$): δ 7.18 (d, J=2.82 Hz, 1H), 7.05 (d, J=8.49 Hz, 1H), 7.18 (dd, J$_1$=8.49 Hz, J$_2$=2.82 Hz, 1H), 2.88 (s, 6H), 2.32 (s, 3H).

1,5-Difluoro-3-iodo-2-(trifluoromethyl)benzene

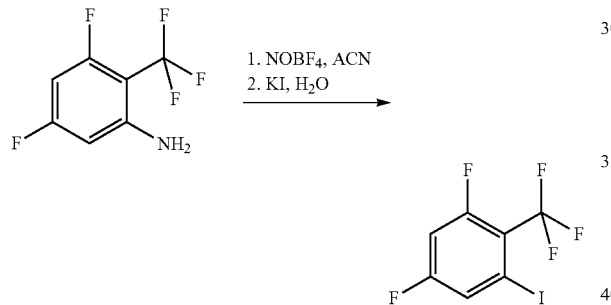

1,5-Difluoro-3-iodo-2-(trifluoromethyl)benzene: To a solution of nitrosonium tetrafluoroborate (5.6 g, 48 mmol) in 20 mL of ACN was added solution of 3,5-difluoro-2-(trifluoromethyl)aniline (7.88 g, 40 mmol) in 10 mL of ACN at −20° C. The mixture was stirred for 1 h raising temperature to 0° C. A white precipitate formed. Then a solution of KI (7.97 g, 48 mmol) in 20 mL of water was added dropwise while cooling in an ice bath. The mixture was stirred for 1 h, then added 2 mL of saturated sodium sulfite, and the mixture was extracted with EtOAc/hexane 1:1 (2×10 mL). Extract was dried over Na$_2$SO$_4$ and concentrated under light vacuum at 20° C. to give crude reddish oil that was distilled under vacuum to give pure 1,5-difluoro-3-iodo-2-(trifluoromethyl)benzene as pale oil (9.14 g, 62%). $^1$H NMR (300 MHz, CDCl$_3$): δ 7.63 (d, J=7.17 Hz, 1H), 6.94 (t, J=9.6 Hz, 1H).

2-Iodo-4-methoxy-1-methylbenzene

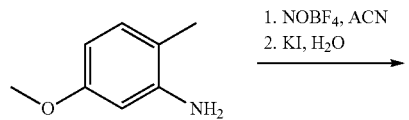

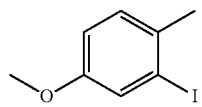

2-Iodo-4-methoxy-1-methylbenzene: To a solution of nitrosonium tetrafluoroborate (5.6 g, 48 mmol) in 30 mL of ACN was added solution of 5-methoxy-2-methylaniline (5.49 g, 40 mmol) in 20 mL of ACN at −20° C. The mixture was stirred for 15 min at 0° C. A dark mixture formed. Then a solution of KI (7.97 g, 48 mmol) in 20 mL of water was added dropwise while cooling in an ice bath. The mixture was stirred for 1 h, then added 2 mL of saturated sodium sulfite, and the mixture was extracted with EtOAc/hexane 1:1 (2×10 mL). Extract was dried over Na$_2$SO$_4$ and evaporated under vacuum at 20° C. to give crude reddish oil that was passed through silica gel plug with hexane to give pure 2-iodo-4-methoxy-1-methylbenzene as colorless oil (3.71 g, 32%). $^1$H NMR (300 MHz, CDCl$_3$): δ 7.35 (s, 1H), 7.11 (d, J=8.46 Hz, 1H), 6.80 (d, J=8.46 Hz, 1H), 3.76 (s, 3H), 2.36 (s, 3H).

(2R)-1-(2-Chloro-5-fluorophenyl)propan-2-ol

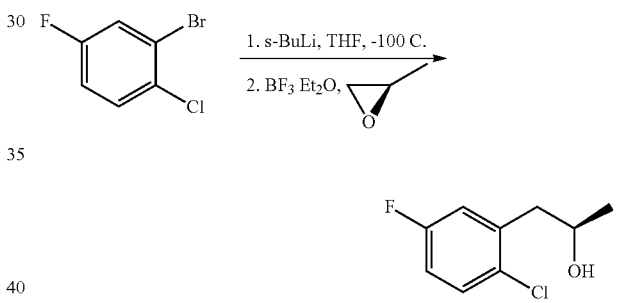

(2R)-1-(2-Chloro-5-fluorophenyl)propan-2-ol: A solution of 2-bromo-1-chloro-4-fluorobenzene (4.19 g, 20 mmol) in 100 mL of anhydrous THF was cooled to −100° C. (liquid nitrogen/EtOH) under nitrogen. Then 1.4M solution of sec-BuLi in cyclohexane (15 mL, 21 mmol) was added dropwise at −100° C. to −90° C. The mixture was stirred at −100° C. to −90° C. for 10 min, then a solution of R-(+)-propylene oxide (1.51 g, 1.8 mL, 26 mmol) in 15 mL of THF was added dropwise at −100° C. to −90° C., then the mixture was cooled to −105° C. and a 46.5% solution of BF$_3$ in diethyl ether (4.18 mL, 30 mmol) was added dropwise. The mixture was stirred at −100° C. to −90° C. for 2 h, then the reaction was quenched with 20 mL of sat. aq. NH$_4$Cl at −90° C. The mixture was stirred and warmed to 0° C. overnight. Then 20 mL of water was added and mixture was extracted with EtOAc (2×60 mL), the extract was dried over Na$_2$SO$_4$ and evaporated to give crude oil, which was purified by column (silica gel, EtOAc/hexane 1:9, Rf=0.52 in EtOAc/hexane 3:7) to give (2R)-1-(2-chloro-5-fluorophenyl)propan-2-ol (2.80 g, 74%) as colorless oil. $^1$H NMR (300 MHz, CDCl$_3$): δ 7.32 (m, 1H), 7.02 (m, 1H), 6.90 (m, 1H), 4.14 (m, 1H), 2.82-2.96 (m, 2H), 1.46 (d, J=4.32 Hz, 1H), 1.28 (d, J=6.21 Hz, 3H).

(2R)-1-(2-Bromo-5-fluorophenyl)propan-2-ol

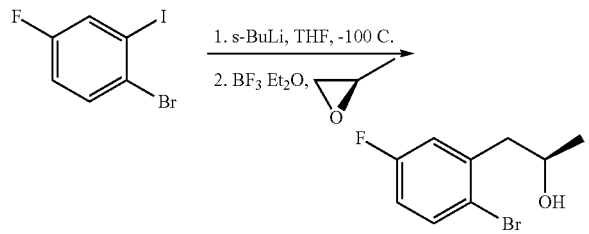

(2R)-1-(2-Bromo-5-fluorophenyl)propan-2-ol: A solution of 1-bromo-4-fluoro-2-iodobenzene (6.02 g, 20 mmol) in 100 mL of anhydrous THF was cooled to −100° C. (liquid nitrogen/EtOH) under nitrogen. Then 1.4M solution of sec-BuLi in cyclohexane (15 mL, 21 mmol) was added dropwise at −100° C. to −90° C. The mixture was stirred at −100° C. to −90° C. for 10 min, then a solution of R-(+)-propylene oxide (1.51 g, 1.8 mL, 26 mmol) in 15 mL of THF was added dropwise at −100° C. to −90° C., then the mixture was cooled to −105° C. and a 46.5% solution of $BF_3$ in diethyl ether (4.18 mL, 30 mmol) was added dropwise. The mixture was stirred at −100° C. to −90° C. for 2 h, then the reaction was quenched with 20 mL of sat. aq. $NH_4Cl$ at −90° C. The mixture was stirred and warmed to 0° C. overnight. Then 20 mL of water was added and mixture was extracted with EtOAc (2×60 mL), the extract was dried over $Na_2SO_4$ and evaporated to give crude oil, which was purified by column (silica gel, EtOAc/hexane 1:9, Rf=0.52 in EtOAc/hexane 3:7) to give (2R)-1-(2-bromo-5-fluorophenyl)propan-2-ol (1.67 g, 35%) as white solid. $^1$H NMR (300 MHz, $CDCl_3$): δ 7.50 (m, 1H), 7.02 (m, 1H), 6.84 (m, 1H), 4.14 (m, 1H), 2.78-2.96 (m, 2H), 1.45 (d, J=4.53 Hz, 1H), 1.29 (d, J=6.24 Hz, 3H).

(2R)-1-[5-(Dimethylamino)-2-methylphenyl]propan-2-ol

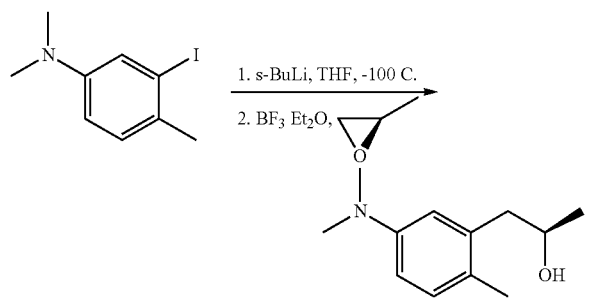

(2R)-1-[5-(Dimethylamino)-2-methylphenyl]propan-2-ol: A solution of N-(3-iodo-4-methylphenyl)-N,N-dimethylamine (5.22 g, 20 mmol) in 100 mL of anhydrous THF was cooled to −100° C. (liquid nitrogen/EtOH) under nitrogen. Then 1.4M solution of sec-BuLi in cyclohexane (15 mL, 21 mmol) was added dropwise at −100° C. to −90° C. The mixture was stirred at −100° C. to −90° C. for 10 min, then a solution of R-(+)-propylene oxide (1.51 g, 1.8 mL, 26 mmol) in 15 mL of THF was added dropwise at −100° C. to −90° C., then the mixture was cooled to −105° C. and a 46.5% solution of $BF_3$ in diethyl ether (4.18 mL, 30 mmol) was added dropwise. The mixture was stirred at −100° C. to −90° C. for 2 h, then the reaction was quenched with 20 mL of sat. aq. $NH_4Cl$ at −90° C. The mixture was stirred and warmed to 0° C. overnight. Then 20 mL of water was added and mixture was extracted with EtOAc (2×60 mL), the extract was dried over $Na_2SO_4$ and evaporated to give crude oil, which was purified by column (silica gel, EtOAc/hexane 1:9, Rf=0.25 in EtOAc/hexane 3:7) to give (2R)-1-[5-(dimethylamino)-2-methylphenyl]propan-2-ol (0.15 g, 4%) as brown oil. $^1$H NMR (300 MHz, $CDCl_3$): δ 7.03 (m, 1H), 6.58 (m, 2H), 4.02 (m, 1H), 2.90 (s, 6H), 2.65-2.78 (m, 2H), 2.23 (s, 3H), 1.62 (br, 1H), 1.29 (d, J=6.21 Hz, 3H).

(2R)-1-[2-Methyl-5-(trifluoromethyl)phenyl]propan-2-ol

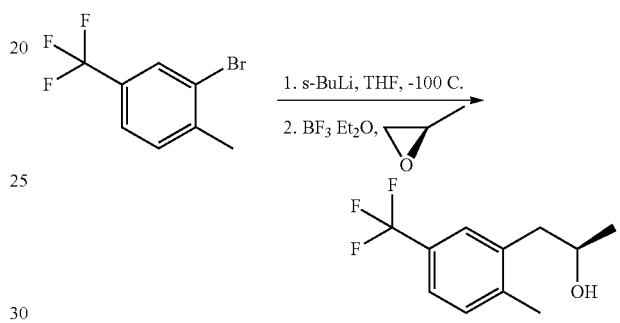

(2R)-1-[2-Methyl-5-(trifluoromethyl)phenyl]propan-2-ol: A solution of 2-bromo-1-methyl-4-(trifluoromethyl)benzene (4.78 g, 20 mmol) in 100 mL of anhydrous THF was cooled to −100° C. (liquid nitrogen/EtOH) under nitrogen. Then 1.4M solution of sec-BuLi in cyclohexane (15 mL, 21 mmol) was added dropwise at −100° C. to −90° C. The mixture was stirred at −100° C. to −90° C. for 10 min, then a solution of R-(+)-propylene oxide (1.51 g, 1.8 mL, 26 mmol) in 15 mL of THF was added dropwise at −100° C. to −90° C., then the mixture was cooled to −105° C. and a 46.5% solution of $BF_3$ in diethyl ether (4.18 mL, 30 mmol) was added dropwise. The mixture was stirred at −100° C. to −90° C. for 2 h, then the reaction was quenched with 20 mL of sat. aq. $NH_4Cl$ at −90° C. The mixture was stirred and warmed to 0° C. overnight. Then 20 mL of water was added and mixture was extracted with EtOAc (2×60 mL), the extract was dried over $Na_2SO_4$ and evaporated to give crude oil, which was purified by column (silica gel, EtOAc/hexane 1:9, Rf=0.45 in EtOAc/hexane 3:7) to give (2R)-1-[2-methyl-5-(trifluoromethyl)phenyl]propan-2-ol (2.87 g, 66%) as white solid. $^1$H NMR (300 MHz, $CDCl_3$): δ 7.42 (s, 1H), 7.39 (d, J=8.1 Hz, 1H), 7.27 (d, J=8.1 Hz, 1H), 4.06 (m, 1H), 2.81 (d, J=6.39 Hz, 2H), 2.39 (s, 3H), 1.43 (d, J=4.14 Hz, 1H), 1.29 (d, J=6.21 Hz, 3H).

(2R)-1-(2,3,5-Trifluorophenyl)propan-2-ol

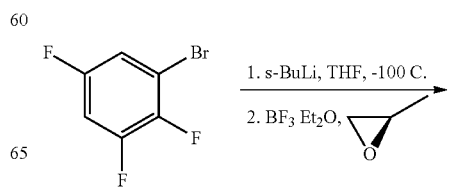

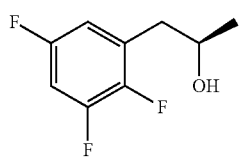

(2R)-1-(2,3,5-Trifluorophenyl)propan-2-ol: A solution of 1-bromo-2,3,5-trifluorobenzene (4.22 g, 20 mmol) in 100 mL of anhydrous THF was cooled to −100° C. (liquid nitrogen/EtOH) under nitrogen. Then 1.4M solution of sec-BuLi in cyclohexane (15 mL, 21 mmol) was added dropwise at −100° C. to −90° C. The mixture was stirred at −100° C. to −90° C. for 10 min, then a solution of R-(+)-propylene oxide (1.51 g, 1.8 mL, 26 mmol) in 15 mL of THF was added dropwise at −100° C. to −90° C., then the mixture was cooled to −105° C. and a 46.5% solution of $BF_3$ in diethyl ether (4.18 mL, 30 mmol) was added dropwise. The mixture was stirred at −100° C. to −90° C. for 2 h, then the reaction was quenched with 20 mL of sat. aq. $NH_4Cl$ at −90° C. The mixture was stirred and warmed to 0° C. overnight. Then 20 mL of water was added and mixture was extracted with EtOAc (2×60 mL), the extract was dried over $Na_2SO_4$ and evaporated to give crude oil, which was purified by column (silica gel, EtOAc/hexane 1:9, Rf=0.52 in EtOAc/hexane 3:7) to give (2R)-1-(2,3,5-trifluorophenyl)propan-2-ol (3.14 g, 83%) as pale yellow oil. $^1$H NMR (300 MHz, $CDCl_3$): δ 7.12-7.26 (m, 1H), 6.76-6.96 (m, 1H), 4.09 (m, 1H), 2.85-2.88 (m, 2H), 1.47 (d, J=5.46 Hz, 1H), 1.26 (d, J=6.03 Hz, 3H).

(1S)-2-(2-Chloro-5-fluorophenyl)-1-methylethyl azide

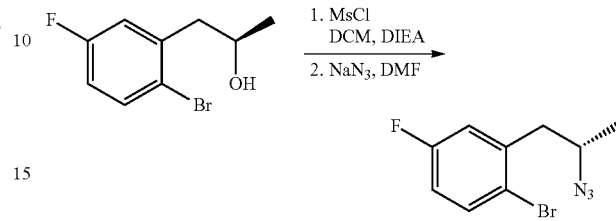

(1S)-2-(2-Chloro-5-fluorophenyl)-1-methylethyl azide: A solution of (2R)-1-(2-chloro-5-fluorophenyl)propan-2-ol (1.40 g, 7.42 mmol) and DIEA (2.58 mL, 14 mmol) in 20 mL of anhydrous DCM was cooled to −10° C. Then MSCl (1.02 g, 8.9 mmol) was carefully added and the mixture was warmed to RT and stirred for 30 min. Then 10 mL of sat. $NaHCO_3$ was added and the mixture was extracted with DCM (2×20 mL). The extract was dried over $Na_2SO_4$ and evaporated to give crude oil of mesylate. This oil was dissolved in 6 mL of anh. DMF. Then $NaN_3$ (965 mg, 14.84 mmol) was added and the mixture was heated at 80° C. for 2 h. Then 30 mL of water added and extracted with 20 mL of EtOAc/hexane 1:1 mixture. The extract was dried over $Na_2SO_4$ and evaporated to give crude oil, which was passed through silica gel plug eluting with 5% DCM in hexane, then evaporated to give (1S)-2-(2-chloro-5-fluorophenyl)-1-methylethyl azide (1.22 g, 77%) as pale yellow oil. $^1$H NMR (300 MHz, $CDCl_3$): δ 7.32 (m, 1H), 6.98 (m, 2H), 3.80 (m, 1H), 2.88 (d, J=5.1 Hz, 2H), 1.31 (d, J=6.39 Hz, 3H).

(1S)-2-(2-Bromo-5-fluorophenyl)-1-methylethyl azide

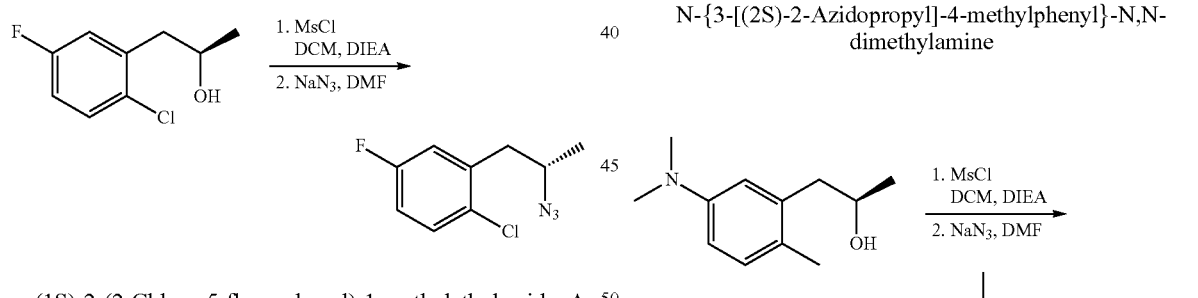

(1S)-2-(2-Bromo-5-fluorophenyl)-1-methylethyl azide: A solution of (2R)-1-(2-bromo-5-fluorophenyl)propan-2-ol (1.06 g, 4.55 mmol) and DIEA (1.58 mL, 9.1 mmol) in 20 mL of anhydrous DCM was cooled to −10° C. Then MSCl (625 mg, 5.46 mmol) was carefully added and the mixture was warmed to RT and stirred for 30 min. Then 10 mL of sat. $NaHCO_3$ was added and the mixture was extracted with DCM (2×20 mL). The extract was dried over $Na_2SO_4$ and evaporated to give crude oil of mesylate. This oil was dissolved in 4 mL of anh. DMF. Then $NaN_3$ (592 mg, 9.1 mmol) was added and the mixture was heated at 80° C. for 2 h. Then 30 mL of water added and extracted with 20 mL of EtOAc/hexane 1:1 mixture. The extract was dried over $Na_2SO_4$ and evaporated to give crude oil, which was passed through silica gel plug eluting with 5% DCM in hexane, then evaporated to give (1S)-2-(2-bromo-5-fluorophenyl)-1-methylethyl azide (997 mg, 85%) as pale yellow oil. $^1$H NMR (300 MHz, $CDCl_3$): δ 7.51 (m, 1H), 6.99 (m, 1H), 6.86 (m, 1H), 3.81 (m, 1H), 2.88 (d, J=4.9 Hz, 2H), 1.32 (d, J=4.35 Hz, 3H).

N-{3-[(2S)-2-Azidopropyl]-4-methylphenyl}-N,N-dimethylamine

N-{3-[(2S)-2-Azidopropyl]-4-methylphenyl}-N,N-dimethylamine: A solution of (2R)-1-[5-(dimethylamino)-2-methylphenyl]propan-2-ol (150 mg, 0.77 mmol) and DIEA (0.27 mL, 1.54 mmol) in 10 mL of anhydrous DCM was cooled to −10° C. Then MsCl (107 mg, 0.93 mmol) was carefully added and the mixture was warmed to RT and stirred for 30 min. Then 5 mL of sat. $NaHCO_3$ was added and the mixture was extracted with DCM (2×10 mL). The extract was dried over $Na_2SO_4$ and evaporated to give crude oil of mesylate. This oil was dissolved in 2 mL of anh. DMF. Then $NaN_3$ (100 mg, 1.54 mmol) was added and the mixture was heated at 80° C. for 2 h. Then 20 mL of water added and extracted with 2×10 mL of EtOAc/hexane 1:1 mixture. The extract was dried over Na$_2$SO$_4$ and evaporated to give crude oil, which was passed through silica gel plug eluting with 5% DCM in hexane, then evaporated to give N-{3-[(2S)-2-azidopropyl]-4-methylphenyl}-N,N-dimethylamine (71 mg, 42%) as pale yellow oil. $^1$H NMR (300 MHz, CDCl$_3$): δ 7.02 (m, 1H), 6.57 (m, 2H), 3.66 (m, 1H), 2.90 (s, 6H), 2.64-2.84 (m, 2H), 2.23 (s, 3H), 1.28 (d, J=6.42 Hz, 3H).

(1S)-1-Methyl-2-[2-methyl-5-(trifluoromethyl)phenyl]ethyl azide

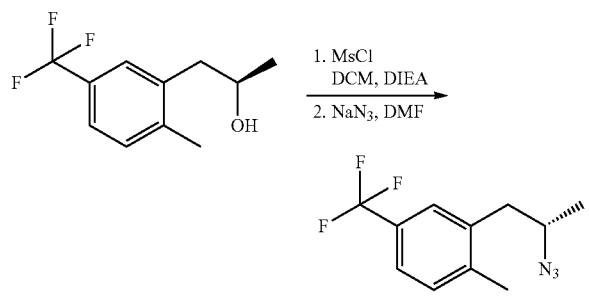

(1S)-1-Methyl-2-[2-methyl-5-(trifluoromethyl)phenyl]ethyl azide: A solution of (2R)-1-[2-methyl-5-(trifluoromethyl)phenyl]propan-2-ol (1.62 g, 7.42 mmol) and DIEA (2.58 mL, 14 mmol) in 20 mL of anhydrous DCM was cooled to −10° C. Then MsCl (1.02 g, 8.9 mmol) was carefully added and the mixture was warmed to RT and stirred for 30 min. Then 10 mL of sat. NaHCO$_3$ was added and the mixture was extracted with DCM (2×20 mL). The extract was dried over Na$_2$SO$_4$ and evaporated to give crude oil of mesylate. This oil was dissolved in 6 mL of anh. DMF. Then NaN$_3$ (965 mg, 14.84 mmol) was added and the mixture was heated at 80° C. for 2 h. Then 30 mL of water added and extracted with 20 mL of EtOAc/hexane 1:1 mixture. The extract was dried over Na$_2$SO$_4$ and evaporated to give crude oil, which was passed through silica gel plug eluting with 5% DCM in hexane, then evaporated to give (1S)-1-methyl-2-[2-methyl-5-(trifluoromethyl)phenyl]ethyl azide (1.64 g, 91%) as pale yellow oil. $^1$H NMR (300 MHz, CDCl$_3$): δ 7.40 (m, 2H), 7.27 (m, 1H), 3.70 (m, 1H), 2.73-2.92 (m, 2H), 2.39 (s, 3H), 1.31 (d, J=6.39 Hz, 31-1).

(1S)-1-Methyl-2-(2,3,5-trifluorophenyl)ethyl azide

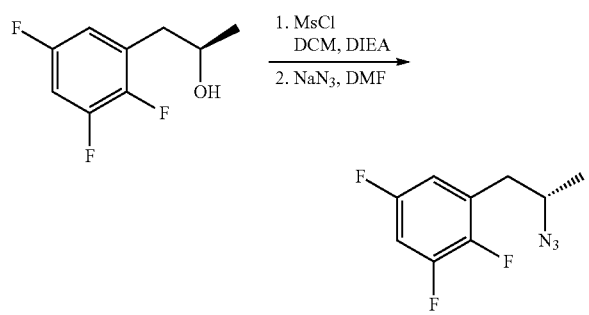

(1S)-1-Methyl-2-(2,3,5-trifluorophenyl)ethyl azide: A solution of (2R)-1-(2,3,5-trifluorophenyl)propan-2-ol (1.41 g, 7.42 mmol) and DIEA (2.58 mL, 14 mmol) in 20 mL of anhydrous DCM was cooled to −10° C. Then MsCl (1.02 g, 8.9 mmol) was carefully added and the mixture was warmed to RT and stirred for 30 min. Then 10 mL of sat. NaHCO$_3$ was added and the mixture was extracted with DCM (2×20 mL). The extract was dried over Na$_2$SO$_4$ and evaporated to give crude oil of mesylate. This oil was dissolved in 6 mL of anh. DMF. Then NaN$_3$ (965 mg, 14.84 mmol) was added and the mixture was heated at 80° C. for 2 h. Then 30 mL of water added and extracted with 20 mL of EtOAc/hexane 1:1 mixture. The extract was dried over Na$_2$SO$_4$ and evaporated to give crude oil, which was passed through silica gel plug eluting with 5% DCM in hexane, then evaporated to give (1S)-1-methyl-2-(2,3,5-trifluorophenyl)ethyl azide (931 mg, 58%) as pale yellow oil. $^1$H NMR (300 MHz, CDCl$_3$): δ 7.03 (m, 1H), 6.81 (m, 1H), 3.73 (m, 1H), 2.84 (m, 2H), 1.32 (d, J=6.6 Hz, 3H).

(1S)-2-(2-Chloro-5-fluorophenyl)-1-methylethylamine

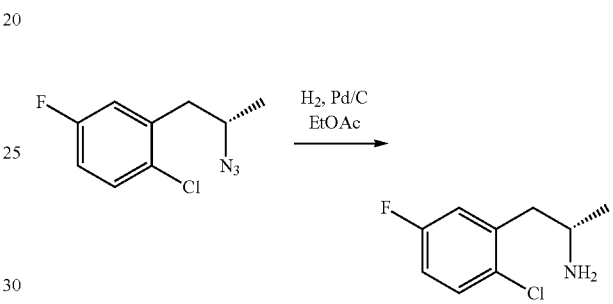

(1S)-2-(2-Chloro-5-fluorophenyl)-1-methylethylamine:
To a solution of (1S)-2-(2-chloro-5-fluorophenyl)-1-methylethyl azide (1.10 g, 5.15 mmol) in 100 mL of EtOAc was added Pd/C (300 mg of 10% Pd) and the mixture was hydrogenated under hydrogen balloon for 30 min. The catalyst was removed by filtration through celite, then passed through silica gel plug eluting first with EtOAc (40 mL), then MeOH/EtOAc/NH$_4$OH 20:75:5 (120 mL). The fraction with product was evaporated to give (1S)-2-(2-chloro-5-fluorophenyl)-1-methylethylamine (721 mg, 67%) as pale yellow oil. ESI-MS: m/z (MH$^+$) 188.3. $^1$H NMR (300 MHz, CDCl$_3$): δ 7.30 (m, 1H), 6.86-6.97 (m, 2H), 3.26 (m, 1H), 2.66-2.84 (m, 2H), 1.40 (s, 2H), 1.15 (d, J=6.42 Hz, 3H).

(1S)-2-(2-Bromo-5-fluorophenyl)-1-methylethylamine

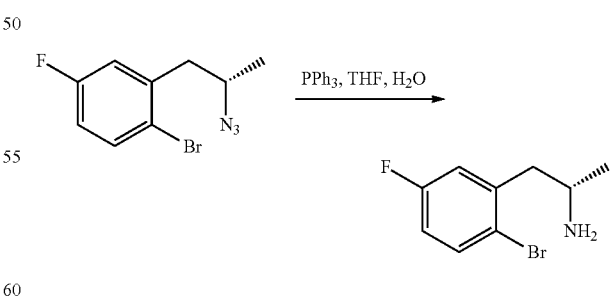

(1S)-2-(2-Bromo-5-fluorophenyl)-1-methylethylamine:
To a solution of (1S)-2-(2-bromo-5-fluorophenyl)-1-methylethyl azide (1.00 g, 3.87 mmol) in 20 mL of THF and 4 mL of water was added PPh$_3$ (2.03 g, 7.74 mmol) and the mixture was stirred for 4 h. The solvent was evaporated and the residue was purified by silica gel column eluting first with DCM, then DCM:MeOH:NH$_4$OH (94:5:1). The fraction with product was evaporated to give (1S)-2-(2-bromo-5-fluorophenyl)-1-methylethylamine (134 mg, 15%) as colorless oil. $^1$H NMR (300 MHz, CDCl$_3$): δ 7.50 (m, 1H), 6.97 (m, 1H), 6.83 (m, 1H), 3.28 (m, 1H), 2.66-2.87 (m, 2H), 1.68 (s, 2H), 1.17 (d, J=6.21 Hz, 3H).

N-{3-[(2S)-2-Aminopropyl]-4-methylphenyl}-N,N-dimethylamine

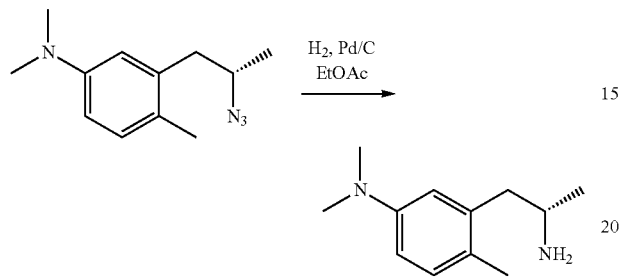

N-{3-[(2S)-2-Aminopropyl]-4-methylphenyl}-N,N-dimethylamine: To a solution of N-{3-[(2S)-2-azidopropyl]-4-methylphenyl}-N,N-dimethylamine (71 mg, 0.325 mmol) in 10 mL of EtOAc was added Pd/C (30 mg of 10% Pd) and the mixture was hydrogenated under hydrogen balloon for 1 h. The catalyst was removed by filtration through celite, then passed through silica gel plug eluting first with EtOAc (10 mL), then MeOH/EtOAc/NH$_4$OH 20:75:5 (20 mL). The fraction with product was evaporated to give N-{3-[(2S)-2-aminopropyl]-4-methylphenyl}-N,N-dimethylamine (53 mg, 85%) as pale yellow oil. ESI-MS: m/z (MH$^+$) 193.1. $^1$H NMR (300 MHz, CDCl$_3$): δ 7.02 (m, 1H), 6.57 (m, 2H), 3.16 (m, 1H), 2.90 (s, 6H), 2.44-2.74 (m, 2H), 2.22 (s, 3H), 1.48 (s, 2H), 1.14 (d, J=6.42 Hz, 3H).

(1S)-1-Methyl-2-[2-methyl-5-(trifluoromethyl)phenyl]ethylamine

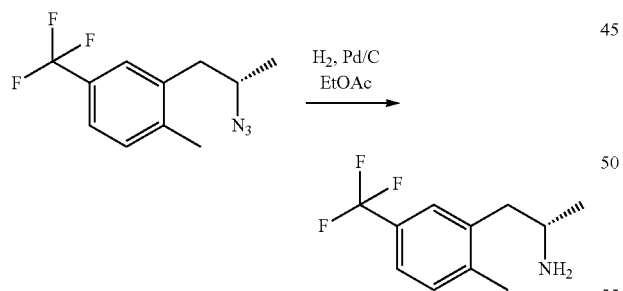

(1S)-1-Methyl-2-[2-methyl-5-(trifluoromethyl)phenyl]ethylamine: To a solution of (1S)-1-methyl-2-[2-methyl-5-(trifluoromethyl)phenyl]ethyl azide (1.64 g, 6.74 mmol) in 100 mL of EtOAc was added Pd/C (300 mg of 10% Pd) and the mixture was hydrogenated under hydrogen balloon for 1 h. The catalyst was removed by filtration through celite, then passed through silica gel plug eluting first with EtOAc (40 mL), then MeOH/EtOAc/NH$_4$OH 20:75:5 (120 mL). The fraction with product was evaporated to give (1S)-1-methyl-2-[2-methyl-5-(trifluoromethyl)phenyl]ethylamine (1.10 g, 75%) as pale yellow oil. ESI-MS: m/z (MH$^+$) 218.4. $^1$H NMR (300 MHz, CDCl$_3$): δ 7.37 (m, 2H), 7.20 (m, 1H), 3.20 (m, 1H), 2.58-2.77 (m, 2H), 2.38 (s, 3H), 1.42 (s, 2H), 1.14 (d, J=6.21 Hz, 3H).

(1S)-1-Methyl-2-(2,3,5-trifluorophenyl)ethylamine

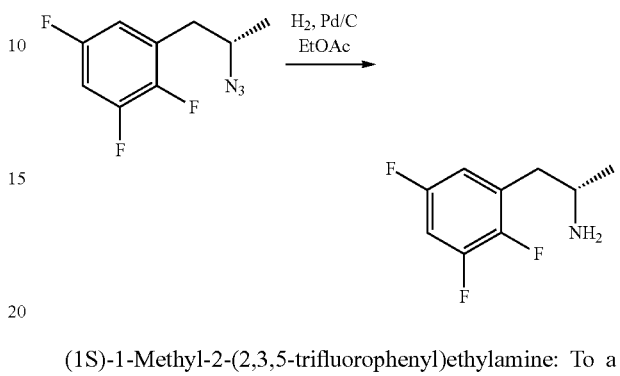

(1S)-1-Methyl-2-(2,3,5-trifluorophenyl)ethylamine: To a solution of (1S)-1-methyl-2-(2,3,5-trifluorophenyl)ethyl azide (930 mg, 4.32 mmol) in 100 mL of EtOAc was added Pd/C (300 mg of 10% Pd) and the mixture was hydrogenated under hydrogen balloon for 1 h. The catalyst was removed by filtration through celite, then passed through silica gel plug eluting first with EtOAc (40 mL), then MeOH/EtOAc/NH$_4$OH 20:75:5 (120 mL). The fraction with product was evaporated to give (1S)-1-methyl-2-(2,3,5-trifluorophenyl)ethylamine (475 mg, 58%) as pale yellow oil. ESI-MS: m/z (MH$^+$) 190.1. $^1$H NMR (300 MHz, CDCl$_3$): δ 7.04 (m, 1H), 6.83 (m, 1H), 4.06 (s, 2H), 3.42 (m, 1H), 2.92 (m, 2H), 1.29 (d, J=6.21 Hz, 3H).

2-(4-((1S)-2-(2-Chloro-5-fluorophenyl)-1-methylethylamino)-2-oxo-1,2-dihydropyridin-3-yl)-6-(2-pyrrolidin-1-ylethyl)-6,7-dihydroimidazo[4,5-f]isoindol-5(3H)-one

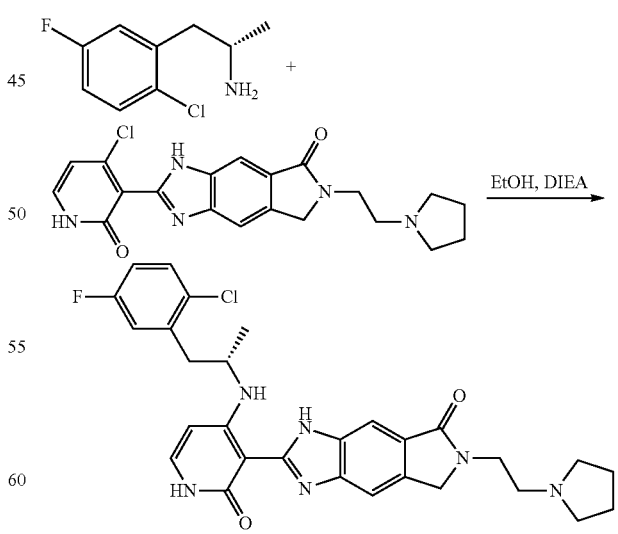

2-(4-((1S)-2-(2-Chloro-5-fluorophenyl)-1-methylethylamino)-2-oxo-1,2-dihydropyridin-3-yl)-6-(2-pyrrolidin-1-ylethyl)-6,7-dihydroimidazo[4,5-f]isoindol-5(3H)-one: A solution of 2-(4-chloro-2-oxo-1,2-dihydropyridin-3-yl)-6-

(2-pyrrolidin-1-ylethyl)-6,7-dihydroimidazo[4,5-f]isoindol-5(3H)-one (50 mg, 0.126 mmol), (1S)-2-(2-chloro-5-fluorophenyl)-1-methylethylamine (30 mg, 0.164 mmol) and DIEA (66 uL, 0.38 mmol) in 2 mL of EtOH was heated at 80° C. for 24 h. Then the solvent was evaporated and the residue was purified by column (silica gel, DCM:MeOH 9:1) to give 2-(4-((1S)-2-(2-chloro-5-fluorophenyl)-1-methylethylamino)-2-oxo-1,2-dihydropyridin-3-yl)-6-(2-pyrrolidin-1-ylethyl)-6,7-dihydroimidazo[4,5-f]isoindol-5(3H)-one (25 mg, 36%) as pale yellow oil. ESI-MS: m/z (MH$^+$) 549.5. $^1$H NMR (300 MHz, CD$_3$OD): δ 8.0 (d, J=60.6 Hz, 1H), 7.67 (d, J=52.5 Hz, 1H), 7.33 (m, 1H), 7.15 (m, 2H), 6.89 (m, 1H), 6.09 (m, 1H), 4.66 (m, 2H), 3.98 (m, 2H), 3.68 (m, 1H), 3.30 (m, 2H), 3.15 (m, 6H), 2.02 (m, 4H), 1.43 (d, J=6.60 Hz, 3H).

2-(4-((1S)-2-(2-Bromo-5-fluorophenyl)-1-methylethylamino)-2-oxo-1,2-dihydropyridin-3-yl)-6-(2-pyrrolidin-1-ylethyl)-6,7-dihydroimidazo[4,5-f]isoindol-5(3H)-one

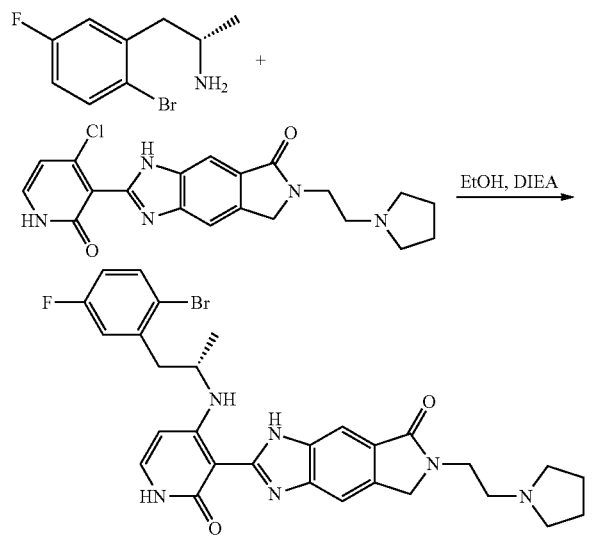

2-(4-((1S)-2-(2-Bromo-5-fluorophenyl)-1-methylethylamino)-2-oxo-1,2-dihydropyridin-3-yl)-6-(2-pyrrolidin-1-ylethyl)-6,7-dihydroimidazo[4,5-f]isoindol-5(3H)-one: A solution of 2-(4-chloro-2-oxo-1,2-dihydropyridin-3-yl)-6-(2-pyrrolidin-1-ylethyl)-6,7-dihydroimidazo[4,5-f]isoindol-5(3H)-one (50 mg, 0.126 mmol), (1S)-2-(2-bromo-5-fluorophenyl)-1-methylethylamine (48 mg, 0.164 mmol) and DIEA (66 uL, 0.38 mmol) in 2 mL of EtOH was heated at 80° C. for 24 h. Then the solvent was evaporated and the residue was purified by column (silica gel, DCM:MeOH 9:1) to give 2-(4-((1S)-2-(2-bromo-5-fluorophenyl)-1-methylethylamino)-2-oxo-1,2-dihydropyridin-3-yl)-6-(2-pyrrolidin-1-ylethyl)-6,7-dihydroimidazo[4,5-f]isoindol-5(3H)-one (17 mg, 23%) as yellow solid. ESI-MS: m/z (MH$^+$) 593.0. $^1$H NMR (300 MHz, CDCl$_3$): δ 8.04 (d, J=58.6 Hz, 1H), 7.53 (d, J=80.9 Hz, 1H), 7.47 (m, 1H), 7.15 (m, 2H), 6.80 (m, 1H), 6.00 (m, 1H), 4.56 (m, 2H), 4.13 (m, 1H), 3.82 (m, 2H), 3.10 (m, 2H), 2.83 (m, 2H), 2.65 (m, 4H), 1.80 (m, 4H), 1.43 (d, J=6.60 Hz, 3H).

2-(4-((1S)-2-(5-Cloro-2-methylphenyl)-1-methylethylamino)-2-oxo-1,2-dihydropyridin-3-yl)-6-(2-pyrrolidin-1-ylethyl)-6,7-dihydroimidazo[4,5-f]isoindol-5(3H)-one

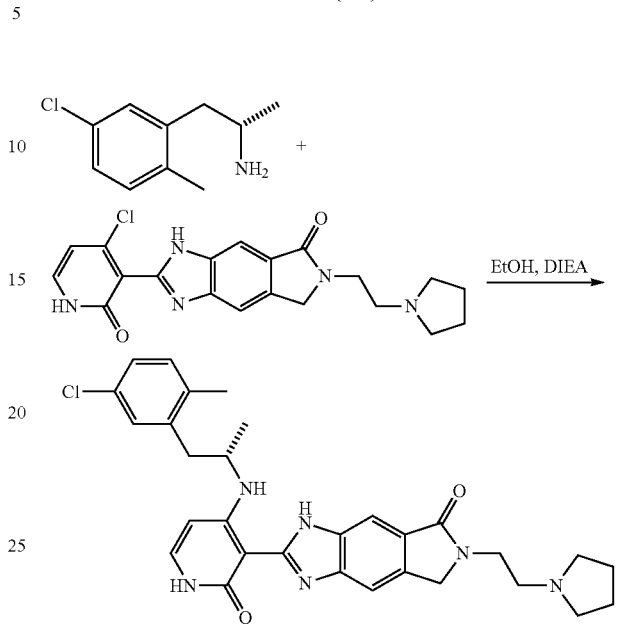

2-(4-((1S)-2-(5-Cloro-2-methylphenyl)-1-methylethylamino)-2-oxo-1,2-dihydropyridin-3-yl)-6-(2-pyrrolidin-1-ylethyl)-6,7-dihydroimidazo[4,5-f]isoindol-5(3H)-one: A solution of 2-(4-chloro-2-oxo-1,2-dihydropyridin-3-yl)-6-(2-pyrrolidin-1-ylethyl)-6,7-dihydroimidazo[4,5-f]isoindol-5(3H)-one (50 mg, 0.126 mmol), (1S)-2-(5-chloro-2-methylphenyl)-1-methylethylamine (30 mg, 0.164 mmol) and DIEA (66 uL, 0.38 mmol) in 2 mL of EtOH was heated at 80° C. for 24 h. Then the solvent was evaporated and the residue was purified by column (silica gel, DCM:MeOH 95:5) to give 2-(4-((1S)-2-(5-cloro-2-methylphenyl)-1-methylethylamino)-2-oxo-1,2-dihydropyridin-3-yl)-6-(2-pyrrolidin-1-ylethyl)-6,7-dihydroimidazo[4,5-f]isoindol-5(3H)-one (41 mg, 59%) as yellow solid. ESI-MS: m/z (MH$^+$) 545.5. $^1$H NMR (300 MHz, CDCl$_3$): δ 7.96 (d, J=44.8 Hz, 1H), 7.51 (d, J=66.3 Hz, 1H), 7.20 (m, 2H), 7.03 (m, 2H), 5.86 (m, 1H), 4.59 (m, 2H), 3.93 (m, 3H), 2.96-3.13 (m, 8H), 2.32 (s, 3H), 1.91 (m, 4H), 1.38 (d, J=7.35 Hz, 3H).

(2R)-1-(5-Chloro-2-methylphenyl)propan-2-ol

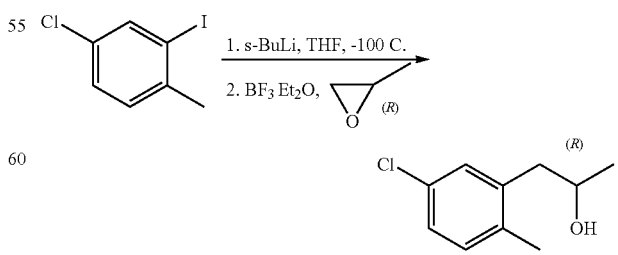

(2R)-1-(5-Chloro-2-methylphenyl)propan-2-ol: A solution of 4-chloro-2-iodo-1-methylbenzene (5.05 g, 20 mmol)

in 100 mL of anhydrous THF was cooled to −100° C. (liquid nitrogen/EtOH) under nitrogen. Then 1.4M solution of sec-BuLi in cyclohexane (15 mL, 21 mmol) was added dropwise at −100° C. to −90° C. The mixture was stirred at −100° C. to −90° C. for 10 min, then a solution of R-(+)-propylene oxide (1.51 g, 1.8 mL, 26 mmol) in 15 mL of THF was added dropwise at −100° C. to −90° C., then the mixture was cooled to −105° C. and a 46.5% solution of BF$_3$ in diethyl ether (4.18 mL, 30 mmol) was added dropwise. The mixture was stirred at −100° C. to −90° C. for 2 h, then the reaction was quenched with 20 mL of sat. aq. NH$_4$Cl at −90° C. The mixture was stirred and warmed to 0° C. overnight. Then 20 mL of water was added and mixture was extracted with EtOAc (2×60 mL), the extract was dried over Na$_2$SO$_4$ and evaporated to give crude oil, which was purified by column (silica gel, EtOAc/hexane 1:9, Rf=0.43 in EtOAc/hexane 3:7) to give (2R)-1-(5-chloro-2-methylphenyl)propan-2-ol (1.39 g, 38%) as pale yellow oil. $^1$H NMR (300 MHz, CDCl$_3$): δ 7.16 (s, 1H), 7.10 (m, 2H), 4.03 (m, 1H), 2.73 (m, 2H), 2.29 (s, 3H), 1.86 (s, 1H), 1.27 (d, J=6.24 Hz, 3H).

(2R)-1-(3,4-Difluoro-2-methylphenyl)propan-2-ol

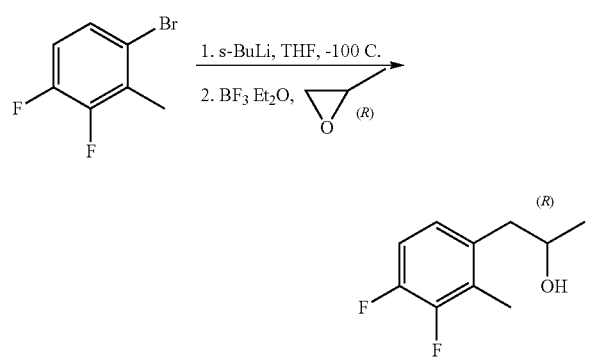

(2R)-1-(3,4-Difluoro-2-methylphenyl)propan-2-ol: A solution of 1-bromo-3,4-difluoro-2-methylbenzene (4.14 g, 20 mmol) in 100 mL of anhydrous THF was cooled to −100° C. (liquid nitrogen/EtOH) under nitrogen. Then 1.4M solution of sec-BuLi in cyclohexane (15 mL, 21 mmol) was added dropwise at −100° C. to −90° C. The mixture was stirred at −100° C. to −90° C. for 10 min, then a solution of R-(+)-propylene oxide (1.51 g, 1.8 mL, 26 mmol) in 15 mL of THF was added dropwise at −100° C. to −90° C., then the mixture was cooled to −105° C. and a 46.5% solution of BF$_3$ in diethyl ether (4.18 mL, 30 mmol) was added dropwise. The mixture was stirred at −100° C. to −90° C. for 2 h, then the reaction was quenched with 20 mL of sat. aq. NH$_4$Cl at −90° C. The mixture was stirred and warmed to 0° C. overnight. Then 20 mL of water was added and mixture was extracted with EtOAc (2×60 mL), the extract was dried over Na$_2$SO$_4$ and evaporated to give crude oil, which was purified by column (silica gel, EtOAc/hexane 1:9, Rf=0.37 in EtOAc/hexane 3:7) to give (2R)-1-(3,4-difluoro-2-methylphenyl)propan-2-ol (2.64 g, 71%) as pale oil. $^1$H NMR (300 MHz, CDCl$_3$): δ 6.85-7.26 (m, 2H), 3.98 (m, 1H), 2.73 (m, 2H), 2.25 (m, 3H), 1.45 (d, J=3.75 Hz, 1H), 1.26 (d, J=6.21 Hz, 3H).

(2R)-1-(3,5-Difluoro-2-methylphenyl)propan-2-ol

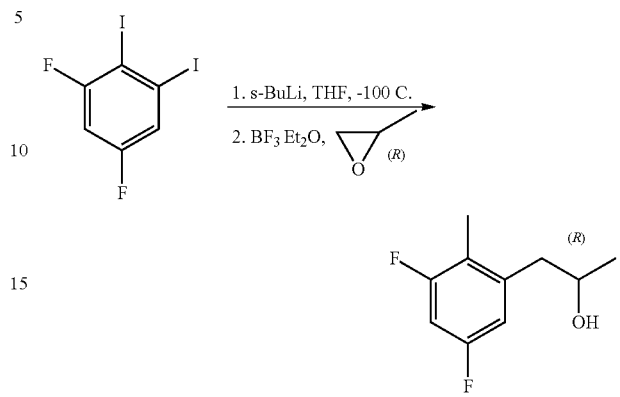

(2R)-1-(3,5-Difluoro-2-methylphenyl)propan-2-ol: A solution of 1,5-difluoro-3-iodo-2-methylbenzene (5.08 g, 20 mmol) in 100 mL of anhydrous THF was cooled to −100° C. (liquid nitrogen/EtOH) under nitrogen. Then 1.4M solution of sec-BuLi in cyclohexane (15 mL, 21 mmol) was added dropwise at −100° C. to −90° C. The mixture was stirred at −100° C. to −90° C. for 10 min, then a solution of R-(+)-propylene oxide (1.51 g, 1.8 mL, 26 mmol) in 15 mL of THF was added dropwise at −100° C. to −90° C., then the mixture was cooled to −105° C. and a 46.5% solution of BF$_3$ in diethyl ether (4.18 mL, 30 mmol) was added dropwise. The mixture was stirred at −100° C. to −90° C. for 2 h, then the reaction was quenched with 20 mL of sat. aq. NH$_4$Cl at −90° C. The mixture was stirred and warmed to 0° C. overnight. Then 20 mL of water was added and mixture was extracted with EtOAc (2×60 mL), the extract was dried over Na$_2$SO$_4$ and evaporated to give crude oil, which was purified by column (silica gel, EtOAc/hexane 1:9, Rf=0.45 in EtOAc/hexane 3:7) to give (2R)-1-(3,5-difluoro-2-methylphenyl)propan-2-ol (1.20 g, 32%) as pale yellow oil. $^1$H NMR (300 MHz, CDCl$_3$): δ 7.02 (t, J=8.47 Hz, 1H), 6.75 (t, J=9.6 Hz, 1H), 4.04 (m, 1H), 2.69-2.76 (m, 2H), 2.22 (s, 3H), 1.46 (d, J=4.35 Hz, 1H), 1.24 (d, J=6.21 Hz, 3H).

(2R)-1-(2,3,5,6-Tetrafluorophenyl)propan-2-ol

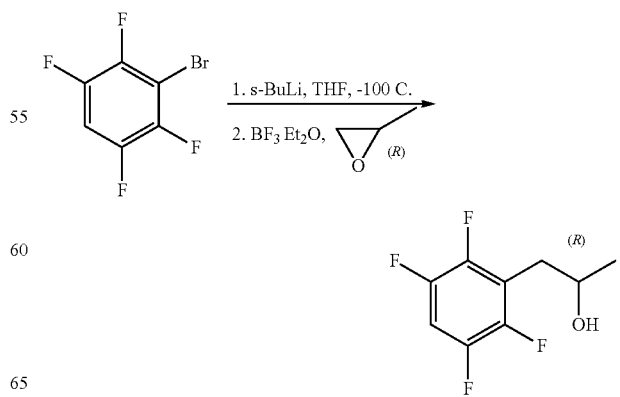

(2R)-1-(2,3,5,6-Tetrafluorophenyl)propan-2-ol: A solution of 1-bromo-2,3,5,6-tetrafluorobenzene (4.58 g, 20 mmol) in 100 mL of anhydrous THF was cooled to −100° C. (liquid nitrogen/EtOH) under nitrogen. Then 1.4M solution of sec-BuLi in cyclohexane (15 mL, 21 mmol) was added dropwise at −100° C. to −90° C. The mixture was stirred at −100° C. to −90° C. for 10 min, then a solution of R-(+)-propylene oxide (1.51 g, 1.8 mL, 26 mmol) in 15 mL of THF was added dropwise at −100° C. to −90° C., then the mixture was cooled to −105° C. and a 46.5% solution of BF$_3$ in diethyl ether (4.18 mL, 30 mmol) was added dropwise. The mixture was stirred at −100° C. to −90° C. for 2 h, then the reaction was quenched with 20 mL of sat. aq. NH$_4$Cl at −90° C. The mixture was stirred and warmed to 0° C. overnight. Then 20 mL of water was added and mixture was extracted with EtOAc (2×60 mL), the extract was dried over Na$_2$SO$_4$ and evaporated to give crude oil, which was purified by column (silica gel, EtOAc/hexane 1:9, Rf=0.57 in EtOAc/hexane 3:7) to give (2R)-1-(2,3,5,6-tetrafluorophenyl)propan-2-ol (2.57 g, 62%) as a white solid. $^1$H NMR (300 MHz, CDCl$_3$): δ 6.96 (m, 1H), 4.11 (m, 1H), 2.89 (m, 2H), 1.47 (d, J=5.46 Hz, 1H), 1.29 (d, J=6.21 Hz, 3H).

(1S)-2-(5-Chloro-2-methylphenyl)-1-methylethyl azide

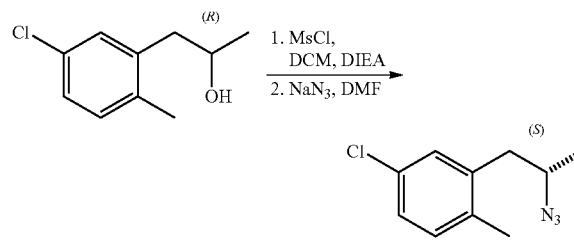

(1S)-2-(5-Chloro-2-methylphenyl)-1-methylethyl azide: A solution of (2R)-1-(5-chloro-2-methylphenyl)propan-2-ol (840 mg, 4.55 mmol) and DIEA (1.58 mL, 9.1 mmol) in 20 mL of anhydrous DCM was cooled to −10° C. Then MsCl (625 mg, 5.46 mmol) was carefully added and the mixture was warmed to RT and stirred for 30 min. Then 10 mL of sat. NaHCO$_3$ was added and the mixture was extracted with DCM (2×20 mL). The extract was dried over Na$_2$SO$_4$ and evaporated to give crude oil of mesylate. This oil was dissolved in 4 mL of anh. DMF. Then NaN$_3$ (592 mg, 9.1 mmol) was added and the mixture was heated at 80° C. for 2 h. Then 30 mL of water added and extracted with 20 mL of EtOAc/hexane 1:1 mixture. The extract was dried over Na$_2$SO$_4$ and evaporated to give crude oil, which was passed through silica gel plug eluting with 5% DCM in hexane, then evaporated to give (1S)-2-(5-chloro-2-methylphenyl)-1-methylethyl azide (745 mg, 78%) as pale oil. $^1$H NMR (300 MHz, CDCl$_3$): δ 7.13 (m, 3H), 3.67 (m, 1H), 2.64-2.85 (m, 2H), 2.29 (s, 3H), 1.29 (d, J=6.6 Hz, 3H).

(1S)-2-(5-Chloro-2-methylphenyl)-1-methylethylamine

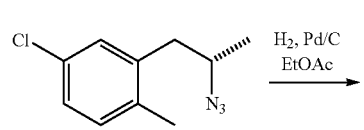

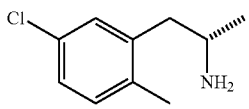

(1S)-2-(5-Chloro-2-methylphenyl)-1-methylethylamine: To a solution of (1S)-2-(5-chloro-2-methylphenyl)-1-methylethyl azide (500 mg, 2.38 mmol) in 50 mL of EtOAc was added Pd/C (150 mg of 10% Pd) and the mixture was hydrogenated under hydrogen balloon for 20 min. The catalyst was removed by filtration through celite, then passed through silica gel plug eluting first with EtOAc (40 mL), then MeOH/EtOAc/NH$_4$OH 20:75:5 (120 mL). The fraction with product was evaporated to give (1S)-2-(5-chloro-2-methylphenyl)-1-methylethylamine (210 mg, 48%) as pale oil. ESI-MS: m/z (MH$^+$) 184.4. $^1$H NMR (300 MHz, CDCl$_3$): δ 7.12 (s, 1H), 7.08 (s, 2H), 3.16 (m, 1H), 2.48-2.70 (m, 2H), 2.28 (s, 3H), 1.23 (s, 2H), 1.13 (d, J=6.21 Hz, 3H).

(1S)-2-(3,4-Difluoro-2-methylphenyl)-1-methylethyl azide

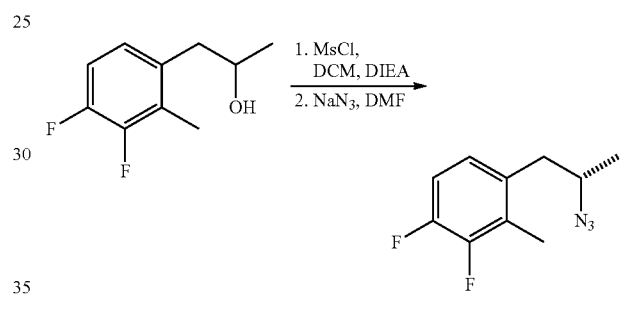

(1S)-2-(3,4-Difluoro-2-methylphenyl)-1-methylethyl azide: A solution of (2R)-1-(3,4-difluoro-2-methylphenyl)propan-2-ol (847 mg, 4.55 mmol) and DIEA (1.58 mL, 9.1 mmol) in 20 mL of anhydrous DCM was cooled to −10° C. Then MsCl (625 mg, 5.46 mmol) was carefully added and the mixture was warmed to RT and stirred for 30 min. Then 10 mL of sat. NaHCO$_3$ was added and the mixture was extracted with DCM (2×20 mL). The extract was dried over Na$_2$SO$_4$ and evaporated to give crude oil of mesylate. This oil was dissolved in 4 mL of anh. DMF. Then NaN$_3$ (592 mg, 9.1 mmol) was added and the mixture was heated at 80° C. for 2 h. Then 30 mL of water added and extracted with 20 mL of EtOAc/hexane 1:1 mixture. The extract was dried over Na$_2$SO$_4$ and evaporated to give crude oil, which was passed through silica gel plug eluting with 5% DCM in hexane, then evaporated to give (1S)-2-(3,4-difluoro-2-methylphenyl)-1-methylethyl azide (771 mg, 80%) as pale oil. $^1$H NMR (300 MHz, CDCl$_3$): δ 6.86 (m, 2H), 3.62 (m, 1H), 2.79 (m, 2H), 2.26 (s, 3H), 1.28 (d, J=6.6 Hz, 3H).

(1S)-2-(3,4-Difluoro-2-methylphenyl)-1-methylethylamine

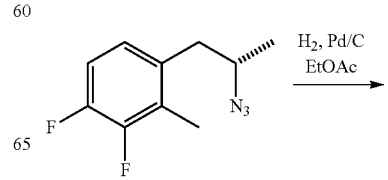

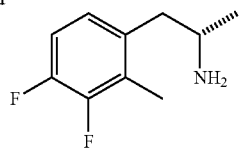

(1S)-2-(3,4-Difluoro-2-methylphenyl)-1-methylethylamine: To a solution of (1S)-2-(3,4-difluoro-2-methylphenyl)-1-methylethyl azide (503 mg, 2.38 mmol) in 50 mL of EtOAc was added Pd/C (150 mg of 10% Pd) and the mixture was hydrogenated under hydrogen balloon for 1 h. The catalyst was removed by filtration through celite, then passed through silica gel plug eluting first with EtOAc (40 mL), then MeOH/EtOAc/NH$_4$OH 20:75:5 (120 mL). The fraction with product was evaporated to give (1S)-2-(3,4-difluoro-2-methylphenyl)-1-methylethylamine (376 mg, 85%) as pale oil. ESI-MS: m/z (MH$^+$) 186.4. $^1$H NMR (300 MHz, CDCl$_3$): δ 6.82-6.97 (m, 2H), 3.12 (m, 1H), 2.48-2.73 (m, 2H), 2.25 (s, 3H), 1.34 (s, 2H), 1.12 (d, J=6.39 Hz, 3H).

(2R)-1-(2,5-Dimethoxyphenyl)propan-2-ol

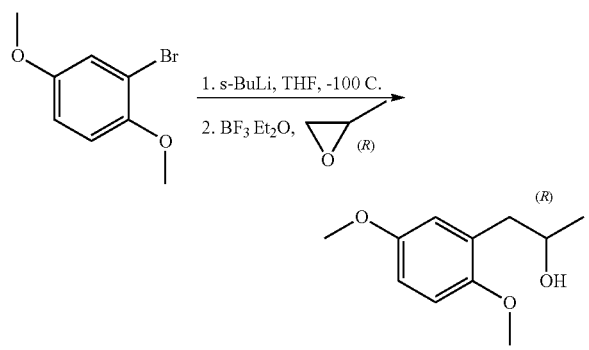

(2R)-1-(2,5-Dimethoxyphenyl)propan-2-ol: A solution of 2-bromo-1,4-dimethoxybenzene (4.35 g, 20 mmol) in 100 mL of anhydrous THF was cooled to −100° C. (liquid nitrogen/EtOH) under nitrogen. Then 1.4M solution of sec-BuLi in cyclohexane (15 mL, 21 mmol) was added dropwise at −100° C. to −90° C. The mixture was stirred at −100° C. to −90° C. for 10 min, then a solution of R-(+)-propylene oxide (1.51 g, 1.8 mL, 26 mmol) in 15 mL of THF was added dropwise at −100° C. to −90° C., then the mixture was cooled to −105° C. and a 46.5% solution of BF$_3$ in diethyl ether (4.18 mL, 30 mmol) was added dropwise. The mixture was stirred at −100° C. to −90° C. for 2 h, then the reaction was quenched with 20 mL of sat. aq. NH$_4$Cl at −90° C. The mixture was stirred and warmed to 0° C. overnight. Then 20 mL of water was added and mixture was extracted with EtOAc (2×60 mL), the extract was dried over Na$_2$SO$_4$ and evaporated to give crude oil, which was purified by column (silica gel, EtOAc/hexane 1:9, Rf=0.45 in EtOAc/hexane 3:7) to give (2R)-1-(2,5-dimethoxyphenyl)propan-2-ol (2.78 g, 71%) as colorless oil. $^1$H NMR (300 MHz, CDCl$_3$): δ 6.79 (m, 1H), 6.74 (m, 2H), 4.05 (m, 1H), 3.79 (s, 3H), 3.77 (s, 3H), 2.65-2.86 (m, 2H), 2.10 (d, J=3.39 Hz, 1H), 1.22 (d, J=6.21 Hz, 3H).

(2R)-1-(5-Methoxy-2-methylphenyl)propan-2-ol

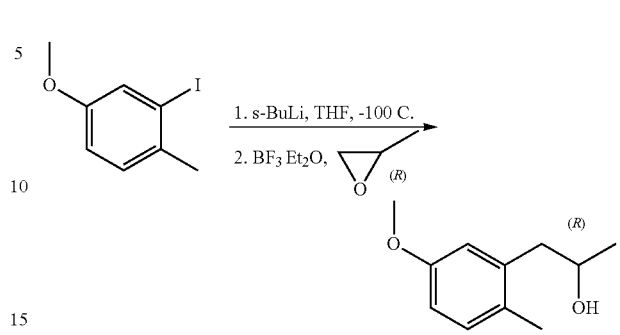

(2R)-1-(5-Methoxy-2-methylphenyl)propan-2-ol: A solution of 2-iodo-4-methoxy-1-methylbenzene (3.70 g, 14.9 mmol) in 100 mL of anhydrous THF was cooled to −100° C. (liquid nitrogen/EtOH) under nitrogen. Then 1.4M solution of sec-BuLi in cyclohexane (11.3 mL, 15.8 mmol) was added dropwise at −100° C. to −90° C. The mixture was stirred at −100° C. to −90° C. for 10 min, then a solution of R-(+)-propylene oxide (1.35 mL, 19.4 mmol) in 15 mL of THF was added dropwise at −100° C. to −90° C., then the mixture was cooled to −105° C. and a 46.5% solution of BF$_3$ in diethyl ether (3.14 mL, 22.5 mmol) was added dropwise. The mixture was stirred at −100° C. to −90° C. for 2 h, then the reaction was quenched with 20 mL of sat. aq. NH$_4$Cl at −90° C. The mixture was stirred and warmed to 0° C. overnight. Then 20 mL of water was added and mixture was extracted with EtOAc (2×60 mL), the extract was dried over Na$_2$SO$_4$ and evaporated to give crude oil, which was purified by column (silica gel, EtOAc/hexane 1:9, Rf=0.50 in EtOAc/hexane 3:7) to give (2R)-1-(5-methoxy-2-methylphenyl)propan-2-ol (0.49 g, 18%) as pale oil. $^1$H NMR (300 MHz, CDCl$_3$): δ 7.08 (d, J=8.31 Hz, 1H), 6.73 (m, 2H), 4.02 (m, 1H), 3.78 (s, 3H), 2.64-2.80 (m, 2H), 2.26 (s, 3H), 1.54 (d, J=3.39 Hz, 1H), 1.27 (d, J=6.03 Hz, 3H).

(2R)-1-(2,3-Difluoro-5,6-dimethoxyphenyl)propan-2-ol

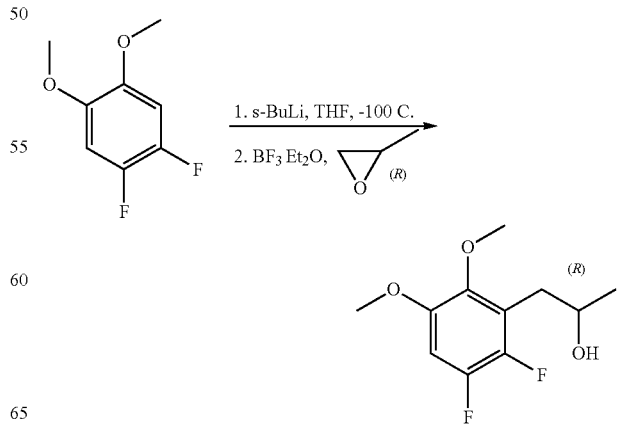

(2R)-1-(2,3-Difluoro-5,6-dimethoxyphenyl)propan-2-ol: A solution of 1,2-difluoro-4,5-dimethoxybenzene (3.48 g, 20 mmol) in 10 mL of anhydrous THF was slowly added to a cooled at −78° C. solution of sec-BuLi in THF/cyclohexane (1.4M in cyclohexane, 15 mL, 21 mmol mixed with 80 mL of THF). The mixture was stirred at −70° C. for 10 min, then a solution of R-(+)-propylene oxide (1.51 g, 1.8 mL, 26 mmol) in 15 mL of THF was added dropwise at −100° C. to −90° C., then the mixture was cooled to −105° C. and a 46.5% solution of BF₃ in diethyl ether (4.18 mL, 30 mmol) was added dropwise. The mixture was stirred at −100° C. to −90° C. for 2 h, then the reaction was quenched with 20 mL of sat. aq. NH₄Cl at −90° C. The mixture was stirred and warmed to 0° C. overnight. Then 20 mL of water was added and mixture was extracted with EtOAc (2×60 mL), the extract was dried over Na₂SO₄ and evaporated to give crude oil, which was purified by column (silica gel, EtOAc/hexane 1:9, Rf=0.29 in EtOAc/hexane 3:7) to give (2R)-1-(2,3-difluoro-5,6-dimethoxyphenyl)propan-2-ol (883 mg, 19%) as pale oil. $^1$H NMR (300 MHz, CDCl₃): δ 6.65 (m, 1H), 4.06 (m, 1H), 3.83 (s, 3H), 3.82 (s, 3H), 2.87 (m, 2H), 2.05 (d, J=4.71 Hz, 1H), 1.25 (d, J=6.24 Hz, 3H).

(2R)-1-(2-Ethylphenyl)propan-2-ol

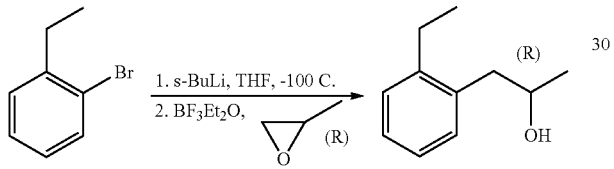

(2R)-1-(2-Ethylphenyl)propan-2-ol: A solution of 1-bromo-2-ethylbenzene (3.70 g, 20 mmol) in 100 mL of anhydrous THF was cooled to −78° C. (liquid nitrogen/EtOH) under nitrogen. Then 1.4M solution of sec-BuLi in cyclohexane (15 mL, 21 mmol) was added dropwise at −78° C. The mixture was stirred for 10 min, then a solution of R-(+)-propylene oxide (1.51 g, 1.8 mL, 26 mmol) in 15 mL of THF was added dropwise at −100° C. to −90° C., then the mixture was cooled to −105° C. and a 46.5% solution of BF₃ in diethyl ether (4.18 mL, 30 mmol) was added dropwise. The mixture was stirred at −100° C. to −90° C. for 2 h, then the reaction was quenched with 20 mL of sat. aq. NH₄Cl at −90° C. The mixture was stirred and warmed to 0° C. overnight. Then 20 mL of water was added and mixture was extracted with EtOAc (2×60 mL), the extract was dried over Na₂SO₄ and evaporated to give crude oil, which was purified by column (silica gel, EtOAc/hexane 1:9, Rf=0.55 in EtOAc/hexane 3:7) to give (2R)-1-(2-ethylphenyl)propan-2-ol (877 mg, 26%) as pale yellow oil. $^1$H NMR (300 MHz, CDCl₃): δ 7.19 (m, 4H), 4.02 (m, 1H), 2.80 (m, 2H), 2.68 (q, J=7.53 Hz, 2H), 1.51 (s, 1H), 1.28 (d, J=6.21 Hz, 3H), 1.22 (t, J=7.53 Hz, 3H).

(S)-2-(5-Methoxy-2-methyl-phenyl)-1-methyl-ethylamine

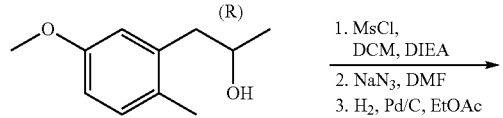

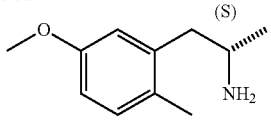

(S)-2-(5-Methoxy-2-methyl-phenyl)-1-methyl-ethylamine: A solution of (R)-1-(5-methoxy-2-methyl-phenyl)-propan-2-ol (487 mg, 2.7 mmol) and DIEA (0.94 mL, 5.4 mmol) in 20 mL of anhydrous DCM was cooled to −10° C. Then MsCl (371 mg, 3.24 mmol) was carefully added and the mixture was warmed to RT and stirred for 30 min. Then 10 mL of sat. NaHCO₃ was added and the mixture was extracted with DCM (2×20 mL). The extract was dried over Na₂SO₄ and evaporated to give crude oil of mesylate. This oil was dissolved in 3 mL of anh. DMF. Then NaN₃ (351 mg, 5.4 mmol) was added and the mixture was heated at 80° C. for 2 h. Then 30 mL of water added and extracted with 20 mL of EtOAc/hexane 1:1 mixture. The extract was dried over Na₂SO₄ and evaporated to give crude oil of azide, which was dissolved in 50 mL of EtOAc, then Pd/C (150 mg of 10% Pd) was added and the mixture was hydrogenated under hydrogen balloon for 1 h. The catalyst was removed by filtration through celite, the mixture was evaporated and the crude residue was used directly in the next step.

(S)-2-(2,3-Difluoro-5,6-dimethoxy-phenyl)-1-methyl-ethylamine

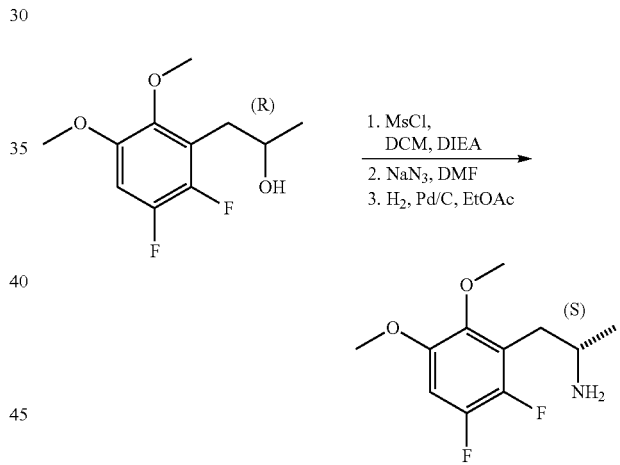

(S)-2-(2,3-Difluoro-5,6-dimethoxy-phenyl)-1-methyl-ethylamine: A solution of (R)-1-(2,3-difluoro-5,6-dimethoxy-phenyl)-propan-2-ol (672 mg, 2.7 mmol) and DIEA (0.94 mL, 5.4 mmol) in 20 mL of anhydrous DCM was cooled to −10° C. Then MsCl (371 mg, 3.24 mmol) was carefully added and the mixture was warmed to RT and stirred for 30 min. Then 10 mL of sat. NaHCO₃ was added and the mixture was extracted with DCM (2×20 mL). The extract was dried over Na₂SO₄ and evaporated to give crude oil of mesylate. This oil was dissolved in 3 mL of anh. DMF. Then NaN₃ (351 mg, 5.4 mmol) was added and the mixture was heated at 80° C. for 2 h. Then 30 mL of water added and extracted with 20 mL of EtOAc/hexane 1:1 mixture. The extract was dried over Na₂SO₄ and evaporated to give crude oil of azide, which was dissolved in 50 mL of EtOAc, then Pd/C (150 mg of 10% Pd) was added and the mixture was hydrogenated under hydrogen balloon for 1 h. The catalyst was removed by filtration through celite, then purified by column (MeOH/EtOAc/NH₄OH 5:93:2) to give (S)-2-(2,3-difluoro-5,6- dimethoxy-phenyl)-1-methyl-ethylamine (300 mg, 48%) as pale oil. ESI-MS: m/z (MH⁺) 232.2. ¹H NMR (300 MHz, CDCl₃): δ 6.63 (m, 1H), 3.82 (s, 3H), 3.80 (s, 3H), 3.17 (m, 1H), 2.63-2.78 (m, 2H), 1.32 (br., 2H), 1.13 (d, J=6.21 Hz, 3H).

(S)-2-(2-Ethyl-phenyl)-1-methyl-ethylamine

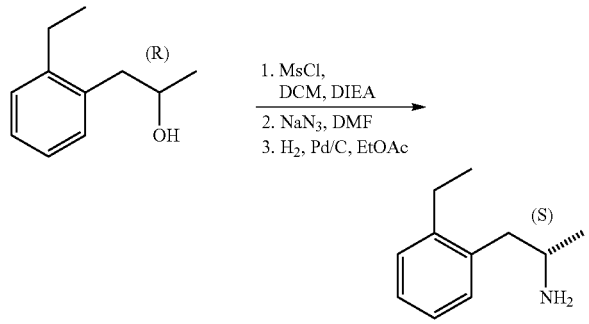

(S)-2-(2-Ethyl-phenyl)-1-methyl-ethylamine: A solution of (R)-1-(2-ethyl-phenyl)-propan-2-ol (443 mg, 2.7 mmol) and DIEA (0.94 mL, 5.4 mmol) in 20 mL of anhydrous DCM was cooled to −10° C. Then MSCl (371 mg, 3.24 mmol) was carefully added and the mixture was warmed to RT and stirred for 30 min. Then 10 mL of sat. NaHCO₃ was added and the mixture was extracted with DCM (2×20 mL). The extract was dried over Na₂SO₄ and evaporated to give crude oil of mesylate. This oil was dissolved in 3 mL of anh. DMF. Then NaN₃ (351 mg, 5.4 mmol) was added and the mixture was heated at 80° C. for 2 h. Then 30 mL of water added and extracted with 20 mL of EtOAc/hexane 1:1 mixture. The extract was dried over Na₂SO₄ and evaporated to give crude oil of azide, which was dissolved in 50 mL of EtOAc, then Pd/C (150 mg of 10% Pd) was added and the mixture was hydrogenated under hydrogen balloon for 1 h. The catalyst was removed by filtration through celite, then purified by column (MeOH/EtOAc/NH₄OH 5:93:2) to give (S)-2-(2-ethyl-phenyl)-1-methyl-ethylamine (328 mg, 74%) as pale oil. ESI-MS: m/z (MH⁺) 164.4. ¹H NMR (300 MHz, CDCl₃): δ 7.16 (m, 4H), 3.16 (m, 1H), 2.52-2.78 (m, 4H), 1.30 (br., 2H), 1.22 (t, J=7.53 Hz, 3H), 1.14 (d, J=6.21 Hz, 3H).

(S)-2-(3,5-Difluoro-2-methyl-phenyl)-1-methyl-ethylamine

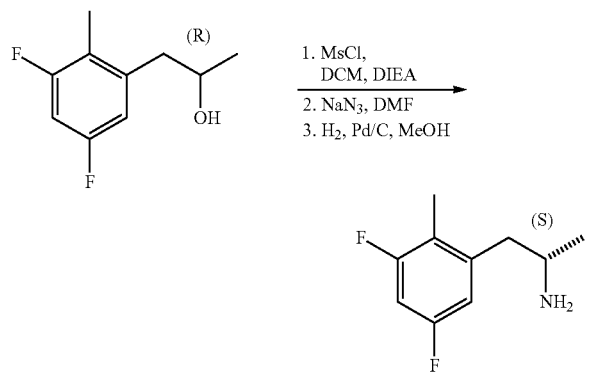

(S)-2-(3,5-Difluoro-2-methyl-phenyl)-1-methyl-ethylamine: A solution of (R)-1-(3,5-difluoro-2-methyl-phenyl)-propan-2-ol (500 mg, 2.7 mmol) and DIEA (0.94 mL, 5.4 mmol) in 20 mL of anhydrous DCM was cooled to −10° C. Then MsCl (371 mg, 3.24 mmol) was carefully added and the mixture was warmed to RT and stirred for 30 min. Then 10 mL of sat. NaHCO₃ was added and the mixture was extracted with DCM (2×20 mL). The extract was dried over Na₂SO₄ and evaporated to give crude oil of mesylate. This oil was dissolved in 3 mL of anh. DMF. Then NaN₃ (351 mg, 5.4 mmol) was added and the mixture was heated at 80° C. for 2 h. Then 30 mL of water added and extracted with 20 mL of EtOAc/hexane 1:1 mixture. The extract was dried over Na₂SO₄ and evaporated to give crude oil of azide, which was dissolved in 20 mL of MeOH, then Pd/C (150 mg of 10% Pd) was added and the mixture was hydrogenated under hydrogen balloon for 16 h. The catalyst was removed by filtration through celite, then purified by column (MeOH/EtOAc/NH₄OH 5:93:2) to give (S)-2-(3,5-difluoro-2-methyl-phenyl)-1-methyl-ethylamine (197 mg, 39%) as pale oil. ESI-MS: m/z (MH⁺) 186.3. ¹H NMR (300 MHz, CDCl₃): δ 6.98 (t, J=8.37 Hz, 1H), 6.73 (t, J=9.69 Hz, 1H), 3.14 (m, 1H), 2.46-2.69 (m, 2H), 2.23 (s, 3H), 1.25 (br., 2H), 1.10 (d, J=6.42 Hz, 3H).

(S)-1-Methyl-2-(2,3,5,6-tetrafluoro-phenyl)-ethylamine

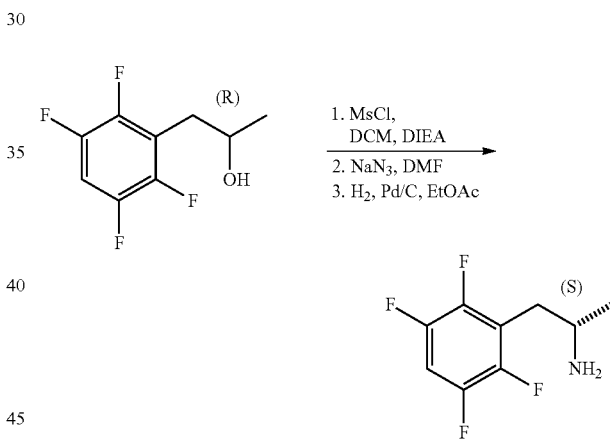

(S)-1-Methyl-2-(2,3,5,6-tetrafluoro-phenyl)-ethylamine: A solution of (R)-1-(2,3,5,6-tetrafluoro-phenyl)-propan-2-ol (1.12 g, 5.4 mmol) and DIEA (1.88 mL, 10.8 mmol) in 20 mL of anhydrous DCM was cooled to −10° C. Then MSCl (742 mg, 6.48 mmol) was carefully added and the mixture was warmed to RT and stirred for 30 min. Then 10 mL of sat. NaHCO₃ was added and the mixture was extracted with DCM (2×20 mL). The extract was dried over Na₂SO₄ and evaporated to give crude oil of mesylate. This oil was dissolved in 5 mL of anh. DMF. Then NaN₃ (702 mg, 10.8 mmol) was added and the mixture was heated at 80° C. for 2 h. Then 30 mL of water added and extracted with 20 mL of EtOAc/hexane 1:1 mixture. The extract was dried over Na₂SO₄ and evaporated to give crude oil of azide, which was dissolved in 50 mL of EtOAc, then Pd/C (150 mg of 10% Pd) was added and the mixture was hydrogenated under hydrogen balloon for 3 h. The catalyst was removed by filtration through celite, then purified by column (MeOH/EtOAc/NH₄OH 5:93:2) to give (S)-1-methyl-2-(2,3,5,6-tetrafluoro-phenyl)-ethylamine (268 mg, 24%) as a white solid. ESI-MS: m/z (MH⁺) 208.3.

¹H NMR (300 MHz, DMSO-d₆): δ 7.91 (br, 2H), 7.89 (m, 1H), 3.44 (m, 1H), 2.88-3.09 (m, 2H), 1.15 (d, J=6.60 Hz, 3H).

(S)-2-(2,5-Dimethoxy-phenyl)-1-methyl-ethylamine

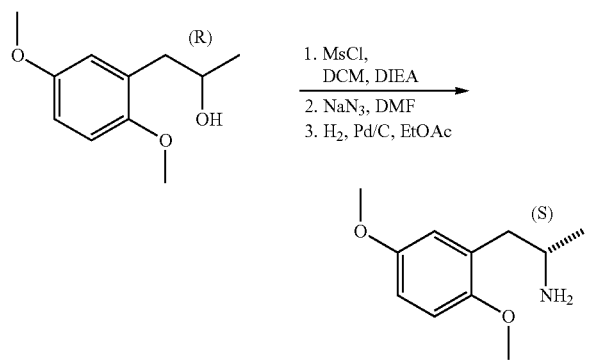

(S)-2-(2,5-Dimethoxy-phenyl)-1-methyl-ethylamine: A solution of (R)-1-(2,5-dimethoxy-phenyl)-propan-2-ol (1.2 g, 5.4 mmol) and DIEA (1.88 mL, 10.8 mmol) in 20 mL of anhydrous DCM was cooled to −10° C. Then MsCl (742 mg, 6.48 mmol) was carefully added and the mixture was warmed to RT and stirred for 30 min. Then 10 mL of sat. NaHCO₃ was added and the mixture was extracted with DCM (2×20 mL). The extract was dried over Na₂SO₄ and evaporated to give crude oil of mesylate. This oil was dissolved in 5 mL of anh. DMF. Then NaN₃ (702 mg, 10.8 mmol) was added and the mixture was heated at 80° C. for 2 h. Then 30 mL of water added and extracted with 20 mL of EtOAc/hexane 1:1 mixture. The extract was dried over Na₂SO₄ and evaporated to give crude oil of azide, which was dissolved in 50 mL of EtOAc, then Pd/C (150 mg of 10% Pd) was added and the mixture was hydrogenated under hydrogen balloon for 3 h. The catalyst was removed by filtration through celite, the mixture was evaporated and the crude residue was used directly in the next step.

Scheme 5
Preparation of chiral aryl and/or heteroaryl isopropylamines

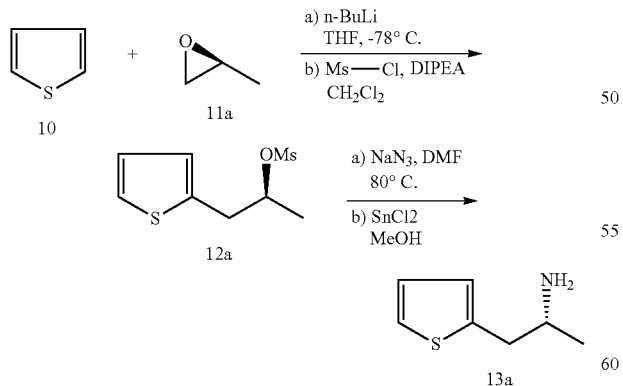

To a cooled (−78° C.) solution of thiophene (10a) (3.18 g, 37.87 mmol) in THF (20.0 mL) was slowly added n-BuLi (15.15 mL, 2.5 M solution in hexane). After 30 minutes, a solution of (S)-(−)-propylene oxide (11a) (2.0 g, 34.43 mmol) in THF (10 mL) was added followed by BF3.Et2O (4.9 g, 34.43 mmol). The resulting solution was slowly brought to room temperature and stirred for over night. The reaction was quenched with NH₄Cl solution (20 mL) and extracted with ether (3×50 mL). The organic extracts were dried and solvent was distilled off. The obtained crude product was dissolved in DCM (50 mL) and DIPEA (6.67 g, 51.6 mmol) and cooled to 0° C. A solution of methanesulfonyl chloride (10.0 g, 87.3 mmol) in DCM (4.93 g, 34.43 mmol) was added and resulting mixture was stirred at room temperature for over night. The reaction mixture was washed with water (3×30 mL), dried and concentrated to give crude compound that was purified on silica gel column using 20% EtOAc/hexane to afford (1S)-1-methyl-2-thien-2-ylethyl methanesulfonate (12a, 5.2 g, 68%) ¹H NMR (CDCl₃) δ 1.48 (d, 3H, J=6.0 Hz), 2.71 (s, 3H), 3.05-3.22 (m, 2H), 4.85-4.95 (m, 1H), 6.90-6.98 (m, 2H), 7.19 (d, 1H, J=3.0 Hz).

A mixture of (1S)-1-methyl-2-thien-2ylethyl methanesulfonate (12a) (2.5 g, 11.34 mmol) and sodium azide (3.6 g, 56.73 mmol) in DMF (25 mL) was stirred at 70° C. for over night. The reaction mixture was diluted with cold water (60 mL) and extracted with ethyl acetate (2×50 mL). The combined extract was washed with water (2×20 mL), dried and concentrated to get crude azide that was purified by silica gel column using 10% ethyl acetate/hexane to get pure azide (1.5 g, 78%). ¹H NMR (CDCl₃) δ 1.21 (d, 3H, J=3.0 Hz), 2.91 (m, 2H), 3.60-3.75 (m, 1H), 6.86 (d, 1H, J=3.0 Hz), 6.95 (t, 1H, J=3.0 Hz), 7.13 (d, 1H, J=3.0 Hz). To a 0° C. cooled solution of SnCl₂ (91.2 g, 5.97 mmol) was added a solution of azide (0.5 g, 2.9 mmol) in methanol (3 mL). After stirring at room temperature for 7 h, and solvent was removed under reduced pressure. To the residue were added DCM (20 mL) and saturated KOH solution (pH ~12). The aqueous layer was extracted with DCM (3×20 mL). The combined extracts were dried and concentrated at room temperature to get (1R)-1-methyl-2-thien-2-ylethylamine (13a, 320 mg, 76%). ¹H NMR (CDCl₃) δ 1.03 (d, 3H, J=6.0 Hz), 2.73 (ABq, 1H, J=6.0, 15.0 Hz), 2.91 (ABq, 1H, J=6.0, 15.0 Hz), 3.01-3.23 (m, 1H), 6.83 (d, 1H, J=3.0 Hz), 6.94 (t, 1H, J=3.0 Hz), 7.15 (d, 1H, J=3.0 Hz).

The following amines were synthesized using this procedure, unless otherwise noted.

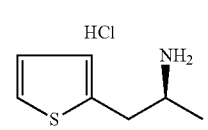

(1S)-1-methyl-2-thien-2-ylethylamine hydrochloride (13b) was prepared from (R)-(+)-propylene oxide and converted as hydrochloride salt. (19.8 g, 39%, 4 steps). ¹H NMR (CDCl₃) δ 1.17 (d, 3H, J=6.0 Hz), 2.93 (ABq, 1H, J=6.0, 15.0 Hz), 3.20 (ABq, 1H, J=6.0, 15.0 Hz), 3.34-3.42 (m, 1H), 6.97-7.02 (m, 2H), 7.43 (d, 1H, J=6.0 Hz), 8.19 (bs, 1H, 3H).

(1S)-2-(3-chlorothien-2-yl)-1-methylethylamine (13c)

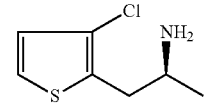

(1S)-2-(3-chlorothien-2-yl)-1-methylethylamine (13c):
Note: BuLi was added to a solution of 3-chlorothiophene at 0° C.

(750 mg, 50.6% four steps). $^1$H NMR (CDCl$_3$) δ 1.15 (d, 3H, J=9.0 Hz), 2.75 (ABq, 1H, J=6.0, 15.0 Hz), 2.87 (ABq, 1H, J=6.0, 15.0 Hz), 3.17-3.27 (m, 1H), 6.88 (d, 1H, J=3.0 Hz), 7.13 (d, 1H, J=3.0 Hz).

(1S)-2-(3-methoxythien-2-yl)-1-methylethylamine (13d)

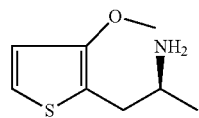

13d (1S)-2-(3-methoxythien-2-yl)-1-methylethylamine (13d).
Note: BuLi was added to a solution of 3-methoxythiophene at 0° C.

(400 mg, 53%) $^1$H NMR (CDCl$_3$) δ 1.16 (d, 3H, J=6.0 Hz), 2.60-2.82 (m, 2H), 3.10-3.25 (m, 1H), 3.82 (s, 3H), 6.82 (d, 1H, J=3.0 Hz), 7.03 (d, 1H, J=3.0 Hz).

(1S)-2-(3-methylthien-2-yl)-1-methylethylamine (13e)

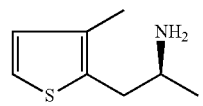

13e (1S)-2-(3-methylthien-2-yl)-1-methylethylamine (13e).
Note n-BuLi was added to the solution of 2-bromo-3-methylthiophene at 21-25° C.

(560 mg, 62%) $^1$H NMR (CDCl$_3$) δ 1.27 (d, 3H, J=6.0 Hz), 2.18 (s, 3H), 2.65-2.84 (m, 2H), 3.13-3.45 (m, 1H), 6.80 (d, 1H, J=3.0 Hz), 7.06 (d, 1H, J=3.0 Hz).

(1S)-2-(2-furyl)-1-methylethylamine (13f)

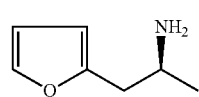

13f (1S)-2-(2-furyl)-1-methylethylamine (13f) was prepared from freshly distilled furan.

(500 mg, 27%). $^1$H NMR (CDCl$_3$) δ 1.14 (d, 3H, J=6.0 Hz), 2.53-2.78 (m, 2H), 3.14-3.30 (m, 1H), 6.07 (d, 1H, J=3.0 Hz), 7.30 (d, 1H, J=3.0 Hz).

(S)-1-methyl-2-o-tolyl-ethylamine

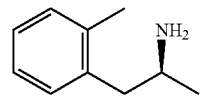

13g (S)-1-methyl-2-o-tolyl-ethylamine (13g) was prepared from 2-bromotoluene. (600 mg, 65%) $^1$H NMR (CDCl$_3$) δ 1.14 (d, 3H, J=6.0 Hz), 2.33 (s, 3H), 2.54-2.77 (m, 2H), 3.14-3.25 (m, 1H), 7.07-7.18 (m, 4H).

Scheme 6
Synthesis of (1S)-2-(2,6-dichloro-phenyl)-1-methyl-1-ethylamine (16a).

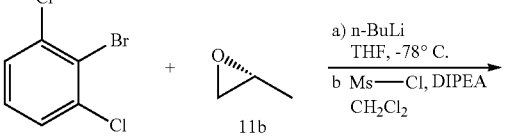

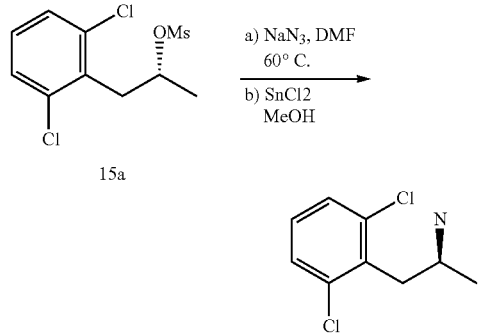

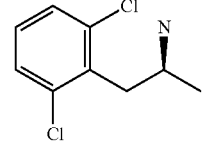

To a cooled (−78° C.) solution of 2,6-dichlorobromobenzene (14a) (970 mg, 4.3 mmol) in THF (10.0 mL) was slowly added n-BuLi (1.75 mL, 2.5 M solution in hexane). After 20 minutes, a solution of (R)-(+)-propylene oxide (11b) (250 mg, 4.3 mmol) was added. The resulting solution was slowly brought to room temperature and stirred for 7 h. The reaction was cooled to 0° C. and methanesulfonyl chloride (0.5 g, 4.3 mmol) was slowly added and stirred at room temperature for over night. The reaction mixture was diluted with water (15 mL) and extracted with ethyl acetate (3×10 mL). The extracts were dried and concentrated to get crude product (15a) that was stirred with sodium azide (1.4 g, 21.5 mmol) in DMF (15 mL) at 70° C. for 3 h. The reaction mixture was diluted with cold water (30 mL) and extracted with ethyl acetate (2×25 mL). The combined extract was washed with water (2×20 mL), dried and concentrated to get crude azide that was purified by silica gel column using 10% ethyl acetate/hexane to get pure azide. To a 0° C. cooled solution of SnCl$_2$ (1.5 g, 7.9 mmol) was added a solution of crude azide in methanol (3 mL). After stirring at room temperature for 7 h, and solvent was removed under reduced pressure. To the residue were added DCM (20 mL) and saturated KOH solution (pH ~12).

The aqueous layer was extracted with DCM (3×20 mL). The combined extracts were dried and concentrated at room temperature to get crude (1S)-2-(2,6-dichloro-phenyl)-1-methyl-1-ethylamine (16a) (500 mg) ESI-MS m/z 204.6 (M$^+$+1). The obtained amine was used for next reaction without further purification.

The following amines were synthesized using the same procedure unless otherwise noted.

(1S)-2-(2,5-dichloro-phenyl)-1-methyl-1-ethylamine

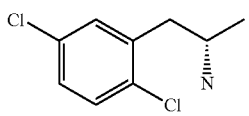

16b (1S)-2-(2,5-dichloro-phenyl)-1-methyl-1-ethylamine (16b) (600 mg) ESI-MS m/z 204.6 (M$^+$+1).

(1S)-2-(2,3-dichloro-phenyl)-1-methyl-1-ethylamine

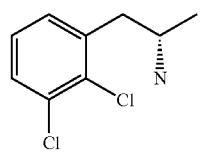

16c (1S)-2-(2,3-dichloro-phenyl)-1-methyl-1-ethylamine (16C) (450 mg) ESI-MS m/z 204.6 (M$^+$+1).

(1S)-2-(2,6-dimethyl-phenyl)-1-methyl-1-ethylamine

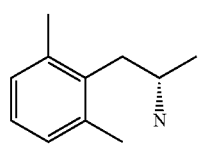

16d (1S)-2-(2,6-dimethyl-phenyl)-1-methyl-1-ethylamine (16d) (400 mg) ESI-MS m/z 164.3 (M$^+$+1).

(1S)-2-(5-fluoro-2-methyl-phenyl)-1-methyl-1-ethylamine

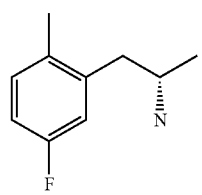

16e (1S)-2-(5-fluoro-2-methyl-phenyl)-1-methyl-1-ethylamine (16e) (600 mg) ESI-MS m/z 168.3 (M$^+$).

(1S)-2-(4-fluoro-2-methyl-phenyl)-1-methyl-1-ethylamine

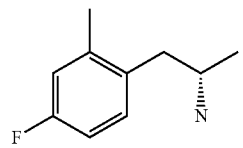

16f (1S)-2-(4-fluoro-2-methyl-phenyl)-1-methyl-1-ethylamine (16l) (600 mg) ESI-MS m/z 168.3 (M$^+$).

(1S)-2-(3-fluoro-2-methyl-phenyl)-1-methyl-1-ethylamine

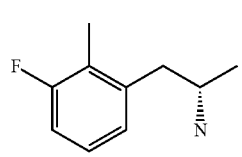

16g (1S)-2-(3-fluoro-2-methyl-phenyl)-1-methyl-1-ethylamine (16g) (600 mg) ESI-MS m/z 168.3 (M$^+$).

Scheme 7
Synthesis of 2-[4-((S)-1-methyl-2-thiophen-2-yl-ethylamino)-2-oxo-1,2-dihydro-pyridin-3-yl]-6-(3-pyrrolidin-1-yl-propyl)-6,7-dihydro-1H-1,3,6-triaza-s-indacen-5-one trifluoroacetic acid salt (18a).

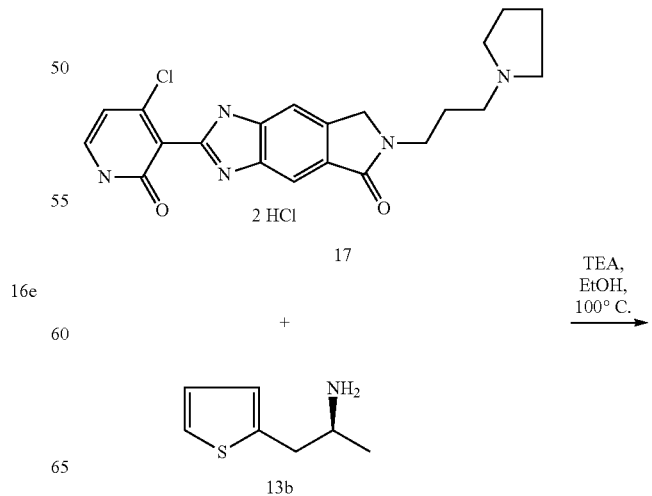

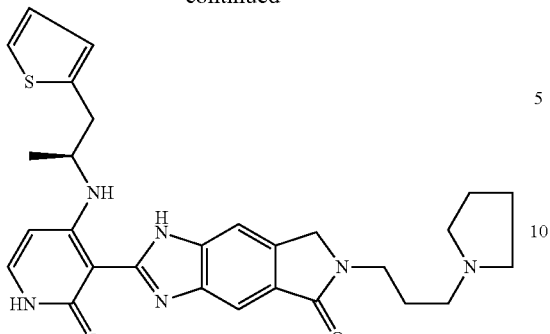

18a

A mixture of 2-(4-chloro-2-oxo-1,2-dihydro-pyridin-3-yl)-6-(3-pyrrolidin-1-yl-propyl)-6,7-dihydro-1H-1,3,6-triaza-s-indacen-5-one dihydrochloride (17) (2.2 g, 4.9 mmol), (1S)-1-methyl-2-thien-2-ylethylamine hydrochloride (13b) (870 mg, 4.9 mmol) and Et₃N (3.44 mL, 24.5 mmol) in EtOH (20 mL) was heated at 100° C. for 12 h. The mixture was concentrated, diluted with water (20 mL) and extracted with CHCl₃ (5×20 mL) the combined organic layer was dried, concentrated to a residue that was purified on silica gel column using 10% NH4OH/methanol in CH₂Cl₂ to get pure 2-[4-((S)-1-methyl-2-thiophen-2-yl-ethylamino)-2-oxo-1,2-dihydro-pyridin-3-yl]-6-(3-pyrrolidin-1-yl-propyl)-6,7-dihydro-1H-1,3,6-triaza-s-indacen-5-one (18a) (1.2 g, 51%). ¹H NMR (DMSO-d₆) δ 1.33 (d, 3H, J=3.0 Hz), 1.55-1.85 (m, 6H), 2.3-2.45 9 m, 6H), 3.15-3.25– (m, 2H), 3.56 (t, 2H, J=6.0 Hz), 3.95-4.15 (m, 1H), 4.51 (s, 2H), 6.15 (d, 1H, J=9.0 Hz), 6.91-6.96 (m, 1H), 7.05 (t, 1H, J=3.0 Hz), 7.31-7.36 (m, 2H), 7.66 (s, 0.5H), 7.79 (d, 1H, J=3.0 Hz), 7.93 (s, 0.5H), 11.14 (d, 1H, J=9.0 Hz), 11.24 (bs, 1H). ESI-MS m/z 517.67 (M⁺+1).

2-[4-((S)-1-methyl-2-thiophen-2-yl-ethylamino)-2-oxo-1,2-dihydro-pyridin-3-yl]-6-(3-pyrrolidin-1-yl-ethyl)-6,7-dihydro-1H-1,3,6-triaza-s-indacen-5-one 18d

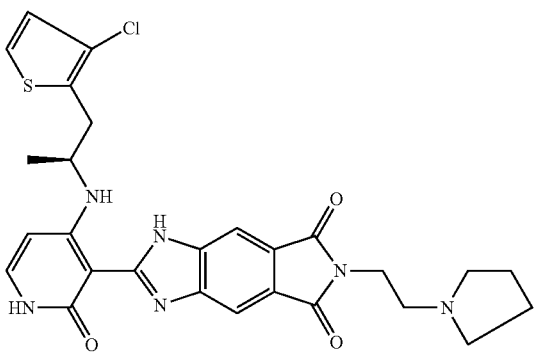

2-[4-((S)-1-methyl-2-thiophen-2-yl-ethylamino)-2-oxo-1,2-dihydro-pyridin-3-yl]-6-(3-pyrrolidin-1-yl-ethyl)-6,7-dihydro-1H-1,3,6-triaza-s-indacen-5-one (18d) was prepared from (1S)-2-(3-chlorothien-2-yl)-1-methylethylamine (13c) and 2-(4-chloro-2-oxo-1,2-dihydro-pyridin-3-yl)-6-(3-pyr-rolidin-1-yl-ethyl)-6,7-dihydro-1H-1,3,6-triaza-s-indacen-5-one dihydrochloride. ESI-MS m/z 551.5 (M⁺) and 553.0 (M⁺+2).

2-[4-((S)-1-methyl-2-thiophen-2-yl-ethylamino)-2-oxo-1,2-dihydro-pyridin-3-yl]-6-(3-pyrrolidin-1-yl-ethyl)-6,7-dihydro-1H-1,3,6-triaza-s-indacen-5-one 18e

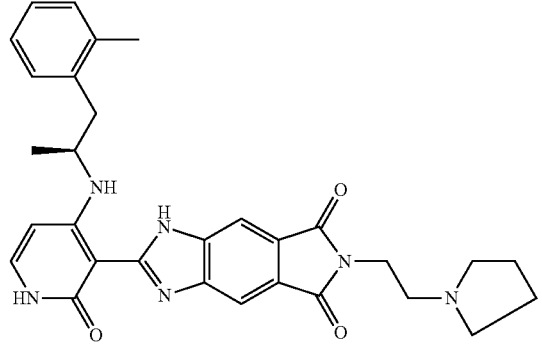

2-[4-((S)-1-methyl-2-thiophen-2-yl-ethylamino)-2-oxo-1,2-dihydro-pyridin-3-yl]-6-(3-pyrrolidin-1-yl-ethyl)-6,7-dihydro-1H-1,3,6-triaza-s-indacen-5-one (18e) was prepared from (S)-1-methyl-2-o-tolyl-ethylamine (13g) and 2-(4-chloro-2-oxo-1,2-dihydro-pyridin-3-yl)-6-(3-pyrrolidin-1-yl-ethyl)-6,7-dihydro-1H-1,3,6-triaza-s-indacen-5-one dihydrochloride (14). ESI-MS m/z 525 (M⁺+1).

2-[4-((S)-2-furan-2-yl-1-methyl-ethylamino)-2-oxo-1,2-dihydro-pyridin-3-yl]-6-(2-pyrrolidin-1-yl-ethyl)-6,7-dihydro-1H-1,3,6-triaza-s-indacen-5-one 18f

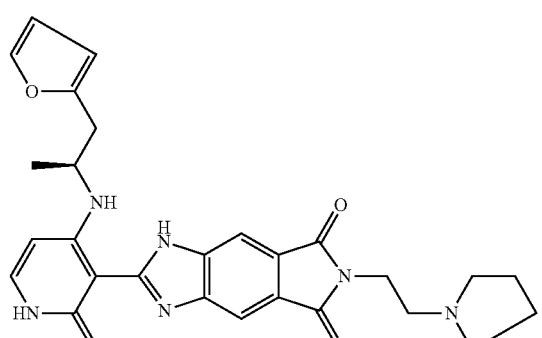

2-[4-((S)-2-furan-2-yl-1-methyl-ethylamino)-2-oxo-1,2-dihydro-pyridin-3-yl]-6-(2-pyrrolidin-1-yl-ethyl)-6,7-dihydro-1H-1,3,6-triaza-s-indacen-5-one (18f) was prepared from (1S)-2-(2-furyl)-1-methylethylamine (131) and 2-(4-chloro-2-oxo-1,2-dihydro-pyridin-3-yl)-6-(3-pyrrolidin-1-yl-ethyl)-6,7-dihydro-1H-1,3,6-triaza-s-indacen-5-one dihydrochloride (14). ESI-MS m/z 501.4 (M⁺+1).

Scheme 8
Synthesis of 2-{4-[(S)-1-methyl-2-(3-methyl-thiophen-2-yl)-ethylamino)-2-oxo-1,2-dihydro-pyridin-3-yl]-6-(2-pyrrolidin-1-yl-ethyl)-6,7-dihydro-1H-1,3,6-triaza-s-indacen-5-one trifluoroacetic acid salt (20a).

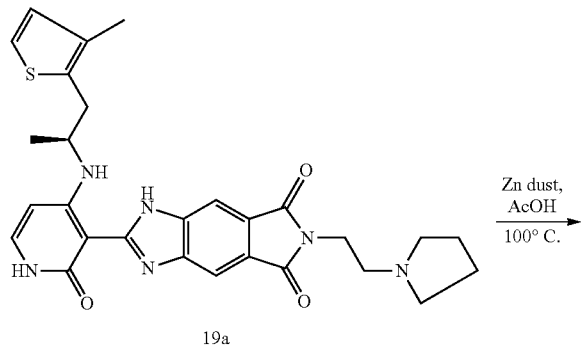

19a

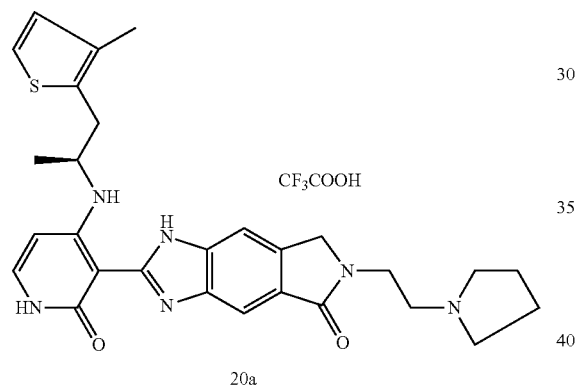

20a

Crude 2-[4-((S)-1-methyl-2-(3-methylthiophen-2-yl)-ethylamino)-2-oxo-1,2-dihydro-pyridin-3-yl]-6-(3-pyrrolidin-1-yl-ethyl)-6,7-dihydro-1H-1,3,6-triaza-s-indacen-5,7-dione (19a) (50 mg) was mixed with zinc dust (123 mg) in AcOH (2 mL) and heated at 100° C. for 2.5 h. The mixture was cooled, filtered through celite and solid was washed with 1:1 MeOH/CH$_2$Cl$_2$ (5 mL). The filtrate was concentrated and the residue was passed through small silica gel column (10% NH4OH in MeOH/CH$_2$Cl$_2$ (1:9). Column fractions were concentrated and obtained compound was subjected to HPLC purification to afford 2-{4-[(S)-1-methyl-2-(3-methyl-thiophen-2-yl)-ethylamino)-2-oxo-1,2-dihydro-pyridin-3-yl]-6-(2-pyrrolidin-1-yl-ethyl)-6,7-dihydro-1H-1,3,6-triaza-s-indacen-5-one trifluoroacetic acid salt (20a). (10 mg). ESI-MS m/z 517.5 (M$^+$+1).

In a similar manner the following compounds were synthesized.

2-{4-[(S)-1-methyl-2-(3-chloro-thiophen-2-yl)-ethylamino)-2-oxo-1,2-dihydro-pyridin-3-yl]-6-(2-pyrrolidin-1-yl-ethyl)-6,7-dihydro-1H-1,3,6-triaza-s-indacen-5-one trifluoroacetic acid salt (20b)

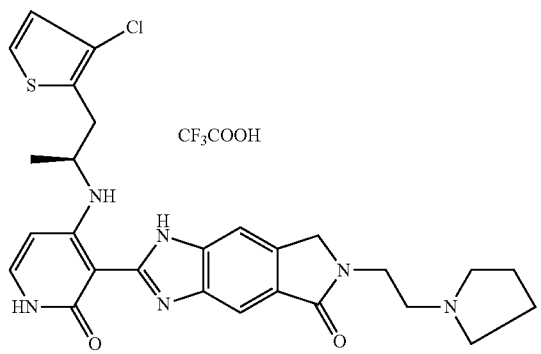

20b (11 mg). ESI-MS m/z 537.5 (M$^+$).

2-{4-[(S)-1-methyl-2-(3-trifluoromethyl-thiophen-2-yl)-ethylamino)-2-oxo-1,2-dihydro-pyridin-3-yl]-6-(2-pyrrolidin-1-yl-ethyl)-6,7-dihydro-1H-1,3,6-triaza-s-indacen-5-one trifluoroacetic acid salt (20c)

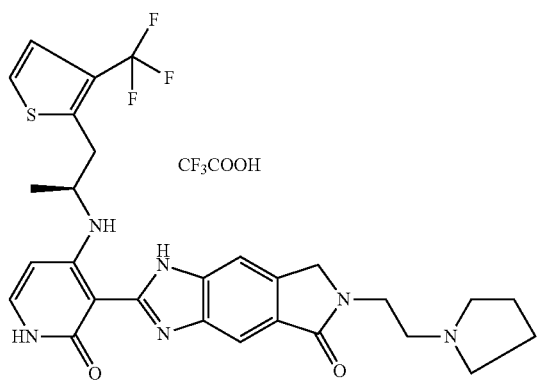

20c (11 mg). ESI-MS m/z 571.5 (M$^+$+1).

2-{4-[(S)-1-methyl-2-otolyl-ethylamino)-2-oxo-1,2-dihydro-pyridin-3-yl]-6-(2-pyrrolidin-1-yl-ethyl)-6,7-dihydro-1H-1,3,6-triaza-s-indacen-5-one trifluoroacetic acid salt (20d)

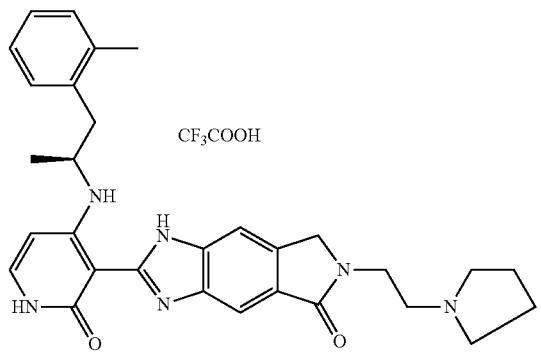

20d (15 mg). ESI-MS m/z 511.5 (M$^+$+1).

2-[4-((S)-2-furan-2yl-1-methyl-ethylamino)-2-oxo-1,2-dihydro-pyridin-3-yl]-6-(2-pyrrolidin-1-yl-ethyl)-6,7-dihydro-1H-1,3,6-triaza-s-indacen-5-one trifluoroacetic acid salt (20e)

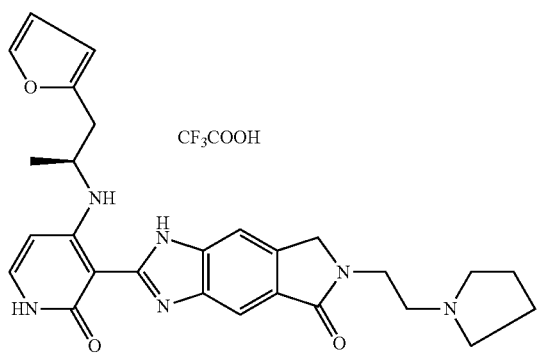

20e 15 mg). ESI-MS m/z 487.1 (M$^+$+1).

Scheme 9
Synthesis of N-alkylated nitro-amino-phthalimide (Method A)
Synthesis of 5-Amino-6-nitro-2-(2-pyrrolidin-1-ylethyl)-1H-isoindole-1,3(2H)-dione
(Method B)

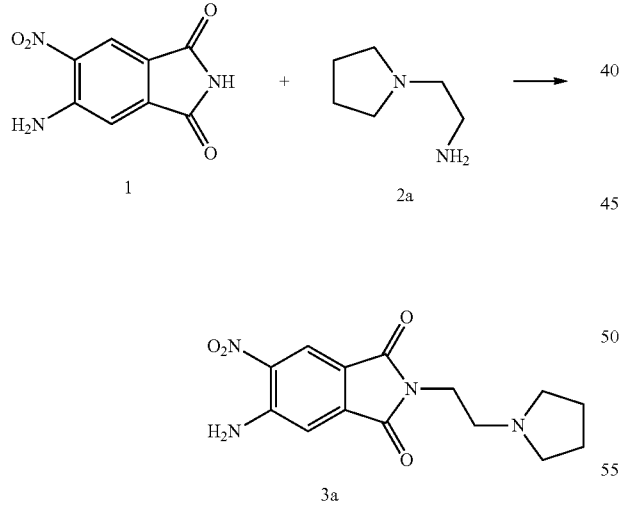

A mixture containing phthalimide (1; 2 g, 9.7 mmol, 1.0 eq.), 2-pyrrolidin-1-ylethanamine (2a, 1.1 g, 9.7 mmol, 1.0 eq.) and imidazole 0.17 g, 2.43 mmol, 0.25 eq.) in dioxane (40 mL) was heated in a capped vial at 110° C. for 14 h. Additional 0.25 eq. of imidazole was added and reaction heated for 24 h. The mixture was cooled to room temperature and concentrated in vacuo to a solid which was used as such in the next step.

The following compounds were prepared using either of the above methods:

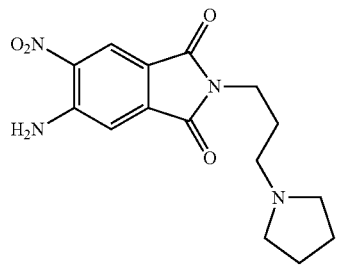
3b
(crude)

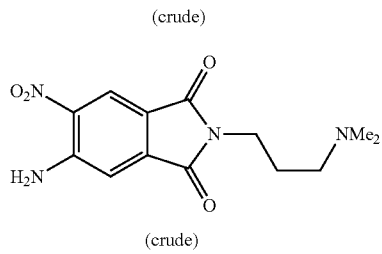
3c
(crude)

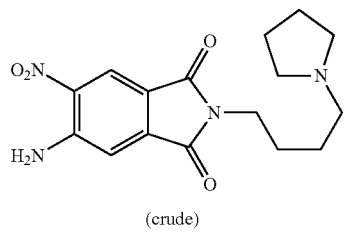
3d
(crude)

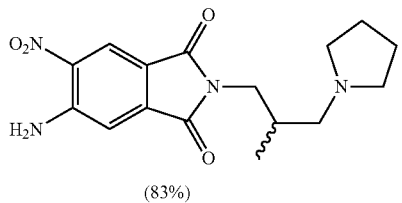
3e
(83%)

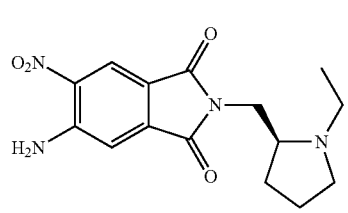
3f
(58%)

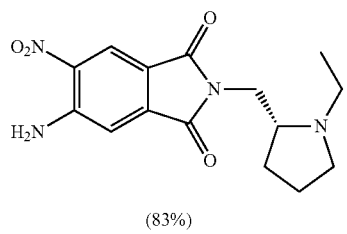
3g
(83%)

3b: Crude used in next step; ESMS (m/z) 318.5 (M + H)$^+$
3c: Crude used in next step; ESMS (m/z) 293.3 (M + H)$^+$
3d: Crude used in next step; ESMS (m/z) 319.5 (M + H)$^+$
3e: 83%; ESMS (m/z) 333.4 (M + H)$^+$
3f: (58%), ESMS (m/z) 319.3 (M + H)$^+$.
3g: (83%), ESMS (m/z) 319.4 (M + H)$^+$.

Synthesis of Phthalimide Halopyridones

Method A 2-(4-Iodo-2-methoxypyridin-3-yl)-6-(3-pyrrolidin-1-ylpropyl)imidazo[4,5-f]isoindole-5,7(1H,6H)-dione (6b)

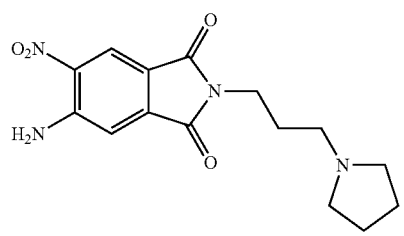

3b

↓ H₂/Pd—C

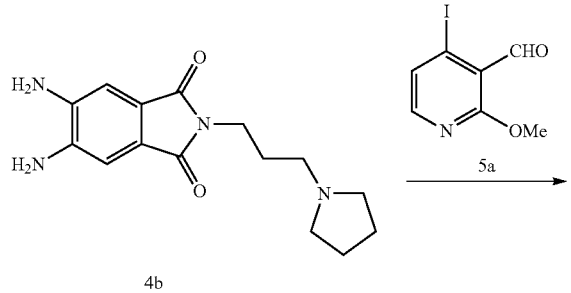

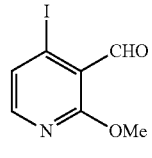

5a

6b

Pd/C (250 mg) was added to a solution of crude 3b in MeOH/AcOH (100 mL/5 mL) and hydrogenated for 5 h. The mixture was filtered through Celite and the filtrate was treated with 4-iodo-2-methoxynicotinaldehyde (3.2 g, 12.07 mmol) and stirred at ambient temperature open to air for 12 h and at 80° C. for 5 h. The reaction mixture was cooled to ambient temperature and concentrated in vacuo to dryness. Purification by flash chromatography gave the title phthalimide 6b as a solid (2.02 g, 32% over 4 steps). $^1$H NMR (MeOD): δ 8.15 (s, 2H), 8.01-8.08 (t, J=3 Hz 1H), 7.64 (t, J=3 Hz, 1H), 3.89-3.78 (m, 2H), 3.41-3.22 (m, 2H), 2.95-2.81 (m, 6H), 2.15-1.82 (m, 7H). ESMS (m/z) 532 (M+H)$^+$.

2-(4-Halo-2-oxo-1,2-dihydropyridin-3-yl)-6-(3-pyrrolidin-1-ylpropyl)imidazo[4,5-f]isoindole-5,7(1H,6H)-dione dihydrochloride (7b)

6b

→

7b: X = Cl/I

A mixture of concentrated HCl (6 mL) and 2-methoxypyridine (1.97 g, 33.7 mmol) in 45 mL of dioxane was stirred at ambient temperature protected from light for 30 h. THF (25 mL) was added to the reaction mixture and the solid was isolated by filtration, washed with Et₂O (4×15 mL), dried at 45° C. in a vacuum oven to afford the title compound as a light chocolate colored solid (1.82 g). $^1$H NMR (MeOH-d₄): δ 12.74 (br s, 1H), 10.60 (br s, 1H), 8.14 (s, 2H), 7.73 (d, J=9 Hz, 1H), 6.65 (d, J=9 Hz, 1H), 3.72-3.64 (m, 1H), 3.51-3.43 (m, 1H), 3.21-3.15 (m, 1H), 2.99-2.93 (m, 1H), 2.07-1.82 (m, 3H). ESMS (m/z) 426.1 (M+H)$^+$ for X=Cl and 518.2 (M+H)$^+$ for X=I.

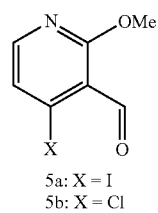

5a: X = I
5b: X = Cl

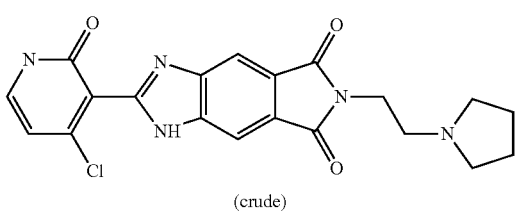

7a
(crude)

111
-continued

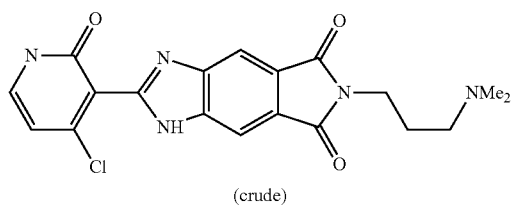

(crude)

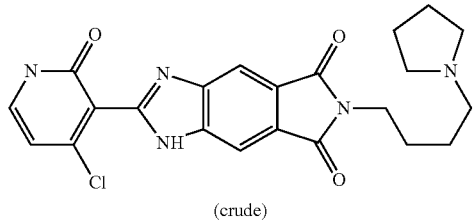

(crude)

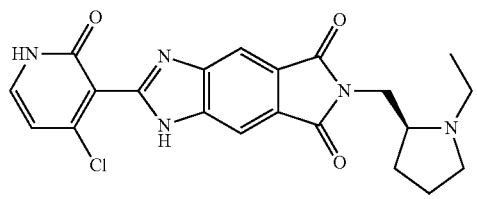

Note 1: All Phthalimides were synthesized using aldehyde 5b.
Note 2: All compounds were identified using LCMS-ELSD Synthesis of Phthalimido Halopyridones Method B

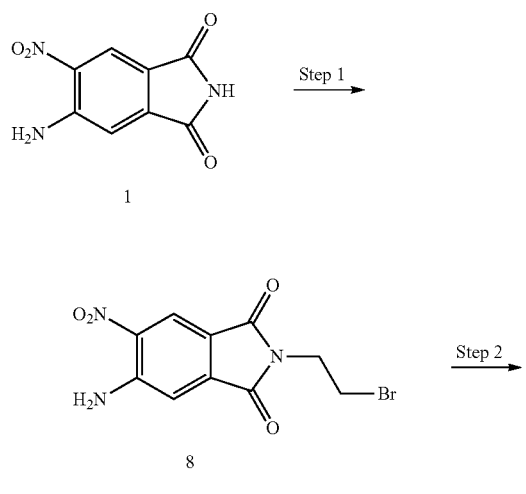

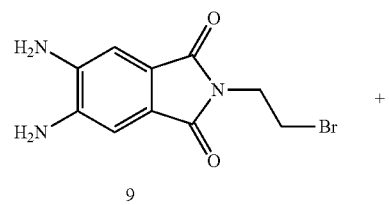

112
-continued

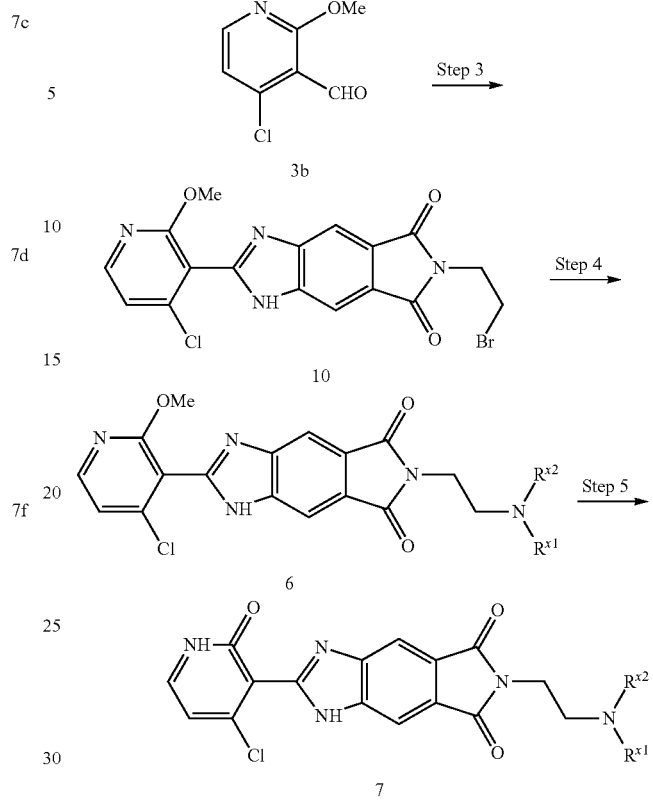

Step 1:

NaH (2.05 g, 60 wt % dispersion in oil, 5.13 mmol, 1.06 eq.) was added portion wise to a solution of the phthalimide (10.0 g, 48.3 mmol, 1.0 eq.) in degassed DMF (50 mL) and heated at 60° C. for 45 min. The mixture was cooled to room temperature and stirred overnight. Then, a solution of dibromoethane (18.1 g, 96.6 mmol) in acetone (50 mL) was added drop wise. The cake was broken up and thick slurry was refluxed overnight. The reaction mixture was cooled to room temperature and filtered. The filtrate was concentrated in vacuo to a residual oil. The filter cake was washed with MeOH and filtered into the residual oil. Additional MeOH was added and the yellow powder obtained was isolated and washed with hexanes to afford 10.14 g (67%) of the desired product. The filtrate cake was taken up in EtOAc (100 mL) and washed with water (50 mL). The aqueous layer was back extracted with EtOAc (50 mL). The organic extracts were combined, dried (Na$_2$SO$_4$), filtered and concentrated in vacuo to afford a yellow solid (2.11 g, 14%) after drying in an oven under high vacuum. Overall yield (12.26 g, 81%). $^1$H NMR (DMSO-d$_6$) 8.45 (br s, 2H) 8.35 (s, 1H), 7.48 (s, 1H), 3.96 (t, J=6.33 Hz, 2H), 3.70 (t, J=6.33 Hz, 2H).

Step 2:

A mixture of the bromophthalimide (1.0 g, 3.2 mmol), AcOH (10 drops) in MeOH (15 mL) was hydrogenated at atmospheric pressure and ambient temperature for 3 h. The mixture was filtered through Celite, Celite was washed well with MeOH, and the filtrate was concentrated in vacuo to afford a residual solid (840 mg; 92%). $^1$H NMR (CDCl$_3$) 7.11 (s, 2H), 4.02 (t, J=6.72 Hz, 2H), 3.86 (br s, 4H), 3.57 (t, J=6.72 Hz, 2H)

Step 3:

Aldehyde (508 mg, 2.96 mmol, 1.0 eq.) was added to a heterogeneous mixture of the diaminophthalimide (840 mg, 2.96 mmol, 1.0 eq.) in MeOH/AcOH (3/1; 40 mL) and stirred at ambient temperature for 48 h. The reaction mixture was concentrated in vacuo to a residual solid and purified by flash chromatography (R$_f$=0.30; 20% EtOAc/DCM) to isolate fractions corresponding to the desired product (1.25 g, 97%, 84% pure). $^1$H NMR (CDCl$_3$) 10.90 (br s, 1H), 8.18 (d, J=5.5 Hz, 1H), 7.15 (d, J=5.5 Hz, 1H), 4.15 (t, J=6.7 Hz, 2H), 3.65 (t, J=6.7 Hz, 2H). ESMS (m/z) 435.

Step 4:

Bromoethylphthalimide (1 eq.) and the secondary amine (3.0 eq.) [Note: 1.2 eq. of powdered K$_2$CO$_3$ was added if secondary amine was HCl salts as in preparation of 5j and 5k) in degassed, anhydrous DMF (0.13 M solution) and heated in capped vial at 75-80° C. for 6-48 h. The desired products were purified by flash chromatography to afford products as shown below.

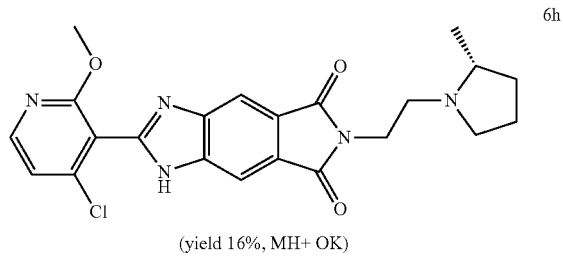

(yield 16%, MH+ OK)

6h

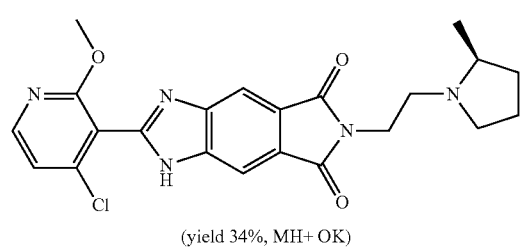

(yield 34%, MH+ OK)

6i

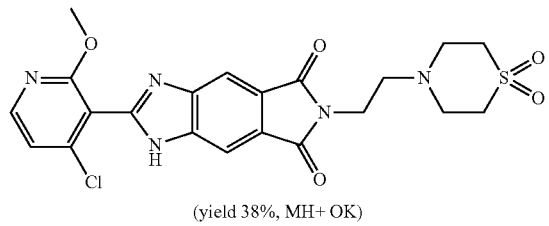

(yield 38%, MH+ OK)

6j

Analytical data for 2-(4-Chloro-2-methoxypyridin-3-yl)-6-{(2-[(2S)-2-methylpyrrolidin-1-yl]ethyl}imidazo[4,5-f]isoindole-5,7(1H,6H)-dione (6i): $^1$H NMR (CDCl$_3$) 8.28 (br s, 1H), 8.17 (d, J=5.5 Hz, 1H), 8.02 (br s, 1H), 7.14 (d, J=5.5 Hz, 1H), 4.01 (s, 3H), 3.41-3.09 (m, 2H), 2.47-2.19 (m, 3H), 1.91-1.78 (m, 1H), 1.65-1.52 (m, 1H), 1.45-1.29 (m, 1H), 1.25 (br s, 1H), 1.19-1.17 (m, 1H), 1.03 (d, J=3.3 Hz, 3H) 0.91-0.72 (m, 1H). ESMS (m/z) 440.91.

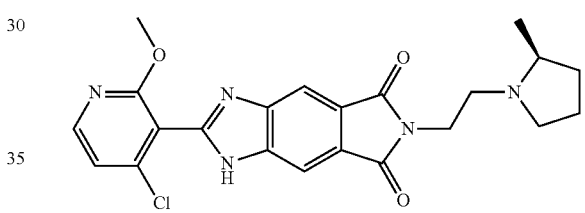

Analytical data for 2-(4-Chloro-2-methoxypyridin-3-yl)-6-[2-(1,1-dioxidothiomorpholin-4-yl)ethyl]imidazo[4,5-f]isoindole-5,7(1H,6H)-dione. $^1$H NMR (MeOH-d$_4$) 8.32 (d, J=5.6 Hz, 1H), 8.14 (s, 2H), 7.29 (d, J=5.6 Hz, 1H), 4.05-3.94 (m, 5H), 3.53-3.37 (m, 4H), 3.29-3.10 (m, 6H). ESMS (m/z) 490.3.

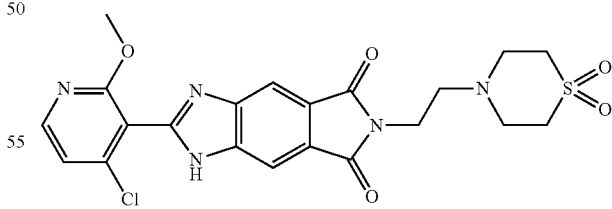

Step 5:

The crude product from Step 4 above was dissolved in dioxane/con HCl (5/1) and stirred at ambient temperature overnight. The reaction mixture was concentrated in vacuo to dryness, azeotroped with EtOH (2×) to obtain the monoHCl salts 5j, 5k, and 5l as a powder. These were used in the next steps as such.

Synthesis of Lactam-Containing Chloropyridones

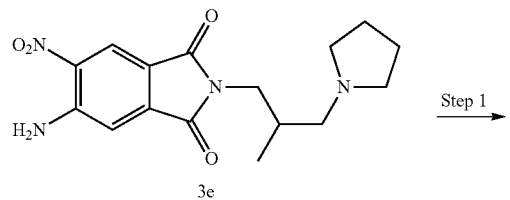
3e

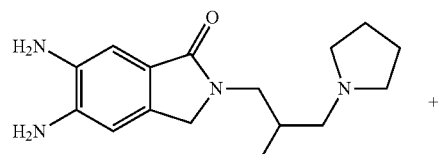
4e

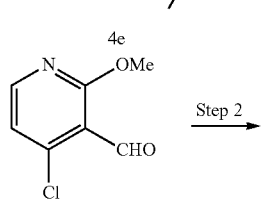
3b

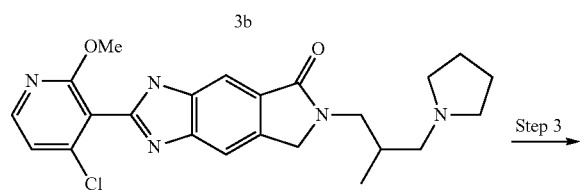
6e

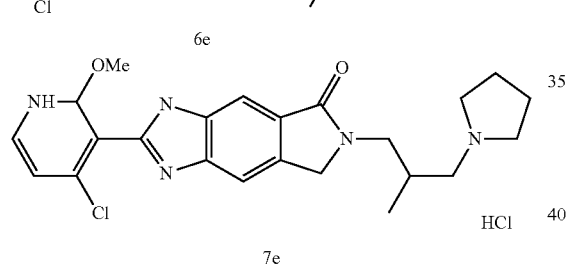
7e

Step 1:
Tin powder (1.96 g, 16.5 mmol, 10.0 eq.) was added to a solution of aminophthalimide (550 mg, 1.65 mmol) in EtOH (7 mL)/con HCl (1.7 mL) and refluxed for 24 h. Another batch of tin powder (1.96 g, 16.5 mmol) and con Hcl (1.7 mL) were added and reflux continued for 15 h. The reaction mixture was decanted to remove tin, and concentrated in vacuo to a residue. The residue was dissolved in MeOH and conc. aq. NH$_4$OH was added until no more precipitation was observed. The reaction mixture was filtered and silica gel was added to the filtrate and concentrated in vacuo. The residue was adsorbed on silica gel and purified by flash chromatography [10% (5% aq. NH$_4$OH/MeOH)/DCM; R$_f$=0.32] to afford the desired product as a thick yellow oil (314 mg, 66%).

Step 2:
A solution of the aldehyde (189 mg, 1.1 mmol, 1.0 eq.) in MeOH (10 mL) was added drop wise to a 0-5° C. solution of the lactam (0.31 g, 1.1 mmol; from step 1) in MeOH (10 mL) and stirred at room temperature for 14 h and at 50° C. for 1 d. The reaction mixture was filtered through Celite, and the filtrate was concentrated in vacuo to a residue and purified by flash chromatography [10% (5% aq. NH$_4$OH/MeOH)/DCM; R$_f$=0.40) to isolate fractions corresponding to the desired product. The isolated product was used as such in the next step.

Step 3:
Con HCl (0.8 mL) was added to a solution of the product from step 2 (225 mg, 0.51 mmol) in dioxane (3 mL) and stirred at ambient temperature overnight and at 60° C. for 2 h. The reaction mixture was concentrated in vacuo to dryness to afford 279 mg of the desired product as a grey solid. ESMS (m/z) 426.4. This was used as such in the next steps.

In a similar fashion was synthesized 2-(4-Chloro-2-oxo-1,2-dihydropyridin-3-yl)-6-{[(2R)-1-ethylpyrrolidin-2-yl]methyl}imidazo[4,5-f]isoindole-5,7(1H,6H)-dione

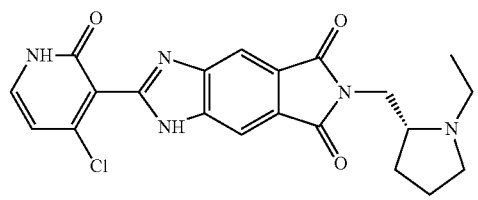 [SMILES: CCN1CCC[C@@H]1CN1C(=O)c2cc3nc(-c4c(Cl)cc[nH]c4=O)[nH]c3cc2C1=O]

Synthesis of Amino-Substituted Phthalimides

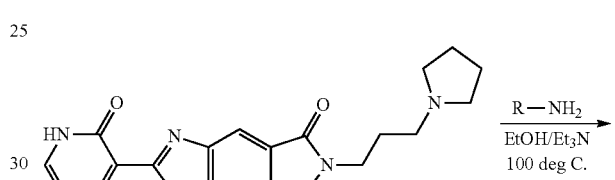

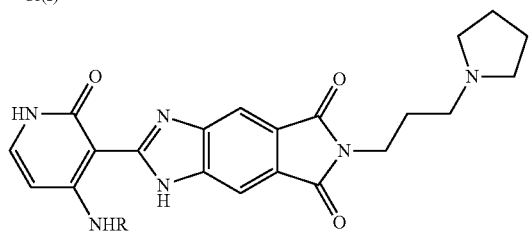

The synthesis of amino-substituted tricyclic phthalimido-derivatives was performed using general methodology described in WO 2008021369 A2 20080221.

The following compounds were synthesized by application of the above methodology.

2-(4-{[(1S)-1-Methyl-2-(2-thienyl)ethyl]amino}-2-oxo-1,2-dihydropyridin-3-yl)-6-(2-pyrrolidin-1-ylethyl)imidazo[4,5-f]isoindole-5,7(1H,6H)-dione (13b) ESMS (m/z) 517.5 (M+H)$^+$; Yield (32%)

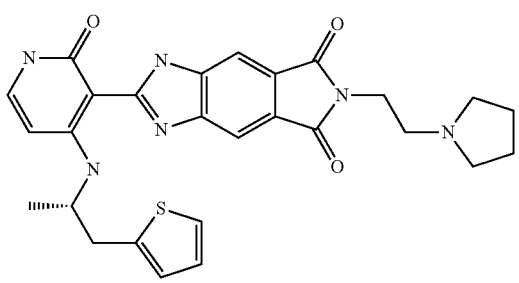 [SMILES: C[C@@H](Cc1cccs1)Nc1cc[nH]c(=O)c1-c1nc2cc3c(cc2[nH]1)C(=O)N(CCN1CCCC1)C3=O]

2-(4-{[1-Methyl-2-(2-thienyl)ethyl]amino}-2-oxo-1,2-dihydropyridin-3-yl)-6-(3-pyrrolidin-1-ylpropyl)imidazo[4,5- f]isoindole-5,7(1H,6H)-dione (15b) ESMS (m/z) 613.5 (M+H)+ 531.3; Yield (64%); Purity 99%

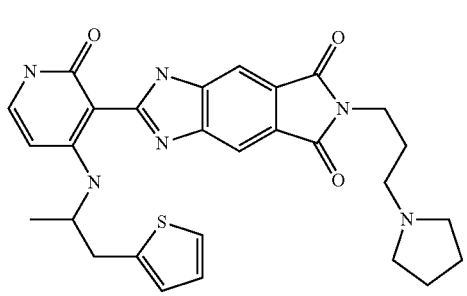 [SMILES: CC(Cc1cccs1)Nc1cc[nH]c(=O)c1-c1nc2cc3c(cc2[nH]1)C(=O)N(CCCN1CCCC1)C3=O]

2-(4-{[1-Methyl-2-(3-thienyl)ethyl]amino}-2-oxo-1,2-dihydropyridin-3-yl)-6-(3-pyrrolidin-1-ylpropyl)imidazo[4,5-f]isoindole-5,7(1H,6H)-dione (19b) ESMS (m/z) 531.5 (M+H+); Yield (66%)

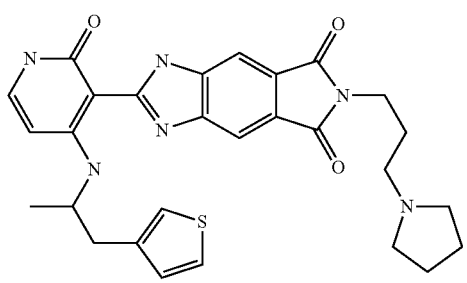 [SMILES: CC(Cc1ccsc1)Nc1cc[nH]c(=O)c1-c1nc2cc3c(cc2[nH]1)C(=O)N(CCCN1CCCC1)C3=O]

2-(2-oxo-4-{[1-(2-thienylmethyl)propyl]amino}-1,2-dihydropyridin-3-yl)-6-(3-pyrrolidin-1-ylpropyl)imidazo[4,5-f]isoindole-5,7(1H,6H)-dione (20b) ESMS (m/z) 545.5 (M+H+); Yield (77%). [Reference for thienyl amine: Gilsdorf, R. T.; Nord, F. F. *J. Org. Chem.* V15, No. 4, 1950, 807-811]

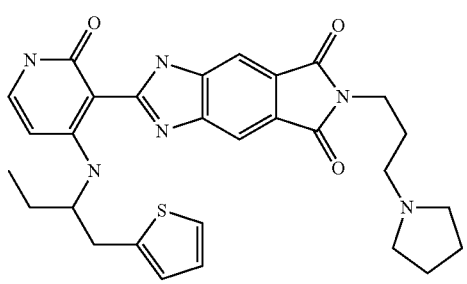 [SMILES: CCC(Cc1cccs1)Nc1cc[nH]c(=O)c1-c1nc2cc3c(cc2[nH]1)C(=O)N(CCCN1CCCC1)C3=O]

2-(4-{[2-(3,5-Dimethylisoxazol-4-yl)-1-methylethyl]amino}-2-oxo-1,2-dihydropyridin-3-yl)-6-(3-pyrrolidin-1-ylpropyl)imidazo[4,5-f]isoindole-5,7(1H,6H)-dione (21b) ESMS (m/z) 544.5 (M+H+); Yield (40%); Purity 99%. [The isoxazolyl derived primary amine was synthesized as in Gilsdorf, R. T.; Nord, F. F. *J. Org. Chem.* V15, No. 4, 1950, 807-811]

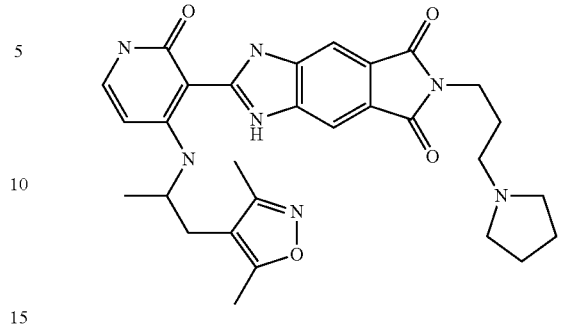

2-(4-{[(1R)-1-methyl-2-(2-thienyl)ethyl]amino}-2-oxo-1,2-dihydropyridin-3-yl)-6-(3-pyrrolidin-1-ylpropyl)imidazo[4,5-f]isoindole-5,7(1H,6H)-dione (22b) ESMS (m/z) 531.3 (M+H+); Yield (81%); Purity 99%

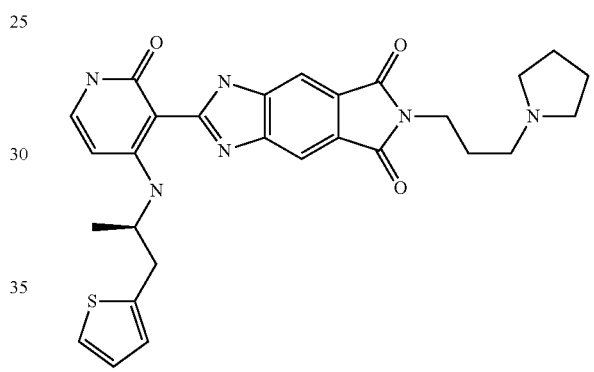

2-(4-{[2-(4-fluorophenyl)-1,1-dimethylethyl]amino}-2-oxo-1,2-dihydropyridin-3-yl)-6-(3-pyrrolidin-1-ylpropyl)imidazo[4,5-f]isoindole-5,7(1H,6H)-dione (24b) ESMS (m/z) 557.5 (M+H+); Yield (27%); Purity 96%

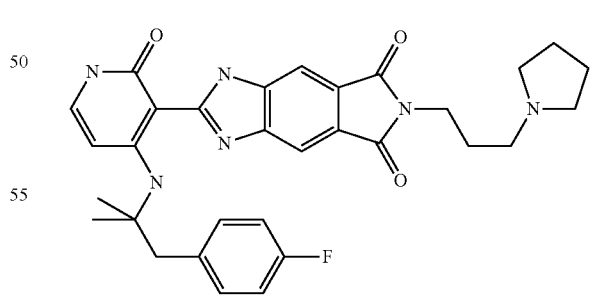

2-(4-{Methyl[1-methyl-2-(2-thienyl)ethyl]amino}-2-oxo-1,2-dihydropyridin-3-yl)-6-(3-pyrrolidin-1-ylpropyl)imidazo[4,5-f]isoindole-5,7(1H,6H)-dione (25b) ESMS (m/z) 545 (M+H+); Yield (74%); Purity 95%. [The thienyl amine was synthesized as in *J. Am. Chem. Soc.* V64, No. 3, 1942, 477-479]

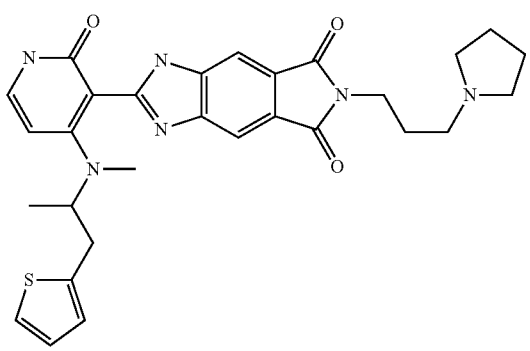 [SMILES: CC(Cc1cccs1)N(C)c1cc[nH]c(=O)c1-c1nc2cc3c(cc2[nH]1)C(=O)N(CCCN1CCCC1)C3=O]

2-(4-{[2-(5-Chloro-2-thienyl)-1-methylethyl]amino}-2-oxo-1,2-dihydropyridin-3-yl)-6-(3-pyrrolidin-1-ylpropyl)imidazo[4,5-f]isoindole-5,7(1H,6H)-dione (26b) ESMS (m/z) 565.3 (M+H⁺); Yield (52%); Purity 99%. Thienyl amine synthesized as in *J. Org. Chem.* V15, No. 4, 1950, 807-811]

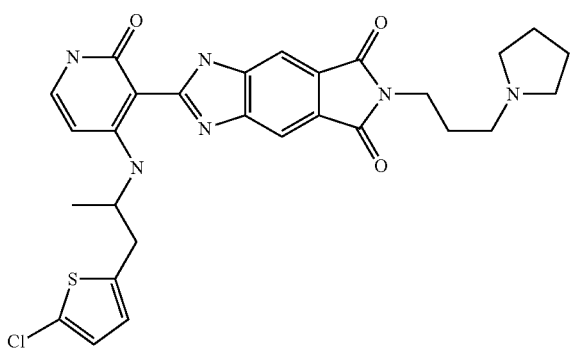 [SMILES: CC(Cc1ccc(Cl)s1)Nc1cc[nH]c(=O)c1-c1nc2cc3c(cc2[nH]1)C(=O)N(CCCN1CCCC1)C3=O]

2-(4-{[(1S,2R)-2-Hydroxy-1-methyl-2-phenylethyl]amino}-2-oxo-1,2-dihydropyridin-3-yl)-6-(3-pyrrolidin-1-ylpropyl)imidazo[4,5-f]isoindole-5,7(1H,6H)-dione (27b) ESMS (m/z) 541.3 (M+H⁺); Yield (60%); Purity 99%

Synthesis of Amino-Substituted Lactams

Method A

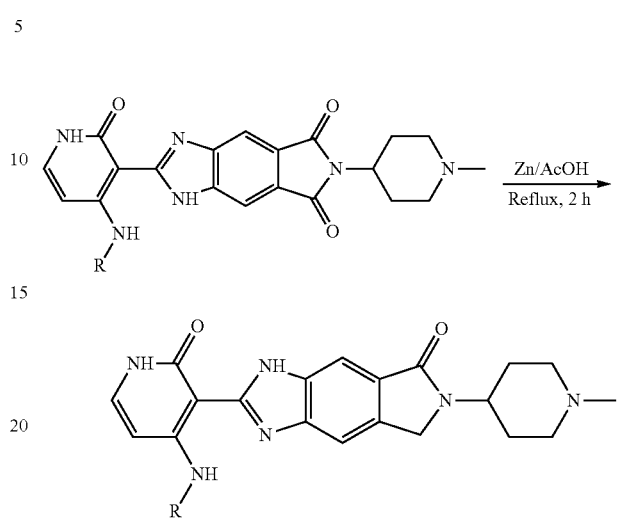

Zn (246 mg, 3.8 g atoms, 23.3 eq.) was added to a solution of the phthalimide 23b (95 mg, 0.163 mmol) and heated at 120° C. for 2 h. Reaction mixture was cooled to ambient temperature and the mixture was filtered through Celite. Celite was washed with MeOH (3×10 mL) and the filtrate was concentrated in vacuo and azeotroped with toluene (3×15 mL). Flash chromatography purification of the resultant residue [10% (5% aq. NH₄OH/MeOH)/DCM] afforded the desired compound as a cream solid (41 mg, 44%). $R_f$=0.40; more polar of the two UV and fluorescent spots of the crude material. ¹H NMR (DMSO-d₆): δ 12.62 (s, 1H), 11.27 (br s, 1H), 11.06 and 10.75 (br singlets, 1H), 7.93 and 7.87 (s, 1H), 7.1629 (br s, 1H), 6.99-6.92 (m, 1H), 6.76 (d, J=7.1 Hz, 1H), 6.07 (br s, 1H), 4.55-4.35 (m, 2H), 4.18-4.07 (m, 2H), 3.80-3.51 (m, 2H), 3.21-3.05 (br s, 2H), 2.71-2.59 (m, 2H), 2.58-2.38 (m, 5H), 2.29-2.59 (m, 4H), 2.40-1.98 (m, 5H), 1.98-1.78 (m, 3H), 1.31-1.05 (m, 3H). ESMS (m/z) 571.5 (M+H)⁺.

Synthesis of Amine-Substituted Lactams

Method B

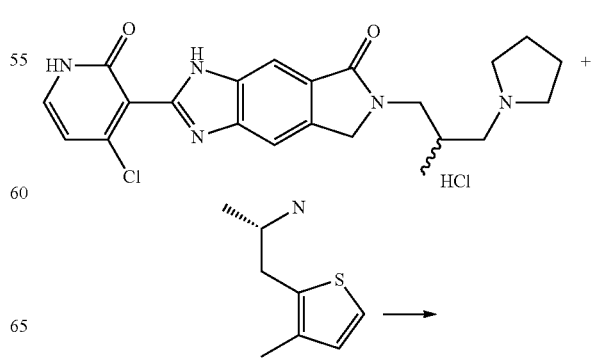

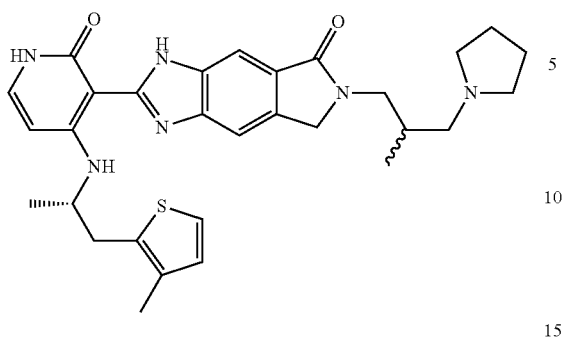

Et₃N 0.15 mL, 1.1 mmol, 5.0 eq.) was added to a mixture containing 2-(4-Chloro-2-oxo-1,2-dihydropyridin-3-yl)-6-(2-methyl-3-pyrrolidin-1-ylpropyl)-6,7-dihydroimidazo[4,5-f]isoindol-5(3H)-one (100 mg, 0.22 mmol) and (2S)-1-(3-methyl-2-thienyl)propan-2-amine (38 mg, 0.24 mmol) in EtOH (1 mL) and heated in a capped vial at 100° C. for 14 h. The mixture was concentrated in vacuo and purified by prep HPLC to afford fractions corresponding to the desired product (45 mg, 38%). ¹H NMR (MeOH-d₄) 7.96 (s, 1H), 7.70 (s, 1H), 7.24 (d, J=7.5 Hz, 1H), 7.08 (d, J=4.41 Hz, 1H), 6.73 (d, J=5.13 Hz, 1H), 6.15 (d, J=7.5 Hz, 1H), 4.67 (s, 2H), 4.19-4.07 (m, 1H), 3.86-3.77 (m, 3H), 3.68-3.56 (m, 1H), 3.23-3.02 (m, 6H), 2.54-2.41 (m, 1H), 2.26-2.02 (m, 7H), 1.46 (d, J=6.3 Hz, 3H), 1.17 (d, J=6.6 Hz, 3H). ESMS (m/z) 545.3 (M+H)⁺.

The following lactams were obtained using Method A unless otherwise specified 2-(4-{[1-methyl-2-(2-thienyl)ethyl]amino}-2-oxo-1,2-dihydropyridin-3-yl)-6-(3-pyrrolidin-1-ylpropyl)-6,7-dihydroimidazo[4,5-f]isoindol-5(3H)-one (32b) ESMS (m/z) 613.5 (M+H)⁺ 517.3; Yield (75%)

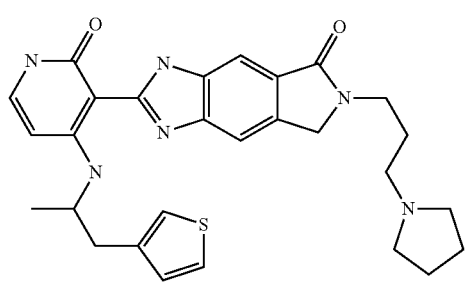 [SMILES: CC(Cc1ccsc1)Nc1cc[nH]c(=O)c1-c1nc2cc3c(cc2[nH]1)C(=O)N(CCCN1CCCC1)C3]

2-(2-Oxo-4-{[1-(2-thienylmethyl)propyl]amino}-1,2-dihydropyridin-3-yl)-6-(3-pyrrolidin-1-ylpropyl)-6,7-dihydroimidazo[4,5-f]isoindol-5(3H)-one (37b) ESMS (m/z) 531.5 (M+H⁺); Yield (83%)

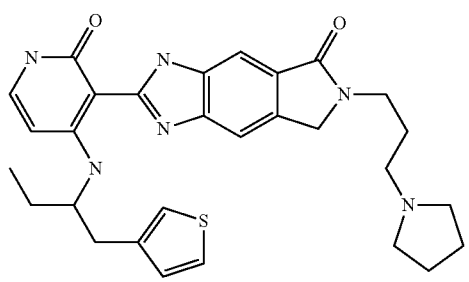 [SMILES: CCC(Cc1ccsc1)Nc1cc[nH]c(=O)c1-c1nc2cc3c(cc2[nH]1)C(=O)N(CCCN1CCCC1)C3]

2-(4-{[2-(3,5-Dimethylisoxazol-4-yl)-1-methylethyl]amino}-2-oxo-1,2-dihydropyridin-3-yl)-6-(3-pyrrolidin-1-ylpropyl)-6,7-dihydroimidazo[4,5-f]isoindol-5(3H)-one (38b) ESMS (m/z) 530.5 (M+H⁺); Yield (38%); Purity 91%

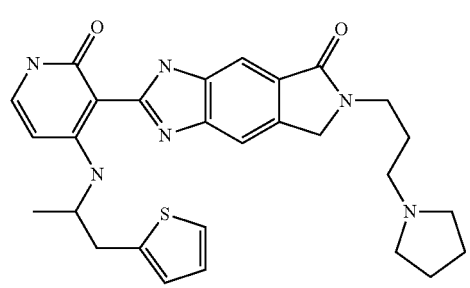

2-(4-{[1-methyl-2-(3-thienyl)ethyl]amino}-2-oxo-1,2-dihydropyridin-3-yl)-6-(3-pyrrolidin-1-ylpropyl)-6,7-dihydroimidazo[4,5-f]isoindol-5(3H)-one (R/S-36b) ESMS (m/z) 517.5 (M+H⁺); Yield (72%)

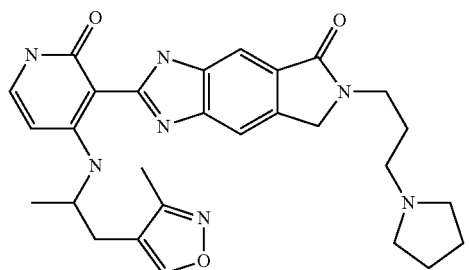

2-(4-{[(1R)-1-Methyl-2-(2-thienyl)ethyl]amino}-2-oxo-1,2-dihydropyridin-3-yl)-6-(3-pyrrolidin-1-ylpropyl)-6,7-dihydroimidazo[4,5-f]isoindol-5(3H)-one [(R)-36b] ESMS (m/z) 531.3 (M+H⁺); Yield (76%); Purity 100%

123

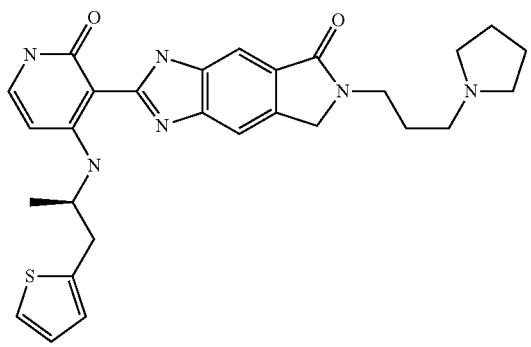 [SMILES: C[C@H](Cc1cccs1)Nc1cc[nH]c(=O)c1-c1nc2cc3c(cc2[nH]1)C(=O)N(CCCN1CCCC1)C3]

2-(4-{[2-(4-Fluorophenyl)-1,1-dimethylethyl]amino}-2-oxo-1,2-dihydropyridin-3-yl)-6-(3-pyrrolidin-1-ylpropyl)-6,7-dihydroimidazo[4,5-f]isoindol-5(3H)-one (40b) ESMS (m/z) 543.5 (M+H$^+$); Yield (100%); Purity 96%

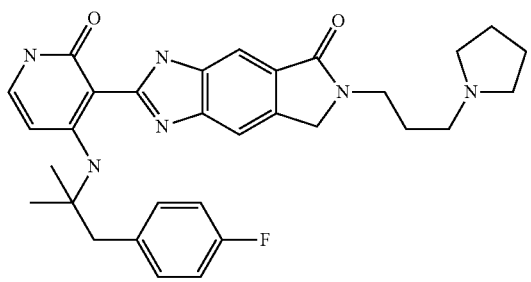 [SMILES: CC(C)(Cc1ccc(F)cc1)Nc1cc[nH]c(=O)c1-c1nc2cc3c(cc2[nH]1)C(=O)N(CCCN1CCCC1)C3]

2-(4-{Methyl[1-methyl-2-(2-thienyl)ethyl]amino}-2-oxo-1,2-dihydropyridin-3-yl)-6-(3-pyrrolidin-1-ylpropyl)-6,7-dihydroimidazo[4,5-f]isoindol-5(3H)-one (41b) ESMS (m/z) 531 (M+H$^+$); Yield (49%); Purity 95%

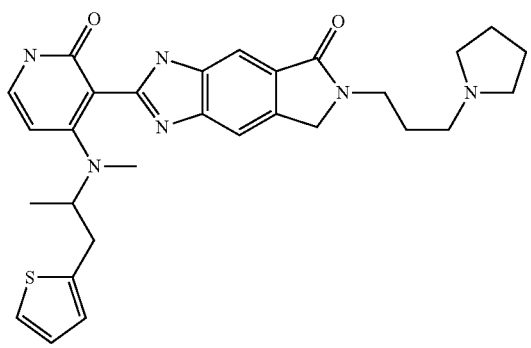 [SMILES: CC(Cc1cccs1)N(C)c1cc[nH]c(=O)c1-c1nc2cc3c(cc2[nH]1)C(=O)N(CCCN1CCCC1)C3]

2-(4-{[2-(5-Chloro-2-thienyl)-1-methylethyl]amino}-2-oxo-1,2-dihydropyridin-3-yl)-6-(3-pyrrolidin-1-ylpropyl)-6,7-dihydroimidazo[4,5-f]isoindol-5(3H)-one (42b) ESMS (m/z) 551.3 (M+H$^+$); Yield (63%); Purity 99%

124

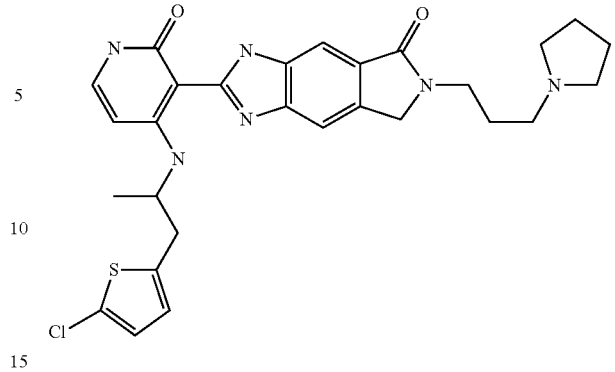

2-(4-{[(1S,2R)-2-Hydroxy-1-methyl-2-phenylethyl]amino}-2-oxo-1,2-dihydropyridin-3-yl)-6-(3-pyrrolidin-1-ylpropyl)-6,7-dihydroimidazo[4,5-f]isoindol-5(3H)-one (43b) ESMS (m/z) 551.3 (M+H$^+$); Yield (63%); Purity 99%

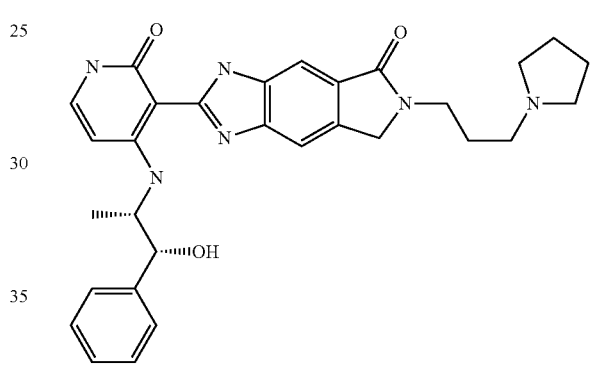

6-[2-(1,1-Dioxidothiomorpholin-4-yl)ethyl]-2-(4-{[(1S)-1-methyl-2-(3-methyl-2-thienyl)ethyl]amino}-2-oxo-1,2-dihydropyridin-3-yl)-6,7-dihydroimidazo[4,5-f]isoindol-5(1H)-one (44j) ESMS (m/z) 581.3 (M+H$^+$); Yield (63%); Purity 99%

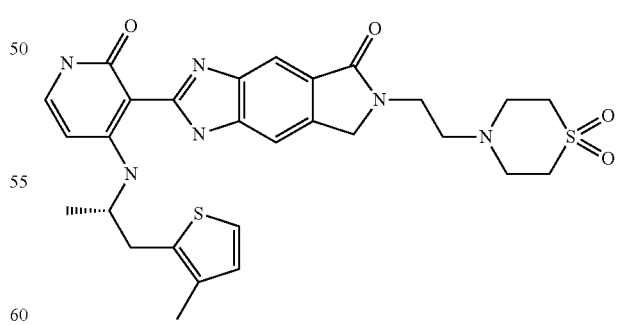

6-{[(2S)-1-Ethylpyrrolidin-2-yl]methyl}-2-(4-{[(1S)-1-methyl-2-(3-methyl-2-thienyl)ethyl]amino}-2-oxo-1,2-dihydropyridin-3-yl)-6,7-dihydroimidazo[4,5-f]isoindol-5(3H)-one (45g) ESMS (m/z) 531.3 (M+H$^+$); Yield (22%); Purity 99%

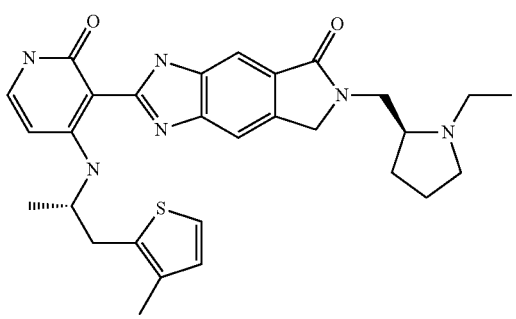 [SMILES: CCN1CCC[C@H]1CN1Cc2cc3nc(-c4c(N[C@@H](C)Cc5sccc5C)cc[nH]c4=O)[nH]c3cc2C1=O]

6-{[(2R)-1-Ethylpyrrolidin-2-yl]methyl}-2-(4-{[(1S)-1-methyl-2-(3-methyl-2-thienyl)ethyl]amino}-2-oxo-1,2-dihydropyridin-3-yl)-6,7-dihydroimidazo[4,5-f]isoindol-5 (3H)-one (45h) [Method B] ESMS (m/z) 531.3 (M+H$^+$); Yield (20%); Purity 99%

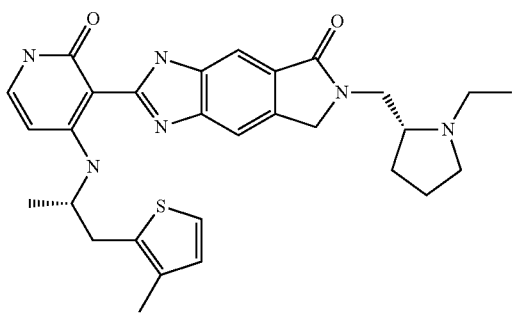 [SMILES: CCN1CCC[C@@H]1CN1Cc2cc3nc(-c4c(N[C@@H](C)Cc5sccc5C)cc[nH]c4=O)[nH]c3cc2C1=O]

2-(4-{[(1S)-1-Methyl-2-(2-thienyl)ethyl]amino}-2-oxo-1,2-dihydropyridin-3-yl)-6-(2-pyrrolidin-1-ylethyl)-6,7-dihydroimidazo[4,5-f]isoindol-5(3H)-one (48a) ESMS (m/z) 503.5 (M+H$^+$); Yield (48%); purity 100%

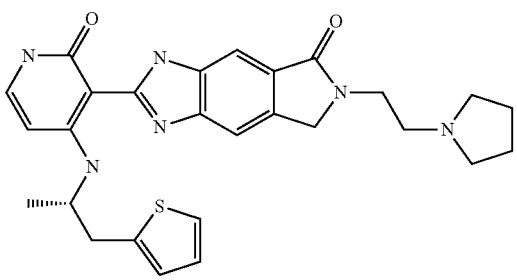 [SMILES: C[C@@H](Cc1cccs1)Nc1cc[nH]c(=O)c1-c1nc2cc3c(cc2[nH]1)C(=O)N(CCN1CCCC1)C3]

Preparation of 5,6-diaminoisoindolin-1-one

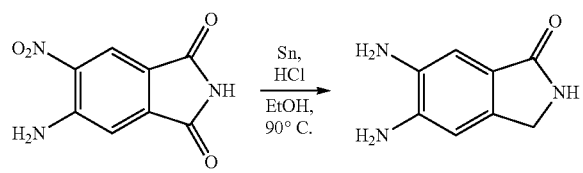 [SMILES: Nc1cc2c(cc1[N+](=O)[O-])C(=O)NC2=O ; Nc1cc2c(cc1N)C(=O)NC2]

A solution of 5-Amino-6-nitroisoindoline-1,3-dione (1.0 g, 4.83 mmol) and tin powder (5.8 g, 48.3 mmol) in EtOH (30 mL) was heated at 90° C. for 4 h. The reaction mixture was cooled to RT, filtered the precipitated solid, washed with EtOH (10 mL) and dried to afford 5,6-diaminoisoindolin-1-one (0.75 g, 95%) as a yellow solid. LCMS: 164 (M+1). $^1$H NMR (300 MHz, DMSO-d$_6$): δ 4.25 (s, 2H); 7.93 (s, 1H), 7.41 (s, 1H); 8.22 (s, 1H); 9.0 (br.s, 4H).

Preparation of (S)-2-(4-(1-(5-fluoro-2-methylphenyl)propan-2-ylamino)-2-oxo-1,2-dihydropyridin-3-yl)-6,7-dihydroimidazo[4,5-f]isoindol-5(1H)-one

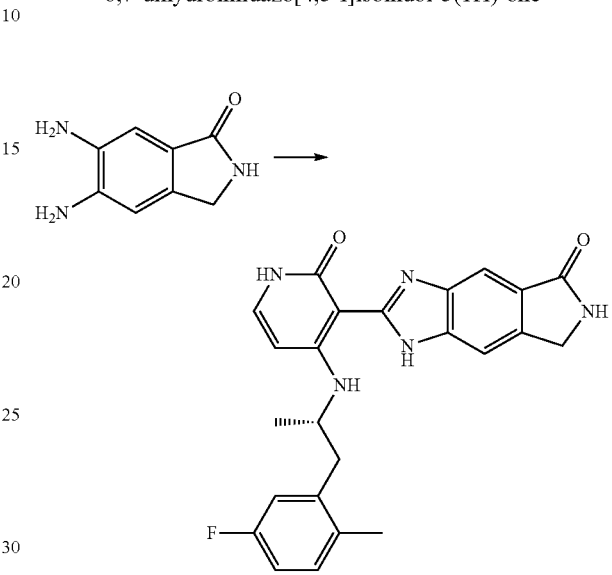

Yield: 40 mg (10%)
LCMS: 432 (M+1). $^1$H NMR (300 MHz, DMSO-d$_6$): δ 1.35 (d, J=3.0 Hz, 1H); 2.48 (s, 3H); 3.02 (m, 2H); 4.17 (m, 1H); 4.55 (s, 2H); 6.15 (m, 1H); 6.95 (m, 1H); 7.1-7.4 (m, 3H); 7.70-8.05 (m, 2H); 8.40 (s, 1H); 11.00-11.23 (m, 2H).

Preparation of 5-Amino-2-(2-(dimethylamino)ethyl)-6-nitroisoindoline-1,3-dione

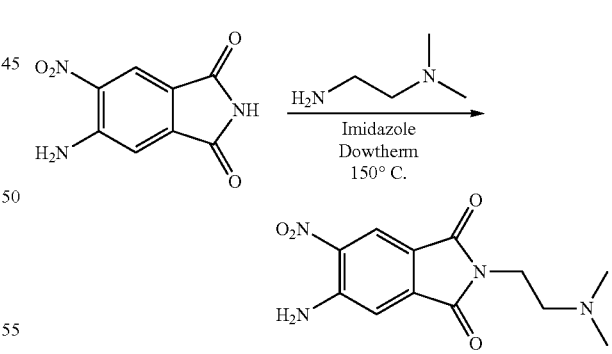

To a suspension of 5-Amino-6-nitroisoindoline-1,3-dione (5.0 g, 24.15 mmol) in Dowtherm (75 mL) were added imidazole (1.64 g, 24.15 mmol) and N$^1$,N$^1$-dimethylethane-1,2-diamine (3.16 mL, 24.15 mmol) and the resulting mixture was heated at 150° C. for overnight. The reaction mixture was cooled to RT, was added ether (100 mL). The yellow precipitate was collected by filtration and washed with ether (2×50 mL) and dried to afford 5-Amino-2-(2-(dimethylamino)ethyl)-6-nitroisoindoline-1,3-dione (6.4 g, 95%) as a yellow solid.

LCMS: 279 (M+1). ¹H NMR (300 MHz, DMSO-d₆): δ 2.21 (s, 6H); 2.50 (t, 2H), 3.65 (t, 2H); 7.55 (s, 1H); 8.31 (s, 1H); 8.40 (br.s, 2H).

Preparation of 5,6-Diamino-2-(2-(dimethylamino)ethyl)isoindoline-1,3-dione

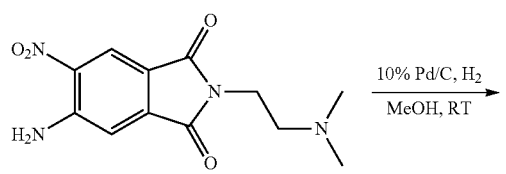

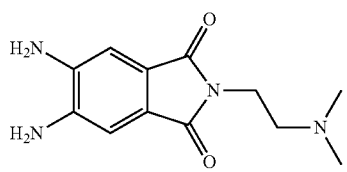

Following the general procedure for hydrogenation in the preparation of analogs, 5,6-diamino-2-(2-(dimethylamino)ethyl)isoindoline-1,3-dione was isolated in quantitative yield (5.7 g, 100%).

LCMS: 249 (M+1). ¹H NMR (300 MHz, DMSO-d₆): δ 2.14 (s, 6H); 2.39 (t, 2H); 3.51 (t, 2H); 5.54 (br.s, 4H); 6.85 (s, 2H).

Preparation of 2-(4-chloro-2-oxo-1,2-dihydropyridin-3-yl)-6-(2-(dimethylamino)ethyl)imidazo[4,5-f]isoindole-5,7(1H,6H)-dione hydrochloride

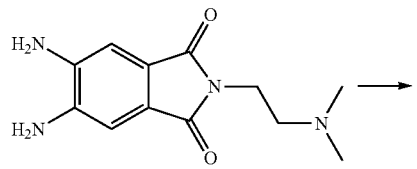

Yield: 8.0 g from 5.7 g of diamine (82%).
LCMS: 386 (M+1). ¹H NMR (300 MHz, DMSO-d₆): δ 2.83 (br.s, 6H); 3.35 (t, 2H); 4.00 (m, 2H); 6.45 (d, J=6.0 Hz, 1H); 6.8 (br.s, 3H); 7.81 (d, J=6.0 Hz, 1H); 8.22 (s, 2H); 10.8 (br.s, 1H).

Preparation of (S)-6-(2-(dimethylamino)ethyl)-2-(4-(1-(5-fluoro-2-methylphenyl)propan-2-ylamino)-2-oxo-1,2-dihydropyridin-3-yl)-6,7-dihydroimidazo[4,5-f]isoindol-5(1H)-one

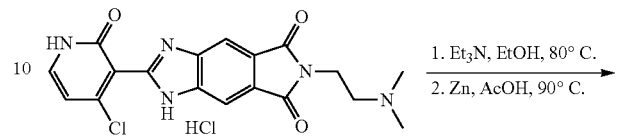

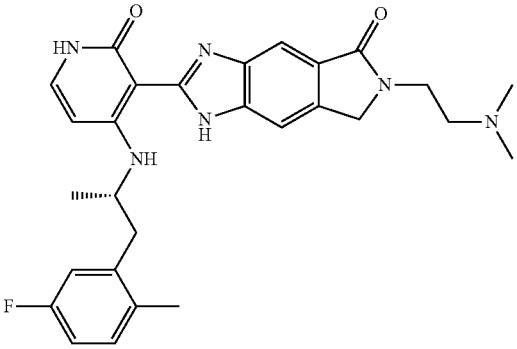

Yield: 45 mg (38%).
LCMS: 503 (M+1). ¹H NMR (300 MHz, DMSO-d₆): δ 1.34 (d, J=3.0 Hz, 3H); 2.19 (s, 6H); 2.35 (s, 3H); 2.50 (m, 2H); 2.99 (t, 2H); 3.69 (t, 2H); 4.17 (m, 1H); 6.14 (d, J=6.0 Hz, 1H); 6.84-6.89 (m, 1H); 7.10-7.31 (m, 3H); 7.94 (s, 1H); 8.06 (s, 1H); 10.87 (d, J=6.0 Hz, 1H); 11.28 (br.s, 1H).

Preparation of (S)-6-(2-(dimethylamino)ethyl)-2-(4-(1-(5-fluoro-2-methoxyphenyl)propan-2-ylamino)-2-oxo-1,2-dihydropyridin-3-yl)-6,7-dihydroimidazo[4,5-f]isoindol-5(1H)-one

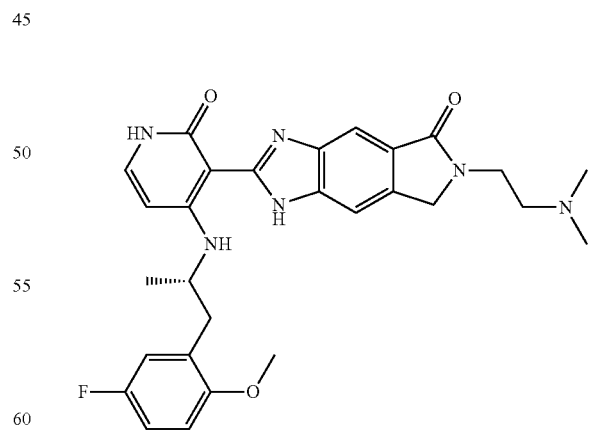

LCMS: 519 (M+1). ¹H NMR (300 MHz, DMSO-d₆): δ 1.28 (d, J=3.0 Hz, 3H); 2.20 (s, 6H); 2.76-2.83 (m, 1H); 2.86-3.07 (m, 1H); 3.62-3.64 (m, 2H); 3.80 (s, 3H); 4.02-4.10 (m, 1H); 4.53 (s, 2H); 6.23 (d, J=9.0 Hz, 1H); 6.90-7.40 (m, 4H); 7.65-7.94 (m, 2H); 10.97-11.20 (2 br.s, 2H).

Preparation of (S)-6-(2-(dimethylamino)ethyl)-2-(4-(1-(2-methyl-5-(trifluoromethyl)phenyl)propan-2-ylamino)-2-oxo-1,2-dihydropyridin-3-yl)-6,7-dihydroimidazo[4,5-f]isoindol-5(1H)-one

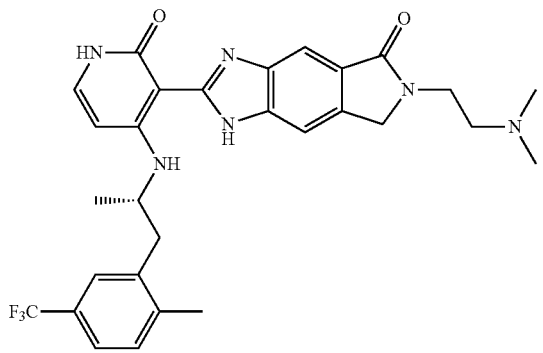 [SMILES: Cc1ccc(C(F)(F)F)cc1C[C@H](C)Nc1cc[nH]c(=O)c1-c1nc2cc3c(cc2[nH]1)CN(CCN(C)C)C3=O]

LCMS: 553 (M+1). $^1$H NMR (300 MHz, DMSO-$d_6$): δ 1.28 (d, J=3.0 Hz, 3H); 2.20 (s, 6H); 2.50 (s, 3H); 2.96-2.99 (m, 2H); 3.62-3.64 (m, 2H); 4.18 (s, 1H); 4.53 (s, 2H); 6.18 (d, J=9.0 Hz, 1H); 7.10-7.40 (m, 3H); 7.65-7.94 (m, 3H); 10.97-11.20 (2 br.s, 2H); 13.10 (s, 1H)

Preparation of (S)-6-(2-(dimethylamino)ethyl)-2-(2-oxo-4-(1-(2,3,5-trifluorophenyl)propan-2-ylamino)-1,2-dihydropyridin-3-yl)-6,7-dihydroimidazo[4,5-f]isoindol-5(1H)-one

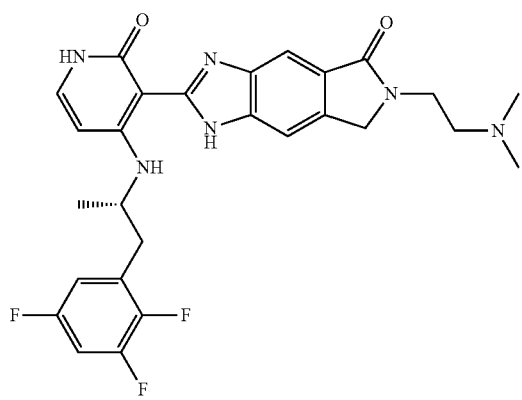

LCMS: 525 (M+1). $^1$H NMR (300 MHz, DMSO-$d_6$): δ 1.28 (d, J=3.0 Hz, 3H); 2.20 (s, 6H); 2.96-2.99 (m, 2H); 3.62-3.64 (m, 2H); 4.18 (s, 1H); 4.53 (s, 2H); 6.18 (d, J=9.0 Hz, 1H); 7.10-7.40 (m, 3H); 7.65-7.94 (m, 2H); 10.97-11.20 (2 br.s, 2H); 13.10 (s, 1H).

Preparation of (S)-2-(4-(1-(3,4-difluoro-2-methylphenyl)propan-2-ylamino)-2-oxo-1,2-dihydropyridin-3-yl)-6-(2-(dimethylamino)ethyl)-6,7-dihydroimidazo[4,5-f]isoindol-5(1H)-one

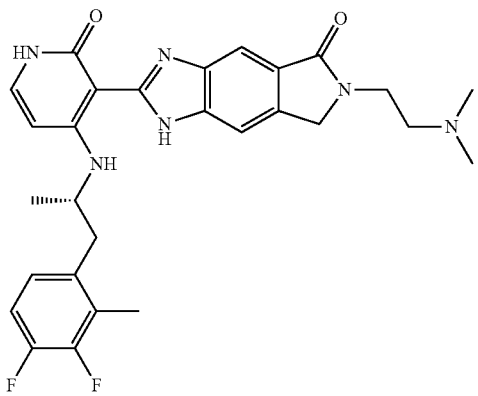 [SMILES: Cc1c(C[C@H](C)Nc2cc[nH]c(=O)c2-c2nc3cc4c(cc3[nH]2)CN(CCN(C)C)C4=O)ccc(F)c1F]

LCMS: 521 (M+1). $^1$H NMR (300 MHz, DMSO-$d_6$): δ 1.34 (d, J=3.0 Hz, 3H); 2.19 (s, 6H); 2.35 (s, 3H); 2.50 (m, 2H); 2.99 (t, 2H); 3.69 (t, 2H); 4.17 (m, 1H); 6.14 (d, J=6.0 Hz, 1H); 6.84-6.89 (m, 1H); 7.10-7.31 (m, 2H); 7.94 (s, 1H); 8.06 (s, 1H); 10.87 (d, J=6.0 Hz, 1H); 11.28 (br.s, 1H); 13.50 (s, 1H).

Preparation of (S)-2-(4-(1-(3,5-difluoro-2-methylphenyl)propan-2-ylamino)-2-oxo-1,2-dihydropyridin-3-yl)-6-(2-(dimethylamino)ethyl)-6,7-dihydroimidazo[4,5-f]isoindol-5(1H)-one

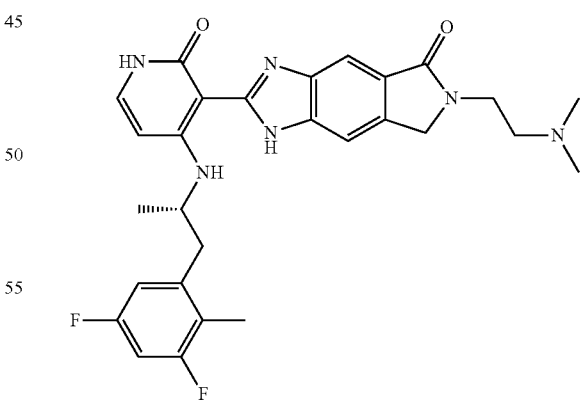

LCMS: 521 (M+1). $^1$H NMR (300 MHz, DMSO-$d_6$): δ 1.24 (d, J=3.0 Hz, 3H); 2.01 (br.s, 4H); 2.19 (s, 6H); 2.50 (s, 3H); 2.80-2.99 (m, 2H); 3.69 (t, 2H); 4.17 (m, 1H); 6.14 (d, J=6.0 Hz, 1H); 6.84-6.89 (m, 1H); 7.10-7.31 (m, 2H); 7.94 (s, 1H); 8.06 (s, 1H); 10.87 (d, J=6.0 Hz, 1H); 11.28 (br.s, 1H); 13.50 (s, 1H).

Preparation of (S)-2-(4-(1-(5-fluoro-2-methoxyphenyl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

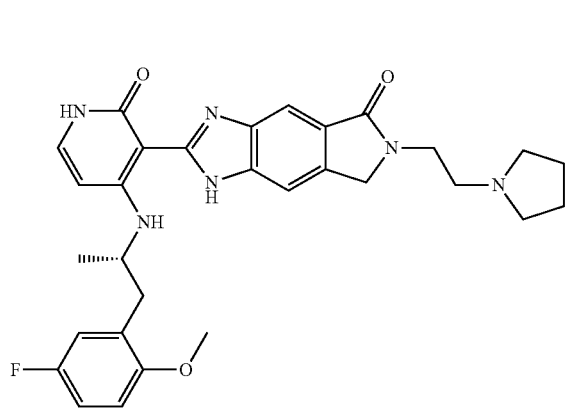 [SMILES: COc1ccc(F)cc1C[C@H](C)Nc1cc[nH]c(=O)c1-c1nc2cc3c(cc2[nH]1)CN(CCN1CCCC1)C3=O]

LCMS: 545 (M+1). $^1$H NMR (300 MHz, DMSO-d$_6$): δ 1.23 (m, 3H); 1.79-1.82 (m, 4H); 2.60-2.70 (m, 4H); 2.76-2.83 (m, 1H); 2.86-3.07 (m, 1H); 3.62-3.64 (m, 2H); 3.80 (s, 3H); 4.02-4.10 (m, 1H); 4.53 (s, 2H); 6.23 (d, J=9.0 Hz, 1H); 6.90-7.40 (m, 4H); 7.65-7.94 (m, 2H); 11.20 (2 br.s, 2H); 13.00 (s, 1H).

Preparation of (5)-2-(2-oxo-4-(1-(2,3,5-trifluorophenyl)propan-2-ylamino)-1,2-dihydropyridin-3-yl)-6-(2-(pyrrolidin-1-yl)ethyl)-6,7-dihydroimidazo[4,5-f]isoindol-5(1H)-one

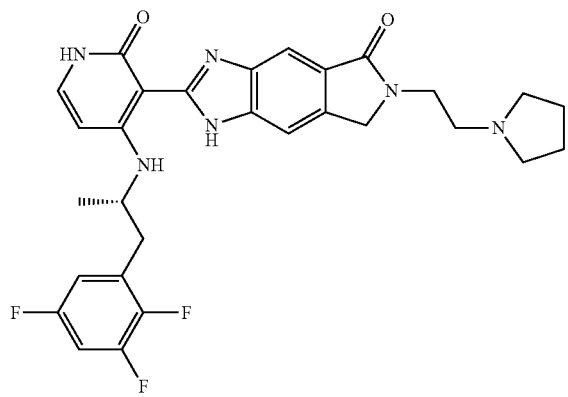 [SMILES: C[C@@H](Cc1cc(F)cc(F)c1F)Nc1cc[nH]c(=O)c1-c1nc2cc3c(cc2[nH]1)CN(CCN1CCCC1)C3=O]

LCMS: 551 (M+1). $^1$H NMR (300 MHz, DMSO-d$_6$): δ 1.23 (m, 3H); 1.79-1.82 (m, 4H); 2.60-2.70 (m, 4H); 2.76-2.83 (m, 1H); 2.86-3.07 (m, 1H); 3.62-3.64 (m, 2H); 3.80 (s, 3H); 4.02-4.10 (m, 1H); 4.53 (s, 2H); 6.23 (d, J=9.0 Hz, 1H); 6.90-7.40 (m, 3H); 7.65-7.94 (m, 2H); 11.20 (2 br.s, 2H); 13.00 (s, 1H).

Preparation of (S)-2-(4-(1-(5-(dimethylamino)-2-methylphenyl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

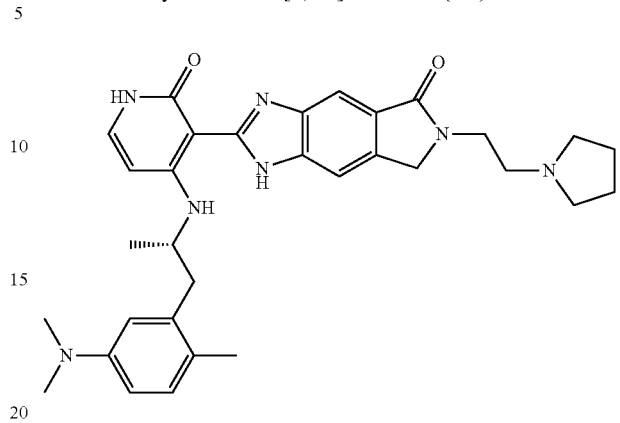

LCMS: 554 (M+1).

Preparation of (S)-2-(4-(1-(2-methyl-5-(trifluoromethyl)phenyl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

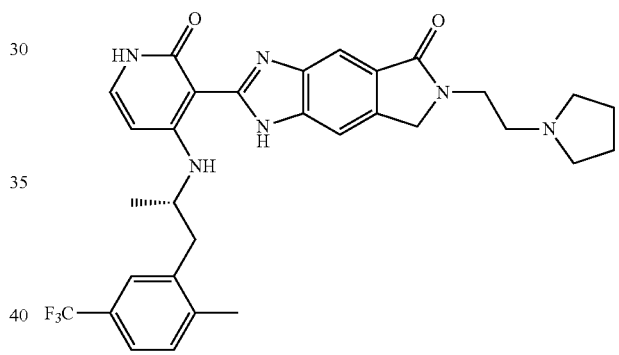

Preparation of (S)-2-(4-(1-(2-fluorophenyl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

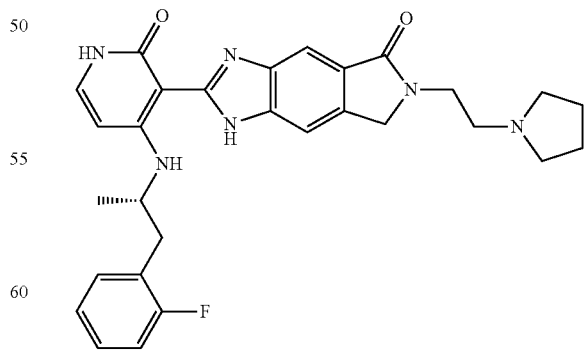

LCMS: 515 (M+1).
$^1$H NMR (300 MHz, DMSO-d$_6$): δ 1.32 (m, 3H); 1.69 (m, 4H); 2.60-2.70 (m, 4H); 2.73 (m, 2H); 3.02-3.11 (m, 2H);

3.66-3.69 (m, 2H); 4.08-4.11 (m, 1H); 4.55 (s, 2H); 6.16 (d, J=9.0 Hz, 1H); 7.01-7.40 (m, 4H); 7.65-7.94 (m, 3H); 11.11, 11.20 (2 br.s, 2H); 13.00 (s, 1H).

Preparation of (S)-2-(4-(1-(2-chlorophenyl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

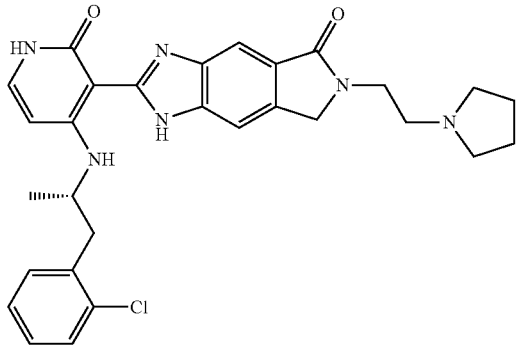 [SMILES: C[C@@H](Cc1ccccc1Cl)Nc1cc[nH]c(=O)c1-c1nc2cc3c(cc2[nH]1)CN(CCN1CCCC1)C3=O]

LCMS: 531 (M+1).

$^1$H NMR (300 MHz, DMSO-d$_6$): δ 1.32 (m, 3H); 1.69 (m, 4H); 2.60-2.70 (m, 4H); 2.73 (m, 2H); 3.02-3.11 (m, 2H); 3.66-3.69 (m, 2H); 4.08-4.11 (m, 1H); 4.55 (s, 2H); 6.16 (d, J=9.0 Hz, 1H); 7.01-7.40 (m, 4H); 7.65-7.94 (m, 3H); 11.11, 11.20 (2 br.s, 2H); 13.00 (s, 1H).

Preparation of (S)-2-(4-(1-(3,4-difluoro-2-methylphenyl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

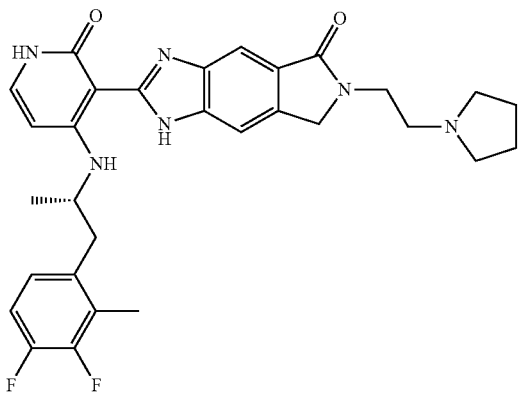 [SMILES: Cc1c(C[C@H](C)Nc2cc[nH]c(=O)c2-c2nc3cc4c(cc3[nH]2)CN(CCN2CCCC2)C4=O)ccc(F)c1F]

LCMS: 547 (M+1).

$^1$H NMR (300 MHz, DMSO-d$_6$): δ 1.23 (m, 3H); 1.79-1.82 (m, 4H); 2.60-2.70 (m, 4H); 2.76-2.83 (m, 1H); 2.86-3.07 (m, 1H); 3.62-3.64 (m, 2H); 3.80 (s, 3H); 4.02-4.10 (m, 1H); 4.53 (s, 2H); 6.23 (d, J=9.0 Hz, 1H); 6.90-7.40 (m, 3H); 7.65-7.94 (m, 2H); 11.20 (2 br.s, 2H); 13.00 (s, 1H).

Preparation of (S)-2-(4-(1-(2,5-dimethoxyphenyl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

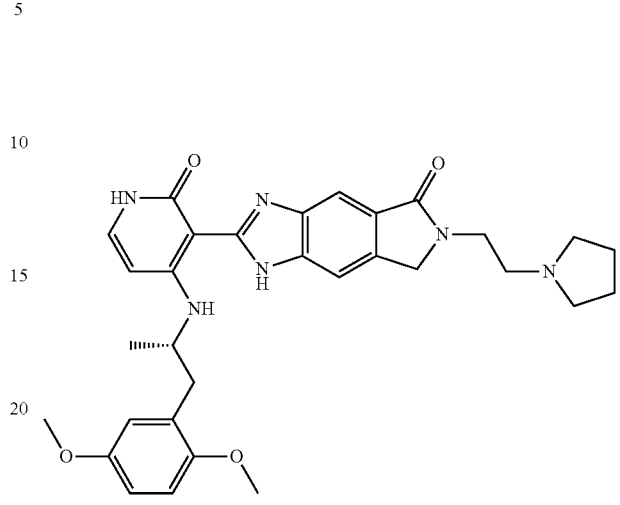

LCMS: 557 (M+1).

$^1$H NMR (300 MHz, DMSO-d$_6$): δ 1.27 (d, J=6.0 Hz, 3H); 1.73 (br.s, 4H); 2.65-2.80 (m, 3H); 3.00-3.04 (m, 1H); 3.39-3.57 (m, 3H); 3.61 (s, 3H); 3.63-3.69 (m, 3H); 3.73 (s, 3H); 3.95-4.09 (m, 1H); 4.55 (d, J=3.0 Hz, 2H); 6.25 (d, J=6.0 Hz, 2H); 6.87-6.93 (m, 3H); 7.38 (d, 1H); 7.65-7.99 (m, 2H); 11.10 (m, 2H); 13.50 (s, 1H).

Preparation of (S)-2-(4-(1-(5-methoxy-2-methylphenyl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

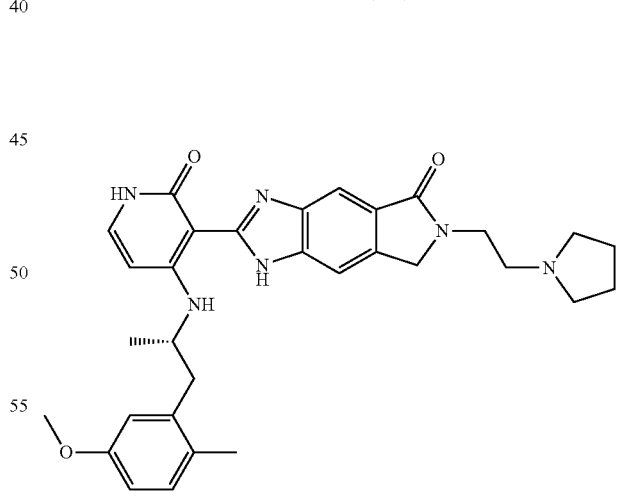

LCMS: 541 (M+1).

$^1$H NMR (300 MHz, DMSO-d$_6$): δ 1.33 (d, J=6.0 Hz, 3H); 1.67 (br.s, 4H); 2.32 (s, 3H); 2.65-2.69 (m, 2H); 2.94-2.96 (m, 2H); 3.39-3.57 (m, 2H); 3.63 (s, 3H); 3.67-3.69 (m, 2H); 4.09-4.12 (m, 1H); 4.55 (d, J=3.0 Hz, 2H); 6.25 (d, J=6.0 Hz, 2H); 6.61-7.99 (m, 7H); 11.10 (m, 2H); 13.50 (s, 1H).

135

Preparation (S)-2-(4-(1-(2-ethylphenyl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

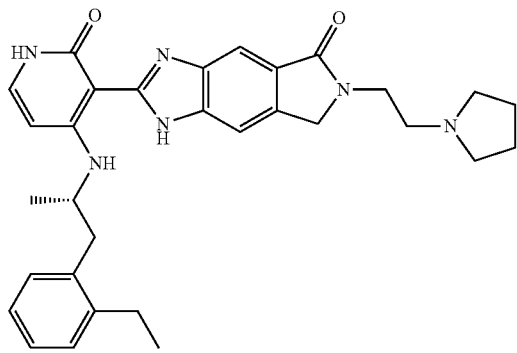 [SMILES: CCc1ccccc1C[C@H](C)Nc1cc[nH]c(=O)c1-c1nc2cc3c(cc2[nH]1)CN(CCN1CCCC1)C3=O]

LCMS: 525 (M+1).

$^1$H NMR (300 MHz, DMSO-d$_6$): δ 1.20 (t, J=6.0 Hz, 3H); 1.33 (d, J=3.0 Hz, 3H); 1.79 (br.s, 4H); 2.65-2.81 (m, 4H); 2.98-3.00 (m, 2H); 3.39-3.51 (m, 4H); 3.63-3.69 (m, 2H); 4.08-4.15 (m, 1H); 4.55 (d, J=3.0 Hz, 2H); 6.12 (d, J=6.0 Hz, 2H); 7.15-7.99 (m, 7H); 11.10 (m, 2H); 13.50 (s, 1H).

Preparation of (S)-2-(4-(1-(2,3-difluoro-5,6-dimethoxyphenyl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

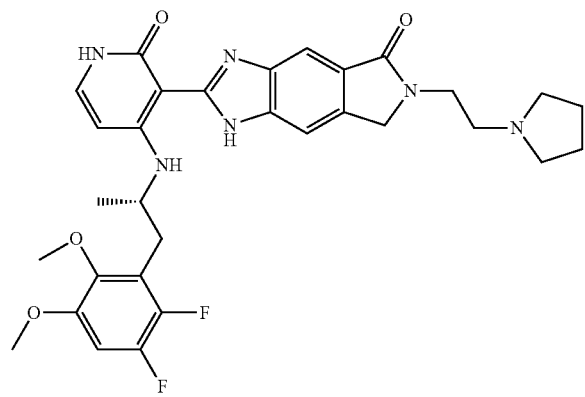 [SMILES: COc1cc(F)c(F)c(C[C@H](C)Nc2cc[nH]c(=O)c2-c2nc3cc4c(cc3[nH]2)CN(CCN2CCCC2)C4=O)c1OC]

LCMS: 593 (M+1).

$^1$H NMR (300 MHz, DMSO-d$_6$): δ 1.32 (d, J=3.0 Hz, 3H); 1.67 (br.s, 4H); 2.65-2.69 (m, 22.85-3.11 (m, 2H); 3.39-3.51 (m, 4H); 3.63-3.69 (m, 2H); 3.75 (2 s, 6H); 3.98-4.05 (m, 1H); 4.55 (s, 2H); 6.20 (d, J=6.0 Hz, 2H); 7.15-7.99 (m, 4H); 11.10 (m, 2H); 1150 (s, 1H).

136

Preparation of (S)-2-(2-oxo-4-(1-(2,3,5,6-tetrafluorophenyl)propan-2-ylamino)-1,2-dihydropyridin-3-yl)-6-(2-(pyrrolidin-1-yl)ethyl)-6,7-dihydroimidazo[4,5-f]isoindol-5(1H)-one

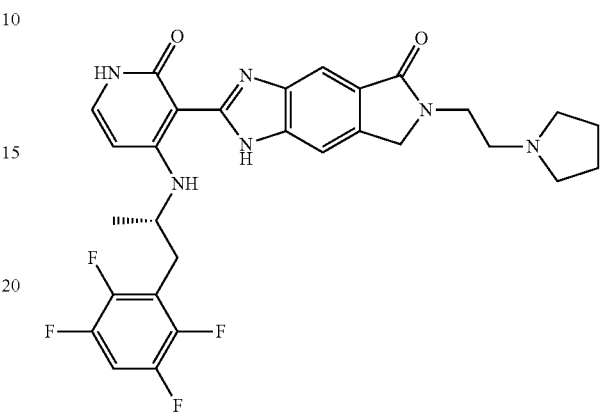

LCMS: 569 (M+1).

$^1$H NMR (300 MHz, DMSO-d$_6$): δ 1.32 (d, J=3.0 Hz, 3H); 1.67 (br.s, 4H); 2.65-2.69 (m, 22.85-3.11 (m, 2H); 3.39-3.51 (m, 4H); 3.63-3.69 (m, 2H); 3.98-4.05 (m, 1H); 4.55 (s, 2H); 6.20 (d, J=6.0 Hz, 2H); 7.15-7.99 (m, 4H); 11.10 (m, 2H); 13.50 (s, 1H).

Preparation of (S)-2-(4-(1-(3,5-difluoro-2-methylphenyl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

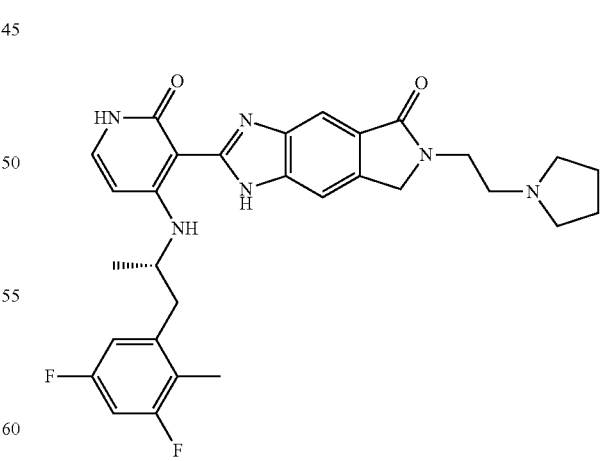

LCMS: 547 (M+1).

$^1$H NMR (300 MHz, DMSO-d$_6$): δ 1.23 (d, J=3.0 Hz, 3H); 1.67 (br.s, 4H); 2.00 (m, 3H); 2.50 (s, 3H); 2.60-2.70 (m, 2H); 2.76-2.83 (m, 1H); 2.86-3.07 (m, 3H); 3.62-3.64 (m, 2H);

4.02-4.20 (m, 1H); 4.53 (s, 2H); 6.13 (d, J=6.0 Hz, 1H); 6.90-7.40 (m, 5H); 11.20 (2 br.s, 2H); 13.00 (s, 1H).

Preparation of 5,6-diamino-4-methyl-2-(2-(pyrrolidin-1-yl)ethyl)isoindoline-1,3-dione

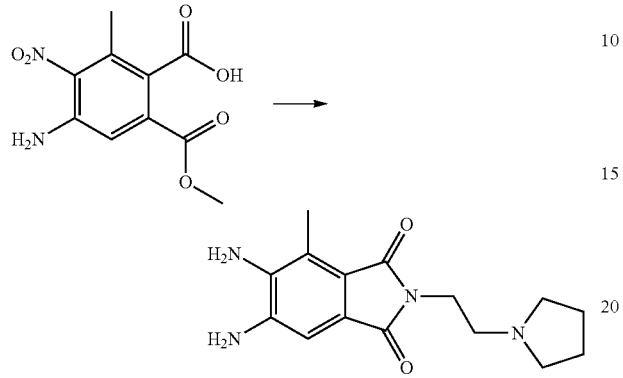

To a solution of 4-amino-6-(methoxycarbonyl)-2-methyl-3-nitrobenzoic acid (380 mg, 1.0 mmol), HATU (114 mg, 1.0 mmol) and DIPEA (129 mg, 1.0 mmol) in THF (20 mL) was added 2-(pyrrolidin-1-yl)ethanamine (114 mg, 1.0 mmol) and stirred at RT for overnight. The reaction mixture was evaporated in vacuo and the residue was triturated with MeOH (10 mL). The yellow precipitate was isolated by filtration and dried to afford the title compound (300 mg) as a yellow solid.

The above residue was further treated with 10% Pd/C, $H_2$ in MeOH at RT to afford 5,6-diamino-4-methyl-2-(2-(pyrrolidin-1-yl)ethyl)isoindoline-1,3-dione (quantitative) as a yellow solid. LCMS: 289 (M+1).

Preparation of (S)-2-(4-(1-(5-fluoro-2-methylphenyl)propan-2-ylamino)-2-oxo-1,2-dihydropyridin-3-yl)-4-methyl-6-(2-(pyrrolidin-1-yl)ethyl)-6,7-dihydroimidazo[4,5-f]isoindol-5(1H)-one

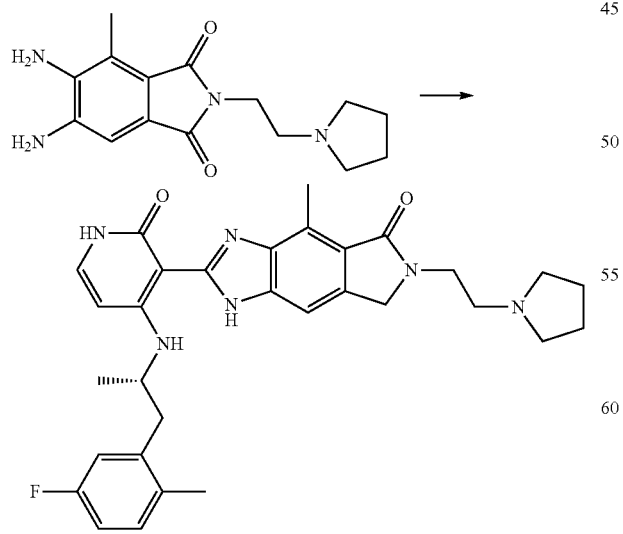

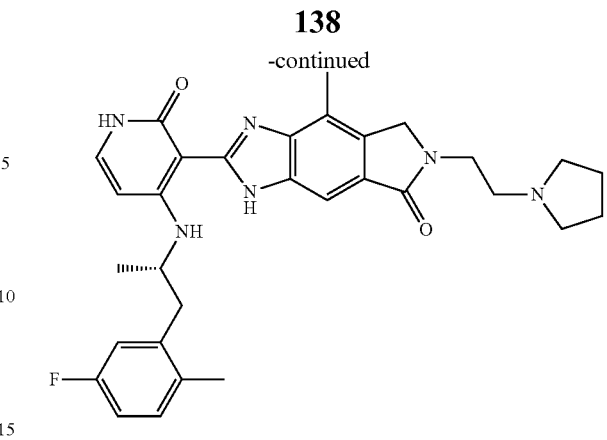

LCMS: 543 (M+1). Two isomers in 8:2 ratio and were not separable by HPLC and column chromatography.

Preparation of (S)-2-(4-(1-(5-fluoro-2-methylphenyl)propan-2-ylamino)-2-oxo-1,2-dihydropyridin-3-yl)-6-(2-morpholinoethyl)-6,7-dihydroimidazo[4,5-f]isoindol-5(1H)-one

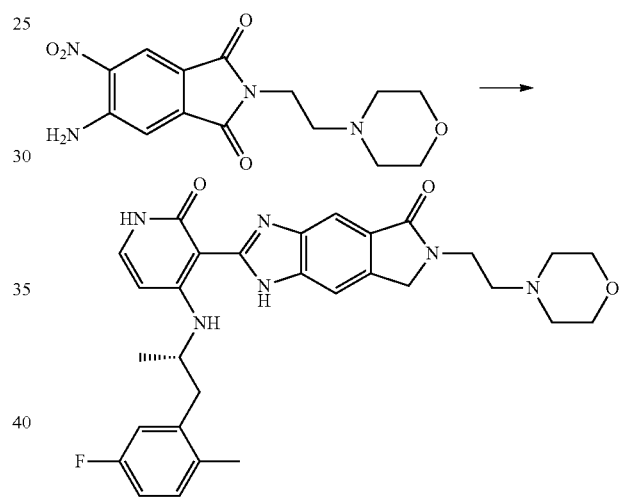

LCMS: 545 (M+1).

Preparation of (S)-6-(2-morpholinoethyl)-2-(2-oxo-4-(1-(2,3,5-trifluorophenyl)propan-2-ylamino)-1,2-dihydropyridin-3-yl)-6,7-dihydroimidazo[4,5-f]isoindol-5(1H)-one

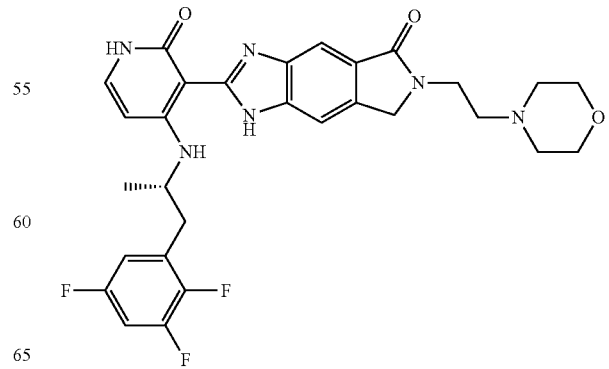

LCMS: 567 (M+1). ¹H NMR (300 MHz, DMSO-d₆): δ 1.37 (d, J=3.0 Hz, 3H); 2.30-2.60 (m, 4H); 2.90-3.12 (m, 2H); 3.35 (br.s, 4H); 3.50-3.74 (m, 4H); 4.10-4.25 (m, 1H); 4.56 (s, 2H); 6.16 (d, J=5.5 Hz, 1H); 6.94-7.03 (m, 1H); 7.25-7.34 (m, 2H); 7.61-7.98 (m, 2H); 11.06-11.28 (m, 2H); 13.10 (s, 1H).

Preparation of (S)-2-(4-(1-(2-methyl-5-(trifluoromethyl)phenyl)propan-2-ylamino)-2-oxo-1,2-dihydropyridin-3-yl)-6-(2-morpholinoethyl)-6,7-dihydroimidazo[4,5-f]isoindol-5(1H)-one

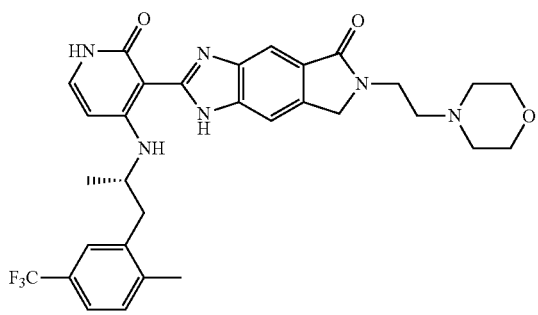 [SMILES: Cc1ccc(C(F)(F)F)cc1C[C@H](C)Nc1cc[nH]c(=O)c1-c1nc2cc3c(cc2[nH]1)CN(CCN1CCOCC1)C3=O]

LCMS: 595 (M+1).

Preparation of 1,5-Difluoro-2-methyl-3-nitrobenzene

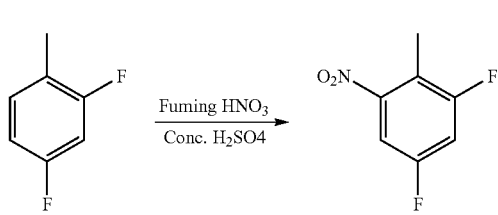

To a stirred solution of 2,4-difluorotoluene (25.0 g, 195.3 mmol) in conc. H₂SO₄ (60 mL) was added fuming HNO₃ (30 mL) drop wise at the rate that temperature was maintained between 40-50° C. over a period of 1.5 h. The reaction mixture was stirred at 40° C. for an additional 1 h. The reaction mixture was poured into ice-cold water (500 mL) and the solid precipitated was filtered and washed with water (2×50 mL). The solid residue was dissolved in EtOAc (200 mL), washed with aq. NaHCO₃ (2×200 mL). The organic layer was dried over Na₂SO₄, filtered and evaporated in vacuo to afford 1,5-difluoro-2-methyl-3-nitrobenzene (21.0 g, 62%) as a light brown liquid.

¹H MNR (CDCl₃, 300 MHz): δ 2.45 (s, 3H); 6.99 (dd, J=6.0 Hz, 1H); 8.00 (dd, J=6.0 Hz, 1H).

Preparation of 3,5-difluoro-2-methylbenzenamine

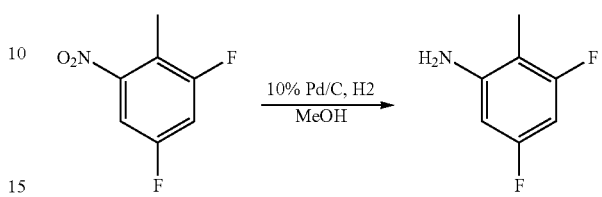

To a suspension of 1,5-difluoro-2-methyl-3-nitrobenzene (21.0 g, 121.4 mmol) and 10% Pd/C (2.0 g) was added MeOH (200 mL) carefully and the flask was evacuated. The reaction mixture was flushed with hydrogen under balloon pressure and stirred at RT for 2 h. The reaction mixture was filtered through Celite bed and evaporated in vacuo to afford 3,5-difluoro-2-methylbenzenamine (18.0 g, 97%) as a dark yellow liquid.

¹H MNR (CDCl₃, 300 MHz): δ 2.25 (s, 3H); 3.49 (br.s, 2H); 6.57 (t, J=9.0 Hz, 1H); 6.71 (t, J=9.0 Hz, 1H).

Preparation of 1,5-difluoro-3-iodo-2-methylbenzene

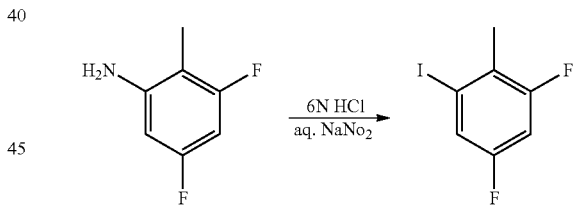

To cold solution of 6N aq. HCl (200 mL) was added 3,5-difluoro-2-methylbenzenamine (11.0 g, 77.0 mmol) in portions and stirred for 10 min. The solution of aq. NaNO₂ (6.37 g in 50 mL of water) wadded drop wise at 0° C. for 20 min. and the resulting mixture was stirred for an additional 30 min. The solution of KI (93.20 mmol) in water was added drop wise at 0° C. and stirred for 1 h. The reaction mixture was extracted with ether (2×100 mL) and washed with aq. solution of Na₂S₂O₃ (2×100 mL). The organic layer was washed with brine (50 mL), dried over Na₂SO₄, filtered and dried to afford 1,5-difluoro-3-iodo-2-methylbenzene (9.0 g, 46%) as a brown liquid.

¹H MNR (CDCl₃, 300 MHz): δ 2.28 (s, 3H); 6.77 (dd, J=6.0 Hz, J=9.0 Hz, 1H); 7.56 (dd, J=6.0 Hz, J=9.0 Hz, 1H).

141

Preparation of 6-(2-((R)-2-methylpyrrolidin-1-yl)ethyl)-2-(2-oxo-4-((S)-1-(2,3,5-trifluorophenyl)propan-2-ylamino)-1,2-dihydropyridin-3-yl)-6,7-dihydroimidazo[4,5-f]isoindol-5(1H)-one

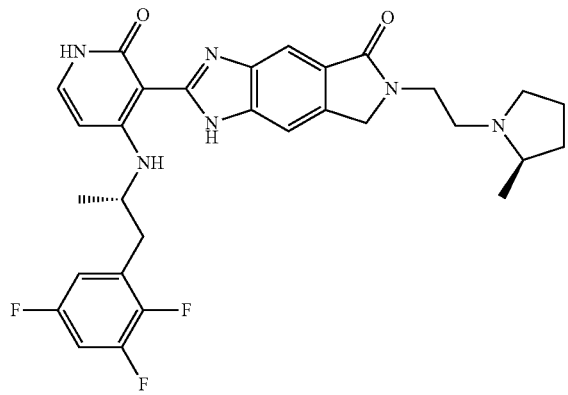 [SMILES: C[C@@H]1CCCN1CCN1Cc2cc3[nH]c(-c4c(N[C@@H](C)Cc5cc(F)cc(F)c5F)cc[nH]c4=O)nc3cc2C1=O]

LCMS: 565 (M+1).

Preparation of (S)-6-(2-(3,3-difluoropyrrolidin-1-yl)ethyl)-2-(4-(1-(5-fluoro-2-methylphenyl)propan-2-ylamino)-2-oxo-1,2-dihydropyridin-3-yl)-6,7-dihydroimidazo[4,5-f]isoindol-5(1H)-one

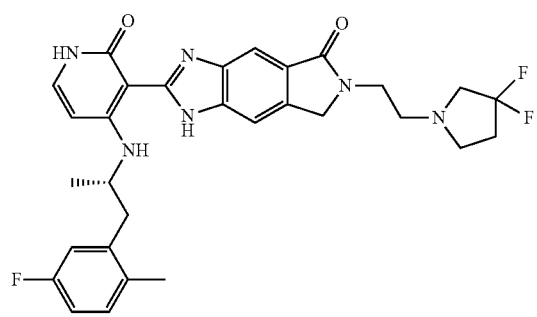 [SMILES: Cc1ccc(F)cc1C[C@H](C)Nc1cc[nH]c(=O)c1-c1nc2cc3c(cc2[nH]1)CN(CCN1CCC(F)(F)C1)C3=O]

LCMS: 565 (M+1).

142

Preparation of (')-2-(4-(1-(5-fluoro-2-methylphenyl)propan-2-ylamino)-2-oxo-1,2-dihydropyridin-3-yl)-6-(2-(methylamino)ethyl)-6,7-dihydroimidazo[4,5-f]isoindol-5(1H)-one

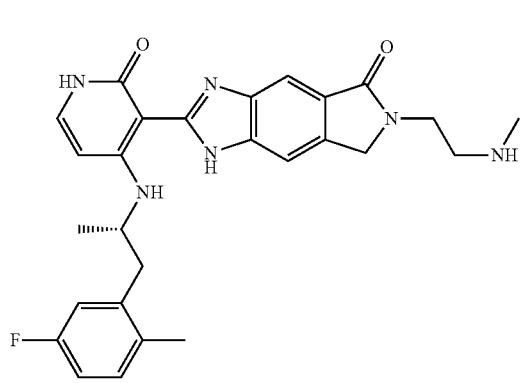 [SMILES: CNCCN1Cc2cc3[nH]c(-c4c(N[C@@H](C)Cc5cc(F)ccc5C)cc[nH]c4=O)nc3cc2C1=O]

LCMS: 489 (M+1).

Chlorinated Compounds

General Structure 1

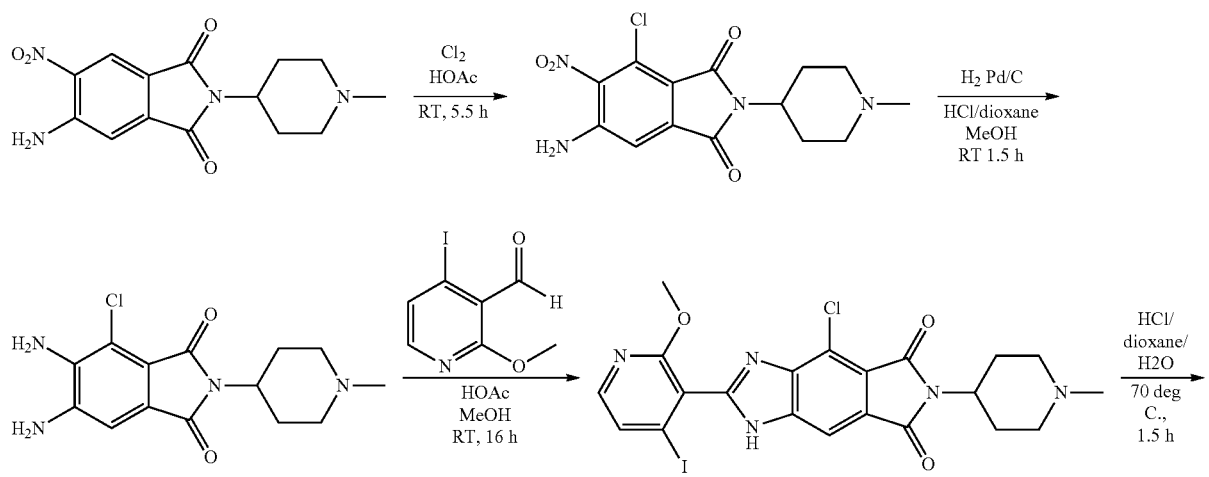

R1 = R2 = H
or R1, R2 = O

Scheme 10

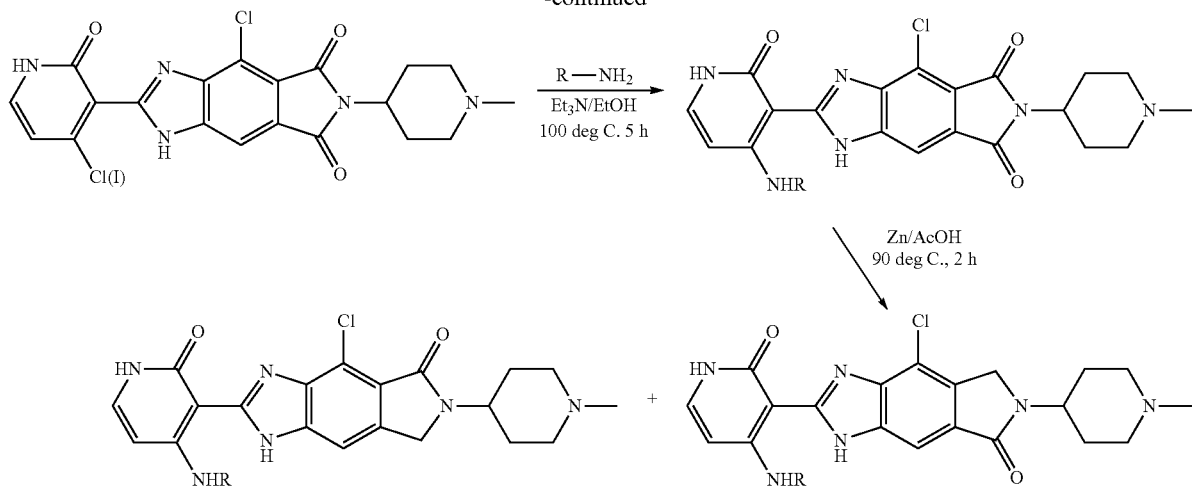

5-Amino-4-chloro-2-(1-methyl-piperidin-4-yl)-6-nitro-isoindole-1,3-dione: A suspension of 5-amino-2-(1-methyl-piperidin-4-yl)-6-nitro-isoindole-1,3-dione (3.04 g, 10 mmol) in HOAc (100 mL) was bubbled with $Cl_2$ gas for 5.5 h and evaporated to dryness. The residue was diluted with aqueous MeOH (25 mL, 80%) and basified with aqueous $NH_4OH$ solution (28%) resulting a solution to which $NaHSO_3$ (10.4 g, 100 mmol) was added. The mixture was sonicated for 30 min and loaded on silica gel. Chromatography of the mixture with mixed solvent of $CH_2Cl_2$/MeOH/28% aqueous $NH_4OH$ (20:10:1) afforded the title compound which is not pure, but was used for the next step reaction directly without further purification.

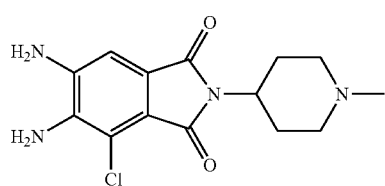 [SMILES: CN1CCC(N2C(=O)c3cc(N)c(N)c(Cl)c3C2=O)CC1]

5,6-Diamino-4-chloro-2-(1-methyl-piperidin-4-yl)-isoindole-1,3-dione: To a mixture of 5-amino-4-chloro-2-(1-methyl-piperidin-4-yl)-6-nitro-isoindole-1,3-dione (1.35 g, not pure) and 10% Pd/C (500 mg) was added 2-propanol (20 mL), HCl in dioxane (4 M, 0.1 mL) and then MeOH (230 mL). After it was stirred under atmospheric hydrogen for 1.5 h, the reaction mixture was filtered over Celite. The filtrate was concentrated, diluted with 50% DCM in MeOH, basified with aqueous $NH_4OH$ solution (28%) and evaporated. Chromatography of the mixture with mixed solvent of $CH_2Cl_2$/MeOH/28% aqueous $NH_4OH$ (50:10:1) afforded the title compound (186 mg, 6% for 2 steps). $^1$H NMR (DMSO-$d_6$) δ 1.51 (m, 2H), 1.90 (m, 2H), 2.29 (m, 2H), 2.81 (m, 2H), 3.80 (m, 1H), 5.61 (br s, 2H, $NH_2$), 5.93 (br s, 2H, $NH_2$), 6.82 (s, 1H, ArH); ESI-MS m/z 309.4 (MH$^+$).

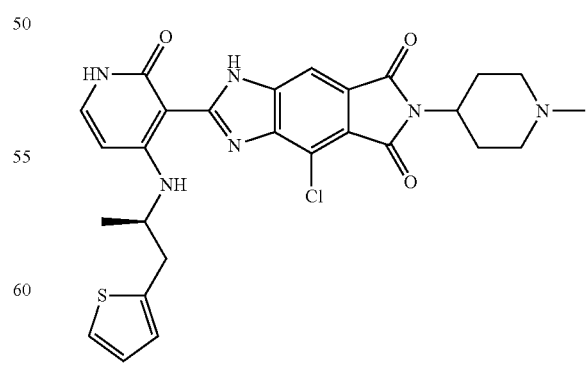

4-Chloro-2-(4-chloro-2-oxo-1,2-dihydro-pyridin-3-yl)-6-(1-methyl-piperidin-4-yl)-1H-1,3,6-triaza-s-indacene-5,7-dione: A solution of 5,6-diamino-4-chloro-2-(1-methyl-piperidin-4-yl)-isoindole-1,3-dione (62.0 mg, 0.2 mmol), 4-iodo-2-methoxynicotinic aldehyde (34.3 mg, 0.2 mmol) and HOAc (1 mL) in MeOH was stirred at the room temperature for 14 h, heated at 80° C. for 4.5 h, and concentrated to result a residue which was then mixed with HCl in dioxane (4 M, 10 mL) and H2O (0.8 mL) and heated for 1.7 h at 70° C. for 1.5 h. The reaction mixture was evaporated, diluted with diluted with a mixed solvent of DCM/MeOH (1:5), basified with aqueous $NH_4OH$ solution (28%) and evaporated. Chromatography of the residue with mixed solvent of $CH_2Cl_2$/MeOH/28% aqueous $NH_4OH$ (40:10:1) afforded the title compound (70.2 mg, 78% for 2 steps). ESI-MS m/z 446.5 (MH$^+$).

4-Chloro-6-(1-methyl-piperidin-4-yl)-2-[4-(1-methyl-2-thiophen-2-yl-ethylamino)-2-oxo-1,2-dihydro-pyridin-3-yl]-1H-1,3,6-triaza-s-indacene-5,7-dione: 4-Chloro-2-{4-[3-

(2,4-dimethyl-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione (18 mg, 0.04 mmol), 1-methyl-2-thiophen-2-yl-ethylamine (8.5 mg, 0.06 mmol) and Et$_3$N (0.2 mL, 1.43 mmol) in EtOH (1.0 mL) was heated at 80° C. for 17 h and then concentrated to result a residue which was subjected to HPLC purification to furnish the title compound in TFA salt form (6.73 mg, 25%). $^1$H NMR (DMSO-d$_6$) δ 1.36 (d, J=6 Hz, 3H, CH$_3$), 1.95 (m, 2H), 2.52 (m, 2H), 2.74 (s, 3H, CH$_3$), 3.02-3.22 (4H), 3.45 (m, 2H), 4.08 (m, 1H), 4.28 (m, 1H), 6.19 (d, J=8 Hz, 1H), 6.89 (m, 1H), 7.00 (m, 1H), 7.29 (m, 1H), 7.39 (m, 1H), 8.09 (s, 1H), 11.01 (d, J=8 Hz, 1H), 11.35 (d, J=6 Hz, 1H); ESI-MS m/z 551.3 (MH$^+$).

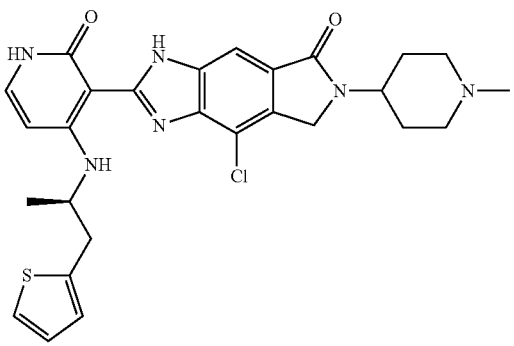 [SMILES: C[C@H](Cc1cccs1)Nc1cc[nH]c(=O)c1-c1nc2c(Cl)c3c(cc2[nH]1)C(=O)N(C1CCN(C)CC1)C3]

8-Chloro-6-(1-methyl-piperidin-4-yl)-2-[4-(1-methyl-2-thiophen-2-yl-ethylamino)-2-oxo-1,2-dihydro-pyridin-3-yl]-6,7-dihydro-3H-1,3,6-triaza-s-indacen-5-one: 4-Chloro-6-(1-methyl-piperidin-4-yl)-2-[4-(1-methyl-2-thiophen-2-yl-ethylamino)-2-oxo-1,2-dihydro-pyridin-3-yl]-1H-1,3,6-triaza-s-indacene-5,7-dione (49 mg, 0.089 mmol) was mixed with zinc dust (196 mg, 1.0 mmol) in HOAc (10 mL). After it was heated at 90° C. for 40 min, the reaction mixture was cooled to 50° C. and diluted with a mixed solvent of MeOH:DCM (45 mL/5 mL) and filtered. The filtrate was evaporated at 95° C. (the bath temperature) under reduced pressure to dryness. The residue was diluted with a mixed solvent of DCM/MeOH (1:5) and basified with 28% aqueous NH$_4$OH solution and concentrated. Chromatography of the residual crude with a mixed solvent of CH$_3$CN/CH$_2$Cl$_2$/MeOH/28% aqueous NH$_4$OH (63:10:37:1) followed by HPLC re-purification afforded the title compound in TFA salt form (6.2 mg, 11%). $^1$H NMR (DMSO-d$_6$) δ 1.37 (d, J=6 Hz, 3H, CH$_3$), 1.95-2.13 (4H), 2.52 (m, 2H), 2.80 (s, 3H, CH$_3$), 3.15 (m, 2H), 3.50-3.65 (4H), 4.05 (m, 1H), 4.31 (m, 1H), 4.50 (br s, 2H), 6.18 (d, J=8 Hz, 1H), 6.89 (m, 1H), 7.01 (m, 1H), 7.29 (m, 1H), 7.37 (m, 1H), 7.99 (s, 1H), 9.60 (br s, 1H), 11.22 (d, J=6 Hz, 1H), 11.30 (d, J=6 Hz, 1H); ESI-MS m/z 537.3 (MH$^+$).

General Structure 2

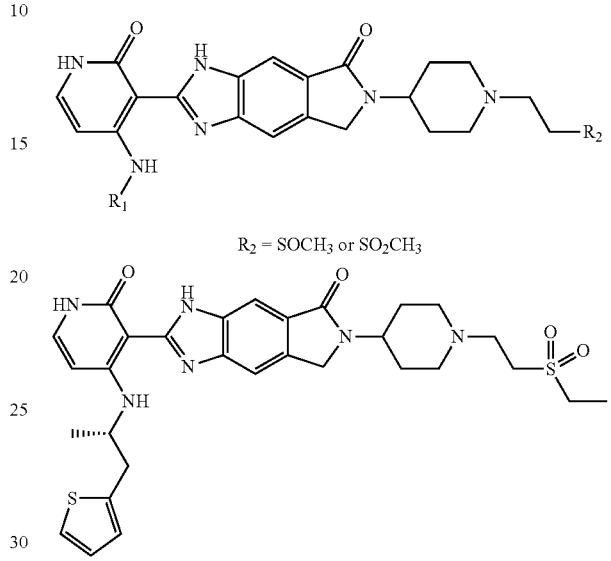

R$_2$ = SOCH$_3$ or SO$_2$CH$_3$ (S)-6-[1-(2-Ethanesulfonyl-ethyl)-piperidin-4-yl]-2-[4-(1-methyl-2-thiophen-2-yl-ethylamino)-2-oxo-1,2-dihydro-pyridin-3-yl]-6,7-dihydro-3H-1,3,6-triaza-s-indacen-5-one: $^1$H NMR (DMSO-d$_6$) δ 1.22 (t, J=6 Hz, 3H, CH$_3$), 1.34 (d, J=6 Hz, 3H, CH$_3$), 1.70-1.82 (4H), 2.12 (m, 2H), 2.73 (m, 2H), 3.02 (m, 2H), 3.12-3.22 (4H), 3.28 (m, 2H), 3.35 (s, 3H, CH$_3$), 4.05 (m, 2H), 4.49 (s, 2H), 6.16 (d, J=6 Hz, 1H), 6.95 (m, 1H), 7.05 (s, 1H), 7.30-7.38 (2H), 7.66 (s, 0.5H), 7.81 (s, 0.5H), 7.82 (s, 0.5H), 7.96 (s, 0.5H), 11.15 (br m, 1H, NH), 11.20 (br m, 1H, NH); ESI-MS m/z 609.7 (MH$^+$).

The synthesis of (S)-6-[1-(2-Ethanesulfonyl-ethyl)-piperidin-4-yl]-2-[4-(1-methyl-2-thiophen-2-yl-ethylamino)-2-oxo-1,2-dihydro-pyridin-3-yl]-6,7-dihydro-3H-1,3,6-triaza-s-indacen-5-one has been accomplished by a general methodology outlined in: WO 2008021369.

Example 2

SAR TABLE 1

| Structure | ALK IC50 | IGF1R IC50 | IRK IC50 | TRKA IC50 |
|---|---|---|---|---|
| 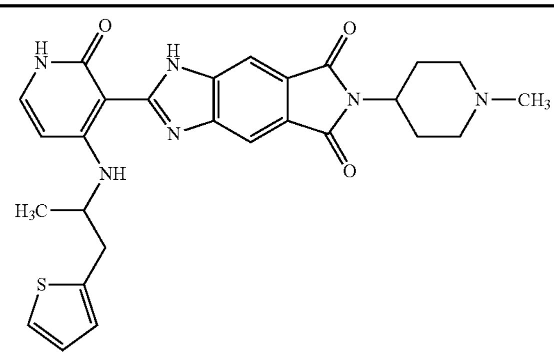 | + | − | − | NT |

SAR TABLE 1
| Structure | | ALK IC50 | IGF1R IC50 | IRK IC50 | TRKA IC50 |
|---|---|---|---|---|---|
| 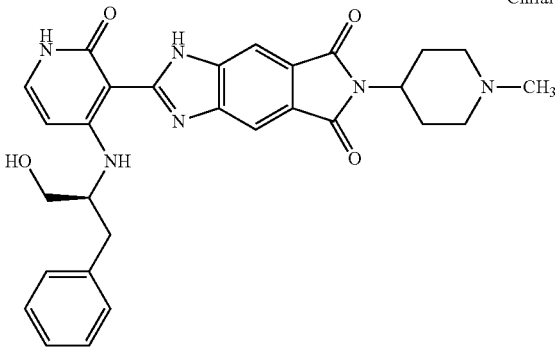 | Chiral | − | NT | NT | NT |
| 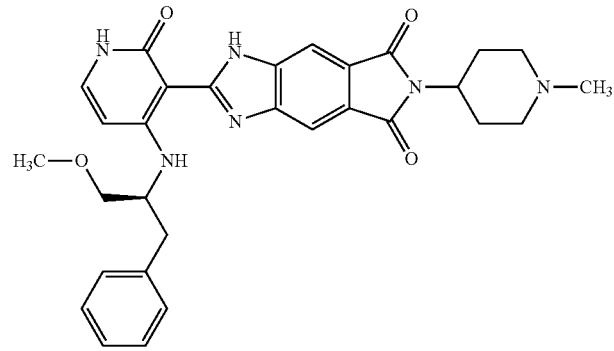 | | − | NT | NT | NT |
| 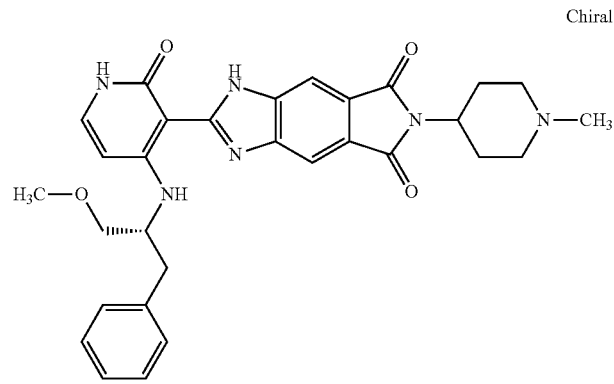 | Chiral | − | NT | NT | NT |
| 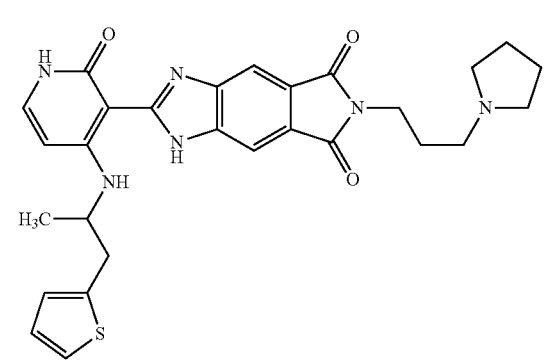 [SMILES: CC(Cc1cccs1)Nc1cc[nH]c(=O)c1-c1nc2cc3c(cc2[nH]1)C(=O)N(CCCN1CCCC1)C3=O] | | ++ | − | − | NT |

SAR TABLE 1

| Structure | ALK IC50 | IGF1R IC50 | IRK IC50 | TRKA IC50 |
| --- | --- | --- | --- | --- |
| | ++ | + | NT | NT |
| | ++ | NT | NT | NT |
| | + | + | NT | NT |
| | + | NT | NT | NT |
| 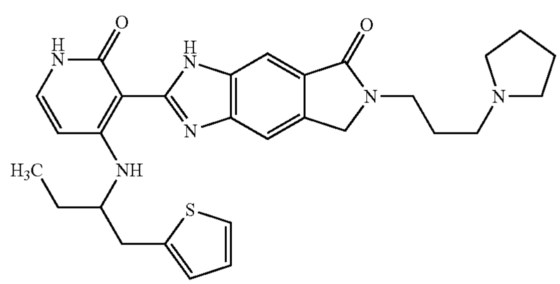 [SMILES: CCC(Cc1cccs1)Nc1cc[nH]c(=O)c1-c1nc2cc3c(cc2[nH]1)C(=O)N(CCCN1CCCC1)C3] | − | NT | NT | NT |

-continued

SAR TABLE 1

| Structure | ALK IC50 | IGF1R IC50 | IRK IC50 | TRKA IC50 |
|---|---|---|---|---|
| | − | − | NT | NT |
| | − | − | NT | NT |
| | − | − | − | NT |
| | − | − | + | NT |

-continued

SAR TABLE 1

| Structure | ALK IC50 | IGF1R IC50 | IRK IC50 | TRKA IC50 |
|---|---|---|---|---|
| | – | – | – | NT |
| | ++ | + | ++ | NT |
| | ++ | +++ | NT | NT |
| | – | + | NT | NT |

SAR TABLE 1 -continued

| Structure | ALK IC50 | IGF1R IC50 | IRK IC50 | TRKA IC50 |
|---|---|---|---|---|
| (structure with Cl-substituted benzimidazole-isoindolinone, N-methylpiperidine, and thiophene-methyl-amine) | + | ++ | NT | NT |
| (structure with pyrrolidinylpropyl isoindolinone and 5-methylthiophene-methyl-amine) | − | ++ | NT | NT |
| (structure with pyrrolidinylpropyl isoindolinone and 2-fluorobenzyl-methyl-amine) | ++ | ++ | − | NT |
| (structure with pyrrolidinylpropyl isoindolinone and 4-methylthiazol-2-yl-methyl-amine) | ++ | ++ | NT | NT |
| (structure with pyrrolidinylpropyl isoindolinone and 4-methylthiophen-2-yl-methyl-amine) | + | + | NT | NT |

-continued
| SAR TABLE 1 | | | | |
|---|---|---|---|---|
| Structure | ALK IC50 | IGF1R IC50 | IRK IC50 | TRKA IC50 |
| 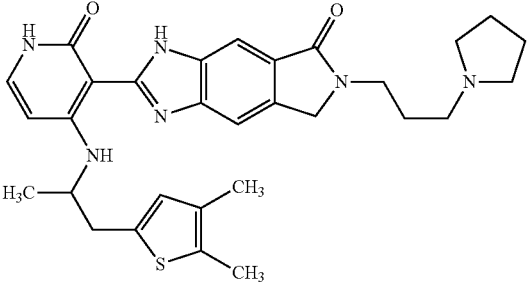 [SMILES: Cc1cc(CC(C)Nc2cc[nH]c(=O)c2-c2nc3cc4c(cc3[nH]2)C(=O)N(CCCN2CCCC2)C4)sc1C] | − | + | NT | NT |
| 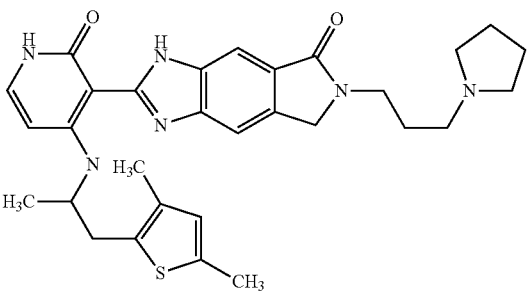 [SMILES: Cc1cc(C)c(CC(C)Nc2cc[nH]c(=O)c2-c2nc3cc4c(cc3[nH]2)C(=O)N(CCCN2CCCC2)C4)s1] | − | ++ | NT | NT |
| 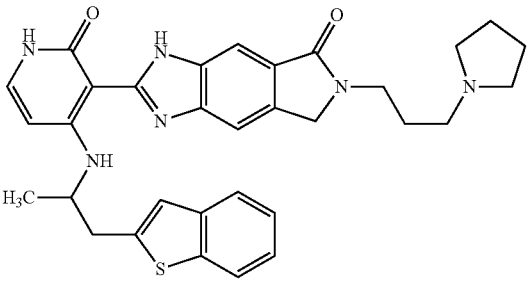 [SMILES: CC(Cc1cc2ccccc2s1)Nc1cc[nH]c(=O)c1-c1nc2cc3c(cc2[nH]1)C(=O)N(CCCN1CCCC1)C3] | − | − | NT | NT |
| 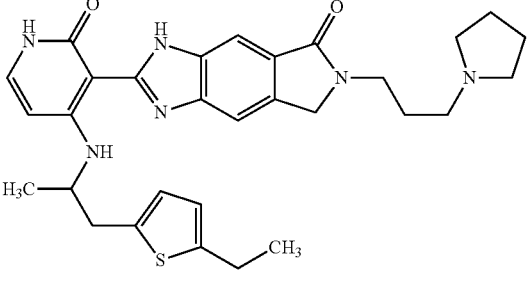 [SMILES: CCc1ccc(CC(C)Nc2cc[nH]c(=O)c2-c2nc3cc4c(cc3[nH]2)C(=O)N(CCCN2CCCC2)C4)s1] | − | − | NT | NT |
| 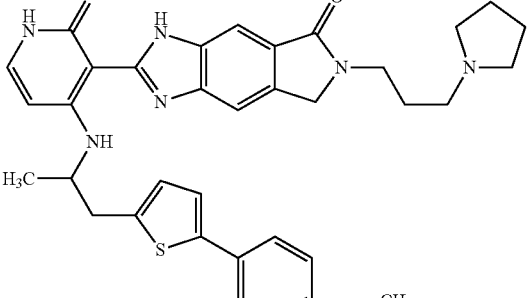 | − | − | NT | NT |

SAR TABLE 1
| Structure | ALK IC50 | IGF1R IC50 | IRK IC50 | TRKA IC50 |
|---|---|---|---|---|
| 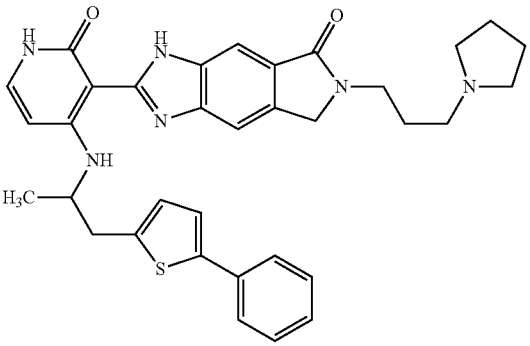 [SMILES: CC(Cc1ccc(-c2ccccc2)s1)Nc1cc[nH]c(=O)c1-c1nc2cc3c(cc2[nH]1)C(=O)N(CCCN1CCCC1)C3] | − | − | NT | NT |
| 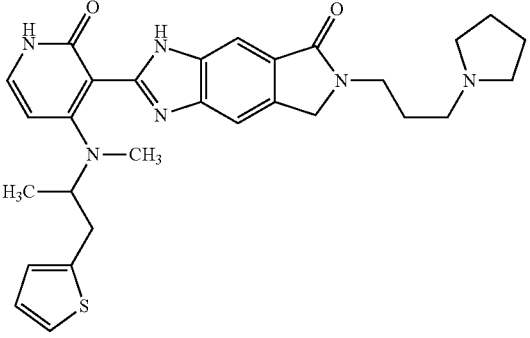 [SMILES: CC(Cc1cccs1)N(C)c1cc[nH]c(=O)c1-c1nc2cc3c(cc2[nH]1)C(=O)N(CCCN1CCCC1)C3] | − | − | − | NT |
| 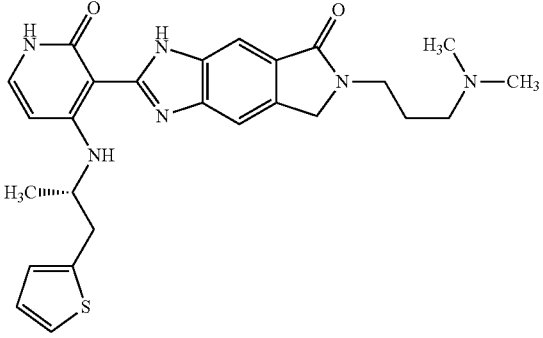 [SMILES: C[C@@H](Cc1cccs1)Nc1cc[nH]c(=O)c1-c1nc2cc3c(cc2[nH]1)C(=O)N(CCCN(C)C)C3] | ++ | + | ++ | NT |
| 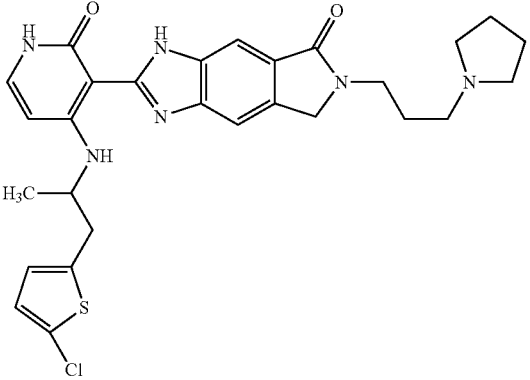 [SMILES: CC(Cc1ccc(Cl)s1)Nc1cc[nH]c(=O)c1-c1nc2cc3c(cc2[nH]1)C(=O)N(CCCN1CCCC1)C3] | + | + | NT | NT |

SAR TABLE 1
| Structure | ALK IC50 | IGF1R IC50 | IRK IC50 | TRKA IC50 |
|---|---|---|---|---|
| 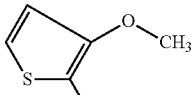 | + | + | NT | NT |
| Chiral  | ++ | + | NT | NT |
| Chiral 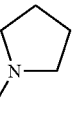 | ++ | + | NT | NT |
| Chiral  | + | + | ++ | NT |

SAR TABLE 1
| Structure | ALK IC50 | IGF1R IC50 | IRK IC50 | TRKA IC50 |
|---|---|---|---|---|
| 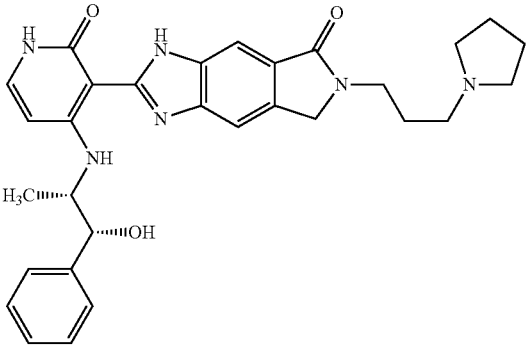 | ++ | + | + | NT |
| 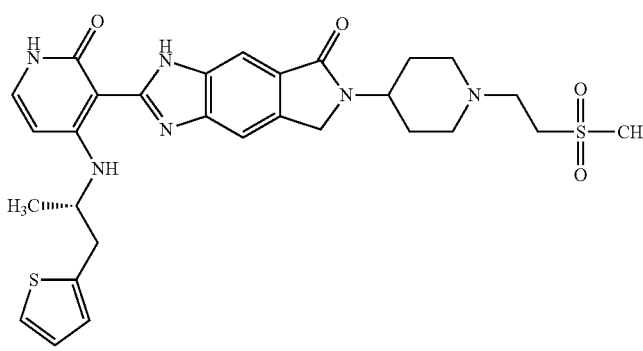 [SMILES: C[C@@H](Cc1cccs1)Nc1cc[nH]c(=O)c1-c1nc2cc3c(cc2[nH]1)C(=O)N(C1CCN(CCS(C)(=O)=O)CC1)C3] | ++ | ++ | + | NT |
| 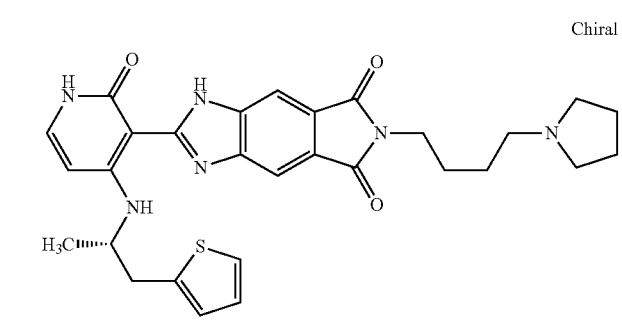 [SMILES: C[C@@H](Cc1cccs1)Nc1cc[nH]c(=O)c1-c1nc2cc3c(cc2[nH]1)C(=O)N(CCCCN1CCCC1)C3=O] | NT | NT | NT | NT |
| 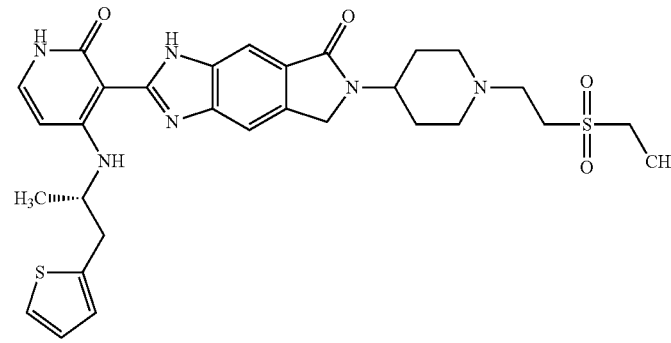 [SMILES: CCS(=O)(=O)CCN1CCC(N2Cc3cc4nc(-c5c(N[C@@H](C)Cc6cccs6)cc[nH]c5=O)[nH]c4cc3C2=O)CC1] | ++ | + | ++ | NT |

-continued

SAR TABLE 1

| Structure | ALK IC50 | IGF1R IC50 | IRK IC50 | TRKA IC50 |
|---|---|---|---|---|
| Chiral structure | ++ | − | NT | NT |
| Structure | ++ | − | NT | NT |
| Structure | +++ | + | +++ | NT |
| Chiral structure | +++ | + | NT | NT |

SAR TABLE 1
| Structure | ALK IC50 | IGF1R IC50 | IRK IC50 | TRKA IC50 |
|---|---|---|---|---|
| 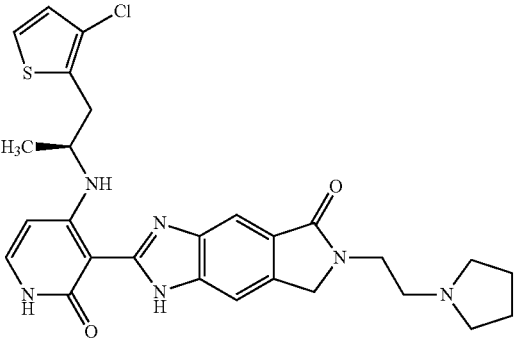 [SMILES: C[C@@H](Cc1sccc1Cl)Nc1cc[nH]c(=O)c1-c1nc2cc3c(cc2[nH]1)CN(CCN1CCCC1)C3=O] | +++ | ++ | ++ | NT |
| 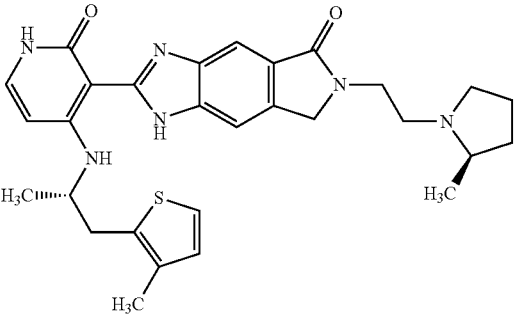 Chiral | +++ | + | ++ | NT |
| 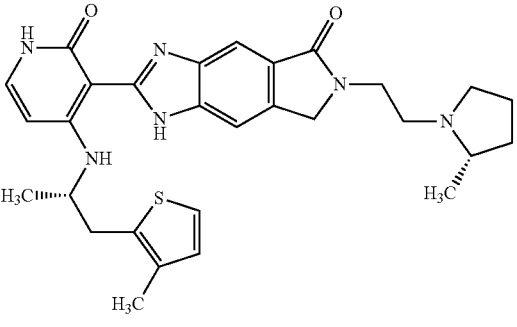 Chiral | ++ | + | NT | NT |
| 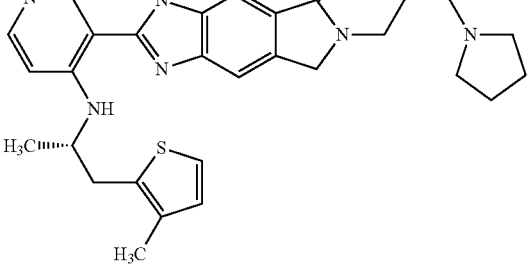 | +++ | + | NT | NT |

-continued
SAR TABLE 1
| Structure | ALK IC50 | IGF1R IC50 | IRK IC50 | TRKA IC50 |
|---|---|---|---|---|
| Chiral 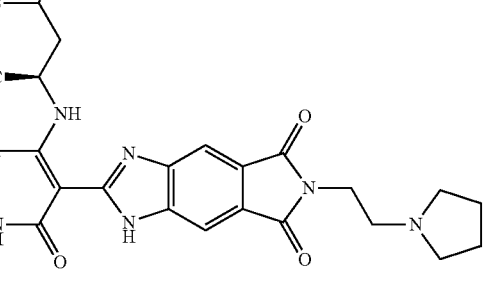 | ++ | + | NT | NT |
| Chiral 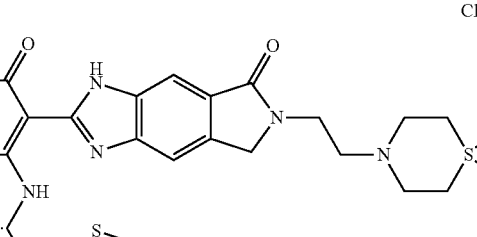 | ++ | + | NT | NT |
| 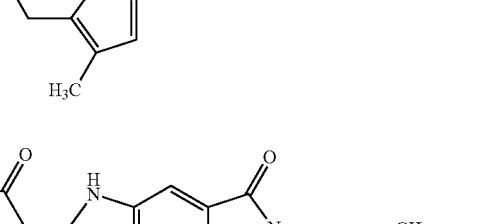 | ++ | − | NT | NT |
| 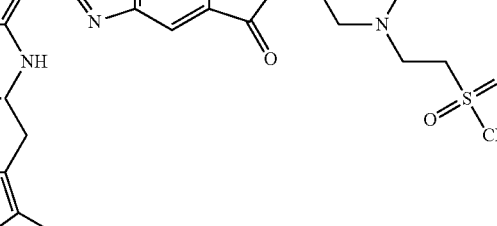 | +++ | + | NT | NT |

SAR TABLE 1
| Structure | ALK IC50 | IGF1R IC50 | IRK IC50 | TRKA IC50 |
|---|---|---|---|---|
| Chiral 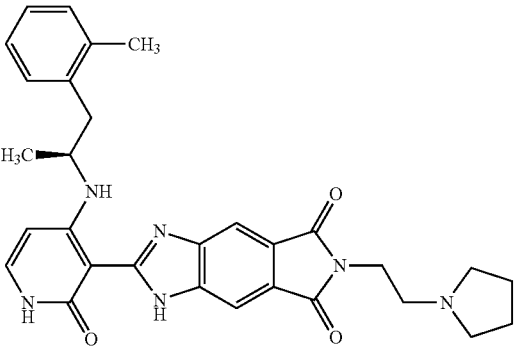 | +++ | − | NT | NT |
| 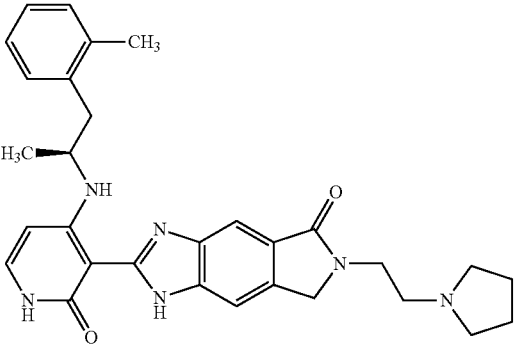 [SMILES: Cc1ccccc1C[C@H](C)Nc1cc[nH]c(=O)c1-c1nc2cc3c(cc2[nH]1)CN(CCN1CCCC1)C3=O] | +++ | + | NT | NT |
| 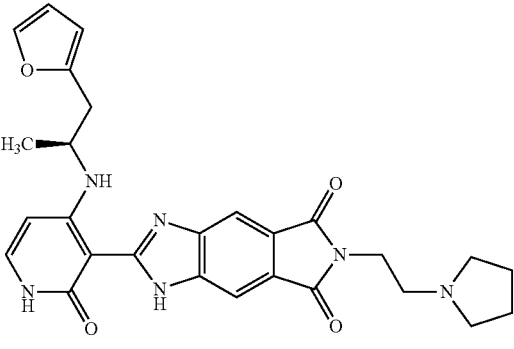 [SMILES: C[C@@H](Cc1ccco1)Nc1cc[nH]c(=O)c1-c1nc2cc3c(cc2[nH]1)C(=O)N(CCN1CCCC1)C3=O] | ++ | − | NT | NT |
| 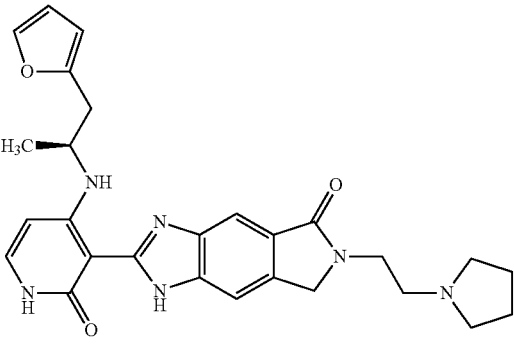 [SMILES: C[C@@H](Cc1ccco1)Nc1cc[nH]c(=O)c1-c1nc2cc3c(cc2[nH]1)CN(CCN1CCCC1)C3=O] | ++ | + | NT | NT |

-continued

SAR TABLE 1

| Structure | ALK IC50 | IGF1R IC50 | IRK IC50 | TRKA IC50 |
|---|---|---|---|---|
| Chiral | ++ | + | NT | NT |
| Chiral | +++ | ++ | NT | NT |
|  | +++ | − | − | ++++ |
| 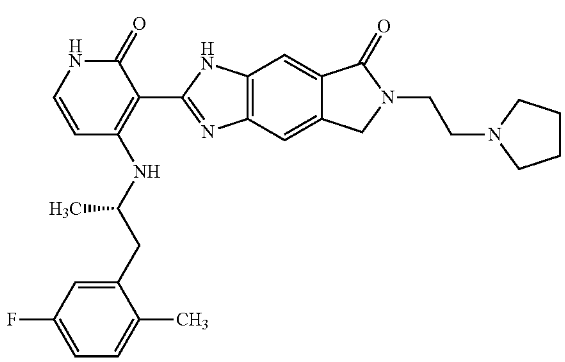 [SMILES: Cc1ccc(F)cc1C[C@H](C)Nc1cc[nH]c(=O)c1-c1nc2cc3c(cc2[nH]1)C(=O)N(CCN1CCCC1)C3] | ++++ | ++ | ++ | ++++ |

SAR TABLE 1 -continued
| Structure | ALK IC50 | IGF1R IC50 | IRK IC50 | TRKA IC50 |
|---|---|---|---|---|
| 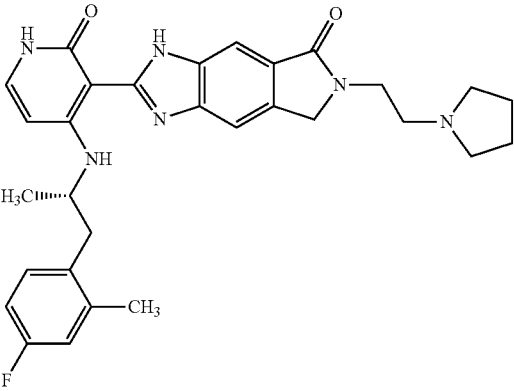 [SMILES: Cc1cc(F)ccc1C[C@H](C)Nc1cc[nH]c(=O)c1-c1nc2cc3c(cc2[nH]1)C(=O)N(CCN1CCCC1)C3] | +++ | − | + | NT |
| 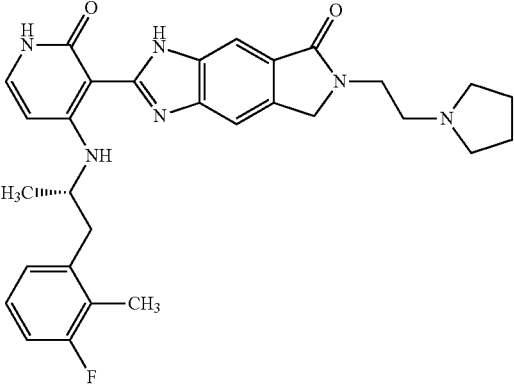 [SMILES: Cc1c(F)cccc1C[C@H](C)Nc1cc[nH]c(=O)c1-c1nc2cc3c(cc2[nH]1)C(=O)N(CCN1CCCC1)C3] | +++ | + | ++ | ++++ |
| 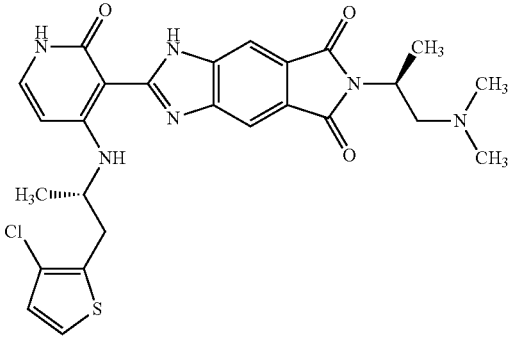 [SMILES: C[C@@H](Cc1sccc1Cl)Nc1cc[nH]c(=O)c1-c1nc2cc3c(cc2[nH]1)C(=O)N([C@@H](C)CN(C)C)C3=O] | +++ | − | NT | NT |
| 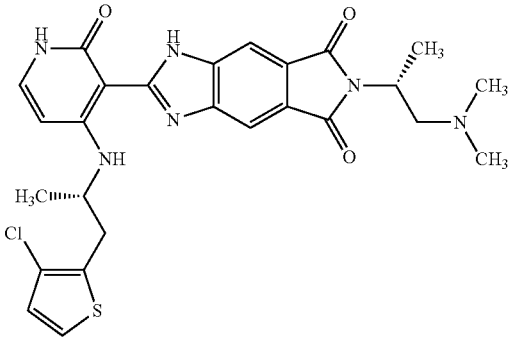 [SMILES: C[C@H](CN(C)C)N1C(=O)c2cc3nc(-c4c(N[C@@H](C)Cc5sccc5Cl)cc[nH]c4=O)[nH]c3cc2C1=O] | +++ | − | NT | NT |

SAR TABLE 1
| Structure | ALK IC50 | IGF1R IC50 | IRK IC50 | TRKA IC50 |
|---|---|---|---|---|
| 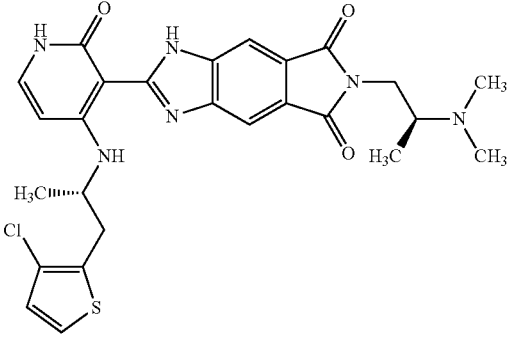 [SMILES: C[C@@H](Cc1sccc1Cl)Nc1cc[nH]c(=O)c1-c1nc2cc3c(cc2[nH]1)C(=O)N(C[C@H](C)N(C)C)C3=O] | +++ | − | NT | NT |
| 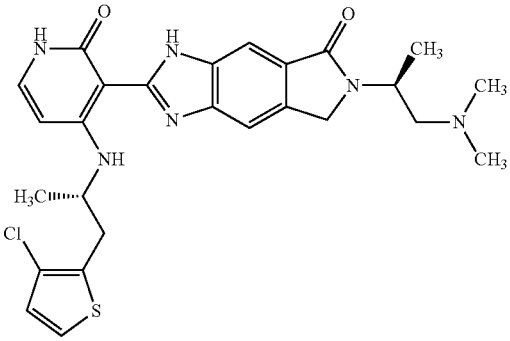 [SMILES: C[C@@H](Cc1sccc1Cl)Nc1cc[nH]c(=O)c1-c1nc2cc3c(cc2[nH]1)C(=O)N([C@@H](C)CN(C)C)C3] | +++ | ++ | NT | NT |
| 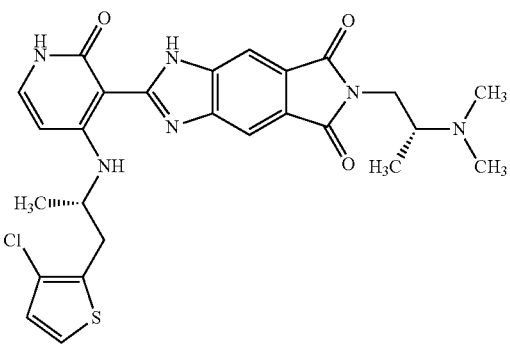 [SMILES: C[C@H](CN1C(=O)c2cc3nc(-c4c(N[C@@H](C)Cc5sccc5Cl)cc[nH]c4=O)[nH]c3cc2C1=O)N(C)C] | +++ | − | NT | NT |
| 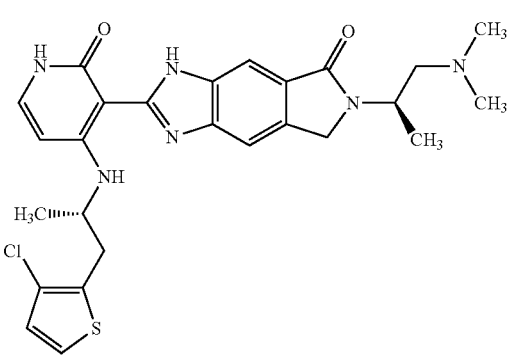 [SMILES: C[C@H](CN(C)C)N1Cc2cc3nc(-c4c(N[C@@H](C)Cc5sccc5Cl)cc[nH]c4=O)[nH]c3cc2C1=O] | +++ | ++ | NT | NT |

-continued
SAR TABLE 1
| Structure | ALK IC50 | IGF1R IC50 | IRK IC50 | TRKA IC50 |
|---|---|---|---|---|
| 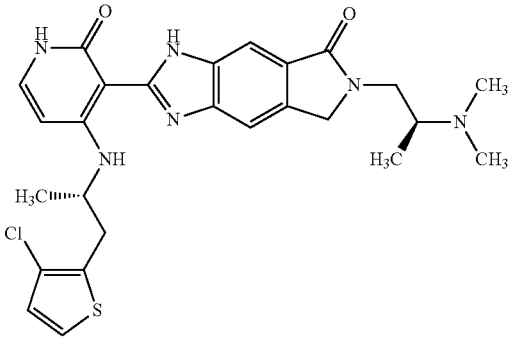 [SMILES: C[C@@H](Cc1sccc1Cl)Nc1cc[nH]c(=O)c1-c1nc2cc3c(cc2[nH]1)C(=O)N(C[C@H](C)N(C)C)C3] | ++++ | + | NT | NT |
| 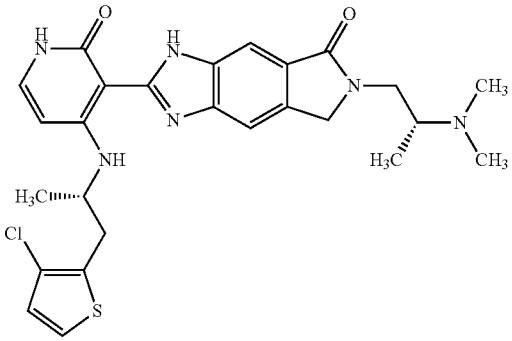 [SMILES: C[C@H](CN1Cc2cc3nc(-c4c(N[C@@H](C)Cc5sccc5Cl)cc[nH]c4=O)[nH]c3cc2C1=O)N(C)C] | ++++ | + | NT | NT |
| 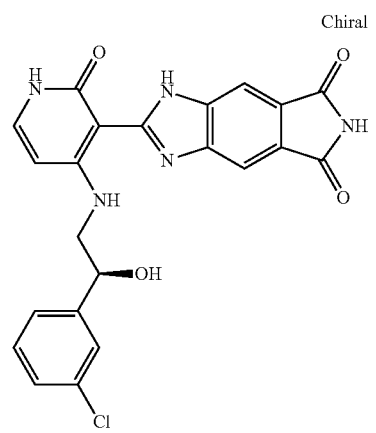 [SMILES: O=C1NC(=O)c2cc3[nH]c(-c4c(NC[C@@H](O)c5cccc(Cl)c5)cc[nH]c4=O)nc3cc21] Chiral | − | + | − | ++ |
| 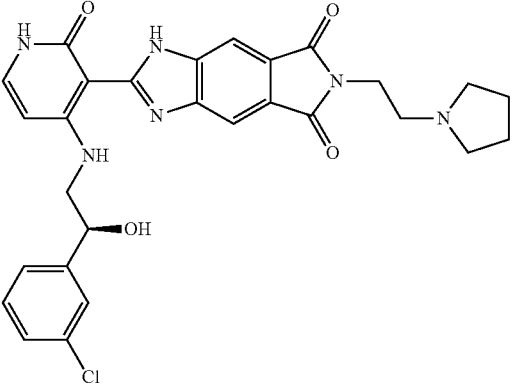 [SMILES: O=C1c2cc3nc(-c4c(NC[C@@H](O)c5cccc(Cl)c5)cc[nH]c4=O)[nH]c3cc2C(=O)N1CCN1CCCC1] | +++ | +++ | ++ | +++ |

SAR TABLE 1

| Structure | ALK IC50 | IGF1R IC50 | IRK IC50 | TRKA IC50 |
|---|---|---|---|---|
| 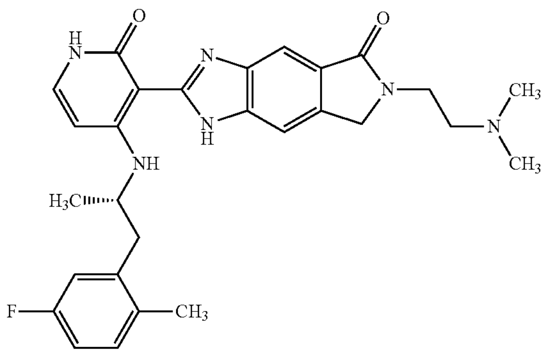 [SMILES: Cc1ccc(F)cc1C[C@H](C)Nc1cc[nH]c(=O)c1-c1nc2cc3c(cc2[nH]1)CN(CCN(C)C)C3=O] | ++++ | ++ | ++ | ++++ |
| 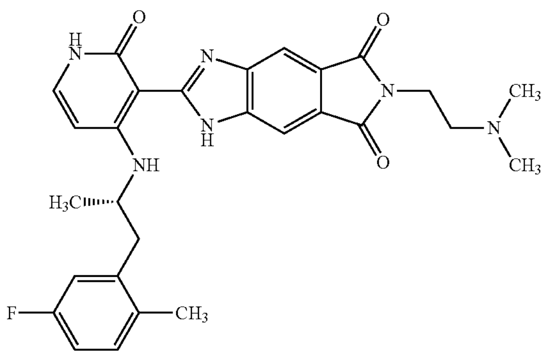 [SMILES: Cc1ccc(F)cc1C[C@H](C)Nc1cc[nH]c(=O)c1-c1nc2cc3c(cc2[nH]1)C(=O)N(CCN(C)C)C3=O] | ++ | ++ | − | NT |
| | +++ | + | − | NT |
| | +++ | ++ | + | NT |

-continued
SAR TABLE 1
| Structure | ALK IC50 | IGF1R IC50 | IRK IC50 | TRKA IC50 |
|---|---|---|---|---|
| 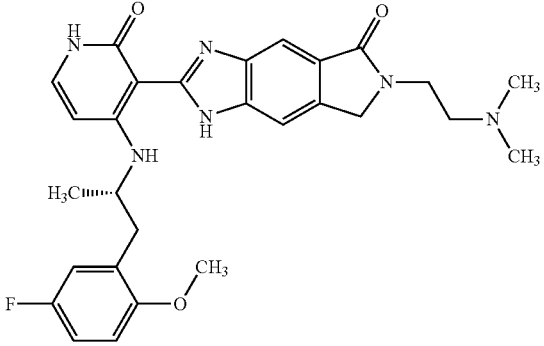 [SMILES: COc1ccc(F)cc1C[C@H](C)Nc1cc[nH]c(=O)c1-c1nc2cc3c(cc2[nH]1)CN(CCN(C)C)C3=O] | +++ | ++ | + | NT |
| 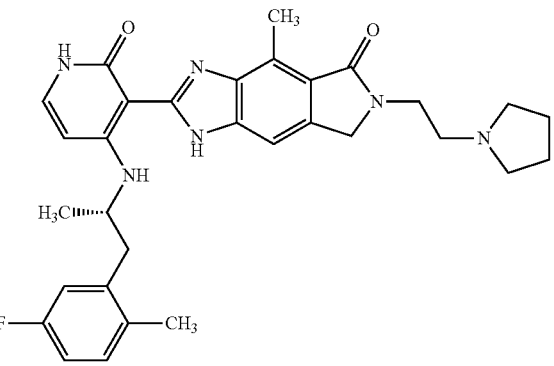 | ++++ | ++ | ++ | NT |
| 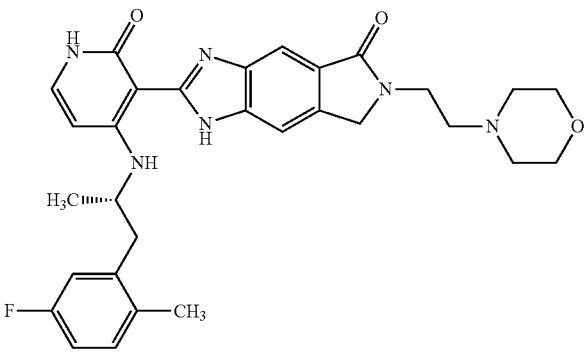 [SMILES: Cc1ccc(F)cc1C[C@H](C)Nc1cc[nH]c(=O)c1-c1nc2cc3c(cc2[nH]1)CN(CCN1CCOCC1)C3=O] | ++ | ++ | − | NT |
| 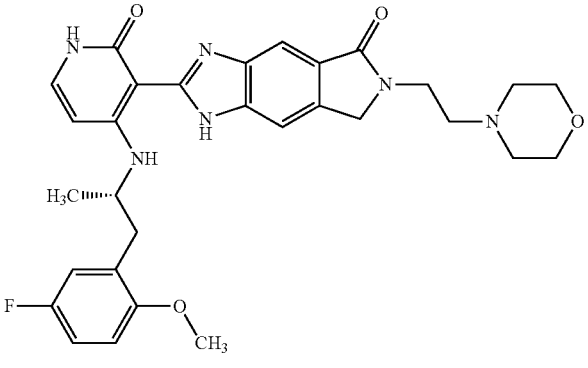 [SMILES: COc1ccc(F)cc1C[C@H](C)Nc1cc[nH]c(=O)c1-c1nc2cc3c(cc2[nH]1)CN(CCN1CCOCC1)C3=O] | ++ | ++ | − | NT |

-continued

SAR TABLE 1

| Structure | ALK IC50 | IGF1R IC50 | IRK IC50 | TRKA IC50 |
|---|---|---|---|---|
| 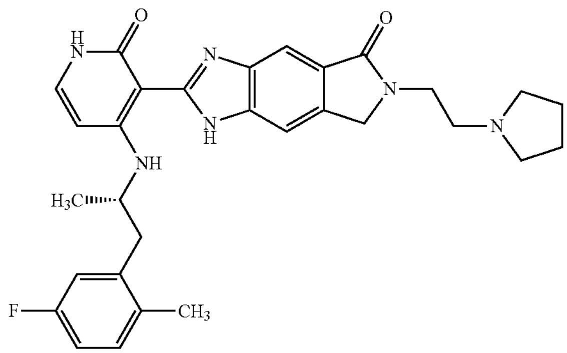 [SMILES: Cc1ccc(F)cc1C[C@H](C)Nc1cc[nH]c(=O)c1-c1nc2cc3c(cc2[nH]1)CN(CCN1CCCC1)C3=O] | ++ | + | + | NT |
| 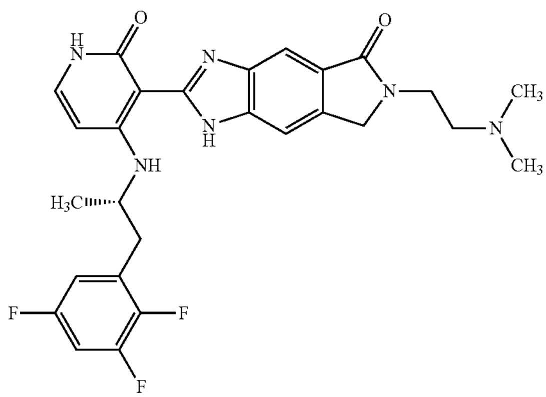 [SMILES: C[C@@H](Cc1cc(F)cc(F)c1F)Nc1cc[nH]c(=O)c1-c1nc2cc3c(cc2[nH]1)CN(CCN(C)C)C3=O] | ++++ | ++ | + | NT |
| 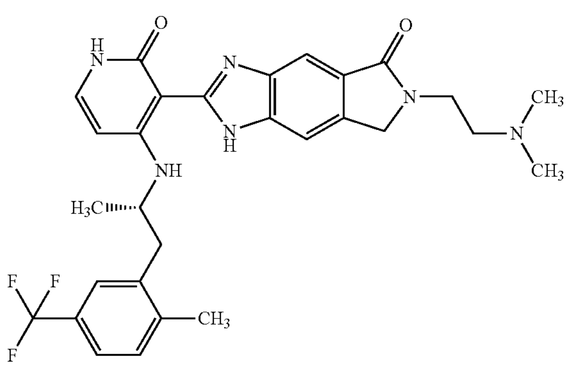 [SMILES: Cc1ccc(C(F)(F)F)cc1C[C@H](C)Nc1cc[nH]c(=O)c1-c1nc2cc3c(cc2[nH]1)CN(CCN(C)C)C3=O] | + | ++ | + | NT |
| 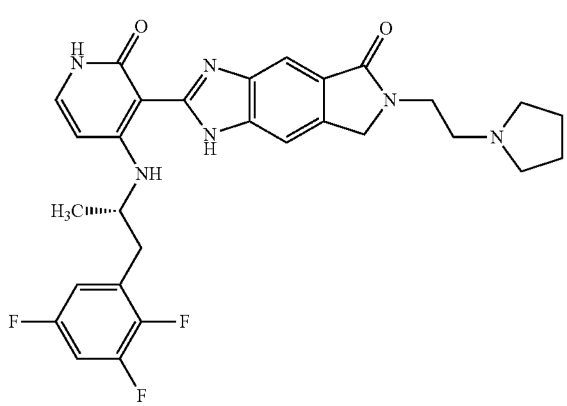 [SMILES: C[C@@H](Cc1cc(F)cc(F)c1F)Nc1cc[nH]c(=O)c1-c1nc2cc3c(cc2[nH]1)CN(CCN1CCCC1)C3=O] | +++ | + | + | NT |

-continued
SAR TABLE 1
| Structure | ALK IC50 | IGF1R IC50 | IRK IC50 | TRKA IC50 |
|---|---|---|---|---|
| 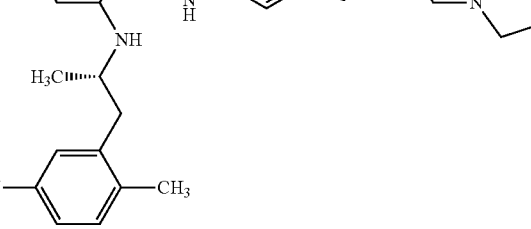 | − | − | − | NT |
| 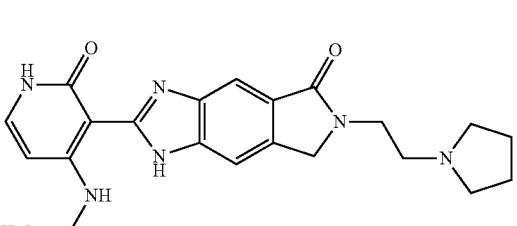 | − | − | + | NT |
| 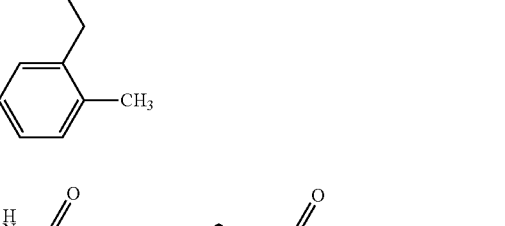 | ++++ | + | ++ | NT |
| 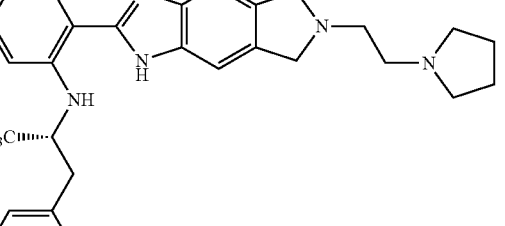 | +++ | + | − | NT |

SAR TABLE 1
| Structure | ALK IC50 | IGF1R IC50 | IRK IC50 | TRKA IC50 |
|---|---|---|---|---|
| 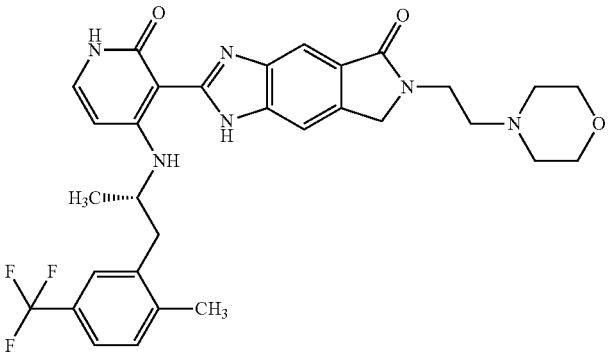 [SMILES: Cc1ccc(C(F)(F)F)cc1C[C@H](C)Nc1cc[nH]c(=O)c1-c1nc2cc3c(cc2[nH]1)CN(CCN1CCOCC1)C3=O] | + | − | − | NT |
| 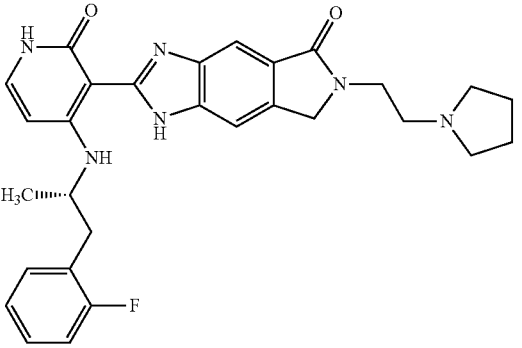 [SMILES: C[C@@H](Cc1ccccc1F)Nc1cc[nH]c(=O)c1-c1nc2cc3c(cc2[nH]1)CN(CCN1CCCC1)C3=O] | ++ | + | NT | NT |
| 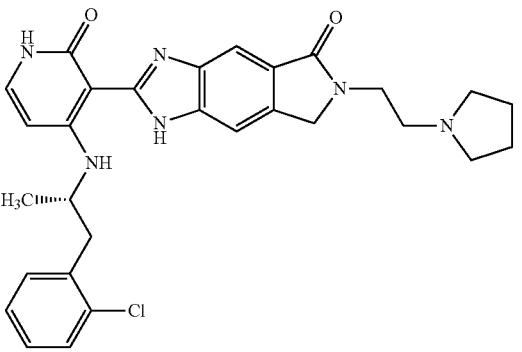 [SMILES: C[C@@H](Cc1ccccc1Cl)Nc1cc[nH]c(=O)c1-c1nc2cc3c(cc2[nH]1)CN(CCN1CCCC1)C3=O] | + | − | ++ | NT |
| 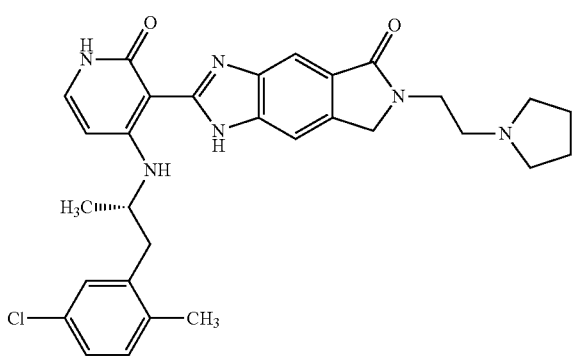 [SMILES: Cc1ccc(Cl)cc1C[C@H](C)Nc1cc[nH]c(=O)c1-c1nc2cc3c(cc2[nH]1)CN(CCN1CCCC1)C3=O] | + | − | ++ | NT |

-continued

SAR TABLE 1

| Structure | ALK IC50 | IGF1R IC50 | IRK IC50 | TRKA IC50 |
|---|---|---|---|---|
| | − | − | NT | NT |
| | − | − | NT | NT |
| 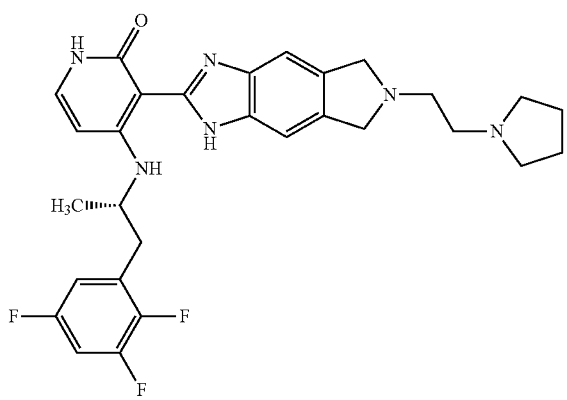 [SMILES: C[C@@H](Cc1cc(F)cc(F)c1F)Nc1cc[nH]c(=O)c1-c1nc2cc3c(cc2[nH]1)CN(CCN1CCCC1)C3] | + | + | NT | NT |
| 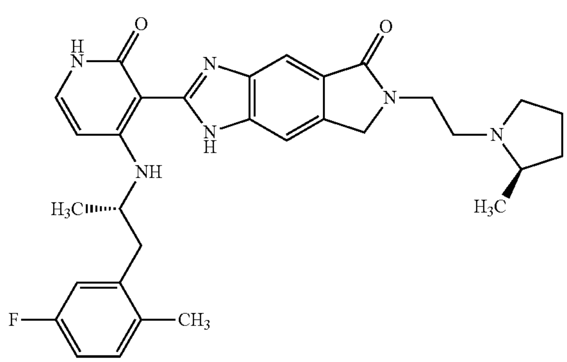 [SMILES: Cc1ccc(F)cc1C[C@H](C)Nc1cc[nH]c(=O)c1-c1nc2cc3c(cc2[nH]1)CN(CCN1CCC[C@H]1C)C3=O] | +++ | − | + | NT |

SAR TABLE 1
| Structure | ALK IC50 | IGF1R IC50 | IRK IC50 | TRKA IC50 |
|---|---|---|---|---|
| 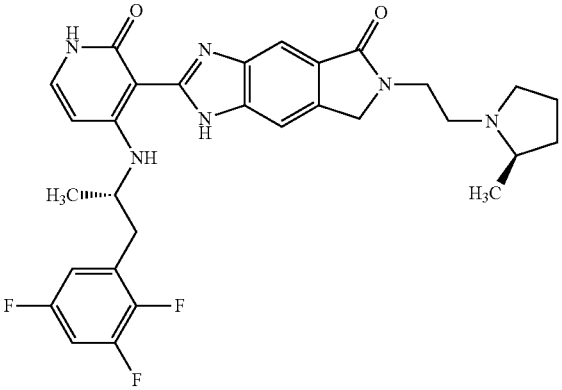 [SMILES: C[C@@H]1CCCN1CCN1Cc2cc3[nH]c(-c4c(N[C@@H](C)Cc5cc(F)cc(F)c5F)cc[nH]c4=O)nc3cc2C1=O] | ++++ | − | + | NT |
| 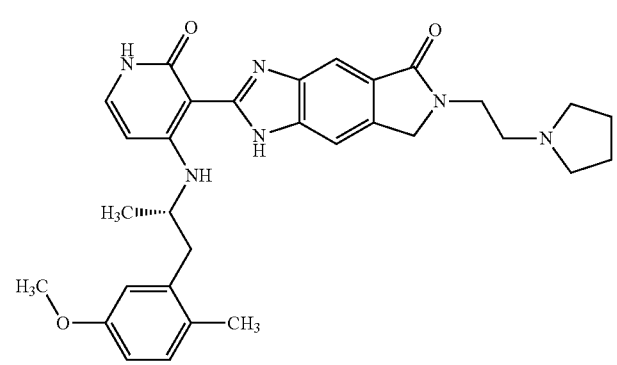 [SMILES: COc1ccc(C)c(C[C@H](C)Nc2cc[nH]c(=O)c2-c2nc3cc4c(cc3[nH]2)CN(CCN2CCCC2)C4=O)c1] | +++ | − | + | NT |
| 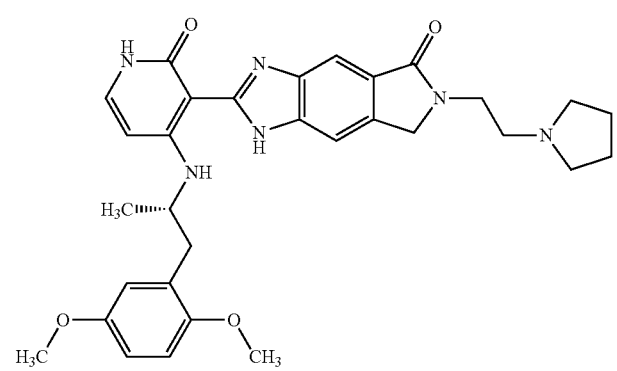 [SMILES: COc1ccc(OC)c(C[C@H](C)Nc2cc[nH]c(=O)c2-c2nc3cc4c(cc3[nH]2)CN(CCN2CCCC2)C4=O)c1] | ++ | − | + | NT |
| 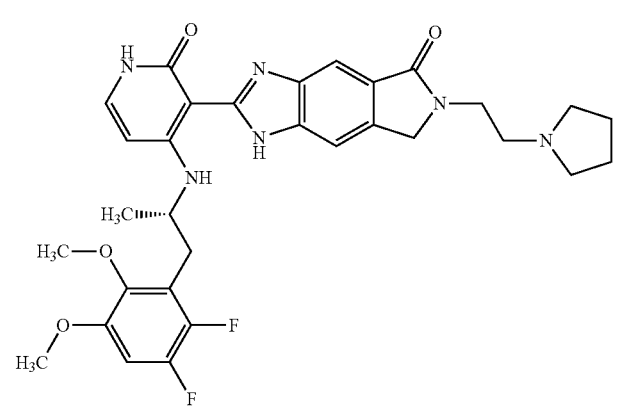 [SMILES: COc1cc(F)c(F)c(C[C@H](C)Nc2cc[nH]c(=O)c2-c2nc3cc4c(cc3[nH]2)CN(CCN2CCCC2)C4=O)c1OC] | +++ | − | + | NT |

-continued

SAR TABLE 1

| Structure | ALK IC50 | IGF1R IC50 | IRK IC50 | TRKA IC50 |
|---|---|---|---|---|
| 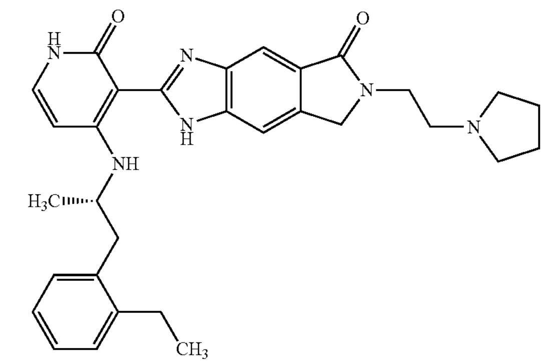 [SMILES: CCc1ccccc1C[C@H](C)Nc1cc[nH]c(=O)c1-c1nc2cc3c(cc2[nH]1)CN(CCN1CCCC1)C3=O] | +++ | − | + | NT |
| 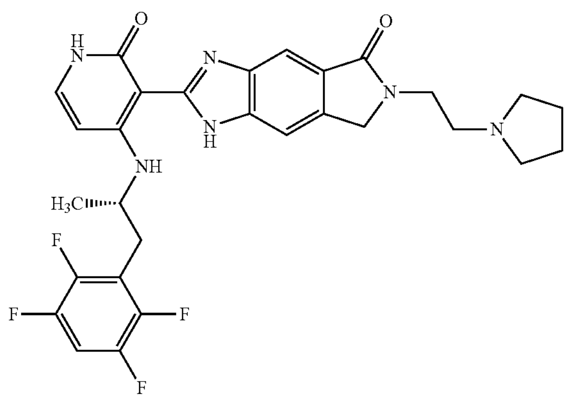 | ++++ | − | + | NT |
| 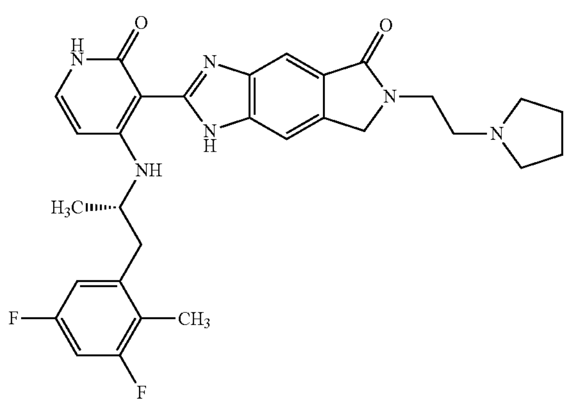 [SMILES: Cc1c(F)cc(F)cc1C[C@H](C)Nc1cc[nH]c(=O)c1-c1nc2cc3c(cc2[nH]1)CN(CCN1CCCC1)C3=O] | − | + | NT | NT |
| 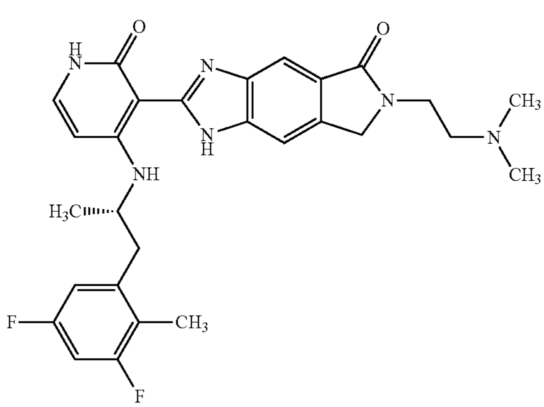 [SMILES: Cc1c(F)cc(F)cc1C[C@H](C)Nc1cc[nH]c(=O)c1-c1nc2cc3c(cc2[nH]1)CN(CCN(C)C)C3=O] | ++ | + | NT | NT |

-continued

SAR TABLE 1

| Structure | ALK IC50 | IGF1R IC50 | IRK IC50 | TRKA IC50 |
|---|---|---|---|---|
| 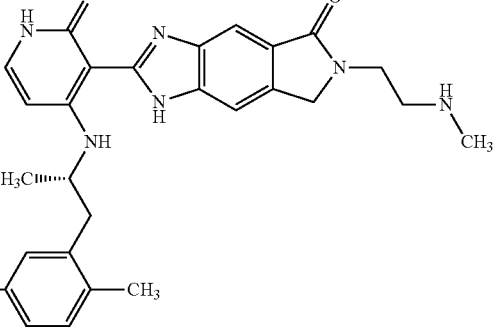 | + | +++ | NT | NT |
| 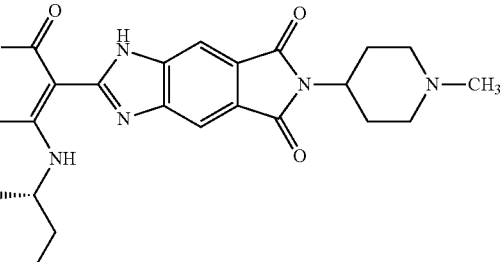 | ++ | – | – | NT |

ALK, IGF1R, IRK, TRKA IC50 (μM) +0.25-1 ++0.1-0.25 +++0.01-0.1 ++++<0.01
NT = not tested Table I above presents the pharmacological data (IC$_{50}$ values) for specific kinases showing the relative degree of potency of inhibition of their activity.

SAR TABLE 2

| Structure | Enzymatic ALK IC50 | Enzymatic IGF1R IC50 | ALCL (ALK) JB6 | IC50 ALCL (ALK) Karpas299 | ALCL (ALK) Uconn | MM (IGF1R) H929 | CONTROL W138 |
|---|---|---|---|---|---|---|---|
| 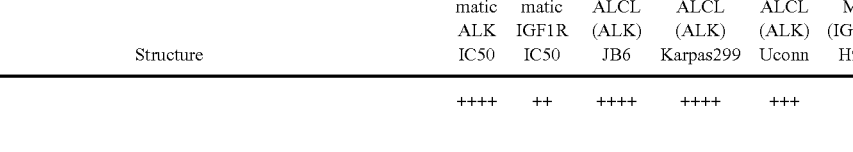 | ++++ | ++ | ++++ | ++++ | +++ | + | – |

-continued

SAR TABLE 2

| Structure | Enzymatic ALK IC50 | Enzymatic IGF1R IC50 | ALCL (ALK) JB6 | IC50 ALCL (ALK) Karpas299 | ALCL (ALK) Uconn | MM (IGF1R) H929 | CONTROL W138 |
|---|---|---|---|---|---|---|---|
| (structure 1) | ++++ | ++ | ++++ | ++++ | +++ | + | − |
| (structure 2) | ++++ | − | ++++ | ++++ | +++ | + | − |
| (structure 3) | ++++ | − | ++++ | ++++ | +++ | + | − |
| (structure 4) | +++ | − | +++ | +++ | +++ | + | − |

SAR TABLE 2
| Structure | Enzymatic ALK IC50 | Enzymatic IGF1R IC50 | ALCL (ALK) JB6 | IC50 ALCL (ALK) Karpas299 | ALCL (ALK) Uconn | MM (IGF1R) H929 | CONTROL W138 |
|---|---|---|---|---|---|---|---|
| 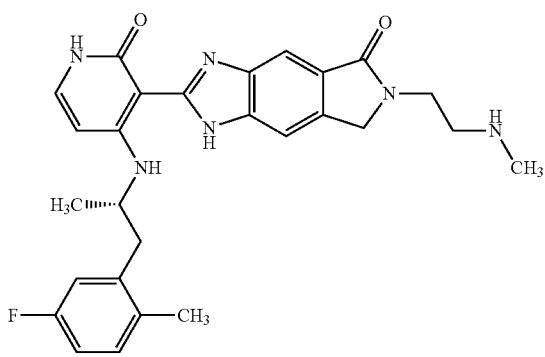 [SMILES: CNCCN1Cc2cc3[nH]c(-c4c(N[C@@H](C)Cc5cc(F)ccc5C)cc[nH]c4=O)nc3cc2C1=O] | ++++ | +++ | ++++ | +++ | +++ | + | − |
| 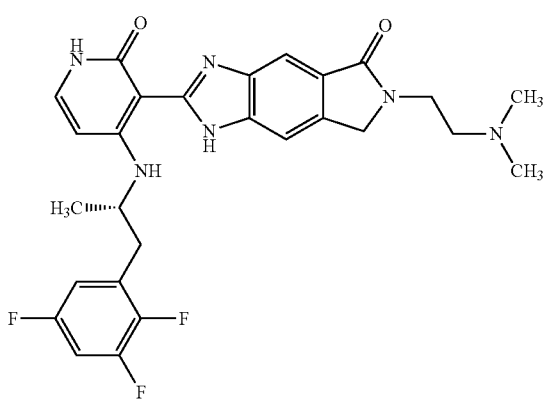 [SMILES: C[C@@H](Cc1cc(F)cc(F)c1F)Nc1cc[nH]c(=O)c1-c1nc2cc3c(cc2[nH]1)CN(CCN(C)C)C3=O] | ++++ | ++ | +++ | +++ | +++ | + | − |
| 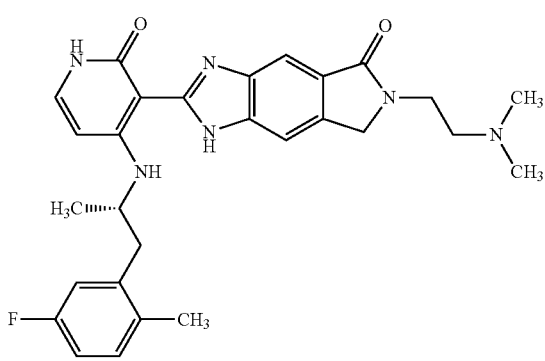 [SMILES: Cc1ccc(F)cc1C[C@H](C)Nc1cc[nH]c(=O)c1-c1nc2cc3c(cc2[nH]1)CN(CCN(C)C)C3=O] | ++++ | ++ | +++ | +++ | +++ | + | − |

-continued

SAR TABLE 2

| Structure | Enzymatic ALK IC50 | Enzymatic IGF1R IC50 | ALCL (ALK) JB6 | IC50 ALCL (ALK) Karpas299 | ALCL (ALK) Uconn | MM (IGF1R) H929 | CONTROL W138 |
|---|---|---|---|---|---|---|---|
| (structure 1) | +++ | + | +++ | +++ | +++ | + | − |
| (structure 2) | +++ | + | +++ | +++ | ++ | + | − |

ALK, IGF1R IC50 (μM) +0.25-1 ++0.1-0.25 +++0.01-0.1 ++++<0.01
Cell lines IC50 +0.25-1 ++0.1-0.25 +++0.01-0.1 ++++<0.01

Table 2 above presents the pharmacological data (IC$_{50}$ values) for specific kinases showing the relative degree of potency of inhibition of their cell-based activity.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings provided herein that certain changes and modifications may be made thereto without departing from the spirit or scope of the appended claims.

What is claimed:

1. A compound according to the formula (I) or a stereoisomer, tautomer, or salt thereof:

formula (I)

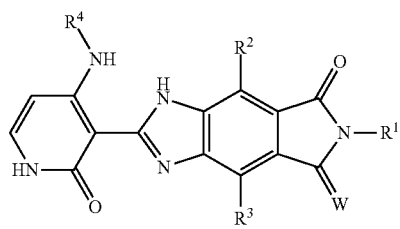

wherein:
R$^2$ and R$^3$ are each independently hydrogen, lower alkyl, lower alkoxy, halogen, cyano, lower alkylamino, or di-lower alkylamino;
W is O, S, or NR$^e$, wherein R$^e$ is selected from hydrogen and lower alkyl;
or W represents bonding of two hydrogen atoms to a carbon atom, forming an optionally substituted methylene group:

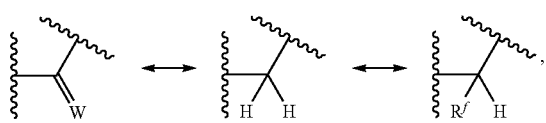

wherein
R$^f$ is selected from hydrogen and lower alkyl;
R$^4$ is

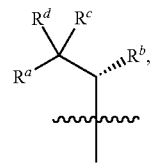

wherein
R$^a$ is optionally substituted aryl or heteroaryl;
R$^b$ is lower alkyl, trifluoromethyl, methoxymethyl, aminomethyl, di-lower alkylaminomethyl, or heterocyclylaminomethyl;
R$^c$ is selected from hydrogen, lower alkoxy, and lower alkyl;
R$^d$ is selected from hydrogen, and lower alkyl; and
R$^1$ is independently selected from optionally substituted heterocyclyl, heterocyclylalkyl, heteroaryl, heteroarylalkyl, heterocyclyloxyalkyl, heteroalkyl, heterocyclylaminoalkyl, aminoalkyl, lower alkylaminoalkyl, di-(lower alkyl)-aminoalkyl, aminocycloalkyl, alkylaminocycloalkyl, di-(lower alkyl)-aminocycloalkyl, and di-(lower alkyl)-aminocycloalkylalkyl, wherein the substituents are selected from hydrogen, lower alkyl, hydroxy, lower alkoxy, amino, amidino, carboxamido, sulfonamido, hydroxy, cyano, primary, secondary or tertiary amino, halo, azido, lower alkoxyalkyl, cyanoalkyl, azidoalkyl, haloalkyl, hydroxyalkyl, methanesulfonylalkyl, primary, secondary or tertiary amino-alkyl, optionally substituted aryl, heteroaryl, heteroalkyl, heterocyclyl, cycloalkyl, alkenyl, and alkynyl.

2. The compound of claim 1, wherein R$^2$ and R$^3$ are hydrogen or methyl.

3. The compound of claim 1, wherein W represents bonding of two hydrogen atoms to a carbon atom, forming methylene.

4. The compound of claim 1, wherein R$^a$ is optionally substituted thienyl or phenyl wherein the optional substituents are alkyl, alkoxy or halo.

5. The compound of claim 1, wherein R$^a$ is optionally substituted thienyl or phenyl wherein the optional substituents are methyl, methoxy or fluoro.

6. The compound of claim 1, wherein R$^a$ is 2-thienyl, phenyl, 3-methyl-2-thienyl, 2-methylphenyl, 5-fluoro-2-methylphenyl, 5-fluoro-2-methoxyphenyl, 2,3,5-trifluorophenyl or 2,3,5,6-tetrafluorophenyl.

7. The compound of claim 1, wherein R$^c$ and R$^d$ are hydrogen.

8. The compound of claim 1, wherein R$^b$ is alkyl.

9. The compound of claim 1, wherein R$^b$ is methyl.

10. The compound according to claim 1, wherein R$^1$ is selected from the group consisting of:

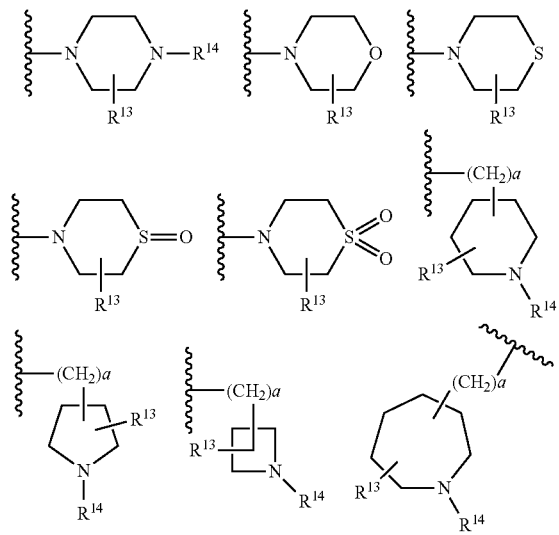

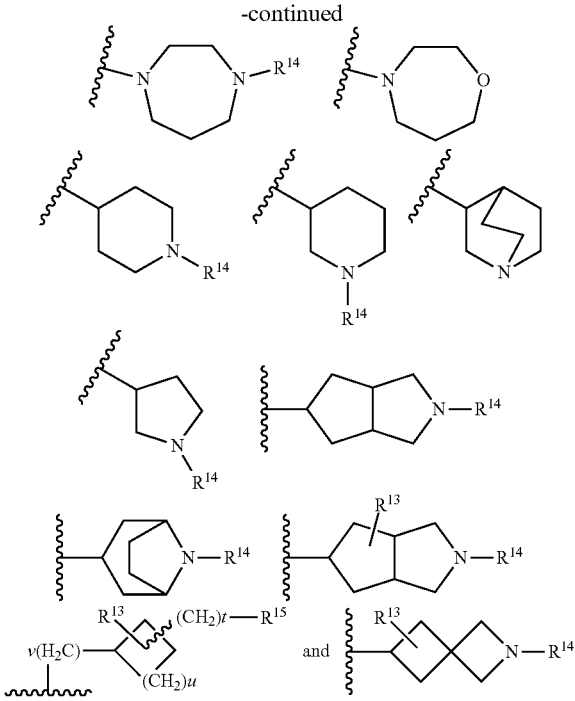

wherein:
R$^{13}$ is selected from hydrogen, lower alkyl, heteroalkyl, heterocyclyl, cycloalkyl, and heterocycloalkyl;
R$^{14}$ is selected from hydrogen, hydroxy, lower alkoxy, di-(lower alkyl)amino, lower alkyl, heteroalkyl, heterocyclyl, cycloalkyl, heterocycloalkyl, lower alkoxyalkyl, cyanoalkyl, azidoalkyl, nitroalkyl, ketoalkyl, methanesulfonylalkyl, aminoalkyl, lower alkylaminoalkyl, di-(lower alkyl)aminoalkyl, optionally substituted aryl, heteroaryl, arylalkyl, and heteroarylalkyl;
R$^{15}$ is selected from hydrogen, amino, lower alkylamino, di-(lower alkyl)amino, hydroxy, lower alkoxy, heteroalkyl, lower alkoxyalkyl, aminoalkyl, lower alkylaminoalkyl, and di-(lower alkyl)aminoalkyl;
a is an integer from 0 to 4; and
t, u, v are independent integers from 0 to 5.

11. The compound according to claim 1, wherein R$^1$ is selected from the group consisting of:

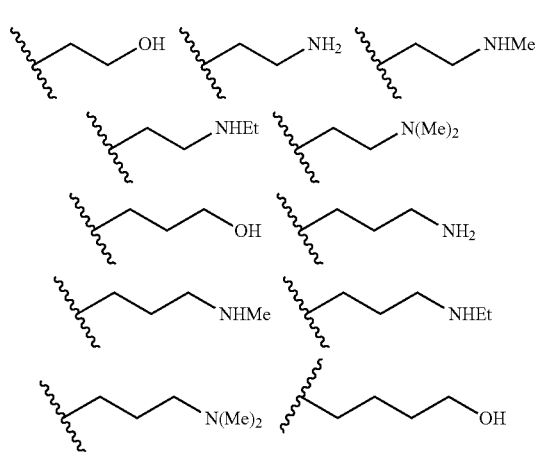

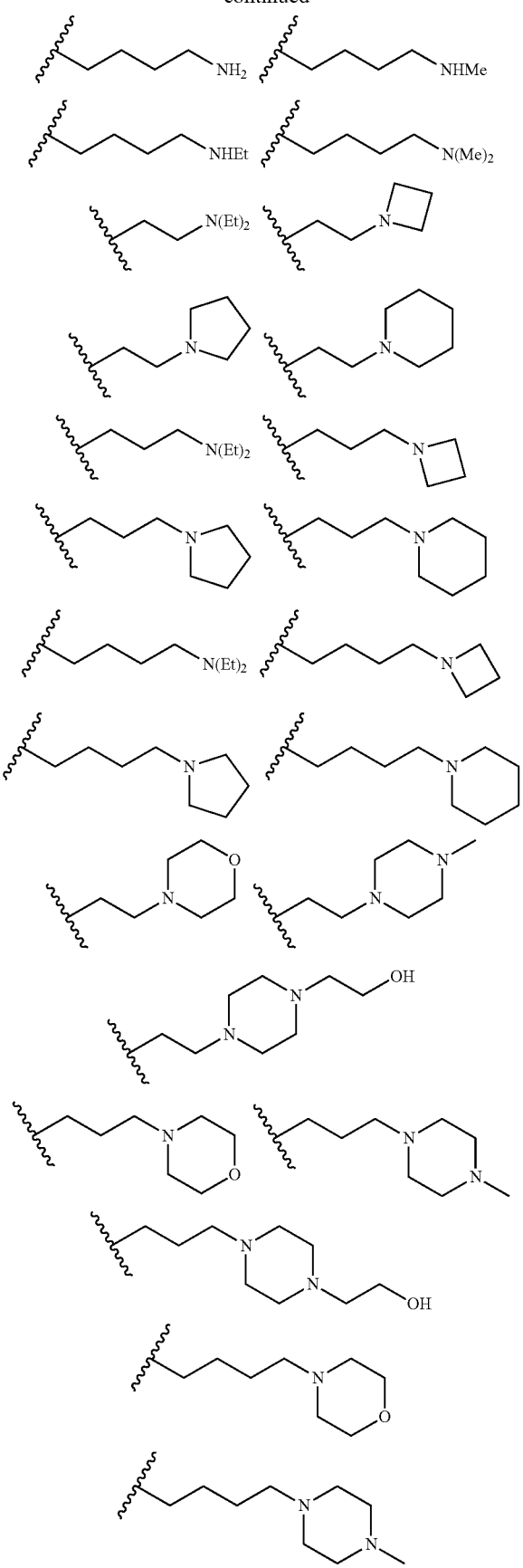
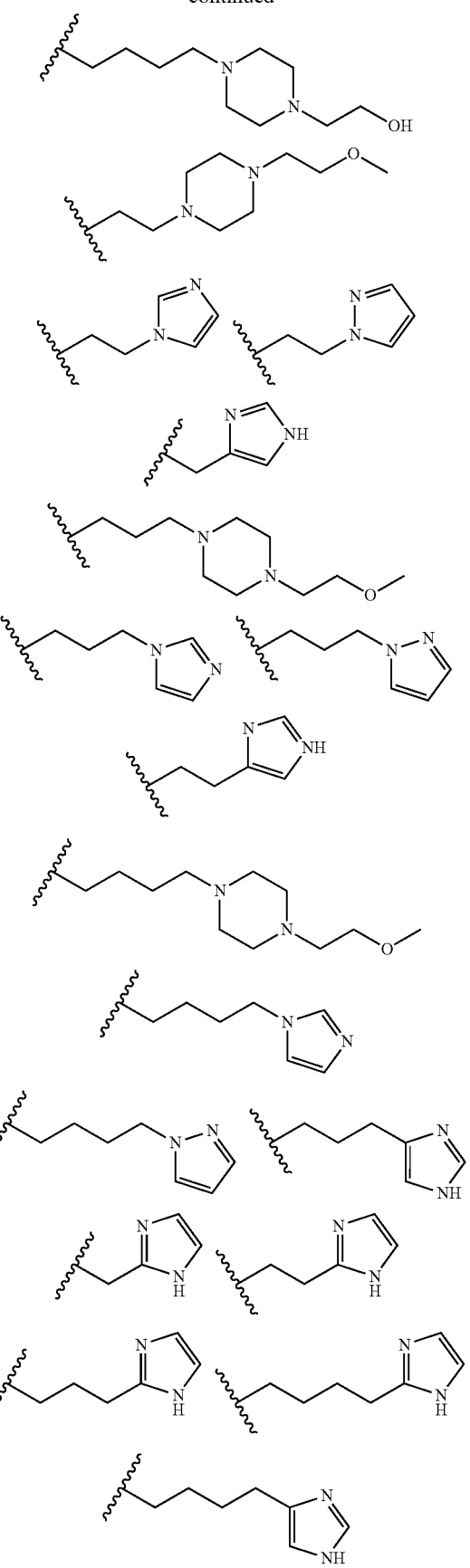

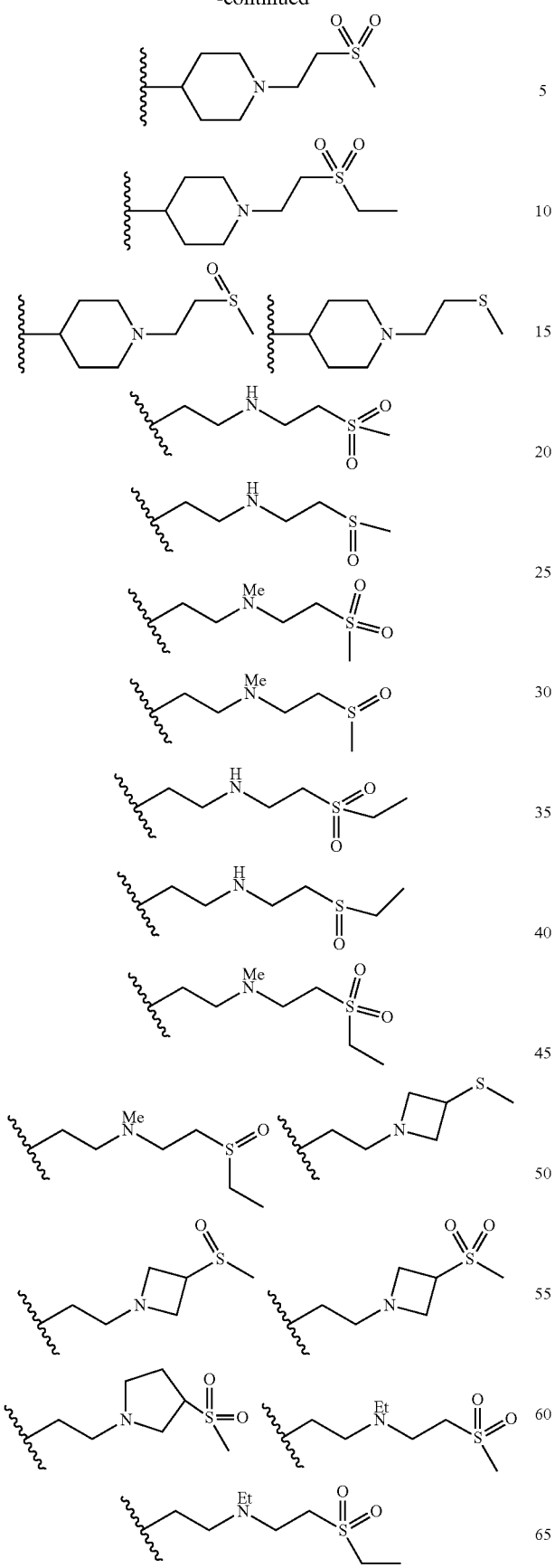
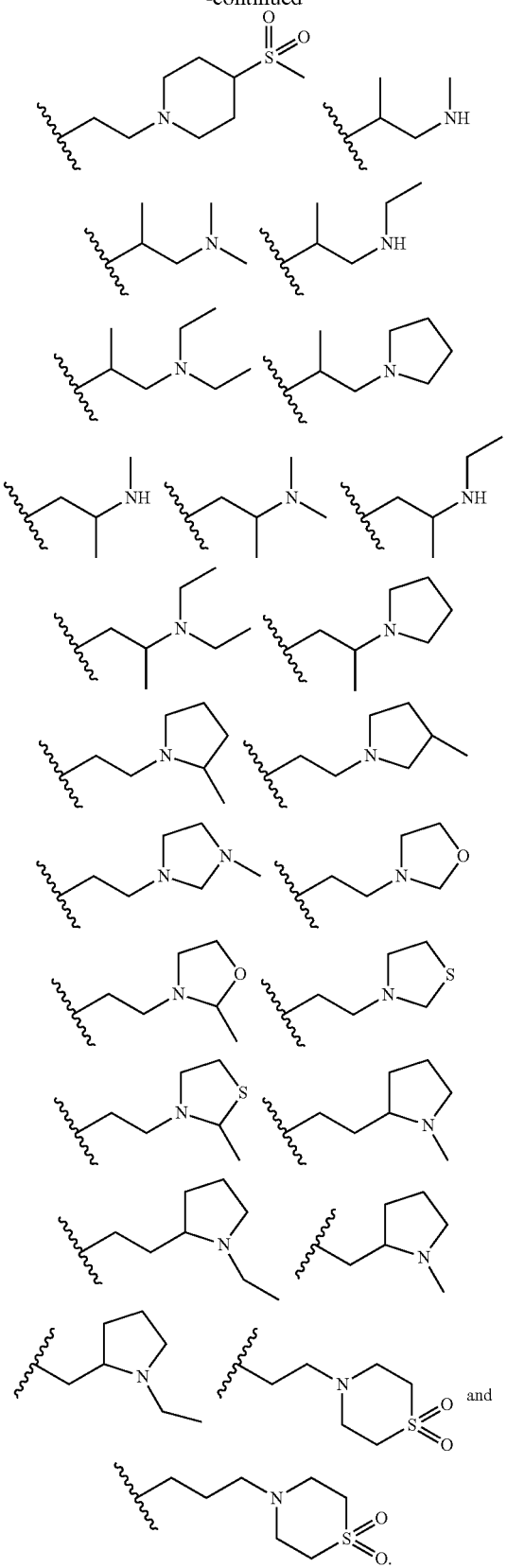
12. The compound according to claim 1, wherein the $R^1$ methylene chain between the connection and the heteroatom is optionally substituted by one or more hydrogen, lower alkyl, hydroxy, hydroxy-lower alkyl, lower alkoxy, carboxamido or sulfonamido.

13. The compound according to claim 1, wherein the $R^1$ methylene groups are optionally substituted by a heteroatom selected from O and S, NR*, S=O, or S(=O)$_2$, wherein R* is selected from hydrogen, hydroxy, lower alkyl, lower alkoxy, heteroalkyl, hydroxyalkyl, aminoalkyl, lower alkylaminoalkyl and di-(lower alkyl)aminoalkyl.

14. The compound according to claim 1, wherein the $R^1$ ring is optionally substituted by a lower alkyl or heteroalkyl group.

15. The compound according to claim 1 having the following formula (Ia):

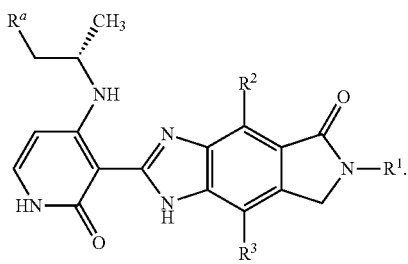

16. A compound according to claim 1, wherein the compound is selected from the group consisting of:

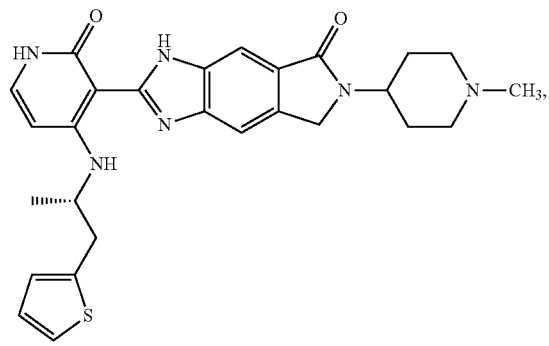

(S)-6-(1-methylpiperidin-4-yl)-2-(2-oxo-4-(1-(thiophen-2-yl)propan-2-ylamino)-1,2-dihydropyridin-3-yl)-6,7-dihydroimidazo[4,5-f]isoindol-5(3H)-one

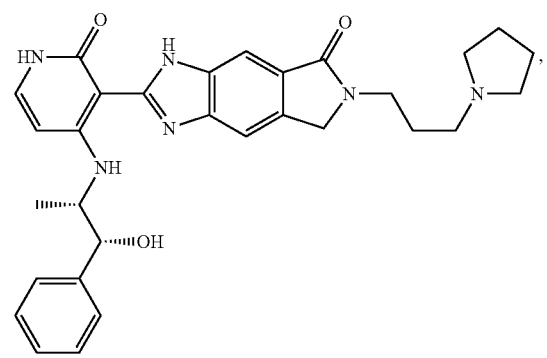

2-(4-((1R,2S)-1-hydroxy-1-phenylpropan-2-ylamino)-2-oxo-1,2-dihydropyridin-3-yl)-6-(3-(pyrrolidin-1-yl)propyl)-6,7-dihydroimidazo[4,5-f]isoindol-5(3H)-one

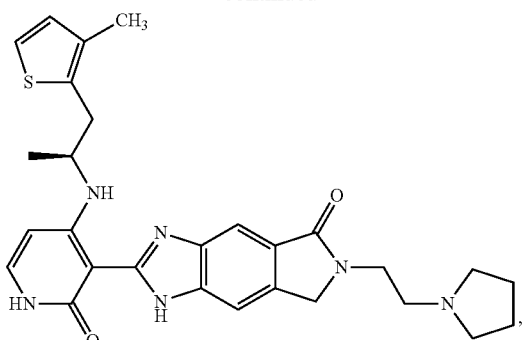

(S)-2-(4-(1-(3-methylthiophen-2-yl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

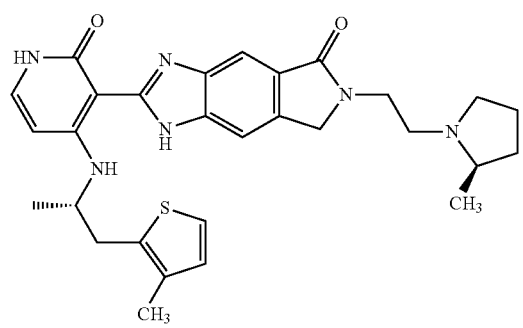

6-(2-((R)-2-methytpyrrolidin-1-yl)ethyl)-2-(4-((S)-1-(3-methylthiophen-2-yl)propan-2-ylamino)-2-oxo-1,2-dihydropyridin-3-yl)-6,7-dihydroimidazo[4,5-f]isoindol-5(1H)-one

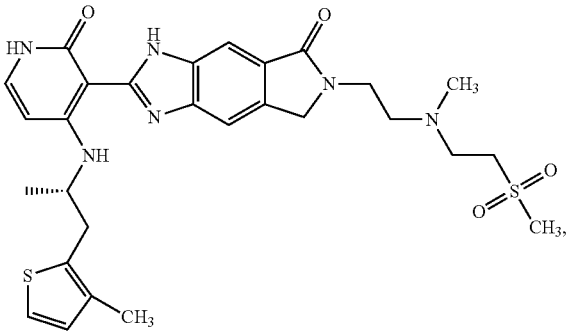

(S)-6-(2-(methyl(2-(methylsulfonyl)ethyl)amino)ethyl)-2-(4-(1-(3-methylthiophen-2-yl)propan-2-ylamino)-2-oxo-1,2-dihydropyridin-3-yl)-6,7-dihydroimidazo[4,5-f]isoindol-5(3H)-one

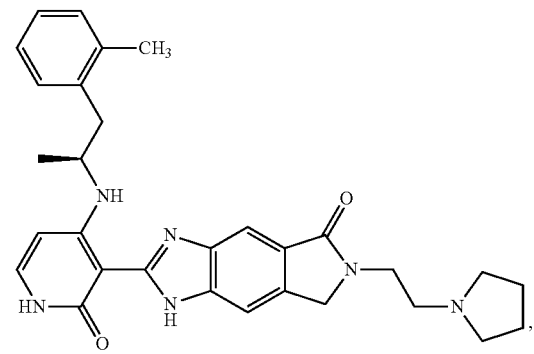

(S)-2-(2-oxo-4-(1-o-tolylpropan-2-ylamino)-1,2-dihydropyridin-3-yl)-6-(2-(pyrrolidin-1-yl)ethyl)-6,7-dihydroimidazo[4,5-f]isoindol-5(1H)-one 213
-continued

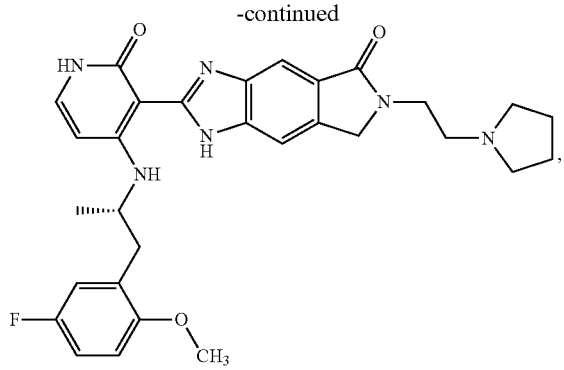

(S)-2-(4-(1-(5-fluoro-2-methoxyphenyl)propan-2-ylamino)-2-oxo-1,2-dihydropyridin-3-yl)-6-(2-(pyrrolidin-1-yl)ethyl)-6,7-dihydroimidazo[4,5-f]isoindol-5(1H)-one

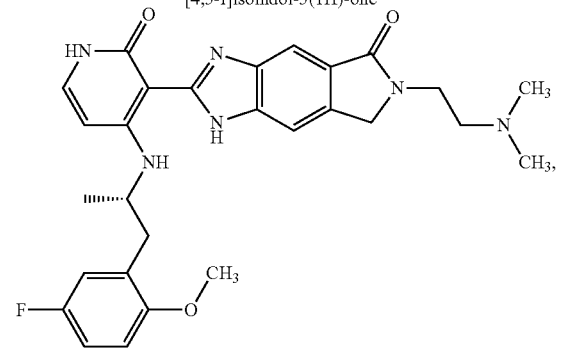

(S)-6-(2-(dimethylamino)ethyl)-2-(4-(1-(5-fluoro-2-methoxyphenyl)propan-2-ylamino)-2-oxo-1,2-dihydropyridin-3-yl)-6,7-dihydroimidazo[4,5-f]isoindol-5(1H)-one

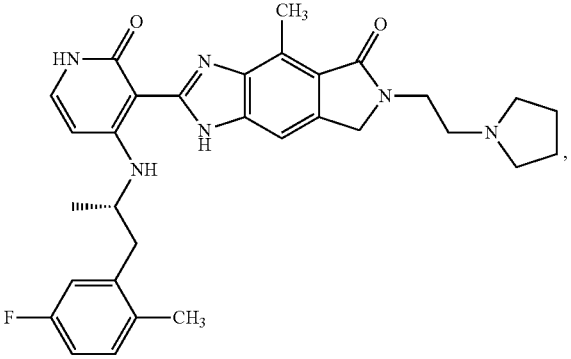

(S)-2-(4-(1-(5-fluoro-2-methylphenyl)propan-2-ylamino)-2-oxo-1,2-dihydropyridin-3-yl)-4-methyl-6-(2-(pyrrolidin-1-yl)ethyl)-6,7-dihydroimidazo[4,5-f]isoindol-5(1H)-one

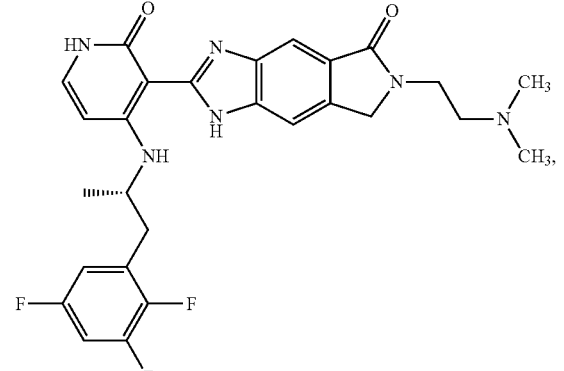

(S)-6-(2-(dimethylamino)ethyl)-2-(2-oxo-4-(1-(2,3,5-trifluorophenyl)propan-2-ylamino)-1,2-dihydropyridin-3-yl)-6,7-dihydroimidazo[4,5-f]isoindol-5(1H)-one 214
-continued

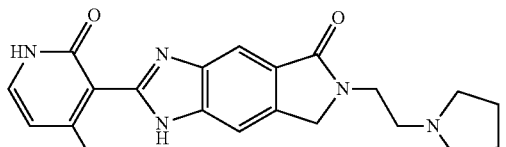

(S)-2-(2-oxo-4-(1-(2,3,5-trifluorophenyl)propan-2-ylamino)-1,2-dihydropyridin-3-yl)-6-(2-(pyrrolidin-1-yl)ethyl)-6,7-dihydroimidazo[4,5-f]isoindol-5(1H)-one

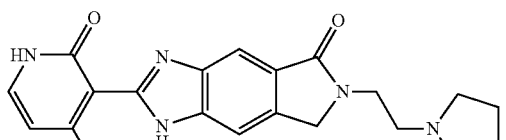

2-(4-((S)-1-(5-fluoro-2-methylphenyl)propan-2-ylamino)-2-oxo-1,2-dihydropyridin-3-yl)-6-(2-((R)-2-methylpyrrolidin-1-yl)ethyl)-6,7-dihydroimidazo[4,5-f]isoindol-5(1H)-one

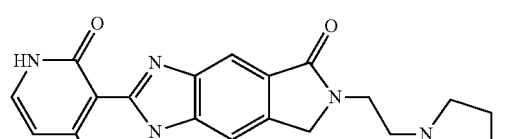

6-(2-((R)-2-methylpyrrolidin-1-yl)ethyl)-2-(2-oxo-4-((S)-1-(2,3,5-trifluorophenyl)propan-2-ylamino)-1,2-dihydropyridin-3-yl)-6,7-dihydroimidazo[4,5-f]isoindol-5(1H)-one -continued

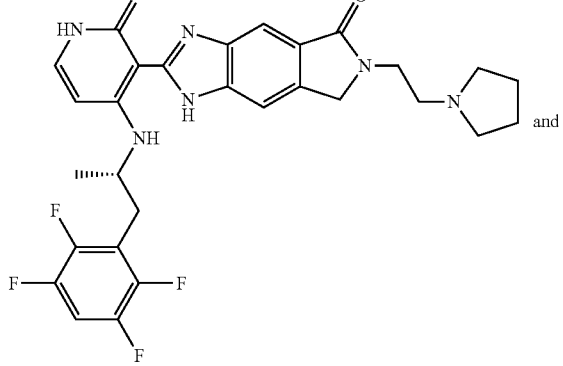

(S)-2-(2-oxo-4-(1-(2,3,5,6-tetrafluorophenyl)propan-2-ylamino)-1,2-dihydropyridin-3-yl)-6-(2-(pyrrolidin-1-yl)ethyl)-6,7-dihydroimidazo[4,5-f]isoindol-5(1H)-one and

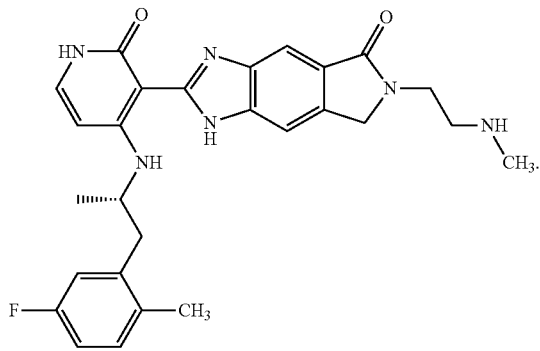

(S)-2-(4-(1-(5-fluoro-2-methylphenyl)propan-2-ylamino)-2-oxo-1,2-dihydropyridin-3-yl)-6-(2-(methylamino)ethyl)-6,7-dihydroimidazo[4,5-f]isoindol-5(1H)-one 17. A compound of any one of claims 1 to 16 which is a selective Alk inhibitor.

18. A pharmaceutical composition comprising a compound according to any one of claims 1 to 16 and one or more pharmaceutically acceptable diluents, excipients or carriers.

19. A method of modulating a tyrosine kinase activity comprising the step of contacting the tyrosine kinase with an amount of a compound according to any one of claims 1 to 16 effective to modulate the tyrosine kinase activity.

20. The method of claim 19, wherein said tyrisone kinase is selected from the group consisting of Alk, Axl, CSFR, DDR1, DDR2, EphB4, EphA2, EGFR, Flt-1, Flt3, Flt4, FGFR1, FGFR2, FGFR3, FGFR4, HER2, HER3, HER4, IR, IGF1R, IRR, Kit, KDR/Flk-1, Met, Mer, PDGFR.alpha., PDGFR.beta., Ret, Ros, Ron, Tie1, Tie2, TrkA, TrkB and TrkC.

21. The method of claim 20, wherein the tyrosine kinase is Alk, Axl, Ret, Ros, TrkA, TrkB or TrkC.

22. The method of claim 20, wherein the tyrosine kinase is Alk.

23. A method of treating a condition or disorder related to tyrosine kinase activity comprising administering to a subject a compound according to any one of claims 1 to 16 wherein said condition or disorder is selected from the group consisting of ALK-positive anaplastic large cell lymphoma, an inflammatory myofibroblastic tumor, diffuse large B-cell non-Hodgkin lymphoma, non-small cell lung cancer, esophageal carcinoma, breast cancer, neuroblastoma and glioblastoma.

24. The method of claim 23, wherein the tyrosine kinase activity is Alk activity.

25. A method of inhibiting a tyrosine kinase activity comprising contacting the tyrosine kinase with a compound according to any one of claims 1 to 16.

26. The method of claim 25, wherein the tyrosine kinase activity is Alk activity.

* * * * *